United States Patent [19]

Isaacs et al.

[11] Patent Number: 5,139,940
[45] Date of Patent: Aug. 18, 1992

[54] ACTIVATION COMPOUNDS AND METHODS OF SYNTHESIS OF ACTIVATION COMPOUNDS

[76] Inventors: Stephen T. Isaacs, 79 Loma Vista Dr., Orinda, Calif. 94563; Goerge D. Cimino, 1435 Liberty St., El Cerrito, Calif. 94530; Kenneth C. Metchette, 2041 Francisco St., #12, Berkeley, Calif. 94709; John W. Tessman, 1342 Northside Ave., Berkeley, Calif. 94702

[21] Appl. No.: 427,303

[22] Filed: Oct. 26, 1989

[51] Int. Cl.$^5$ ............................................. C12Q 1/68
[52] U.S. Cl. ........................................ 435/91; 435/6; 435/810; 436/501; 514/455; 514/457; 536/27; 935/78; 935/88
[58] Field of Search ............................ 435/6, 91, 810; 436/501; 536/27; 935/78, 88; 514/455, 457

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 546/270 |
| 4,196,281 | 4/1980 | Hearst et al. | 536/28 |
| 4,312,883 | 1/1982 | Baccicetti et al. | 424/279 |
| 4,398,031 | 8/1983 | Bender et al. | 549/282 |
| 4,683,195 | 7/1987 | Mullis et al. | 435/6 |
| 4,683,202 | 7/1987 | Mullis | 435/91 |

FOREIGN PATENT DOCUMENTS

84134 A/79  8/1979  Italy.

OTHER PUBLICATIONS

National Institutes of Health, Federal Register 41:27902 (1976).
National Institutes of Health, Federal Register 43:60108 (1978).
E. Fisher and D. R. Lincoln, Recomb. DNA Tech. Bull. 7:1 (1984).
R. W. Old and S. B. Primrose, Principles of Gene Manipulatoin, pp. 157-158 (Univ. of Cal, Press, 2nd Edition 1981).
T. Maniatis et al., Molecular Cloning, pp. 23-24 (Cold Spring Harbor Laboratory 1982).
P. M. Lizardi et al., Biotechnology 6:1197 (1988).
D. L. Kacian et al., Proc. Natl. Acad. Sci. USA 69:3038 (1972).
B. C. F. Chu et al., Nucleic Acids Res. 14:5591 (1986).
P. Knight, Biotechnology 7:609 (1989).
S. Kwok and R. Higuchi, Nature 339:237 (1989).
PCR Technology, H. A. Erlich (ed.) (Stockton Press 1989).
K. Mullis et al., Cold Spring Harbor Symposia, vol. LI, pp. 263-273 (1986).
G. D. Cimino et al., Ann. Rev. Biochem. 54:1151 (1985).
J. E. Hearst et al., Quart. Rev. Biophys. 17:1 (1984).
S. T. Isaacs et al., Biochemistry 16:1058 (1977).
S. T. Isaacs et al., Trends in Photobiology (Plenum) pp. 279-294 (1982).
J. W. Tessman et al., Biochem. 24:1669 (1985).
F. Bordin et al., Experentia 35:1567 (1979).
F. Dall'Acqua et al., Medeline Biologie Envir. 9:303 (1981).
S. Caffieri et al., Medecine Biologie Envir. 11:386 (1983).

(List continued on next page.)

*Primary Examiner*—Amelia Burgess Yarbrough
*Assistant Examiner*—Ardin H. Marschel
*Attorney, Agent, or Firm*—Limbach & Limbach

[57] ABSTRACT

The invention is directed to isopsoralen compound compositions that contain a variety of substitutions which yet permit their binding to nucleic acid polymers. Reaction conditions that activate these bound isopsoralens results in covalent crosslinking to the nucleic acid polymers. The resultant complex is inhibited from being a template for the template-directed enzymatic synthesis of a complementary nucleic acid polymer. Beside the isopsoralens compositions, the invention includes their synthesis, the nucleic acid complex production and detection, and the above inhibitory method of use of the isopsoralens.

42 Claims, 56 Drawing Sheets

OTHER PUBLICATIONS

F. Dall'Acqua et al., Photochem Photobio. 37:373 (1983).
G. Guiotto et al., Eur. J. Med. Chem–Chim. Ther. 16:489 (1981).
F. Dall'Acqua et al., J. Med. Chem. 24:178 (1984).
S. Isaacs et al., Nat. Cancer Inst. Monograph No. 66:21 (1985).
Green et al., Biochem. J. 125:781 (1971).
J. P. Albarella et al., Nucleic Acids Res. 17:4293 (1983).
L. Bretherick, Hazards in the Chemical Laboratory (Royal Society, London 1981) (p. 247).
D. R. Bender et al., J. Org. Chem. 44:2176 (1979).
N. D. Heindel et al., J. Hetero. Chem. 22:73 (1985).
Hyde and Hearst, Biochemistry 17:1251 (1978).
Thompson et al., J. Mol. Biol. 147:417 (1981).
Thompson et al., Biochemistry 21:1363 (1982).
W. I. Wood et al., Proc. Natl. Acad. Sci. 82:1585 (1985).
Guiotto et al., J. Med. Chem. 27:959 (1984).
I. Willis and J. M. Menter, Nat. Cancer Inst. Monograph 66:143 (1985).
P. R. Langer et al., Proc. Natl. Acad. Sci. U.S.A. 78:6633 (1981).
P. D. Moore et al., Proc. Natl. Acad. Sci 78:110 (1981).
P. D. Moore et al., Proc. Natl. Acad. Sci. 79:7166 (1982).
J. G. Piette and P. D. Moore, Photochem. Photobiol. 35:705 (1982).
C. N. Ou et al., Biochemistry 17:1047 (1978).
J. G. Piette and J. E. Hearst, Proc. Natl. Acad. Sci. 80:5540 (1983).
J. G. Piette and J. E. Hearst, Int. J. Radiat. Biol. 48:381 (1985).
G. Ericson and P. Wollenzien, Analytical Biochem. 174:215 (1988).
M. Chamberlin et al., Nature 228:227 (1970).
D. Y. Wu and R. B. Wallace, Genomics 4:560 (1989).
G. J. Murakawa et al., DNA 7:287 (1988).
G. D. Cimino et al., Biochemistry 25:3013 (1986).
C. Y. Ou et al., Science 239:295 (1988).
Bordin et al., Z. Naturforsch. 33:296 (1978).
Bordin et al., Photochem. Photobiol. 29:1063 (1979).

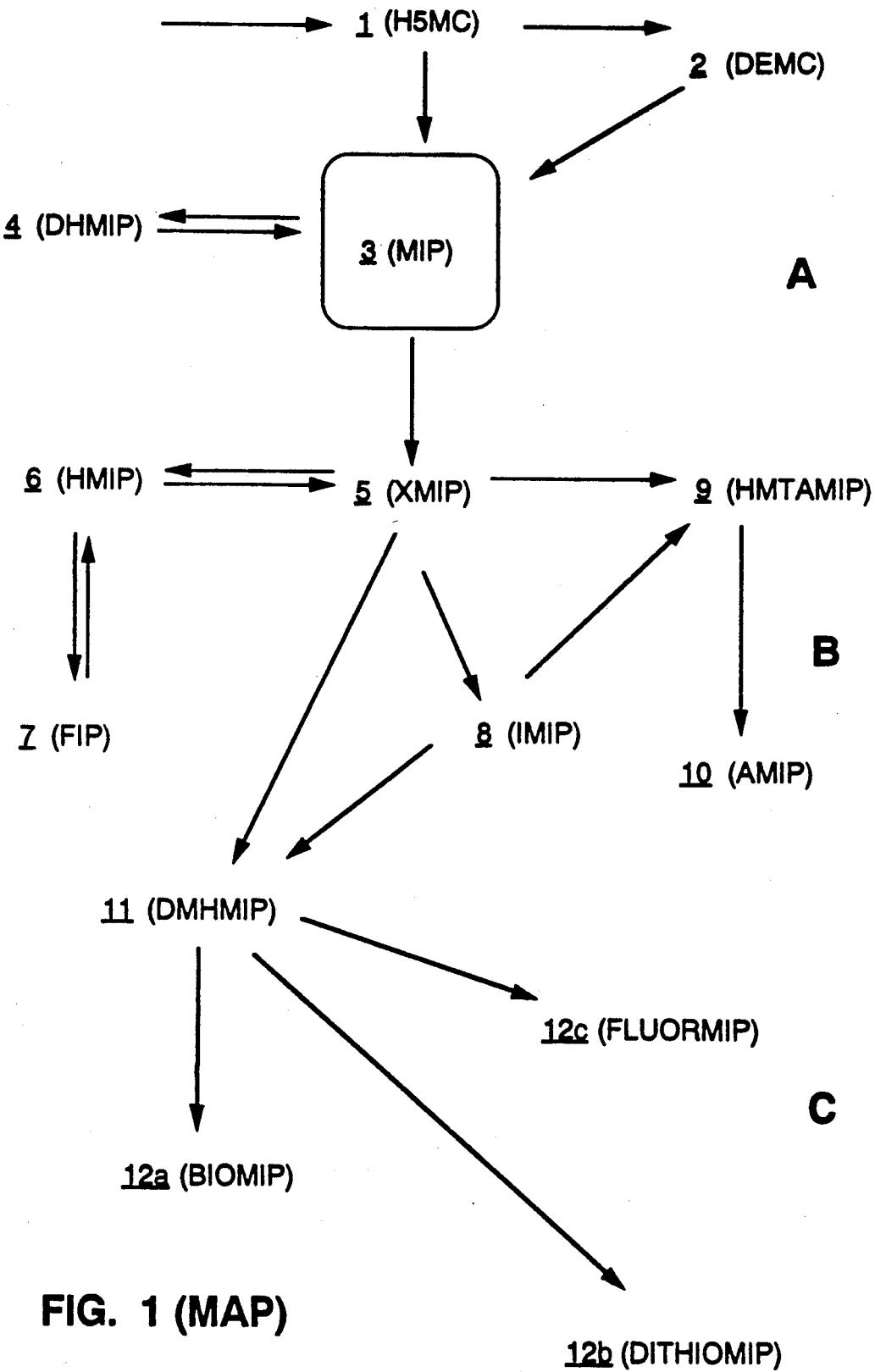
FIG. 1 (MAP)

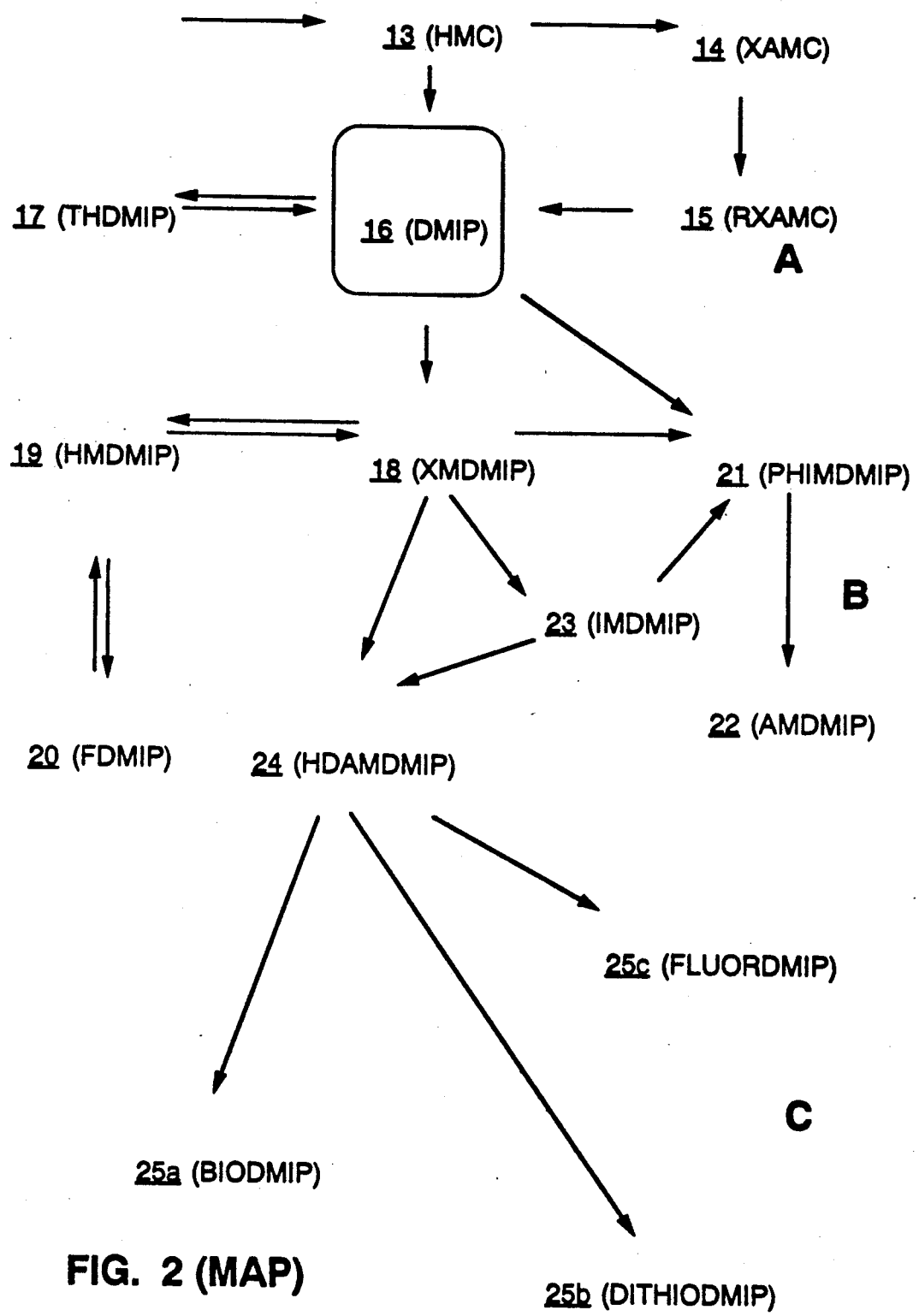
FIG. 2 (MAP)

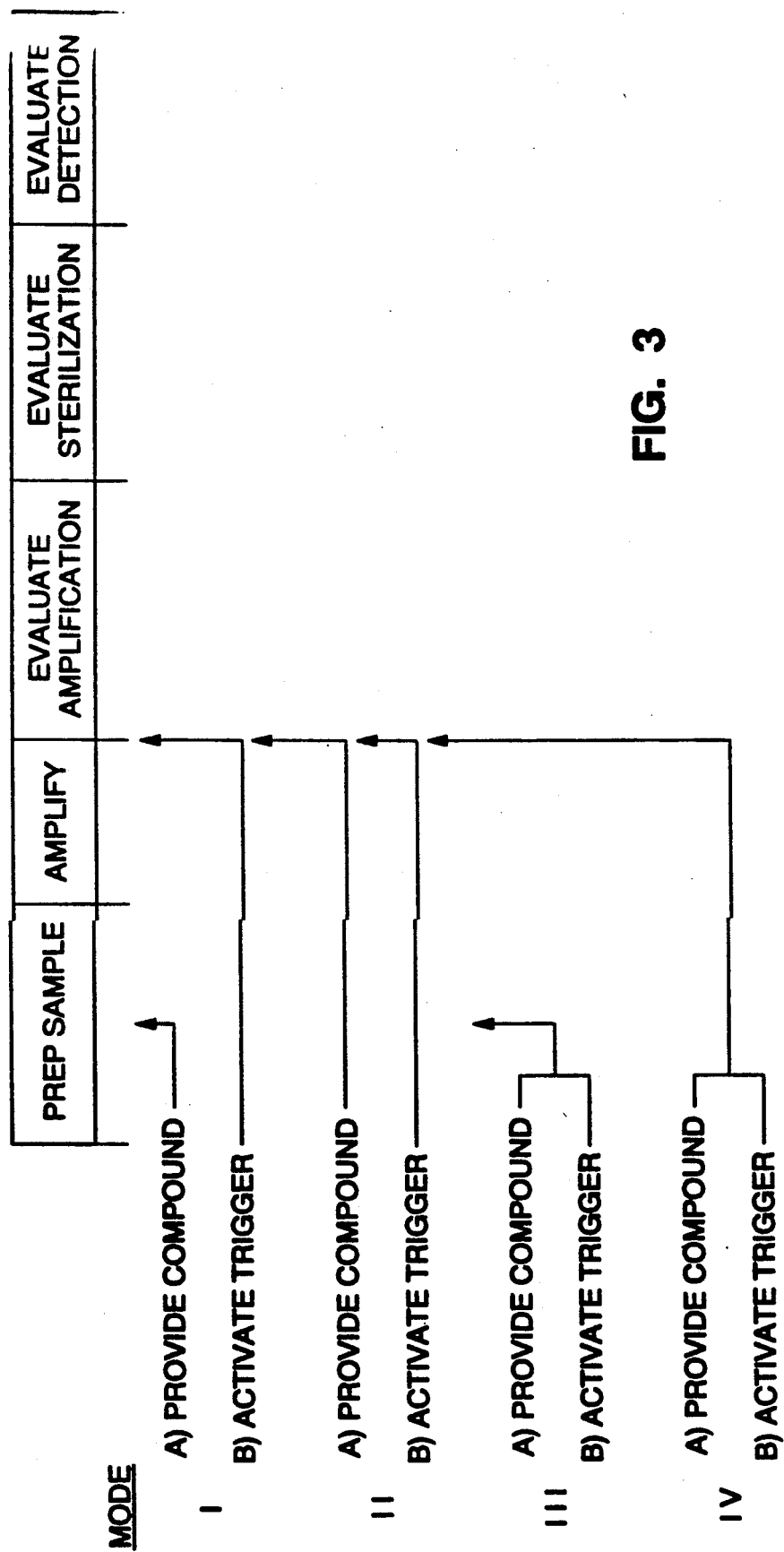

HRI 45   3' - C CCT AAT TTA TTT TAT CAT TCT TAC -5'

HRI 43   3' - C CCT AAT TTA 5'

HRI 42   5' - ATC CTG GGA TTA AAT -3'

HRI 102                              5' - AAA ATA GTA AGA ATG TAT AGC CCT ACC AGC ATT CTG GAC ATA AGA CAA GGA CCA AA -3'

HRI 55   5' - ATC CTG GGA TTA AAT AAA ATA GTA AGA ATG TAT AGC CCT ACC AGC ATT CTG GAC ATA AGA CAA GGA CCA AA -3'

SK39                                 3' - CG TAA GAC CTG TAT TCT GTT CCT GGT TT -5'

FIG. 26

ANALYSIS BY DENATURING PAGE

| PCR DILUTION FACTOR | $10^4$ | $10^6$ | $10^8$ |
| --- | --- | --- | --- |
| CARRYOVER COPIES OF HIV 115-mer | $10^7$ | $10^5$ | $10^3$ |
| hν | − + | − + | − + |
115-mer
FIG. 43

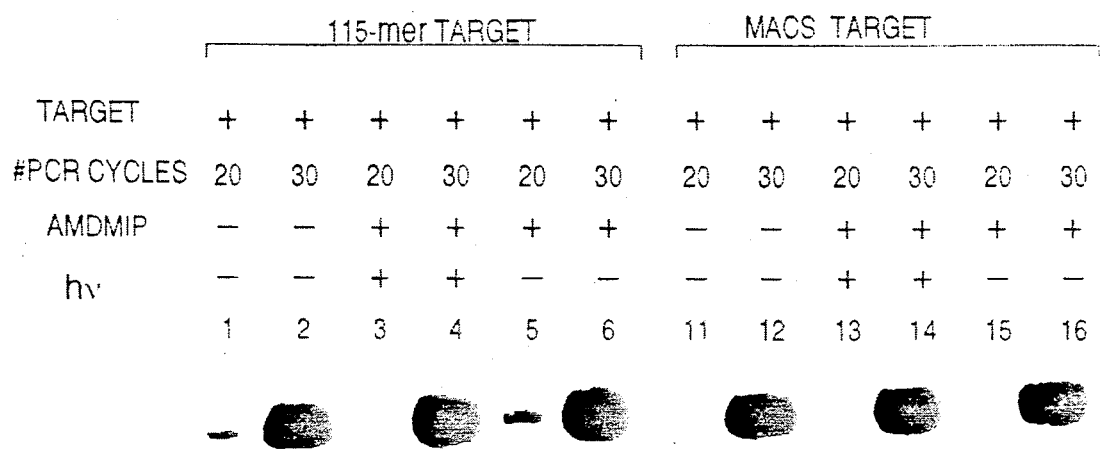
FIG. 46

ACTIVATION COMPOUNDS AND METHODS OF SYNTHESIS OF ACTIVATION COMPOUNDS

FIELD OF THE INVENTION

The present invention relates to i) new methods of synthesis of known compounds, ii) new compounds and methods of synthesis of new compounds, iii) methods for binding new and known compounds to nucleic acid, and iv) methods for using new and known compounds to inhibit template-dependent enzymatic synthesis of nucleic acid.

BACKGROUND

Nucleic acid technology has made possible the manipulation, amplification, selection and characterization of a potentially very large number of eukaryotic, prokaryotic and viral genes. Most importantly, application of nucleic acid techniques allows for the isolation of any nucleic acid sequence within a complex genome, the modification of the sequence, and the introduction of the sequence into diverse species.

With the prospect of advertently or inadvertently releasing nucleic acid sequences into nature that are either a) modified but present in their normal host species, or b) normal but present in a foreign host species, there is some concern that nucleic acid techniques pose a risk to human health. Regulatory approaches to this risk have focused on physical or biological containment of organisms that contain foreign or modified nucleic acid sequences. National Institutes of Health, Federal Register 41:27902 (1976). National Institutes of Health, Federal Register 43:60108 (1978). Such approaches are bolstered by studies that assess the impact of different laboratory protocols and various types of human error and equipment failures on the incidence and extent of uncontained organisms. E. Fisher and D. R. Lincoln, Recomb. DNA Tech. Bull. 7:1 (1984).

With this effort directed at nucleic acids in organisms, little attention has been paid to the problem of naked nucleic acid, i.e. nucleic acid that is free from a host organism. Depending on the particular circumstances, naked nucleic acid can be an infectious or transforming agent. R. W. Old and S. B. Primrose, Principles of Gene Manipulation, pp. 167-168 (Univ. of Cal. press, 2d Edition 1981). Furthermore, naked nucleic acid can interfere with other laboratory reactions because of carryover.

Carryover

Carryover is broadly defined here as the accidental introduction of nucleic acid into a reaction mixture. Of course, the types of accidental introductions are numerous. Nucleic acids can be introduced during a spill or because of poor laboratory technique (e.g. using the same reaction vessel or the same pipette twice). Of more concern, however, is the introduction of nucleic acids that occurs even during normal laboratory procedures, including inadvertent transfer from contaminated gloves. As with modified organisms, one of the most troubling source of this type of accident is aerosolization.

Aerosols are suspensions of fine liquid or solid particles, as in a mist. Aerosols can occur by disturbing a solution (e.g. aerosols are created during a spill), but they can also occur simply by disturbing the small amount of material on a container surface (e.g. the residue on the inner surface of a cap of a plastic tube is frequently aerosolized at the moment the tube is opened). Because of the latter, any container having highly concentrated amounts of nucleic acid is a potential source of nucleic acid carryover.

It should be pointed out that the question of whether there is carryover is only significant to the extent that such carryover interferes with a subsequent reaction. In general, any laboratory reaction that is directed at detecting and/or amplifying a nucleic acid sequence of interest among vastly larger amounts of nucleic acid is susceptible to interference by nucleic acid carryover.

Amplification Techniques

The circumstances in the modern laboratory where both a) containers having highly concentrated amounts of nucleic acid are present, and b) reactions directed at amplifying nucleic acid sequences are performed, are relatively common. The screening of genomic DNA for single copy genes is perhaps the best example of procedure involving both concentrated nucleic acid and amplification. There are a number of alternative methods for nucleic acid amplification, including 1) the replication of recombinant phage through lytic growth, 2) amplification of recombinant RNA hybridization probes, and 3) the Polymerase Chain Reaction.

1. Recombinant Vectors. Most cloning vectors are DNA viruses or bacterial plasmids with genomic sizes from 2 to approximately 50 kilobases (kb). The amplification of genomic DNA into a viral or plasmid library usually involves i) the isolation and preparation of viral or plasmid DNA, ii) the ligation of digested genomic DNA into the vector DNA, iii) the packaging of the viral DNA, iv) the infection of a permissive host (alternatively, the transformation of the host), and v) the amplification of the genomic DNA through propagation of virus or plasmid. At this point, the recombinant viruses or plasmids carrying the target sequence may be identified. T. Maniatis et al., Molecular Cloning, pp. 23-24 (Cold Spring Harbor Laboratory 1982). Identification of the recombinant viruses or plasmids carrying the target sequence is often carried out by nucleic acid hybridization using plasmid-derived probes.

Bacterial viruses (bacteriophage) can infect a host bacterium, replicate, mature, and cause lysis of the bacterial cell. Bacteriophage DNA can, in this manner, be replicated many fold, creating a large quantity of nucleic acid.

Plasmids are extrachromosomal elements found naturally in a variety of bacteria. Like bacteriophages, they are double-stranded and can incorporate foreign DNA for replication in bacteria. In this manner, large amounts of probes can be made.

The use of plasmid-derived probes for the screening of phage libraries in hybridization reactions avoids the problem of hybridization of vector DNA (e.g. phage-phage, plasmid-plasmid). In the construction of a viral library, it is therefore essential that no plasmid DNA carryover into the phage-genomic DNA mixture. If, for example, 10 picograms of clonable plasmid DNA were to carryover into a viral-genomic mixture containing 1 microgram of genomic DNA (0.001% carryover by weight), every 11 clones assessed to contain the target sequence would, on average, represent 10 false positives (i.e. plasmid-plasmid hybridization) and only 1 true positive (probe-target hybridization), assuming a frequency of 1 target insert in $1 \times 10^6$ inserts.

2. Recombinant RNA Probes. P. M. Lizardi et al., Biotechnology 6:1197 (1988), describe recombinant-RNA molecules that function both as hybridization probes and as templates for exponential amplification by QB replicase. Each recombinant consists of a specific sequence (i.e. an "internal probe") within the sequence of MDV-1 RNA. MDV-1 RNA is a natural template for the replicase. D. L. Kacian et al., Proc. Nat. Acad. Sci USA 69:3038 (1972). The recombinant can hybridize to target sequence that is complementary to the internal probe and that is present in a mixture of nucleic acid. Various isolation techniques (e.g. washing) can then be employed to separate the hybridized recombinant/target complex from a) unbound recombinant and b) nucleic acids that are non-complementary to the internal probe. B. C. F. Chu et al., Nucleic Acids Res. 14:5591 (1986). See also Biotechnology 7:609 (1989). Following isolation of the complex, QB replicase is added. In minutes a one-billion fold amplification of the recombinant (i.e. "recombinant RNA probe amplification") occurs, indicating that specific hybridization has taken place with a target sequence.

While a promising technique, recombinant RNA probe amplification works so well that carryover is of particular concern. As little as one molecule of template RNA can, in principle, initiate replication. Thus, the carryover of a single molecule of the amplified recombinant RNA probe into a new reaction vessel can cause RNA to be synthesized in an amount that is so large it can, itself, be a source of further carryover.

3. Polymerase Chain Reaction. K. B. Mullis et al., U.S. Pat. Nos. 4,683,195 and 4,683,202, describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then to annealed to their complementary sequences within the target molecule. Following annealing, the primers are extended with a polymerase so as to form a new pair of complementary strands. The steps of denaturation, primer annealing, and polymerase extension can be repeated many times (i.e. denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g. hybridization with a labelled probe; incorporation of biotinylated primers followed by avidin-enzyme conjugate detection; incorporation of $^{32}P$ labelled deoxynucleotide triphosphates, e.g. dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The PCR amplification process is known to reach a plateau concentration of specific target sequences of approximately $10^{-8}M$. A typical reaction volume is 100 $\mu l$, which corresponds to a yield of $6 \times 10^{11}$ double stranded product molecules. At this concentration, as little as one femtoliter ($10^{-9}$ microliter) of the amplified PCR reaction mixture contains enough product molecules to generate a detectable signal in a subsequent 30 cycle PCR amplification. If product molecules from a previous PCR are carried over into a new PCR amplification, it can result in a false positive signal during the detection step for the new PCR reaction.

Handling of the reaction mixture after PCR amplification can result in carryover such that subsequent PCR amplifications contain sufficient previous product molecules to result in a false positive signal. S. Kwok and R. Higuchi, Nature 339, 286 (1989). PCR Technology, H. A. Erlich (ed.) (Stockton Press 1989). This can occur either through aerosols or through direct introduction, as described above for other types of carryover.

Control of Carryover

At present, there are three approaches for the control of carryover. These can be broadly defined as: 1) containment, 2) elimination, and/or 3) prevention. With the containment approach, amplification is performed in a closed system. Usually, this means a designated part of the laboratory that is closed off from all other space. Of course, the designated area must be appropriately configured for the particular amplification assay. In the case of replication of recombinant phage through lytic growth, the area must allow for the amplification of the genomic DNA through propagation of virus or plasmid. The area must also provide all the requisite equipment and reagents for amplification and subsequent detection of the amplified segment of the target sequence.

The problem with containment is that it is very inconvenient. In order for the containment area to be configured to provide conditions appropriate for all the steps of amplification, the laboratory must commit a separate set of equipment. This duplicate set of equipment, furthermore, is also subject to carryover. Over time it can be rendered unusable.

The elimination approach is used when carryover has already occurred. New stocks of enzymes, buffers, and other reagents are prepared along with a complete and thorough cleaning of the laboratory area where amplification is performed. All surfaces are scrubbed and all disposable supplies replaced. Suspect laboratory equipment is either discarded or removed from the area.

The elimination approach is also unsatisfactory. First, it does not entirely render the area free of carryover. Indeed, the cleaning process can, itself, generate aerosols. Second, the level of thoroughness needed in the cleaning requires too much time. Finally, it is not practical to constantly be discarding or removing laboratory equipment.

One preventative approach to dealing with plasmid carryover in phage libraries is the purification of the probe. Purifying the probe so that it is essentially free of plasmid DNA can reduce the incidence of plasmid-plasmid hybridization.

There are a number of problems with this approach. First, while reducing the incidence of plasmid-plasmid hybridization, this method leaves the carryover in the library. Second, purification is never 100%; the method can only reduce, not eliminate, the problem. This carryover is an inherent problem with all cloning vectors including not only bacterial viruses and plasmids, but also animal and plant viruses and plasmids as well as the more recent technologies such as yeast chromosomal vectors.

There is at present one preventative approach to dealing with recombinant-RNA probe carryover. This involves base treatment to destroy RNA carryover. This approach will not harm DNA target. However, it is obviously inadequate as a treatment for RNA target.

The only prevention method for PCR carryover that has been considered up to now involves the use of nested primers. While originally applied to PCR to improve specificity, the nested primer technique can also be applied to PCR as a means of reducing the problem of carryover. Nested primers are primers that anneal to the target sequence in an area that is inside the annealing boundaries of the two primers used to start PCR. K. B. Mullis et al., Cold Spring Harbor Symposia, Vol. LI, pp. 263–273 (1986). When applied to the carryover problem, nested primers are used that have non-overlapping sequences with the starting primers. Because the nested primers anneal to the target inside the annealing boundaries of the starting primers, the predominant PCR-amplified product of the starting primers is necessarily a longer sequence than that defined by the annealing boundaries of the nested primers. The PCR amplified product of the nested primers is an amplified segment of the target sequence that cannot, therefore, anneal with the starting primers. If this PCR-amplified product of the nested primers is the nucleic acid carried over into a subsequent PCR amplification, the use of the starting primers will not amplify this carryover.

There are at least two problems with the nested primer solution to carryover in PCR reactions. First, the carryover is neither removed, nor inactivated (inactivation is defined as rendering nucleic acid unamplifiable in PCR). Second, the amplified product of the nested primers will be amplified if the same nested primers are used in a subsequent PCR.

Of course, another solution to carryover in subsequent PCR amplifications is to use different primers altogether. This is not, however, a practical solution. First, making new primers for every new PCR amplification would be extremely time consuming and costly. Second, PCR amplification with each primer pair must be individually optimized. Third, for a target sequence of a given length, there is a limit to the number of non-overlapping primers that can be constructed.

The present invention offers the first definitive method for controlling carryover. These methods involve the use of compounds, including psoralens and isopsoralens.

Psoralens. Psoralens are tricyclic compounds formed by the linear fusion of a furan ring with a coumarin. Psoralens can intercalate between the base pairs of double-stranded nucleic acids, forming covalent adducts to pyrimidine bases upon absorption of longwave ultraviolet light. G. D. Cimino et al., Ann. Rev. Biochem. 54:1151 (1985). Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., Biochemistry 16:1058 (1977). S. T. Isaacs et al., Trends in Photobiology (Plenum) pp. 279–294 (1982) J. Tessman et al., Biochem. 24:1669 (1985). Hearst et al., U.S. Pat. No. 4,124,589 (1978). Hearst et al., U.S. Pat. No. 4,169,204 (1980). Hearst et al., U.S. Pat. No. 4,196,281 (1980).

Isopsoralens. Isopsoralens, like psoralens, are tricyclic compounds formed by the fusion of a furan ring with a coumarin. See Baccichetti et al., U.S. Pat. No. 4,312,883. F. Bordin et al., Experientia 35:1567 (1979). F. Dall'Acqua et al., Medeline Biologie Envir. 9:303 (1981). S. Caffieri et al., Medecine Biologie Envir. 11:386 (1983). F. Dall'Acqua et al., Photochem Photobio. 37:373 (1983). G. Guiotto et al., Eur. J. Med. Chem-Chim. Ther. 16:489 (1981). F. Dall'Acqua et al., J. Med. Chem. 24:178 (1984). Unlike psoralens, the rings of isopsoralen are not linearly annulated. While able to intercalate between the base pairs of double-stranded nucleic acids and form covalent adducts to nucleic acid bases upon absorption of longwave ultraviolet light, isopsoralens, due to their angular geometry, normally cannot form crosslinks with DNA. See generally, G. D. Cimino et al., Ann. Rev. Biochem. 54:1151 (1985).

Objects and advantages of the present invention will be apparent from the following description when read in connection with the accompanying figures.

SUMMARY OF THE INVENTION

The present invention relates to i) new methods of synthesis of known compounds, ii) new compounds and methods of synthesis of new compounds, iii) methods for binding new and known compounds to nucleic acid, and iv) methods for using new and known compounds to inhibit template dependent enzymatic synthesis of nucleic acid.

With respect to new methods of synthesis of known compounds, the present invention provides new methods of synthesizing 5-methylisopsoralen. In one embodiment, the method comprises the steps: a) providing 7-hydroxy-5-methylcoumarin; and b) treating 7-hydroxy-5-methylcoumarin so that 5-methylisopsoralen is produced. In another embodiment, the method comprises the steps: a) providing 7-hydroxy-5-methylcoumarin; b) treating 7-hydroxy-5-methylcoumarin so that 7-(2,2-diethoxyethyloxy)-5-methylcoumarin is produced, and c) treating 7-(2,2-diethoxyethyloxy)-5-methylcoumarin so that 5-methylisopsoralen is produced.

With respect to additional new methods of synthesis of known compounds, the present invention provides new methods of synthesizing 4,5'-dimethylisopsoralen. The method comprises the steps: a) providing 7-alkylcarbonyloxy-6-($\beta$-haloallyl)-4-methylcoumarin; and b) treating 7-alkylcarbonyloxy-6-($\beta$-haloallyl)-4-methylcoumarin so that 4,5'-dimethylisopsoralen is produced.

With respect to still additional new methods of synthesis of known compounds, the present invention provides new methods of synthesizing 4'-aminomethyl-4,5'-dimethylisopsoralen. In one embodiment, the method comprises the steps: a) providing 7-alkylcarbonyloxy-6-($\beta$-haloallyl)-4-methylcoumarin; b) treating 7-alkylcarbonyloxy-6-($\beta$-haloallyl)-4-methylcoumarin so that 4,5'-dimethylisopsoralen is produced; and c) treating 4,5'-dimethylisopsoralen so that 4'-aminomethyl-4,5'- dimethylisopsoralen is produced. In another embodiment, the method comprises the steps: a) providing 4,5'-dimethylisopsoralen; and b) reacting 4,5'-dimethylisopsoralen with a nitrogen donor so that 4'-aminomethyl-4,5'-dimethylisopsoralen is produced. The nitrogen donor may be selected from the group consisting of phthalimide salts, N-hydroxymethyl phthalimide and hexamethylenetetramine. In still another embodiment, the method comprises the steps: a) providing 4'-hydroxymethyl-4,5'-dimethylisopsoralen; b) treating 4'-hydroxymethyl-4,5'-dimethylisopsoralen so that 4'-halomethyl-4,5'-dimethylisopsoralen is produced; c) treating 4'-halomethyl-4,5'-dimethylisopsoralen so that 4'-phthalimidomethyl-4,5'-dimethylisopsoralen is produced; and d) treating 4'-phthalimidomethyl-4,5'-dimethylisopsoralen so that 4'-aminomethyl-4,5'-dimethylisopsoralen is produced.

With respect to new compounds, the present invention contemplates a compound having the formula:

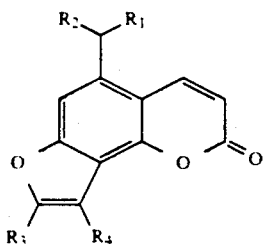

in which $R_1$ is —OH, —Br, —Cl, —I, —NH$_2$, or —NH$_3^+$ X$^-$, where X$^-$ is Br$^-$, Cl$^-$ or I$^-$, and where $R_2$, $R_3$ and $R_4$, which may be the same or different, are —H or —$^3$H.

The present invention further contemplates a new compound having the formula:

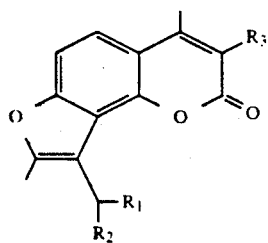

in which $R_1$ is —Br or —I, and where $R_2$ and $R_3$, which may be the same or different, are —H or $^3$H.

The present invention further contemplates a new compound having the formula:

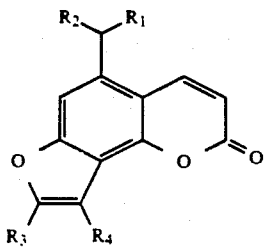

in which $R_1$ is

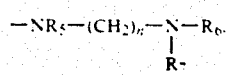

where n is a whole number between 6 and 16, where $R_2$, $R_3$ and $R_4$, which may be the same or different, are —H or $^3$H, and where $R_5 = R_7 =$ —CH$_3$, —C$_2$H$_5$, —C$_3$H$_7$ or —C$_4$H$_9$ and $R_6$ may have the formula —H or:

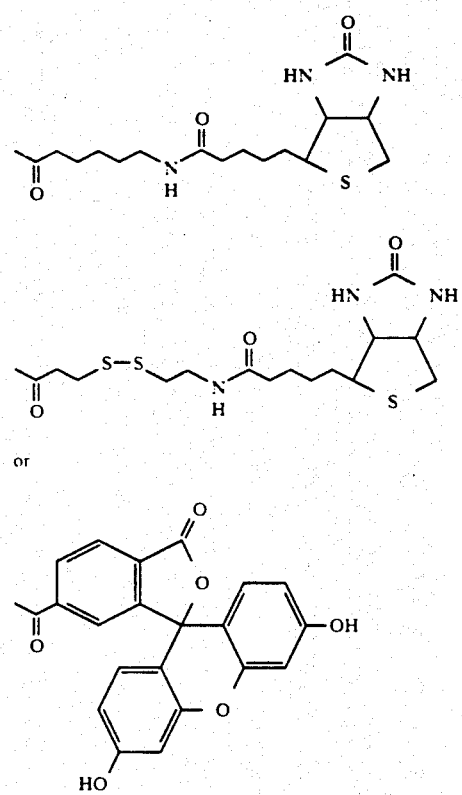

or a salt thereof.

The present invention further contemplates a compound having the formula:

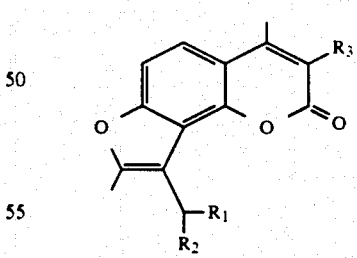

in which $R_1$ is

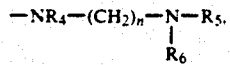

where n is a whole number between 6 and 16, where $R_2$ and $R_3$, which may be the same or different, are —H or $^3$H, and where $R_4 = R_6 =$ —CH$_3$, —C$_2$H$_5$, —C$_3$H$_7$ or —C$_4$H$_9$ and $R_5$ may have the formula —H or:

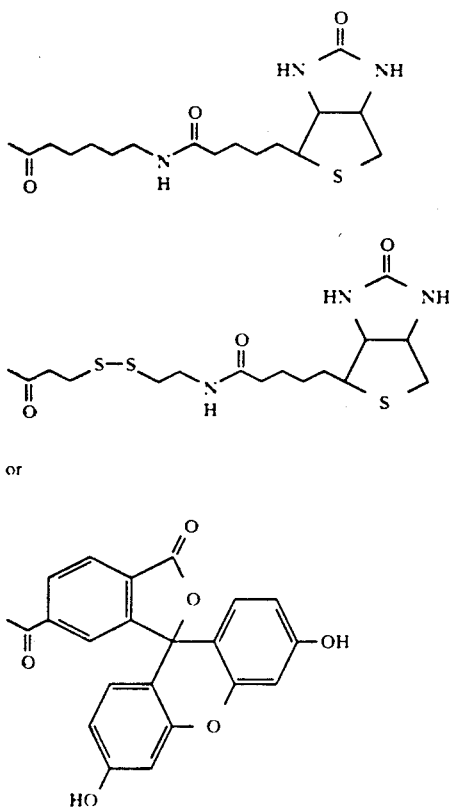

or a salt thereof.

The present invention further contemplates a compound having the formula:

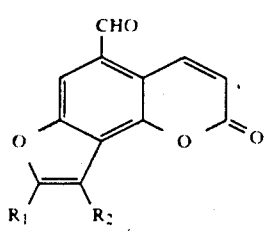

in which $R_1$ and $R_2$, which may be the same or different, are —H or $^3$H.

The present invention further contemplates a compound having the formula:

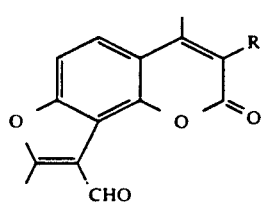

in which R is —H or $^3$H.

The present invention further contemplates a compound having the formula:

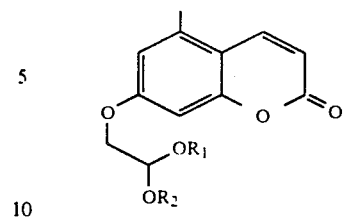

in which $R_1$ and $R_2$, which may be the same or different, are —CH$_3$, —C$_2$H$_5$, —C$_3$H$_7$ or —C$_4$H$_9$.

The present invention further contemplates a compound having the formula:

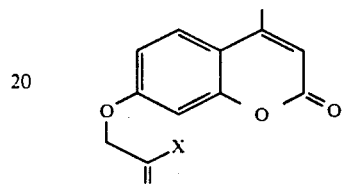

in which X is —Cl, —Br or —I.

The present invention further contemplates a compound having the formula:

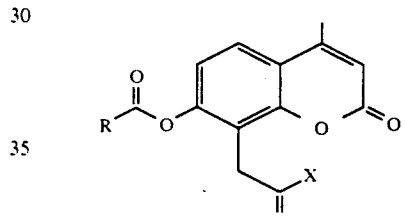

in which X is —Cl, —Br or —I and R is —CH$_3$, —C$_2$H$_5$, —C$_3$H$_7$ or —C$_4$H$_9$.

The present invention further contemplates a compound having the formula:

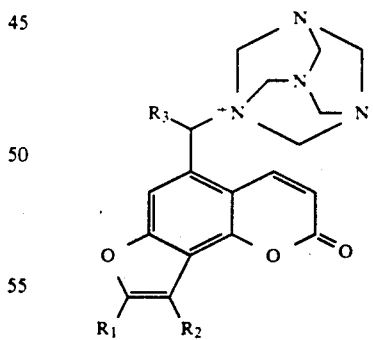

in which $R_1$, $R_2$ and $R_3$, which may be the same or different, are —H or $^3$H.

With respect to methods for synthesizing new compounds, the present invention contemplates a method of synthesizing 5-aminomethylisopsoralen, comprising the steps: a) providing a 5-halomethylisopsoralen; and b) treating said 5-halomethylisopsoralen, so that 5-aminomethylisopsoralen is produced. In one embodiment, the providing of a 5-halomethylisopsoralen comprises synthesizing 5-bromomethylisopsoralen from 5-methylisopsoralen. In another embodiment, the treating of 5-halomethylisopsoralen comprises reacting the 5-halomethylisopsoralen with hexamethylenetetramine.

The present invention further contemplates a method of synthesizing radiolabelled 5-aminomethylisopsoralen, comprising the steps: a) providing formylisopsoralen; and b) treating said formylisopsoralen, so that radiolabelled 5-aminomethylisopsoralen is produced.

The present invention contemplates binding the above-named compounds to nucleic acid. In one embodiment, the present invention contemplates a complex, comprising one or more of the above-named compounds, bound to nucleic acid. In another embodiment, the present invention contemplates a complex, comprising one or more of the above-named compounds, bound to nucleic acid, wherein the binding is non-covalent. In still another embodiment, the present invention contemplates a complex, comprising one or more of the above-named compounds, bound to nucleic acid, wherein the binding is covalent.

The present invention contemplates binding new and known compounds to nucleic acid at a high level of addition. In one embodiment, the present invention contemplates a complex, comprising 5-aminomethylisopsoralen bound to nucleic acid at a level of addition greater than one 5-aminomethylisopsoralen molecule per fifty nucleic acid base pairs. In another embodiment, the present invention contemplates a complex, comprising 4'-aminomethyl-4,5'-dimethylisopsoralen bound to nucleic acid at a level of addition greater than one 4'-aminomethyl-4,5'-dimethylisopsoralen molecule per fifty nucleic acid base pairs.

In one embodiment, the present invention contemplates a method of producing a 5-aminomethylisopsoralen/nucleic acid complex, comprising the steps: a) providing 5-aminomethylisopsoralen and nucleic acid; and b) binding the 5-aminomethylisopsoralen to said nucleic acid.

In one embodiment, the method provides for covalent binding. In one embodiment, the present invention contemplates that covalent binding is achieved by photoactivation of 5-aminomethylisopsoralen. In one embodiment, photoactivation is achieved by exposure of said 5-aminomethylisopsoralen to electromagnetic radiation.

It is not intended that the present invention be limited by the nature of the nucleic acid bound. The present invention contemplates all forms and sources of RNA and DNA. In one embodiment, the nucleic acid is selected from the group consisting of Eukaryotic DNA and Prokaryotic DNA. In another embodiment, the nucleic acid of the above-described complexes is Human Immunodeficiency Virus nucleic acid. In another embodiment, the nucleic acid of the above-described complexes is human nucleic acid. In still another embodiment, the nucleic acid is selected from the group consisting of viral, bacterial, fungal, mycoplasmal and protozoan nucleic acid.

The present invention further contemplates a method for labelling nucleic acid. In one embodiment, the method comprises the steps: a) providing labelled 5-aminomethylisopsoralen and nucleic acid; and b) binding said 5-aminomethylisopsoralen to said nucleic acid.

The present invention further contemplates a method for inhibiting template-dependent enzymatic synthesis of nucleic acid, comprising the steps: a) providing one or more furocoumarins and nucleic acid; and b) coupling one or more furocoumarins to said nucleic acid, so that it cannot be replicated by Taq polymerase.

In another embodiment, the present invention further contemplates a method for inhibiting template-dependent enzymatic synthesis of nucleic acid, comprising the steps: a) providing 5-methylisopsoralen and nucleic acid; and b) binding said 5-methylisopsoralen to nucleic acid, so that it inhibits replication of nucleic acid by reverse transcriptase.

The present invention further contemplates a method for inhibiting template-dependent enzymatic synthesis of nucleic acid, comprising the steps: a) providing 5-methylisopsoralen and nucleic acid; and b) binding said 5-methylisopsoralen to nucleic acid, so that it cannot be replicated by Taq polymerase.

The present invention further contemplates a method for inhibiting template-dependent enzymatic synthesis of nucleic acid, comprising the steps: a) providing 5-methylisopsoralen and nucleic acid; and b) binding said 5-methylisopsoralen to nucleic acid, so that it cannot be replicated by T4 polymerase.

The present invention further contemplates a method for inhibiting template-dependent enzymatic synthesis of nucleic acid, comprising the steps: a) providing 5-aminomethylisopsoralen and nucleic acid; and b) binding said 5-aminomethylisopsoralen to nucleic acid, so that it inhibits replication of nucleic acid by reverse transcriptase.

The present invention further contemplates a method for inhibiting template-dependent enzymatic synthesis of nucleic acid, comprising the steps: a) providing 5-aminomethylisopsoralen and nucleic acid; and b) binding said 5-aminomethylisopsoralen to nucleic acid, so that it cannot be replicated by Taq polymerase.

The present invention further contemplates a method for inhibiting template-dependent enzymatic synthesis of nucleic acid, comprising the steps: a) providing 5-aminomethylisopsoralen and nucleic acid; and b) binding said 5-aminomethylisopsoralen to nucleic acid, so that it cannot be replicated by T4 polymerase.

The present invention further contemplates a method for inhibiting template-dependent enzymatic synthesis of nucleic acid, comprising the steps: a) providing 4'-aminomethyl-4,5'-dimethylisopsoralen and nucleic acid; and b) binding said 4'-aminomethyl-4,5'-dimethylisopsoralen to nucleic acid, so that it cannot be replicated by reverse transcriptase.

The present invention further contemplates a method for inhibiting template-dependent enzymatic synthesis of nucleic acid, comprising the steps: a) providing 4'-aminomethyl-4,5'-dimethylisopsoralen and nucleic acid; and b) binding said 4'-aminomethyl-4,5'-dimethylisopsoralen to nucleic acid, so that it cannot be replicated by Taq polymerase.

The present invention further contemplates a method for inhibiting template-dependent enzymatic synthesis of nucleic acid, comprising the steps: a) providing 4'-aminomethyl-4,5'-dimethylisopsoralen and nucleic acid; and b) binding said 4'-aminomethyl-4,5'-dimethylisopsoralen to nucleic acid, so that it cannot be replicated by T4 polymerase.

The present invention further contemplates a method for inhibiting template-dependent enzymatic synthesis of nucleic acid, comprising the steps: a) providing 4'-aminomethyl-4,5'-dimethylisopsoralen and nucleic acid; and b) binding said 4'-aminomethyl-4,5'-dimethylisopsoralen to nucleic acid, so that it cannot be replicated by E. coli DNA polymerase I.

The present invention further contemplates a method for inhibiting template-dependent enzymatic synthesis of nucleic acid, comprising the steps: a) providing 4'-aminomethyl-4,5'-dimethylisopsoralen and nucleic acid; and b) binding said 4'-aminomethyl-4,5'-dimethylisopsoralen to nucleic acid, so that it cannot be replicated by Klenow polymerase.

DESCRIPTION OF THE DRAWINGS

FIG. 1 sets forth a map of a compound synthesis scheme of the present invention where the starting material is 5-methylresorcinol.

FIG. 2 sets forth a map of a compound synthesis scheme of the present invention where the starting material is resorcinol.

FIG. 3 schematically shows the steps involved in screening activation compounds for sterilizing compounds.

FIG. 26 shows the oligonucleotide system used for the synthesis and extension of 71-mers containing a single monoadduct.

FIG. 43 is an autoradiograph after gel electrophoresis, showing a PCR sterilization.

FIG. 46 is an autoradiograph after gel electrophoresis, showing hybridization after sterilization by Crosslinkable Oligonucleotide Probe Analysis (COP).

DESCRIPTION OF THE INVENTION

Figure 1A:
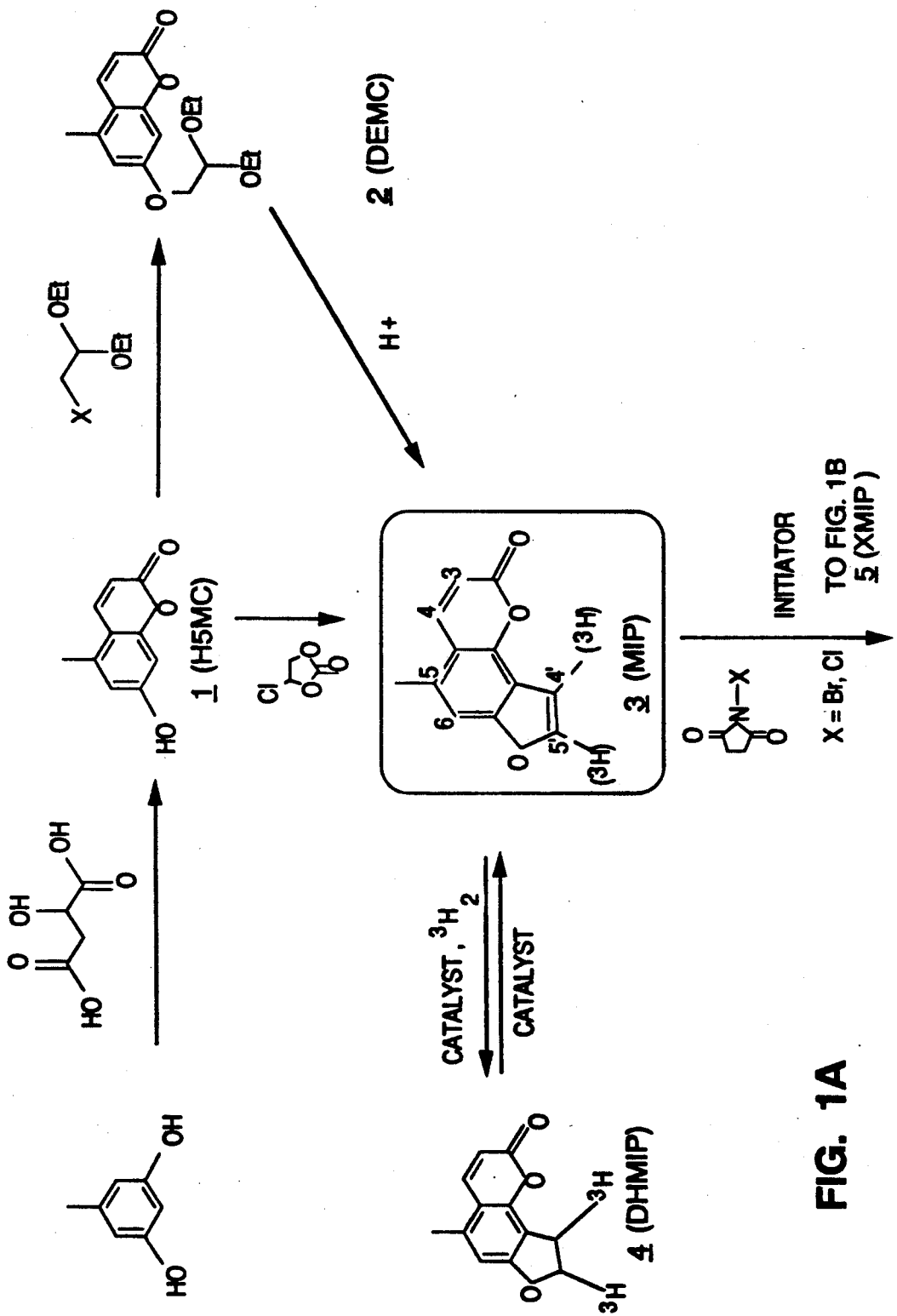
FIG. 1A details the compound synthesis scheme to Compound 3.

The present invention relates to i) new methods of synthesis of known compounds, ii) new compounds and methods of synthesis of new compounds, iii) methods for binding new and known compounds to nucleic acid, and iv) methods for using new and known compounds to inhibit template-dependent enzymatic synthesis of nucleic acid.

The description of the invention is divided into I) Compound Synthesis, II) Photoactivation Devices and Methods, III) Binding of Compounds to Nucleic Acid, IV) Capture of Nucleic Acid, V) Inhibiting Template-Dependent Enzymatic Synthesis, and VI) Sterilization.

I. COMPOUND SYNTHESIS

"Activation compounds" defines a family of compounds that undergo chemical change in response to triggering stimuli. Triggering stimuli include, but are not limited to, thermal stimuli, chemical stimuli and electromagnetic stimuli. "Photoreactive, activation compounds" (or simply "photoreactive compounds"), defines a genus of compounds in the activation compound family that undergo chemical change in response to electromagnetic radiation (Table 1).

TABLE 1

Photoreactive Compounds

Actinomycins
Anthracyclinones
Anthramycin
Benzodipyrones
Fluorenes and fluorenones
Furocoumarins
Mitomycin
Monostral Fast Blue
Norphillin A
Organic dyes
Phenanthridines
Phenazathionium Salts
Phenazines
Phenothiazines
Phenylazides
Polycyclic hydrocarbons
Quinolines
Thiaxanthenones One species of photoreactive compounds described herein is commonly referred to as the furocoumarins. The furocoumarins belong to two main categories: 1) psoralens [7H-furo(3,2-g)-(1)-benzopyran-7-one, or δ-lactone of 6-hydroxy-5-benzofuranacrylic acid], which are linear:

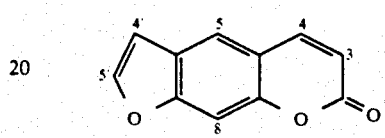

and in which the two oxygen residues appended to the central aromatic moiety have a 1, 3 orientation, and further in which the furan ring moiety is linked to the 6 position of the two ring coumarin system, and 2) the isopsoralens [2H-furo(2,3-h)-(1)-benzopyran-2-one, or δ-lactone of 4-hydroxy-5-benzofuranacrylic acid], which are angular:

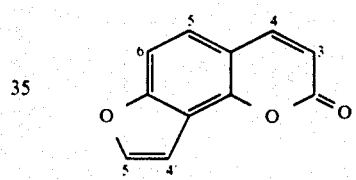

in which the two oxygen residues appended to the central aromatic moiety have a 1, 3 orientation, and further in which the furan ring moiety is linked to the 8 position of the two ring coumarin system. Psoralen derivatives are derived from substitution of the linear furocoumarin at the 3, 4, 5, 8, 4', or 5' positions, while isopsoralen derivatives are derived from substitution of the angular furocoumarin at the 3, 4, 5, 6, 4', or 5 positions.

Tables 2 and 3 set forth the nomenclature used for the furocoumarin derivatives discussed herein. FIGS. 1 and 2 set forth the overall scheme for the synthesis of the furocoumarin derivatives of the present invention.

The present invention contemplates labelled and unlabelled furocoumarin derivatives. FIGS. 1 and 2 set forth how each furocoumarin derivative may be labelled. Where both an unlabelled and radiolabelled version of a compound may be synthesized by methods of the present invention, the radiolabel is indicated in parentheses.

If labelled, the compounds will have at least one label attached or integrated into its structure. Labels are generally intended to facilitate i) the detection of the inhibiting compounds, as well as ii) the detection of molecules bound to the inhibiting compounds (e.g. nucleic acid). Labels are chosen from the group consisting of enzymes, fluorophores, high-affinity conjugates, chemiphores and radioactive atoms ("radiolabels"). While others may be used, 1) enzymes contemplated include alkaline phosphatase, β-galactosidase and glucose oxidase, 2) an affinity conjugate system contemplated is the biotin-avidin system, 3) fluorescein is contemplated as a fluorophore, 4) luminol is contemplated as chemiphore, and 4) the preferred radiolabels contemplated by the present invention include $^3$H and $^{14}$C.

It is not intended that the present invention be limited by the nature of the label used. The present invention contemplates single labelling (e.g. a radiolabel, a fluorophore, etc.) and double labelling (e.g. two radiolabels, a radiolabel and fluorphore, etc.).

TABLE 2

Furocoumarin Derivatives (MIP Series)

| # | Compound | Abbrev. |
|---|---|---|
| 1 | 7-Hydroxy-5-methylcoumarin | H5MC |
| 2 | 7-(2,2-diethoxyethyloxy)-5-methylcoumarin | DEMC |
| 3 | 5-Methylisopsoralen | MIP |
| 4 | [4',5'-H$_2$]-4',5'-dihydro-5-methyl -isopsoralen | DHMIP |
| 5 | 5-Halomethylisopsoralen | XMIP |
|   | 5-Bromomethylisopsoralen | BMIP |
|   | 5-Chloromethylisopsoralen | CMIP |
| 6 | 5-Hydroxymethylisopsoralen | HMIP |
| 7 | 5-Formylisopsoralen | FIP |
| 8 | 5-Iodomethylisopsoralen | IMIP |
| 9 | 5-Hexamethylenetetraminomethylisopsoralen | HMTAMIP |
| 10 | 5-Aminomethylisopsoralen | AMIP |
| 11 | 5-N-(N,N'-Dimethyl-1,6-hexanediamine) -methyl-isopsoralen | DMHMIP |
| 12a | 5-N-[N,N'-Dimethyl-(6-[biotinamido] -hexanoate)-1,6-hexanediamine]) -methyl-isopsoralen | BIOMIP |
| 12b | 5-N-[N,N'-dimethyl-N'-(2-(biotinamido) -ethyl-1,3-dithiopropionate)-1,6 -hexanediamine] -methyl-isopsoralen | DITHIOMIP |
| 12c | 5-N-[N,N'-dimethyl-N'-(carboxyfluorescein ester)-1,6-hexanediamine) -methyl-isopsoralen | FLUORMIP |

TABLE 3

Furocoumarin Derivatives (DMIP Series)

| | | |
|---|---|---|
| 13 | 7-Hydroxy-4-methylcoumarin | H4MC |
| 14 | 7-(β-haloallyloxy)-4-methylcoumarin | XAMC |
|    | 7-(β-chloroallyloxy)-4-methylcoumarin | CAMC |
| 15 | 7-Alkylcarbonyloxy-8-(B-haloallyl) -4-methylcoumarin | RXAMC |
|    | 7-Butyroxy-8-(B-chloroallyl) -4-methylcoumarin | BCAMC |
| 16 | 4,5'-Dimethylisopsoralen | DMIP |
| 17 | [4',5'-$^3$H$_2$]-4',5'-dihydro-4,5' -dimethylisopsoralen | DHDMIP |
| 18 | 4'-Halomethyl-4,5'-dimethylisopsoralen | XMDMIP |
|    | 4'-Chloromethyl-4,5'-dimethylisopsoralen | CMDMIP |
|    | 4'-Bromomethyl-4,5'-dimethylisopsoralen | BMDMIP |
| 19 | 4'-Hydroxymethyl-4,5'-dimethylisopsoralen | HMDMIP |
| 20 | 4'-Formyl-4,5'-dimethylisopsoralen | FDMIP |
| 21 | 4'-Phthalimidomethyl-4,5' -dimethylisopsoralen | PHIMDMIP |
| 22 | 4'-Aminomethyl-4,5'-dimethylisopsoralen | AMDMIP |
| 23 | 4'-Iodomethyl-4,5'-dimethylisopsoralen | IMDMIP |
| 24 | 4'-N-(N,N'-dimethyl-1,6-hexanediamine) -methyl-4,5'-dimethylisopsoralen | HDAMDMIP |
| 25a | 4'-N-[N,N'-dimethyl-N'-(6-(biotinamido) -hexanoate]-1,6-hexanediamine] -methyl-4,5'-dimethylisopsoralen | BIOMIP |
| 25b | 4'-N-[N,N'-dimethyl-N'-(2-(biotinamido) -ethyl-1,3-dithiopropionate)-1,6 -hexanediamine]-methyl-4,5' -dimethylisopsoralen | DITHIODMIP |
| 25c | 4'-N-[N,N'-dimethyl-N'-(6-carboxyfluorescein ester)-1,6-hexanediamine)-methyl -4,5'-dimethylisopsoralen | FLUORDMIP |

While not limited to any particular label, a preferred label of the present invention for facilitating the detection of compounds is tritium ($^3$H). A preferred label of the present invention for facilitating the detection of molecules bound to the compounds is biotin. While FIGS. 1 and 2 have been drafted to show these preferred labels (as well as some other labels), it is not intended thereby to limit the present invention.

As shown in FIGS. 1 and 2, the synthesis pathway for the compounds of the present invention involves starting with:

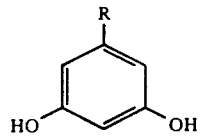

where R is either —CH$_3$ or —H, respectively.

Where R is —CH$_3$ (FIG. 1; Table 2), the starting compound is 5-methylresorcinol. Where R is —H (FIG. 2; Table 3), the starting compound is resorcinol. Accordingly, the description of the compound synthesis methods of the present invention proceeds in two parts.

A. PART ONE: R EQUALS —CH$_3$

Where R is —CH$_3$ (FIG. 1; Table 2), the synthesis proceeds via one of two new synthesis methods to MIP (Compound #3), a known compound. One of these novel synthesis methods for MIP proceeds via new compound DEMC (Compound #2).

After MIP is formed, the synthesis can continue on to create i) new compounds XMIP (Compound #5), HMIP (Compound #6), FMIP (Compound #7), IMIP (Compound #8), HMTAMIP (Compound #9), AMIP (Compound #10), DMHMIP (Compound #11), BIOMIP (Compound #12a), DITHIOMIP (Compound 12b), and/or FLUORMIP (Compound 12c), or ii) radiolabelled compounds. (In FIG. 1, radiolabels are indicated in parathesis where the compound can be synthesised unlabelled as well as labelled.) In addition to the tritiated compounds indicated in FIG. 1, the analogous ¹⁴C derivatives may be prepared ¹⁴C labelled 5-methylresorcinol.

All methods for synthesizing new compounds AMIP, BIOMIP, DITHIOMIP and FLUORMIP proceed via new compound intermediate XMIP. XMIP is defined as either CMIP or BMIP. Some methods for synthesizing AMIP, BIOMIP, DITHIOMIP and FLUORMIP proceed from XMIP through new compound IMIP (Compound #8).

The synthesis methods of the present invention where R equals —CH₃ begins with novel synthesis methods for MIP.

1) MIP Synthesis

The invention contemplates novel approaches to the synthesis of MIP and/or labelled MIP prior to the synthesis of novel MIP derivatives.

Two new methods are provided for the synthesis of MIP (FIG. 1). The first step of the first method for MIP synthesis involves a reaction of 5-methylresorcinol with malic acid to yield H5MC (Compound #1). The second step of the first method involves a reaction of H5MC with a haloacetaldehyde diethylacetal to yield the diethoxyethylether of H5MC, DEMC (Compound #2). The haloacetaldehyde diethylacetal can be chloro-, iodo- or bromoacetaldehyde diethylacetal. In the third step of the first method, DEMC is treated to close the ring to yield the two isomers, 5-methylpsoralen and MIP, which are separated to isolate pure MIP (Compound #3).

The first step of the second method for MIP synthesis is identical to the first step of the first method. The second step of the second method, however, involves the synthesis of MIP directly from H5MC (i.e., compound #2 to #3) via a haloethylene carbonate.

1') Radiolabelled MIP Synthesis

Methods are provided for the synthesis of radiolabelled MIP (FIG. 1). These methods build on the two methods of MIP synthesis with additional known steps: 1) catalytic hydrogenation of the 4',5' (furan-side) double bond using tritium gas to provide the tritiated compound, DHMIP, followed by 2) catalytic reoxidation of this bond with a hydrogen donor to yield the tritiated MIP (³H-MIP). S. Isaacs et al., Nat. Cancer Inst. Monograph No. 66 (1985). Alternatively, the reaction can be continued until catalytic hydrogenation of the 3,4 (pyrone-side) double bond resulting in the formation of the 3,4,4',5'-tetrahydro-[³H₄]-5-methylisopsoralen (THMIP). THMIP has the advantage of allowing for compounds of higher specific activity and the disadvantage of poor yield relative to DHMIP (for convenience only DHMIP is shown in FIG. 1).

The present invention contemplates that the catalyst is selected from the group consisting of palladium on charcoal, palladium on barium sulfate, Adams catalyst [(NH₄)₂PtCl₆], PtO₂, rhoduim, ruthenium, copper chromite and Raney nickel. The present invention contemplates that the hydrogen donor in the reoxidation step is selected from the group consisting of diphenylether and cyclohexene.

2) XMIP Synthesis

As noted above, all methods for synthesizing new compounds AMIP, BIOMIP, DITHIOMIP and FLUORMIP proceed via new compound XMIP as an intermediate. XMIP is defined a halomethylisopsoralen selected from the group consisting of bromomethylisopsoralen (BMIP) and chloromethylisopsoralen (CMIP).

The synthesis method of XMIP of the present invention is a free radical halogenation of MIP with an N-halosuccinimide and a peroxide initiator. The preferred N-halosuccinimide is N-bromosuccinimide but the present invention contemplates the use of N-chlorosuccinimide as well.

2') Radiolabelled XMIP Synthesis

The present invention contemplates radiolabelled XMIP. Methods are provided for the synthesis of radiolabelled XMIP (FIG. 1). In one embodiment, the method builds on the methods of synthesizing radiolabelled MIP (e.g. #3 to #4*, #4* to #3*, and #3* to #5*, where * indicates a radiolabelled compound). In another embodiment, the methods proceed via new compounds HMIP and FMIP (e.g. #5 to #6, #6 to #7, #7 to #6*, and #6* to #5*, where * indicates a radiolabelled compound). Combining the radiolabelling steps for MIP with the HMIP/FMIP radiolabelling method provides for double-radiolabelling of XMIP (e.g., #3 to #4*, #4* to #3*, and #3* to #5*, #5* to #6*, #6* to #7*, #7* to #6, and #6 to #5, where  indicates a double-radiolabelled compound).

3) AMIP Synthesis

As shown in FIG. 1, four alternative synthesis methods are provided when proceeding via new compound intermediate XMIP as starting material to new compound AMIP. One method proceeds in four steps from XMIP to new compound AMIP via new compound intermediate HMIP (i.e., compound #5 to #6, #6 to #5, #5 to #9, and #9 to #10). Another method proceeds in five steps from XMIP to new compound AMIP via new compound intermediates HMIP and IMIP (i.e., #5 to #6, #6 to #5, #5 to #8, #8 to #9, and #9 to #10) Still another proceeds in two steps from XMIP to new compound AMIP (i.e, compound #5 to #9, and #9 to #10). Still another proceeds in three steps from XMIP to new compound AMIP via new compound IMIP (i.e., #5 to #8, #8 to #9, #9 to #10).

Methods one and two allow the synthesis to be interrupted at new compound intermediate HMIP, which is stable and can be stored indefinitely without decomposition. The third method (the preferred method) proceeds in two steps from XMIP to new compound AMIP. While this third method offers the most direct route to new compound AMIP, it is inappropriate if stopping the synthesis sequence prior to completion is anticipated. This follows from the hydrolytic instability of XMIP, which must be maintained in a strictly inert environment to prevent hydrolytic decomposition. Again, XMIP is selected from the group bromomethylisopsoralen (BMIP) and chloromethylisopsoralen (CMIP) (instability increases in the order BMIP>CMIP).

In the four step method and the five step method, XMIP may be the same halomethylisopsoralen or may be a different isopsoralen. (In general, the reactivity of XMIP will increase as X is changed from chloro to bromo; a significant advantage of higher reactivity is correspondingly shorter reaction times for conversions such as XMIP→HMIP.)

In the fourth method for synthesizing AMIP, the synthesis proceeds via IMIP. In this regard, it is known that benzyl iodides are more reactive than the corresponding bromides or chlorides, which follows from the relative ability of each halide to act as a leaving group in an S_N2 (second order, nucleophilic displacement) reaction. Accordingly, to take advantage of the resulting high reactivity and corresponding short reaction times provided by the benzyl iodide analog, the new compound IMIP is prepared in the method of the present invention via the Finkelstein reaction.

When combined with the two methods for producing MIP, the present invention provides eight methods for synthesizing AMIP from 5-methylresorcinol:

| I | #1 to #2, #2 to #3, #3 to #5, #5 to #6, #6 to #5, #5 to #9, and #9 to #10. |
|---|---|
| II | #1 to #3, #3 to #5, #5 to #6, #6 to #5, #5 to #9, and #9 to #10. |
| III | #1 to #2, #2 to #3, #3 to #5, #5 to #9, and #9 to #10. |
| IV | #1 to #3, #3 to #5, #5 to #9, and #9 to #10 |
| V | #1 to #2, #2 to #3, #3 to #5, #5 to #8, #8 to #9, and #9 to #10. |
| VI | #1 to #3, #3 to #5, #5 to #8, and #9 to #10. |
| VII | #1 to #2, #2 to #3, #3 to #5, #5 to #6, #6 to #5, #5 to #8, #8 to #9, and #9 to #10. |
| VIII | #1 to #3, #3 to #5, #5 to #6, #6 to #5, #5 to #8, #8 to #9, and #9 to #10. |

3') Radiolabelled AMIP Synthesis

FIG. 1 also shows two methods provided for proceeding via new compound intermediate XMIP as starting material to new compound, radiolabelled AMIP. Both of the methods proceeding via new compound intermediate XMIP as starting material to new compound, radiolabelled AMIP, proceed via HMIP and new compound FMIP. One method is a six step method (i.e., compound #5 to #6, #6 to #7, #7 to #6*, #6* to #5*, #5* to #9*, and #9* to #10*); the other is a seven step method (i.e., compound #5 to #6, #6 to #7, #7 to #6*, #6* to #5*, #5* to #8*, #8* to #9*, and #9* to #10*).

When combined with the two methods for producing MIP, the present invention provides two additional methods (for a total of four methods) for synthesizing radiolabelled AMIP from 5-methylresorcinol; when combined with the two methods for producing radiolabelled MIP, the present invention provides eight additional methods for producing radiolabelled AMIP for a total of twelve methods:

| I | #1 to #2, #2 to #3, #3 to #4*, #4* to #3*, #3* to #5*, #5* to #6*, #6* to #5*, #5* to #9*, and #9* to #10*. |
|---|---|
| II | #1 to #3, #3 to #4*, #4* to #3*, #3* to #5*, #5* to #6*, #6* to #5*, #5* to #9*, and #9* to #10*. |
| III | #1 to #2, #2 to #3, #3 to #4*, #4* to #3*, #3* to #5*, #5* to #6*, #6* to #5*, #5* to #8*, #8* to #9*, and #9* to #10*. |
| IV | #1 to #3, #3 to #4*, #4* to #3*, #3* to #5*, #5* to #6*, #6* to #5*, #5* to #8*, #8* to #9*, and #9* to #10*. |
| V | #1 to #2, #2 to #3, #3 to #4*, #4* to #3*, #3* to #5*, #5* to #9*, and #9* to #10*. |
| VI | #1 to #3, #3 to #4*, #4* to #3*, #3* to #5*, #5* to #9*, and #9* to #10*. |
| VII | #1 to #2, #2 to #3, #3 to #4*, #4* to #3*, #3* to #5*, #5* to #8*, #8* to #9*, and #9* to #10*. |
| VIII | #1 to #3, #3 to #4*, #4* to #3*, #3* to #5*, #5* to #8*, #8* to #9*, and #9* to #10*. |
| IX | #1 to #2, #2 to #3, #3 to #5, #5 to #6, #6 to #7*, #7* to #6*, #6* to #5*, #5* to #9*, and #9* to #10*. |
| X | #1 to #3, #3 to #5, #5 to #6, #6 to #7*, #7* to #6*, #6* to #5*, #5* to #9*, and #9* to #10*. |
| XI | #1 to #2, #2 to #3, #3 to #5, #5 to #6, #6 to #7*, #7* to #6*, #6* to #5*, #5* to #8*, #8* to #9*, and #9* to #10*. |
| XII | #1 to #3, #3 to #5, #5 to #6, #6 to #7*, #7* to #6*, #6* to #5*, #5* to #8*, #8* to #9*, and #9* to #10*. | where * indicates a labelled compound. Methods V, VI, IX and X are preferred.

The present invention also contemplates double-labelling. In one embodiment, the double-labelling method of the present invention involves the combination of the labelling steps for MIP (Compound #3 to Compound #4) and the labelling steps for AMIP. Where the label is a radiolabel, this provides, among other advantages, the advantage of increasing the specific activity of the compounds of the present invention. The present invention contemplates the following double-radiolabelling methods (where ** indicates a double-labelled compound):

| I | #1 to #2, #2 to #3, #3 to #4*, #4* to #3*, #3* to #5*, #5* to #6*, #6* to #7*, #7* to #6**, #6** to #5**, #5** to #9**, and #9** to #10**. |
|---|---|
| II | #1 to #3, #3 to #4*, #4* to #3*, #3* to #5*, #5* to #6*, #6* to #7*, #7* to #6**, #6** to #5**, #5** to #9**, and #9** to #10** |
| III | #1 to #2, #2 to #3, #3 to #4*, #4* to #3*, #3* to #5*, #5* to #6*, #6* to #7*, #7* to #6**, #6** to #5**, #5** to #8**, #8** to #9**, and #9** to #10**. |
| IV | #1 to #3, #3 to #4*, #4* to #3*, #3* to #5*, #5* to #6*, #6* to #7*, #7* to #6**, #6** to #5**, #5** to #8**, #8** to #9**, and #9** to #10**. |

Methods I and II are preferred.

4) BIOMIP, DITHIOMIP and FLUORMIP Synthesis

The BIO-, DITHIO- and FLUOR- derivatives of MIP of the present invention (compounds #12a, 12b, and 12c, respectively) can each be generally described as a three part compound consisting of the following three units:

MIP—SPACER—LABEL

The spacer contemplated by the present invention has the general formula $R_1HN-(CH_2)_n-NHR_2$. In general, $R_1 = -H, -CH_3, -C_2H_5, -C_3H_7$ or $-C_4H_9$, $R_2 = -H$ or $-CH_3, -C_2H_5, -C_3H_7$ or $-C_4H_9$, and n is between 6 and 16, inclusive. It is contemplated that, where the BIOMIP compound is bound to another molecule (e.g. nucleic acid), sufficient length is provided for the biotin moiety to span the distance between the site of attachment to another molecule and the avidin binding site when $n \geq 6$. Since the biotin binding site is reported to be 9 Å below the surface of the avidin molecule [Green et al., Biochem. J. 125:781 (1971)], shorter spacers [see e.g. J. P. Albarella et al., Nucleic Acids Res. 17:4293 (1983)] may hinder the formation of the biotin-avidin complex. Adequate chain length helps reduce steric hinderance associated with the avidin-biotin interaction, and accordingly, the stability of the avidin-biotin complex should increase when the appropriate chain length is employed.

Chemical (synthetic) considerations come into play when considering the preferred spacer for the BIO—, DITHIO— and FLUOR— derivatives of MIP. While for spacer $R_1HN-(CH_2)_n-NHR_2$, $R_1$ can be $-H$, $-CH_3, -C_2H_5, -C_3H_7$ or $-C_4H_9$, and $R_2$ can be $-H$, $-CH_3, -C_2H_5, C_3H_7$ or $C_4H_7$, most preferably $R_1$ and $R_2$ are both $-CH_3, -C_2H_5, -C_3H_7$ or $C_4H_9$. While not limited to any particular theory, in the reaction to prepare DMHMIP from XMIP (or IMIP) where $R_1$ and $R_2$ are both —$CH_3$, the spacer nitrogens can react at either nitrogen with only one or two equivalents of XMIP (or IMIP).

So that the desired mono-N-substituted product (i.e. DMHMIP) is favored, the present invention contemplates that a high ratio of spacer to XMIP (or IMIP) is employed in the reaction. Nonetheless, even where 1) $R_1$ and $R_2$ are both —$CH_3$, —$C_2H_5$, —$C_3H_7$ or —$C_4H_9$, and 2) a high ratio of spacer to XMIP (or IMIP) is employed, the present invention contemplates side products from the reaction of more than one XMIP (or IMIP) with the spacer. These side products include one di-N,N-substituted product (i.e. two isopsoralens at the same nitrogen on the spacer), one di-N,N'-substituted product (i.e. two isopsoralens at each of the spacer nitrogens), one tri-N,N,N'-substituted product and one tetra-N, N, N', N'-substituted product.

As noted, the present invention does contemplate the case where $R_1$ and $R_2$ are —H. While this spacer can be used, the number of possible multi-substituted spacer side products is increased, making subsequent purification of the desired mono-N-substituted product (i.e. DMHMIP) more difficult.

The label on the BIO-, DITHIO- and FLUOR-derivatives of MIP of the present invention is comprised of two elements: 1) the reporter moiety, and 2) the linking arm which binds the reporter moiety to the spacer. Two types of reporter moieties are shown in FIG. 1. The first, biotin, is an indirect reporter moiety, as it functions to bind avidin, which in turn is attached to the signal generating system (e.g., BluGENE; BRL). The second, fluorescein, is a direct reporter moiety which provides a highly fluorescent signal upon excitation with appropriate wavelengths of light. Both biotin and fluorescein are appended to the spacer via an amide bond, with zero to seven bridging atoms making up the linking arm between the spacer amido carbonyl and the reporter moiety. In some cases (e.g. DITHIOMIP), the linking arm may contain a disulfide linkage, which is useful for subsequent cleavage of the reporter moiety from the isopsoralen.

The reaction to form the amide bond between the spacer nitrogen and the label carbonyl uses an activated ester, preferably the N-hydroxysuccinimide ester. Other active esters, however, are contemplated, such as the imidazolides (from N, N'-carbonyldiimidizoles) and the sulfosuccinimidyl esters.

a) BIOMIP Synthesis

As shown in FIG. 1, the present invention contemplates four alternative synthesis methods for proceeding via new compound intermediate XMIP to new compound BIOMIP (Compound #12a). Two of the four methods proceed via HMIP; one proceeds from HMIP via IMIP (i.e., #5 to #6, #6 to #5, #5 to #8, #8 to #11, and #11 to #12a) and one proceeds from HMIP via DMHMIP (i.e., #5 to #6, #6 to #5, #5 to #11, and #11 to #12a). The other two methods proceed directly from XMIP (i.e. without HMIP); one proceeds from XMIP via IMIP (i.e., #5 to #8, #8 to #11, and #11 to #12a) and one proceeds from XMIP via DMHMIP (i.e., #5 to #11, and #11 to #12a), the latter is preferred.

As discussed above for the synthesis of AMIP, the routes via HMIP offer the advantage of allowing for interruptions in the synthesis (often necessary in a production facility) because of the stability of HMIP. The XMIP route is more direct, however, and should be used where continued synthesis is possible.

When combined with the two methods for synthesizing MIP, the present invention provides eight methods for synthesizing BIOMIP (methods III and IV are preferred):

| | |
|---|---|
| I | #1 to #2, #2 to #3, #3 to #5, #5 to #6, #6 to #5, #5 to #11, and #11 to #12a. |
| II | #1 to #3, #3 to #5, #5 to #6, #6 to #5, #5 to #11, and #11 to #12a. |
| III | #1 to #2, #2 to #3, #3 to #5, #5 to #11, and #11 to #12a. |
| IV | #1 to #3, #3 to #5, #5 to #11, and #11 to #12a. |
| V | #1 to #2, #2 to #3, #3 to #5, #5 to #8, #8 to #11, and #11 to #12a. |
| VI | #1 to #3, #3 to #5, #5 to #8, #8 to #11, and #11 to #12a. |
| VII | #1 to #2, #2 to #3, #3 to #5, #5 to #6, #6 to #5, #5 to #8, #8 to #11, and #11 to #12a. |
| VIII | #1 to #3, #3 to #5, #5 to #6, #6 to #5, #5 to #8, #8 to #11, and #11 to #12a. | a') Radiolabelled BIOMIP Synthesis

The present invention further contemplates synthesis methods for proceeding via new compound intermediate XMIP to radiolabelled BIOMIP. Both methods involve synthesis of HMIP and labelled HMIP. One proceeds via IMIP (i.e., #5 to #6, #6 to #7, #7 to #6*, #6* to #5*, #5* to #8*, #8* to #11*, and #11* to #12a*) and one proceeds directly via DMHMIP (i.e., #5 to #6, #6 to #7, #7 to #6*, #6* to #5*, #5* to #11*, and #12a*).

When combined with the two methods to produce MIP and two methods to produce labelled MIP, the present invention provides twelve methods for synthesizing radiolabelled BIOMIP (methods V, VI, IX and X are preferred):

| | |
|---|---|
| I | #1 to #2, #2 to #3, #3 to #4*, #4* to #3*, #3* to #5*, #5* to #6*, #6* to #5*, #5* to #11*, and #11* to #12a*. |
| II | #1 to #3, #3 to #4*, #4* to #3*, #3* to #5*, #5* to #6*, #6* to #5*, #5* to #11*, and #11* to #12a*. |
| III | #1 to #2, #2 to #3, #3 to #4*, #4* to #3*, #3* to #5*, #5* to #6*, #6* to #5*, #5* to #8*, #8* to #11*, and #11* to #12a*. |
| IV | #1 to #3, #3 to #4*, #4* to #3*, #3* to #5*, #5* to #6*, #6* to #5*, #5* to #8*, #8* to #11*, and #11* to #12a*. |
| V | #1 to #2, #2 to #3, #3 to #4*, #4* to #3*, #3* to #5*, #5* to #11*, and #11* to #12a*. |
| VI | #1 to #3, #3 to #4*, #4* to #3*, #3* to #5*, #5* to #11*, and #11* to #12a*. |
| VII | #1 to #2, #2 to #3, #3 to #4*, #4* to #3*, #3* to #5*, #5* to #8*, #8* to #11*, and #11* to #12a*. |
| VIII | #1 to #3, #3 to #4*, #4* to #3*, #3* to #5*, #5* to #8*, #8* to #11*, and #11* to #12a*. |
| IX | #1 to #2, #2 to #3, #3 to #5, #5 to #6, #6 to #7*, #7* to #6*, #6* to #5*, #5* to #11*, and #11* to #12a*. |
| X | #1 to #3, #3 to #5, #5 to #6, #6 to #7*, #7* to #6*, #6* to #5*, #5* to #11*, and #11* to #12a*. |
| XI | #1 to #2, #2 to #3, #3 to #5, #5 to #6, #6 to #7*, #7* to #6*, #6* to #5*, #5* to #8*, #8* to #11*, and #11* to #12a*. |
| XII | #1 to #3, #3 to #5, #5 to #6, #6 to #7*, #7* to #6*, #6* to #5*, #5* to #8*, #8* to #11*, and #11* to #12a*. |

These twelve methods of radiolabelling BIOMIP offer one approach to double-labelling (the compound has both $^3H$ and biotin). As with labelled AMIP, the present invention also contemplates double-radiolabelling of BIOMIP (in this case, however, to create a triple-labelled compound). The double-radiolabelling method combines the radiolabelling steps for MIP with the radiolabelling steps for BIOMIP.

b) DITHIOMIP Synthesis

As shown in FIG. 1, the present invention contemplates four alternative synthesis methods for proceeding via new compound intermediate XMIP to new compound DITHIOMIP (Compound #12b). As with the synthesis for BIOMIP, two of the four methods proceed via HMIP; one proceeds from HMIP via IMIP (i.e., #5 to #6, #6 to #5, #5 to #8, #8 to #11, and #11 to #12b) and one proceeds from HMIP via DMHMIP (i.e., #5 to #6, #6 to #5, #5 to #11, and #11 to #12b). The other two methods proceed directly from XMIP (i.e. without HMIP); one proceeds from XMIP via IMIP (i.e., 5 #5 to #8, #8 to #11, and #11 to #12b) and one (the preferred) proceeds from XMIP via DMHMIP (i.e., #5 to #11, and #11 to #12b). The HMIP route advantages discussed above must again be balanced with the more direct routes.

When combined with the two methods for synthesizing MIP, the present invention provides eight methods for synthesizing DITHIOMIP (methods III and IV are preferred):

| | |
|---|---|
| I | #1 to #2, #2 to #3, #3 to #5, #5 to #6, #6 to #5, #5 to #11, and #11 to #12b. |
| II | #1 to #3, #3 to #5, #5 to #6, #6 to #5, #5 to #11, and #11 to #12b. |
| III | #1 to #2, #2 to #3, #3 to #5, #5 to #11, and #11 to #12b |
| IV | #1 to #3, #3 to #5, #5 to #11, and #11 to #12b. |
| V | #1 to #2, #2 to #3, #3 to #5, #5 to #8, #8 to #11, and #11 to #12b. |
| VI | #1 to #3, #3 to #5, #5 to #8, #8 to #11, and #11 to #12b. |
| VII | #1 to #2, #2 to #3, #3 to #5, #5 to #6, #6 to #5, #5 to #8, #8 to #11, and #11 to #12b. |
| VIII | #1 to #3, #3 to #5, #5 to #6, #6 to #5, #5 to #8, #8 to #11, and #11 to #12b. | b') Radiolabelled DITHIOMIP Synthesis

The present invention further contemplates synthesis methods for proceeding via new compound intermediate XMIP to radiolabelled DITHIOMIP. Both methods involve synthesis of HMIP and labelled HMIP. One proceeds via IMIP (i.e., #5 to #6, #6 to #7, #7 to #6*, #6* to #5*, #5* to #8*, 8* to #11*, and #11* to #12b*) and one proceeds directly via DMHMIP (i.e., 5 to #6, #6 to #7, #7 to #6*, #6* to #5*, #5* to 11*, and #11* to #12b*).

When combined with the two methods to produce MIP and two methods to produce labelled MIP, the present invention provides twelve methods for synthesizing radiolabelled DITHIOMIP (methods V, VI, IX and X are preferred):

| | |
|---|---|
| I | #1 to #2, #2 to #3, #3 to #4*, #4* to #3*, #3* to #5*, #5* to #6*, #6* to #5*, #5* to #11*, and #11* to #12b*. |
| II | #1 to #3, #3 to #4*, #4* to #3*, #3* to #5*, #5* to #6*, #6* to #5*, #5* to #11*, and #11* to #12b*. |
| III | #1 to #2, #2 to #3, #3 to #4*, #4* to #3*, #3* to #5*, #5* to #6*, #6* to #5*, #5* to #8*, #8* to #11*, and #11* to #12b*. |
| IV | #1 to #3, #3 to #4*, #4* to #3*, #3* to #5*, #5* to #6*, #6* to #5*, #5* to #8*, #8* to #11*, and #11* to #12b*. |
| V | #1 to #2, #2 to #3, #3 to #4*, #4* to #3*, #3* to #5*, #5* to #11*, and #11* to #12b*. |
| VI | #1 to #3, #3 to #4*, #4* to #3*, #3* to #5*, #5* to #11*, and #11* to #12b*. |
| VII | #1 to #2, #2 to #3, #3 to #4*, #4* to #3*, #3* to #5*, #5* to #8*, #8* to #11*, and #11* to #12b*. |
| VIII | #1 to #3, #3 to #4*, #4* to #3*, #3* to #5*, #5* to #8*, #8* to #11*, and #11* to #12b*. |
| IX | #1 to #2, #2 to #3, #3 to #5, #5 to #6, #6 to #7*, #7* to #6*, #6* to #5*, #5* to #11*, and #11* to #12b*. |
| X | #1 to #3, #3 to #5, #5 to #6, #6 to #7*, #7* to #6*, #6* to #5*, #5* to #11*, and #11* to #12b*. |
| XI | #1 to #2, #2 to #3, #3 to #5, #5 to #6, #6 to #7*, #7* to #6*, #6* to #5*, #5* to #8*, #8* to #11*, and #11* to #12b*. |
| XII | #1 to #3, #3 to #5, #5 to #6, #6 to #7*, #7* to #6*, #6* to #5*, #5* to #8*, #8* to #11*, and #11* to #12b*. |

These twelve methods of radiolabelling DITHIOMIP offer one approach to double-labelling (the compound has both $^3H$ and cleavable biotin). As with labelled BIOMIP, the present invention also contemplates double-radiolabelling of DITHIOMIP (creating a triple-labelled compound). The double-radiolabelling method combines the radiolabelling steps for MIP with the radiolabelling steps for DITHIOMIP.

c) FLUORMIP Synthesis

As shown in FIG. 1, the present invention contemplates four alternative synthesis methods for proceeding via new compound intermediate XMIP to new compound FLUORMIP (Compound #12c). As with both BIOMIP and DITHIOMIP, two of the four methods proceed via HMIP; the other two methods proceed directly from XMIP. When combined with the two methods for synthesizing MIP, the present invention provides eight methods for synthesizing FLUORMIP (methods III and IV are preferred):

| | |
|---|---|
| I | #1 to #2, #2 to #3, #3 to #5, #5 to #6, #6 to #5, #5 to #11, and #11 to #12c. |
| II | #1 to #3, #3 to #5, #5 to #6, #6 to #5, #5 to #11, and #11 to #12c. |
| III | #1 to #2, #2 to #3, #3 to #5, #5 to #11, and #11 to #12c. |
| IV | #1 to #3, #3 to #5, #5 to #11, and #11 to #12c. |
| V | #1 to #2, #2 to #3, #3 to #5, #5 to #8, #8 to #11, and #11 to #12c. |
| VI | #1 to #3, #3 to #5, #5 to #8, #8 to #11, and #11 to #12c. |
| VII | #1 to #2, #2 to #3, #3 to #5, #5 to #6, #6 to #5, #5 to #8, #8 to #11, and #11 to #12c. |
| VIII | #1 to #3, #3 to #5, #5 to #6, #6 to #5, #5 to #8, #8 to #11, and #11 to #12c. | c') Radiolabelled FLUORMIP Synthesis

The present invention further contemplates synthesis methods for proceeding via new compound intermediate XMIP to radiolabelled FLUORMIP. As with BIOMIP and DITHIOMIP, both methods involve synthesis of HMIP and labelled HMIP.

When combined with the two methods to produce MIP and two methods to produce labelled MIP, the present invention provides twelve methods for synthesizing radiolabelled FLUORMIP (methods V, VI, IX and X are preferred):

| | |
|---|---|
| I | #1 to #2, #2 to #3, #3 to #4*, #4* to #3*, #3* to #5*, #5* to #6*, #6* to #5*, #5* to #11*, and #11* to #12c*. |
| II | #1 to #3, #3 to #4*, #4* to #3*, #3* to #5*, #5* to #6*, #6* to #5*, #5* to #11*, and #11* to #12c*. |
| III | #1 to #2, #2 to #3, #3 to #4*, #4* to #3*, #3* to #5*, #5* to #6*, #6* to #5*, #5* to #8*, #8* to #11*, and #11* to #12c*. |
| IV | #1 to #3, #3 to #4*, #4* to #3*, #3* to #5*, #5* to #6*, #6* to #5*, #5* to #8*, #8* to #11*, and #11* to #12c*. |
| V | #1 to #2, #2 to #3, #3 to #4*, #4* to #3*, #3* to #5*, #5* to #11*, and #11* to #12c*. |
| VI | #1 to #3, #3 to #4*, #4* to #3*, #3* to #5*, #5* to #11*, and #11* to #12c*. |
| VII | #1 to #2, #2 to #3, #3 to #4*, #4* to #3*, #3* to #5*, #5* to #8*, #8* to #11*, and #11* to #12c*. |
| VIII | #1 to #3, #3 to #4*, #4* to #3*, #3* to #5*, #5* to #8*, #8* to #11*, and #11* to #12c*. |
| IX | #1 to #2, #2 to #3, #3 to #5, #5 to #6, #6 to #7*, #7* to #6*, #6* to #5*, #5* to #11*, and #11* to #12c*. |
| X | #1 to #3, #3 to #5, #5 to #6, #6 to #7*, #7* to #6*, #6* to #5*, #5* to #11*, and #11* to #12c*. |
| XI | #1 to #2, #2 to #3, #3 to #5, #5 to #6, #6 to #7*, #7* to #6*, #6* to #5*, #5* to #8*, #8* to #11*, and #11* to #12c*. |
| XII | #1 to #3, #3 to #5, #5 to #6, #6 to #7*, #7* to #6*, #6* to #5*, #5* to #8*, #8* to #11*, and #11* to #12c* |

These twelve methods of radiolabelling FLUORMIP offer one approach to double-labelling (the compound has both $^3$H and fluorescein). The present invention also contemplates double-radiolabelling of FLUORMIP to create a triple-labelled compound. The double-radiolabelling method combines the radiolabelling steps for MIP with the radiolabelling steps for FLUORMIP.

One important advantage of the synthesis methods of the present invention for new compounds AMIP, BIOMIP, DITHIOMIP, and FLUORMIP (and new compound intermediates) as well as the above-named radiolabelled compounds, is that these synthesis methods avoid the use of toxic compounds. As discussed below, preparation of some isopsoralens derivatives requires the use of chloromethylmethyl ether. This compound is highly volatile, extremely toxic and a well known carcinogen (OSHA regulated carcinogen CFR Title 29, Part 1910.1006; L. Bretherick, Hazards in the Chemical Laboratory, (Royal Society, London 1981) (p.247). Its use requires special equipment and precautions to avoid exposure of the worker or release to the environment. The synthesis methods for providing MIP derivatives of the present invention do not require this hazardous compound.

Other advantages of the synthesis methods of the present invention for the MIP derivatives are i) ease of synthesis (fewer steps) and ii) superior overall yield. In this regard, the preparation of the new compounds first requires the synthesis of MIP, which has been previously reported by Baccichetti et al. U.S. Pat. No. 4,312,883. Eur. J. Med. Chem. 16:489 (1981). The methods of the present invention differ from the methods reported by Baccichetti in that Baccichetti's two methods include a four step procedure:

5-methylresorcinol→H5MC→7-allyloxy-5-methyl-coumarin→8-allyl-7-hydroxy-5-methylcoumarin→MIP and a seven step procedure:

5-methylresorcinol→H5MC→7-allyloxy-5-methylcoumarin→8-allyl-7-hydroxy-5-methylcoumarin→7-acetoxy-8-allyl-5-methylcoumarin→7-acetoxy-8-(2',3'-epoxypropyl)-5-methylcoumarin→8-(7-acetoxy-5-methyl)coumarinylacetaldehyde→MIP.

The overall yields of these two methods of Baccichetti are approximately 3.8% and 2.8%, respectively.

By contrast, the present invention provides a two and a three step method for MIP synthesis (see FIG. 1). The overall yields of these methods of the present invention are approximately 8.4% and 7.1%. Thus, the methods of the present invention for MIP synthesis involve fewer steps and a better overall yield.

B. PART TWO: R EQUALS —H

Where R is —H (FIG. 2; Table 3), the present invention contemplates a novel synthesis method for DMIP (Compound #16), a known compound; the method proceeds via new compounds XAMC (Compound #14) and RXAMC (Compound #15). From DMIP, the synthesis builds on the novel synthesis to yield known compound AMDMIP (Compound #22) or proceeds to new compounds HDMADMIP (Compound #24), BIODMIP (compound #25a), DITHIODMIP (compound #24b), FLUORDMIP (compound #24c). New methods for radiolabelling compounds are also shown. In addition to the tritiated compounds indicated in FIG. 2, the analogous $^{14}$C derivatives may be prepared from labelled 5-methylresorcinol.

1) DMIP Synthesis

The present invention provides a new synthesis method for DMIP. The approach utilizes a Claisen rearrangement to build the furan ring. This approach has heretofore only been used for synthesizing psoralens. See D. R. Bender et al., J. Org. Chem. 44:2176 (1979). D. R. Bender et al., U.S. Pat. No. 4,398,031.

Baccichetti et al. have reported the synthesis of DMIP from 7-hydroxy-4-methylcoumarin in five steps. These workers elected to build the 5'-methylfuran moiety via a five step conversion: 1) o-alkylation with allyl bromide, 2) Claisen rearrangement to provide the mixed isomers (6-allyl and 8-allyl), 3) acetylation of the pheonlic hydroxide, 4) bromination of the allylic bond, and 5) alkaline ring closure to provide DMIP. They report an overall yield for the five steps of 7.7%. Eur. J. Med. Chem. (1981).

The synthesis procedure described in the present invention, by contrast, requires fewer steps and provides a better yield of DMIP. DMIP is prepared in three steps: 1) 0-alkylation with a 2,3-dihaloalkene, 2) Claisen rearrangement to provide the two allylic isomers (6-allyl and 8-allyl), and 3) ring closure to provide DMIP. The overall three step yield is 26%.

The method of the new synthesis improves the prior procedure as follows. First, an alkyl anhydride is used during the Claisen rearrangement, which provides the esterified phenol (instead of esterifying as a separate step). Esterification concomitant with rearrangement enhances the yield of the rearranged product due to protection of the phenolate from subsequent undesired high temperature oxidation. While acetic or proprionic anhydrides may be used, the higher boiling butyric anhydride is preferred because it allows the reaction temperature to remain closer to the boiling point of the solvent (diisopropylbenzene). Second, the present invention uses a 2,3-dihaloalkene instead of the allyl moiety, which obviates the requirement for subsequent bromination prior to the ring closure step. Like the O-allyl moiety, the O-(2-halo)alkene undergoes Claisen rearrangement primarily to the 8 position of the coumarin, but distinct from the allylic moiety, the rearranged haloalkene is in fact a masked ketone. Under acidic conditions, conversion of the haloalkene to the ketone occurs along with simultaneous acid catalyzed cleavage of the alkylester. The resulting phenolic ketone subsequently undergoes conversion to the ring closed compound. A third advantage of the new synthesis is that alkaline conditions are avoided in all steps, which eliminates loss of product due to hydrolysis of the coumarin lactone to the cis cinnimate, which undergoes subsequent (irreversible) isomerization to the thermodynamically more favored trans isomer.

1') Radiolabelled DMIP

The present invention also contemplates labelled DMIP. A two step method is provided: 1) mixing DMIP with a catalyst, acetic acid and tritium gas to yield the tritiated compound DHDMIP, and 2) mixing DHDMIP with a catalyst and diphenyl ether to yield tritiated DMIP ($^3$H-DMIP).

The present invention contemplates that the catalyst is selected from the group consisting of palladium on charcoal, palladium on barium sulfate, Adams catalyst [(NH$_4$)$_2$PtCl$_6$], PtO$_2$, rhoduim, ruthenium, copper chromite and Raney nickel.

2) AMDMIP Synthesis

The present invention contemplates a new approach to the synthesis of known compound AMDMIP and new compound $^3$H-AMDMIP. The approach builds on the novel synthesis method described above for DMIP. AMDMIP is thereafter made in one of two ways: i) with a halomethylation step, or ii) without a halomethylation step.

a) AMDMIP via Halomethylation

In one method of the present invention for synthesizing AMDMIP, DMIP is made by the novel synthesis method described above; AMDMIP is then made by derivatizing DMIP to provide a halomethyl derivative followed by hydrazinolysis of the corresponding phthalimidomethyl derivative (prepared by the Gabriel synthesis) with hydrazine hydrate according to the method described by F. Dall'Acqua et al., J. Med. Chem 24:178 (1981).

Because of the novel synthesis method of the present invention for DMIP, the approach of the present invention has the advantage over other methods of synthesizing AMDMIP. For example, the procedure reported by Baccichetti et al. (U.S. Pat. No. 4,312,883) for the synthesis of AMDMIP relies on a method of DMIP synthesis that, as discussed above, is less efficient.

As shown in FIG. 2, the present invention contemplates a number of variations using the halomethylation step. After XMDMIP (Compound #18) is synthesized, the synthesis can proceed via HMDMIP (Compound #19) in two ways:

XMDMIP→HMDMIP→XMDMIP→PHIMD-
    MIP→AMDMIP or

XMDMIP→HMDMIP→XMDMIP→IMDMIP→
    PHIMDMIP→AMDMIP.

On the other hand, the present invention also contemplates two ways of proceeding to AMDMIP without HMDMIP:

XMDMIP→PHIMDMIP→AMDMIP or

XMDMIP→IMDMIP→PHIMDMIP→AMDMIP

As discussed with respect to the hydroxy derivative of MIP, HMIP, the hydroxy derivative of DMIP HMDMIP, is stable and can be stored. This offers the convenience of interrupting the synthesis scheme. The non-HMDMIP routes, however, are more direct. They are, therefore, preferred where interruptions in the synthesis scheme are not anticipated.

a') Radiolabelled AMDMIP via Halomethylation

The halomethylation route for the synthesis of AMDMIP can further be used to synthesize labelled AMDMIP. In one approach of the present invention, radiolabelled AMDMIP is synthesized via new compound FDMIP (Compound #20). The present invention contemplates two methods that are variations of this approach:

XMDMIP→HMDMIP→FDMIP→*HMD-
    MIP→*XMDMIP→*PHIMDMIP→*AMDMIP and

XMDMIP→HMDMIP→FDMIP→*HMD-
    MIP→*XMDMIP→*IMDMIP→*PHIMD-
    MIP→*AMDMIP where (*) indicates a radiolabelled compound.

Together with the novel radiolabelling method of the present invention for DMIP, the present invention provides the following four (single) radiolabelling methods for AMDMIP (methods I and III are preferred):

| | |
|---|---|
| I | #13 to #14, #14 to #15, #15 to #16, #16 to #17*, #17* to #16*, #16* to #18*, #18* to #21*, #21* to #22*. |
| II | #13 to #14, #14 to #15, #15 to #16, #16 to #17*, #17* to #16*, #16* to #18*, #18* to #23*, #23* to #21*, #21* to #22*. |
| III | #13 to #14, #14 to #15, #15 to #16, #16 to #18, #18 to #19, #19 to #20, #20 to #19*, #19* to #18*, #18* to #21*, #21* to #22*. |
| IV | #13 to #14, #14 to #15, #15 to #16, #16 to #18, #18 to #19, #19 to #20, #20 to #19*, #19* to #18*, #18* to #23*, #23* to #21*, #21* to #22*. |

The present invention also contemplates double-labelling, including double-radiolabelling. FIG. 2 shows two ways for synthesizing double-radiolabelled AMDMIP.

b) AMDMIP without Halomethylation

While the halomethylation route described above, combined with the novel method of the present invention for the synthesis of the AMDMIP precursor, DMIP, provides a novel and useful method for the synthesis of AMDMIP, halomethylation can require toxic compounds. For example, chloromethylation requires the use of chloromethylmethyl ether. This compound, as discussed earlier, is highly volatile, extremely toxic and a well known carcinogen (OSHA regulated carcinogen CFR Title 29, Part 1910.1006). Its use requires special equipment and precautions to avoid exposure of the worker or release to the environment. To avoid the the danger and inconvenience of using chloromethylmethyl ether, the present invention provides a novel method for the synthesis of AMDMIP without halomethylation.

The present invention contemplates conversion of DMIP to PHIMDMIP by direct phthalimidomethylation of the 4' furan position with a nitrogen donor. The present invention contemplates that the nitrogen donor may be selected from the group consisting of N-hydroxymethyl phthalimide and derivatives thereof.

In converting DMIP directly to PHIMDMIP, the present invention adapts and modifies a procedure that has heretofore only been used for psoralens. N. D. Heindel et al., J. Hetero. Chem. 22:73 (1985). The present invention contemplates that this adapted and modified procedure is suitable for isopsoralens which a) do contain a methyl group at the 4 position, and b) do not contain hydroxy, amino or other like substituents which result in poly-substitution.

This approach is an improvement over the reported procedures for PHIMDMIP synthesis in that 1) no carcinogen is used, 2) the method requires one step instead of two, and 3) the method provides product (PHIMDMIP) in higher yield. From PHIMDMIP, the method proceeds to AMDMIP as described above.

b') Radiolabelled AMDMIP without Halomethylation

The route for the synthesis of AMDMIP without halomethylation can further be used to synthesize labelled AMDMIP via radiolabelled DMIP.

where (*) indicates a radiolabelled compound.

With the novel radiolabelling method of the present invention for DMIP, the present invention provides the following single radiolabelling method for AMDMIP without halomethylation:

| 1 | #13 to #14, #14 to #15, #15 to #16, #16 to #17*, #17* to #16*, #16* to #21*, #21* to #22*. |
|---|---|

3) BIODMIP, DITHIODMIP and FLUORDMIP Synthesis

The BIO-, DITHIO- and FLUOR- derivatives of DMIP of the present invention (compounds #25a, 25b, and 25c, respectively) can each be generally described as a three part compound consisting of the following three units:

DMIP—SPACER—LABEL

The spacer contemplated by the present invention has the general formula $R_1HN-(CH_2)_n-NHR_2$. In general, $R_1 = -H$, $-CH_3$, $-C_2H_5$, $-C_3H_7$, or $-C_4H_9$, $R_2 = -H$, $-CH_3$, $-C_2H_5$, $-C_3H_7$ or $-C_4H_9$, and n is between 6 and 16, inclusive. It is contemplated that, where the BIODMIP compound is bound to another molecule (e.g. nucleic acid), sufficient length is provided for the biotin moiety to span the distance between the site of attachment to another molecule and the avidin binding site when $n \geq 6$. As noted earlier, shorter spacers [see e.g. J. P. Albarella et al., 17:4293 (1989)] may hinder the formation of the biotin-avidin complex. Adequate chain length helps reduce steric hinderance associated with the avidin-biotin interaction, and accordingly, the stability of the avidin-biotin complex should increase when the appropriate chain length is employed.

Chemical (synthetic) considerations come into play when considering the preferred spacer for the BIO-, DITHIO- and FLUOR- derivatives of DMIP. While for spacer $R_1HN-(CH_2)_n-NHR_2$. $R_1$ can be $-H$, $-CH_3$, $-C_2H_3$, $-C_2H_5$, $-C_3H_6$ or $-C_4H_7$, and $R_2$ can be $-H$, $-CH_3$, $-C_2H_5$, $-C_3H_7$ or $-C_4H_9$, most preferably $R_1$ and $R_2$ are both $-CH_3$, $-C_2H_5$, $-C_3H_7$ or $-C_4H_9$. While not limited to any particular theory, in the reaction to prepare HDAMDMIP from XMDMIP (or IMDMIP) where $R_1$ and $R_2$ are both $-CH_3$, $-C_2H_5$, $-C_3H_7$ or $-C_4H_9$, the spacer nitrogens can react at either nitrogen with only one or two equivalents of XMDMIP (or IMDMIP).

So that the desired mono-N-substituted product (i.e. HDAMDMIP) is favored, the present invention contemplates that a high ratio of spacer to XMDMIP (or IMDMIP) is employed in the reaction. Nonetheless, even where 1) $R_1$ and $R_2$ are both $-CH_3$, $-C_2H_5$, $-C_3H_7$ or $-C_4H_9$ and 2) a high ratio of spacer to XMDMIP (or IMDMIP) is employed, the present invention contemplates side products from the reaction of more than one XMDMIP (or IMDMIP) with the spacer. These side products include one di-N,N-substituted product (i.e. two isopsoralens at the same nitrogen on the spacer), one di-N,N'- substituted product (i.e. two isopsoralens at each of the spacer nitrogens), one tri-N,N,N'-substituted product and one tetra-N, N, N', N'-substituted product.

As noted, the present invention does contemplate the case where $R_1$ and $R_2$ are $-H$. While this spacer can be used, the number of possible multi-substituted spacer side products is increased, making subsequent purification of the desired mono-N-substituted product (i.e. HDAMDMIP) more difficult.

The label on the BIO-, DITHIO- and FLUOR- derivatives of DMIP of the present invention is comprised of two elements: 1) the reporter moiety, and 2) the linking arm which binds the reporter moiety to the spacer. Two types of reporter moieties are shown in FIG. 2: i) biotin and ii) fluorescein. Both biotin and fluorescein are appended to the spacer via an amide bond, with zero to seven bridging atoms making up the linking arm between the spacer amido carbonyl and the reporter moiety. In some cases (e.g. DITHIODMIP), the linking arm may contain a disulfide linkage, which is useful for subsequent cleavage of the reporter moiety from the isopsoralen.

The reaction to form the amide bond between the spacer nitrogen and the label carbonyl uses an activated ester, preferrably the N-hydroxysuccinimide ester. Other active esters, however, are contemplated, such as the imidazolides (from N, N'-carbonyldiimidizoles) and the sulfosuccinimidyl esters.

a) BIODMIP Synthesis

As shown in FIG. 2, the present invention contemplates four alternative synthesis methods for proceeding via new compound intermediate XMDMIP to new compound BIODMIP (Compound #25a). Two of the four methods proceed via HMDMIP:

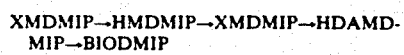

or

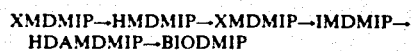

The other two methods (the first of which is perferred) proceed directly from XMDMIP:

XMDMIP→HDAMDMIP→BIODMIP or

XMDMIP→IMDMIP→HDAMDMIP→BIODMIP a') Radiolabelled BIODMIP Synthesis

The present invention also provides methods for radiolabelling BIODMIP. Two methods are provided for synthesizing radiolabelled BIODMIP from DMIP and two methods are provided for synthesizing (single) radiolabelled BIODMIP from radiolabelled DMIP, for a total of four (single) radiolabelling methods:

| I | #16 to #18, #18 to #19, #19 to #20, #20 to #19*, #19* to #18*, #18* to #24*, #24* to #25a*. |
|---|---|
| II | #16 to #18, #18 to #19, #19 to #20, #20 to #19*, #19* to #18*, #18* to #23*, #23* to #24*, #24* to #25a*. |
| III | #16 to #17*, #17* to #16*, #16* to #18*, #18* to #24*, #24* to #25a*. |
| IV | #16 to #17*, #17* to #16*, #16* to #18*, #18* to #23*, #23* to #24*, #24* to #25a*. | where * indicates a labelled compound. Methods I and III are preferred.

The present invention also contemplates double-radiolabelling of BIODMIP. FIG. 2 shows two methods of double-radiolabelling BIODMIP. In one embodiment, the double-radiolabelling method of the present invention involves the combination of the radiolabelling steps for DMIP (Compound #16 to Compound #17*) and the radiolabelling steps for BIODMIP (above). As noted, this provides, among other advantages, the advantage of increasing the specific activity of the compounds of the present invention. The present invention contemplates the following double-radiolabelling methods (where ** indicates a double-labelled compound):

| I | #16 to #17*, #17* to #18*, #18* to #19*, #19* to #20*, #20* to 19**, #19** to #18**, #18** to #24**, #24** to 25a**. |
|---|---|
| II | #16 to #17*, #17* to #18*, #18* to #19*, #19* to #20*, #20* to 19, #19 to #18, #18 to #23, #23 to #24, #24 to 25a**. | b) DIOTHIODMIP Synthesis

As shown in FIG. 2, the present invention contemplates four alternative synthesis methods for proceeding via new compound intermediate XMDMIP to new compound DITHIODMIP (Compound #25b). Two of the four methods proceed via HMDMIP:

XMDMIP→HMDMIP→XMDMIP→HDAMDMIP→DITHIODMIP or

XMDMIP→HMDMIP→XMDMIP→IMDMIP→HDAMDMIP→DITHIODMIP

The other two methods (the first of which is preferred) proceed directly from XMDMIP:

XMDMIP→HDAMDMIP→DITHIODMIP or

XMDMIP→IMDMIP→HDAMDMIP→DITHIODMIP b') Radiolabelled DITHIODMIP

The present invention also provides methods for radiolabelling DITHIODMIP. Two methods are provided for synthesizing radiolabelled DITHIODMIP from DMIP and two methods are provided for synthesizing (single) radiolabelled DITHIODMIP from radiolabelled DMIP, for a total of four (single) radiolabelling methods:

| I | #16 to #18, #18 to #19, #19 to #20, #20 to #19*, #19* to #18*, #18* to #24*, #24* to #25b*. |
|---|---|
| II | #16 to #18, #18 to #19, #19 to #20, #20 to #19*, #19* to #18*, #18* to #23*, #23* to #24*, #24* to #25b*. |
| III | #16 to #17*, #17* to #16*, #16* to #18*, #18* to #24*, #24* to #25b*. |
| IV | #16 to #17*, #17* to #16*, #16* to #18*, #18* to #23*, #23* to #24*, #24* to #25b*. | where * indicates a labelled compound. Methods I and III are preferred.

The present invention also contemplates double-radiolabelling of DITHIODMIP. FIG. 2 shows two methods of double-radiolabelling DITHIODMIP. In one embodiment, the double-radiolabelling method of the present invention involves the combination of the radiolabelling steps for DMIP (Compound #16 to Compound #17*) and the (single) radiolabelling steps for DITHIODMIP (above). As noted, this provides, among other advantages, the advantage of increasing the specific activity of the compounds of the present invention. The present invention contemplates the following double-radiolabelling methods (where ** indicates a double-labelled compound):

| I | #16 to #17*, #17* to #18*, #18* to #19*, #19* to #20*, #20* to 19**, #19** to #18**, #18** to #24**, #24** to 25b**. |
|---|---|
| II | #16 to #17*, #17* to #18*, #18* to #19*, #19* to #20*, #20* to 19, #19 to #18, #18 to #23, #23 to #24, #24 to 25b**. | c) FLUORDMIP Synthesis

As shown in FIG. 2, the present invention contemplates four alternative synthesis methods for proceeding via new compound intermediate XMDMIP to new compound FLUORDMIP (Compound #25c). Two of the four methods proceed via HMDMIP:

XMDMIP→HMDMIP→XMDMIP→HDAMDMIP→FLUORDMIP or

XMDMIP→HMDMIP→XMDMIP→IMDMIP→HDAMDMIP→FLUORDMIP

The other two methods (the first of which is preferred) proceed directly from XMDMIP:

XMDMIP→HDAMDMIP→FLUORDMIP or

XMDMIP→IMDMIP→HDAMDMIP→FLUORDMIP c') Radiolabelled FLUORDMIP Synthesis

The present invention also provides methods for radiolabelling FLUORDMIP. Two methods are provided for synthesizing radiolabelled FLUORDMIP from DMIP and two methods are provided for synthesizing (single) radiolabelled FLUORDMIP from radiolabelled DMIP, for a total of four (single) radiolabelling methods:

| | |
|---|---|
| I | #16 to #18, #18 to #19, #19 to #20, #20 to #19*, #19* to #18*, #18* to #24*, #24* to #25c*. |
| II | #16 to #18, #18 to #19, #19 to #20, #20 to #19*, #19* to #18*, #18* to #23*, #23* to #24*, #24* to #25c*. |
| III | #16 to #17*, #17* to #16*, #16* to #18*, #18* to #24*, #24* to #25c*. |
| IV | #16 to #17*, #17* to #16*, #16* to #18*, #18* to #23*, #23* to #24*, #24* to #25c*. | where * indicates a labelled compound. Methods I and III are preferred.

The present invention also contemplates double-radiolabelling of FLUORDMIP. FIG. 2 shows two methods of double-radiolabelling FLUORDMIP. In one embodiment, the double-radiolabelling method of the present invention involves the combination of the radiolabelling steps for DMIP (Compound #16 to Compound #17*) and the radiolabelling steps for FLUORDMIP (above). The present invention contemplates the following double-radiolabelling methods (where ** indicates a double-labelled compound):

| | |
|---|---|
| I | #16 to #17*, #17* to #18*, #18* to #19*, #19* to #20*, #20* to 19**, #19** to #18**, #18** to #24**, #24** to 25c**. |
| II | #16 to #17*, #17* to #18*, #18* to #19*, #19* to #20*, #20* to 19**, #19** to #18**, #18** to #23**, #23** to #24**, #24** to 25c**. |

II. PHOTOACTIVATION DEVICES AND METHODS

The present invention contemplates devices and methods for photoactivation and specifically, for activation of photoreactive compounds. The present invention contemplates devices having an inexpensive source of electromagnetic radiation that is integrated into a unit. In general, the present invention contemplates a photoactivation device for treating photoreactive compounds, comprising: a) means for providing appropriate wavelengths of electromagnetic radiation to cause activation of at least one photoreactive compound; b) means for supporting a plurality of sample vessels in a fixed relationship with the radiation providing means during activation; and c) means for maintaining the temperature of the sample vessels within a desired temperature range during activation. The present invention also contemplates methods for photoactivating, comprising: a) supporting a plurality of sample vessels, containing one or more photoreactive compounds, in a fixed relationship with a fluorescent source of electromagnetic radiation; b) irradiating the plurality of sample vessels simultaneously with said electromagnetic radiation to cause activation of at least one photoreactive compound; and c) maintaining the temperature of the sample vessels within a desired temperature range during activation.

It is intended that the devices of the present invention serve to replace the specialized instruments of photochemists investigating basic photochemistry of a photoactivator in vitro. These specialized instruments have expensive, high energy, light sources such as high pressure arc lamps or medium pressure mercury lamps. In addition, each has its own peculiar sample holders with varying geometries relative to the lamp source and with varying filter devices (e.g. glass cut-off filters or liquid solutions that transmit only a specific region of the electromagnetic spectrum or ultraviolet spectrum). This lack of standardization makes it difficult to compare data between different labs since there are both intensity variations in each of the different irradiation apparatuses and differences in the spectral energy distribution. Furthermore, the specialized irradiation devices that are available usually lack inherent safety.

The major features of one embodiment of the device of the present invention involve: A) an inexpensive source of ultraviolet radiation in a fixed relationship with the means for supporting the sample vessels, B) rapid photoactivation, C) large sample processing, D) temperature control of the irradiated samples, and E) inherent safety.

A. Electromagnetic Radiation Source

A preferred photoactivation device of the present invention has an inexpensive source of ultraviolet radiation in a fixed relationship with the means for supporting the sample vessels. Ultraviolet radiation is a form of energy that occupies a portion of the electromagnetic radiation spectrum (the electromagnetic radiation spectrum ranges from cosmic rays to radio waves). Ultraviolet radiation can come from many natural and artificial sources. Depending on the source of ultraviolet radiation, it may be accompanied by other (non-ultraviolet) types of electromagnetic radiation (e.g. visible light).

Particular types of ultraviolet radiation are herein described in terms of wavelength. Wavelength is herein described in terms of nanometers ("nm"; $10^{-9}$ meters). For purposes herein, ultraviolet radiation extends from approximately 180 nm to 400 nm. When a radiation source does not emit radiation below a particular wavelength (e.g. 300 nm), it is said to have a "cutoff" at that wavelength (e.g. "a wavelength cutoff at 300 nanometers").

When ultraviolet radiation is herein described in terms of irradiance, it is expressed in terms of intensity flux (milliwatts per square centimeter or "mW $cm^{-2}$"). "Output" is herein defined to encompass both the emission of radiation (yes or no; on or off) as well as the level of irradiance.

A preferred source of ultraviolet radiation is a fluorescent source. Fluorescence is a special case of luminescence. Luminescence involves the absorption of electromagnetic radiation by a substance and the conversion of the energy into radiation of a different wavelength. With fluorescence, the substance that is excited by the electromagnetic radiation returns to its ground state by emitting a quantum of electromagnetic radiation. While fluorescent sources have heretofore been thought to be of too low intensity to be useful for photoactivation, in one embodiment the present invention employs fluorescent sources to achieve results thus far achievable on only expensive equipment.

As used here, fixed relationship is defined as comprising a fixed distance and geometry between the sample and the light source during the sample irradiation. Distance relates to the distance between the source and the sample as it is supported. It is known that light intensity from a point source is inversely related to the square of the distance from the point source. Thus, small changes in the distance from the source can have a drastic impact on intensity. Since changes in intensity can impact photoactivation results, changes in distance are avoided in the devices of the present invention. This provides reproducibility and repeatability.

Geometry relates to the positioning of the light source. For example, it can be imagined that light sources could be placed around the sample holder in many ways (on the sides, on the bottom, in a circle, etc.). The geometry used in a preferred embodiment of the present invention allows for uniform light exposure of appropriate intensity for rapid photoactivation. The geometry of a preferred device of the present invention involves multiple sources of linear lamps as opposed to single point sources. In addition, there are several reflective surfaces and several absorptive surfaces. Because of this complicated geometry, changes in the location or number of the lamps relative to the position of the samples to be irradiated are to be avoided in that such changes will result in intensity changes.

B. Rapid Photoactivation

The light source of the preferred embodiment of the present invention allows for rapid photoactivation. The intensity characteristics of the irradiation device have been selected to be convenient with the anticipation that many sets of multiple samples may need to be processed. With this anticipation, a fifteen minute exposure time is a practical goal.

A fifteen minute exposure, in addition to its convenience, provides for reproducible results. In this regard, it should be noted that the binding levels of photoactive compounds to polynucleotides increases with increasing exposure to activating light. A plateau of binding density is ultimately achieved. This plateau results from competing photochemical reactions. Most photoreactive compounds which undergo addition reactions to the base moieties of nucleic acid also undergo photodecomposition reactions when free in solution. For a given intensity flux (watts/cm$^2$) the relative rates of these competing reactions will determine when, in the course of a time course of an irradiation process, the plateau level will be achieved. For reproducible binding, it is desirable to have irradiation protocols that result in plateau levels of binding. Plateau levels of binding will avoid minor intensity differences that can arise from small differences in sample position (i.e. while the means for supporting the sample vessels can be in a fixed relationship with the source of irradiation, each sample in a large number of samples cannot occupy precisely the same point in space relative to the source). When plateau binding is used, identical reaction mixtures in different positions will show the same level of binding.

In designing the devices of the present invention, relative position of the elements of the preferred device have been optimized to allow for plateau binding in fifteen minutes of irradiation time through Eppendorph tubes for most photoreactive compounds thus far tested. The present invention contemplates for a preferred device: a) a fluorescent source of ultraviolet radiation, and b) a means for supporting a plurality of sample vessels, positioned with respect to the fluorescent source, so that, when measured for the wavelengths between 300 and 400 nanometers, an intensity flux greater than 15 mW cm$^{-2}$ is provided to the sample vessels. Similarly, in the preferred method the present invention, the following steps are contemplated: a) providing a fluorescent source of ultraviolet radiation, and b) supporting a plurality of sample vessels with respect to the fluorescent source of ultraviolet radiation, so that, when measured for the wavelengths between 300 and 400 nanometers, an intensity flux greater than 15 mW cm$^{-2}$ is provided simultaneously to the plurality of sample vessels, and c) simultaneously irradiating the plurality of sample vessels.

C. Processing of Large Numbers of Samples

As noted, another important feature of the photoactivation devices of the present invention is that they provide for the processing of large numbers of samples. In this regard, one element of the devices of the present invention is a means for supporting a plurality of sample vessels. In the preferred embodiment of the present invention the supporting means comprises a sample rack detachably coupled to the housing of the device. The sample rack provides a means for positioning the plurality of sample vessels. The positioning means has been designed to be useful in combination with commonly used laboratory sample vessels. Commonly used laboratory sample vessels include, but are not limited to, test tubes, flasks, and small volume (0.5 − 1.5 ml) plastic tubes (such as Eppendorph tubes). By accepting commonly used laboratory sample vessels, the sample rack of the preferred embodiment of the present invention allows for convenient processing of large numbers of samples.

The detachable aspect of the sample rack in the preferred embodiment also provides for interchangeability of the supporting means. Sample racks having different features suited to different size sample vessels and/or different size photoactivation jobs can be interchanged freely.

The embodiments of the device of the present invention also provide for the processing of a large liquid sample. In the preferred embodiment of the device of the present invention, a trough is provided for holding temperature control liquid (see next section). In an alternative embodiment, it is contemplated that the trough serve as a built-in container for liquid that is to be irradiated. In such a case, the device of the present invention provides a flow-through trough, having inlet and outlet ports for liquid. It is contemplated that the flow-through trough serve as a container for continuous liquid flow during irradiation. Temperature control of this flow-through system can still be achieved by use of an external temperature control means (e.g. a temperature controlled reservoir).

D. Temperature Control

As noted, one of the important features of the photoactivation devices of the present invention is temperature control. Temperature control is important because the temperature of the sample in the sample vessel at the time of exposure to light can dramatically impact the results. For example, conditions that promote secondary structure in nucleic acids also enhance the affinity constants of many psoralen derivatives for nucleic acids. Hyde and Hearst, Biochemistry, 17, 1251 (1978). These conditions are a mix of both solvent composition and temperature. With single stranded 5S ribosomal RNA, irradiation at low temperatures enhances the covalent addition of HMT to 5S rRNA by two fold at 4° C. compared to 20° C. Thompson et al., J. Mol. Biol.

147:417 (1981). Even further temperature induced enhancements of psoralen binding have been reported with synthetic polynucleotides. Thompson et al., Biochemistry 21:1363 (1982).

Temperature control is also an important factor for hybridization assays that detect allele specific nucleic acid targets. Allelic variants of a specific target nucleic acid may differ by a single base. Sickle cell anemia is an example of a human genetic disease that results from the change of a single base (A to T) in the gene for the human β globin molecule. The specific hybridization of a single oligonucleotide probe to one of two allelic variants that differ by only a single base requires very precise temperature control. Wood et al., Proc. Nat. Acad. Sci. 82:1585 (1985). The irradiation of psoralen monoadducted oligonucleotide probes under hybridization equilibrium conditions results in the covalent attachment of these probes to their targets. Allele specific discrimination of a single base change is possible with these crosslinkable probes. However, discrimination is sharply dependant upon temperature. A 2° C. change during the irradiation procedure will have dramatic effect on the level of discrimination that is observed.

5. Inherent Safety

Ultraviolet radiation can cause severe burns. Depending on the nature of the exposure, it may also be carcinogenic. The light source of a preferred embodiment of the present invention is shielded from the user. This is in contrast to the commercial hand-held ultraviolet sources as well as the large, high intensity sources. In a preferred embodiment, the irradiation source is contained within a housing made of material that obstructs the transmission of radiant energy (i.e. an opaque housing). As noted above, sample vessels are placed in the sample rack which is detachably coupled to the housing above the rack. As a final precaution, a sample overlay is provided that extends over and covers the sample vessels. This sample overlay provides two functions. First, it helps to maintain the position of the sample vessels when liquid is in the trough. Second, and more importantly, it closes off the only opening of the housing and, thereby, seals the device. The sealed device allows no irradiation to pass to the user. This allows for inherent safety for the user.

III. BINDING OF COMPOUNDS TO NUCLEIC ACID

The present invention contemplates binding new and known compounds to nucleic acid, including (but not limited to) a) nucleic acid target sequences, probes, and primers, as well as b) nucleic acid used as template, and c) amplified nucleic acid. Target sequences are regions of nucleic acid having one or more segments of known base sequence. Target sequences are "targets" in the sense that they are sought to be detected (i.e. sorted out from other nucleic acid). Detection is frequently performed by hybridization with probes. Probes are nucleic acids having a base sequence that is partially or completely complementary with all or a portion of a target sequence.

Some molecular biological techniques use template and primers. Template is defined simply as nucleic acid that is substrate for enzymatic synthesis. Frequently, it is nucleic acid suspected of containing target sequence(s). Primers act to control the point of initiation of synthesis of target sequences when they are present in the template. Other molecular biological techniques use template and replicating probes.

The present invention contemplates that the binding to all these forms of nucleic acid (as well as others) can be non-covalent binding and/or covalent binding. The present invention contemplates specific embodiments of binding including, but not limited to dark binding and photobinding.

A. Dark Binding

One embodiment of the binding of the present invention involves dark binding. "Dark Binding" is defined as binding to nucleic acid that occurs in the absence of photoactivating wavelengths of electromagnetic radiation. Dark binding can be covalent or non-covalent. "Dark Binding Compounds" are defined as compounds that are capable of dark binding. In one embodiment, the dark binding of the present invention involves the steps: a) providing a dark binding compound; and b) mixing the dark binding compound with nucleic acid in the absence of photoactivation wavelengths of light, where the dark binding compound is selected from the group consisting of DEMC (Compound #2), XMIP (Compound #5), HMIP (Compound #6), FMIP (Compound #7), IMIP (Compound #8), HMTAMIP (Compound #9), AMIP (Compound #10), DMHMIP (Compound #11), BIOMIP (Compound #12a), DITHIOMIP (Compound 12b), FLUORMIP (Compound 12c), XAMC (Compound #14) RXAMC (Compound #15), BMDMIP (Compound #18, where X=Br), FDMIP (Compound #20), IMDMIP (Compound #23), HDMADMIP (Compound #24), BIODMIP (compound #25a), DITHIODMIP (compound #25b), FLUORDMIP (compound #25c), and their radiolabelled derivatives.

The present invention further contemplates the product of dark binding, i.e., a dark binding compound:nucleic acid complex, where the dark binding compound is selected from the group consisting of DEMC (Compound #2), XMIP (Compound #5), HMIP (Compound #6), FMIP (Compound #7), IMIP (Compound #8), HMTAMIP (Compound #9), AMIP (Compound #10), DHMIP (Compound #11), BIOMIP (Compound #12a), DITHIOMIP (Compound 12b), FLUORMIP (Compound 12c), XAMC (Compound #14) RXAMC (Compound #15), BMDMIP (Compound #18, where X=Br), FDMIP (Compound #20), IMDMIP (Compound #23), HDMADMIP (Compound #24), BIODMIP (compound #25a), DITHIODMIP (compound #25b), FLUORDMIP (compound #25c), and their radiolabelled derivatives.

The present invention also contemplates dark binding of photoproduct. "Photoproduct" is defined as a product of the reaction of a compound and activating wavelengths of electromagnetic radiation that, once formed, is later capable of binding to nucleic acid in the absence of electromagnetic radiation.

In considering photoproduct binding, it should be noted that previous work towards the modification of nucleic acids with furocoumarins has historically proceeded by a method having the temporal steps: 1) providing a specific furocoumarin derivative, 2) providing a particular nucleic acid or nucleic acid sequence, and 3) mixing the furocoumarin with the nucleic acid in the presence of activating wavelengths of electromagnetic radiation. Depending on the details of the particular reaction, including the particular furocoumarin derivative, radiation source irradiation time, buffer, temperature and other factors used for the procedure, a given level of covalent modification, with almost exclusively cyclobutyl type 2+2 photocycloaddition products, resulted.

In one embodiment, the present invention contemplates a radical departure from this historical approach to photobinding. In one embodiment of the method of the present invention, the temporal sequence is the following: 1) providing one or more furocoumarin derivatives, 2) exposing the furocoumarin derivative(s) to activating wavelengths of electromagnetic radiation, 3) providing a particular nucleic acid sample or nucleic acid sequence, and 4) mixing the irradiated furocoumarin derivative(s) with the nucleic acid in the absence of activating wavelengths of electromagnetic radiation. In this embodiment, the furocoumarin derivative is irradiated *prior* to mixing with nucleic acid. The experimental investigation of this novel temporal sequence has established the existence of furocoumarin photoproduct. Application of the novel temporal sequence has useful applications but was neither predicted nor expected from the chemical or biochemical literature concerning furocoumarins.

"Photoproduct" is best understood by considering the possible reactions of photoreactive compound when exposed to activating wavelengths of electromagnetic radiation. While not limited to any precise mechanism, it is believed that the reaction of photoreactive compound in its ground state ("C") with activating wavelengths of electromagnetic radiation creates a short-lived excited species ("C*"):

C→C*

What happens next is largely a function of what potential reactants are available to the excited species. Since it is short-lived, a reaction of this species with nucleic acid ("NA") is believed to only be possible if nucleic acid is present at the time the excited species is generated. Thus, the reaction must, in operational terms, be in the presence of activating wavelengths of electromagnetic radiation, i.e. it is "photobinding"; it is not dark binding. The reaction can be depicted as follows:

C*+NA→NA:C

The product of this reaction is hereinafter referred to as "Photoaddition Product" and is to be distinguished from "Photoproduct."

With this reaction described, one can now consider the situation where nucleic acid is not available for binding at the time the compound is exposed to activating wavelengths of electromagnetic radiation. Since the excited species is short-lived and has no nucleic acid to react with, the excited species may simply return to its ground state:

C*→C

On the other hand, the excited species may react with itself (i.e. a ground state or excited species) to create a ground state complex ("C:C"). The product of these self-reactions where two compounds react is referred to as "photodimer" or simply "dimer." The self-reactions, however, are not limited to two compounds; a variety of multimers may be formed (trimers, etc.).

The excited species is not limited to reacting with itself. It may react with its environment, such as elements of the solvent ("E") (e.g. ions, gases, etc.) to produce other products:

C*+E→E:C

Furthermore, it may simply internally rearrange ("isomerize") to a ground state derivative ("["):

C*→[

Finally, the excited species may undergo other reactions than described here.

The present invention and the understanding of "photoproduct" does not depend on which one (if any) of these reactions actually occurs. "Photoproduct"—whatever its nature—is deemed to exist if, following the reaction of a compound and activating wavelengths of electromagnetic radiation, there is a resultant product formed that is later capable of binding to nucleic acid in the absence of electromagnetic radiation, i.e. capable of dark binding (whether non-covalent dark binding or covalent dark binding).

It is important to note that, while the definition of "photoproduct" demands that, once formed by exposure to electromagnetic radiation, the product be "capable" of binding to nucleic acid in the absence of electromagnetic radiation, it is not necessary that the product bind *only* in the dark. Photoproduct may bind under the condition where there is exposure to electromagnetic radiation; it simply does not *require* the condition for binding. Such a definition allows for both "photobinding" and "photoproduct binding" to nucleic acid to occur at the same time. Such a definition also allows a single compound to be "photoproduct" and "photobinding compound."

In one embodiment, the present invention contemplates dark binding of both psoralen photoproduct and isopsoralen photoproduct. With psoralens such as 4'-hydroxymethyl-4,5',8-trimethylpsoralen (HMT), the present invention contemplates there are a number of resultant products produced when the HMT is exposed to activating wavelengths of electromagnetic radiation. The present invention contemplates that a number of resultant products are similarly produced when isopsoralens such as AMIP and AMDMIP are exposed to activating wavelengths of electromagnetic radiation (particularly when irradiated with the CE-III device). The major resultant products of HMT are two cyclobutyl photodimers. In one of the dimers, the two pyrone rings are linked in a cis-syn configuration, while in the other dimer, the linkage occurs between the furan end of one molecule and the pyrone end of the other, again with cis-syn configuration. A third resultant product of HMT is a monomeric HMT photoisomer. In this isomer, the central ring oxygens assume a 1, 4 instead of the normal 1, 3 orientation. While the two photodimers would not be expected to have an intercalating activity due to geometrical considerations, the photoisomer remains planer, and accordingly, it is contemplated that it has a positive intercalative association with double stranded nucleic acid. Analogously, it is contemplated that some of the resultant products of AMIP and AMDMIP also have a positive intercalative association with nucleic acid. While not limited to any particular theory, non-covalent dark binding is anticipated where monomeric isomers are formed, and particularly, where the positively charge aminomethyl moiety is retained in the structure.

B. Photobinding

One approach of the present invention to binding activation compounds to nucleic acid is photobinding. Photobinding, as noted above, is defined as the binding of photobinding compounds in the presence of photoactivating wavelengths of light. Photobinding compounds are compounds that bind to nucleic acid in the presence of photoactivating wavelengths of light. The present invention contemplates a number of methods of photobinding, including 1) photobinding with photobinding compounds of the present invention, 2) high photobinding with new and known compounds, and 3) photobinding to label nucleic acids.

1) Photobinding With New Compounds

One embodiment of the method of the present invention for photobinding involves the steps: a) providing a photobinding compound; and b) mixing the photobinding compound with nucleic acid in the presence of photoactivation wavelengths of electromagnetic radiation, where the photobinding compound is selected from the group consisting of DEMC (Compound #2), XMIP (Compound #5), HMIP (Compound #6), FMIP (Compound #7), IMIP (Compound #8), HMTAMIP (Compound #9), AMIP (Compound #10), DMHMIP (Compound #11), BIOMIP (Compound #12a), DITHIOMIP (Compound 12b), FLUORMIP (Compound 12c), XAMC (Compound #14) RXAMC (Compound #15), BMDMIP (Compound #18, where X=Br), FDMIP (Compound #20), IMDMIP (Compound #23), HDMADMIP (Compound #24), BIODMIP (compound #25a), DITHIODMIP (compound #25b), FLUORDMIP (compound #25c), and their radiolabelled derivatives.

In another embodiment, the steps of the method comprise: a) providing a photobinding compound; b) providing one or more nucleic acid target sequences; and c) mixing the photobinding compound with the nucleic acid target sequences in the presence of photoactivation wavelengths of electromagnetic radiation. Again, in one embodiment, the photobinding compound is selected from the group consisting of DEMC (Compound #2), XMIP (Compound #5), HMIP (Compound #6), FMIP (Compound #7), IMIP (Compound #8), HMTAMIP (Compound #9), AMIP (Compound #10), DMHMIP (Compound #11), BIOMIP (Compound #12a), DITHIOMIP (Compound 12b), FLUORMIP (Compound 12c), XAMC (Compound #14) RXAMC (Compound #15), BMDMIP (Compound #18, where X=Br), FDMIP (Compound #20), IMDMIP (Compound #23), HDMADMIP (Compound #24), BIODMIP (compound #25a), DITHIODMIP (compound #25b), FLUORDMIP (compound #25c), and their radiolabelled derivatives.

The present invention further contemplates the product of photobinding, i.e., a photobinding compound: nucleic acid complex. In one embodiment, the photobinding compound of the complex is selected from the group consisting of DEMC (Compound #2), XMIP (Compound #5), HMIP (Compound #6), FMIP (Compound #7), IMIP (Compound #8), HMTAMIP (Compound #9), AMIP (Compound #10), DMHMIP (Compound #11), BIOMIP (Compound #12a), DITHIOMIP (Compound 12b), FLUORMIP (Compound 12c), XAMC (Compound #14) RXAMC (Compound #15), BMDMIP (Compound #18, where X=Br), FDMIP (Compound #20), IMDMIP (Compound #23), HDMADMIP (Compound #24), BIODMIP (compound #25a), DITHIODMIP (compound #25b), FLUORDMIP (compound #25c), and their radiolabelled derivatives.

The invention further contemplates a method for modifying nucleic acid, comprising the steps: a) providing photobinding compound and nucleic acid; and b) photobinding the photobinding compound to the nucleic acid, so that a compound:nucleic acid complex is formed, wherein the photobinding compound is selected from the group consisting of DEMC (Compound #2), XMIP (Compound #5), HMIP (Compound #6), FMIP (Compound #7), IMIP (Compound #8), HMTAMIP (Compound #9), AMIP (Compound #10), DMHMIP (Compound #11), BIOMIP (Compound #12a), DITHIOMIP (Compound 12b), FLUORMIP (Compound 12c), XAMC (Compound #14) RXAMC (Compound #15), BMDMIP (Compound #18, where X=Br), FDMIP (Compound #20), IMDMIP (Compound #23), HDMADMIP (Compound #24), BIODMIP (compound #25a), DITHIODMIP (compound #25b), FLUORDMIP (compound #25c), and their radiolabelled derivatives.

A preferred embodiment of the method of the present invention for photobinding involves the steps: a) providing a photobinding compound; and b) mixing the photobinding compound with nucleic acid in the presence of photoactivation wavelengths of electromagnetic radiation, where the photobinding compound is selected from the group consisting of AMIP (Compound #10), BIOMIP (Compound #12a), DITHIOMIP (Compound 12b), FLUORMIP (Compound 12c), BIODMIP (compound #25a), DITHIODMIP (compound #25b), FLUORDMIP (compound #25c), and their radiolabelled derivatives.

In another preferred embodiment, the steps of the method comprise: a) providing a photobinding compound; b) providing one or more nucleic acid target sequences; and c) mixing the photobinding compound with the nucleic acid target sequences in the presence of photoactivation wavelengths of electromagnetic radiation, where the photobinding compound is selected from the group consisting of AMIP (Compound #10), BIOMIP (Compound #12a), DITHIOMIP (Compound 12b), FLUORMIP (Compound 12c), BIODMIP (compound #25a), DITHIODMIP (compound #25b), FLUORDMIP (compound #25c), and their radiolabelled derivatives.

In still another preferred embodiment, the present invention contemplates a photobinding compound:nucleic acid complex, where the photobinding compound of the complex is selected from the group consisting of AMIP (Compound #10), BIOMIP (Compound #12a), DITHIOMIP (Compound 12b), FLUORMIP (Compound 12c), BIODMIP (compound #25a), DITHIODMIP (compound #25b), FLUORDMIP (compound #25c), and their radiolabelled derivatives.

In still an additional preferred embodiment, the invention contemplates a method for modifying nucleic acid, comprising the steps: a) providing photobinding compound and nucleic acid; and b) photobinding the photobinding compound to the nucleic acid, so that a compound:nucleic acid complex is formed, wherein the photobinding compound is selected from the group consisting of AMIP (Compound #10), BIOMIP (Compound #12a), DITHIOMIP (Compound 12b), FLUORMIP (Compound 12c), BIODMIP (compound #25a), DITHIODMIP (compound #25b), FLUORD- MIP (compound #25c), and their radiolabelled derivatives.

2) High Photobinding

The present invention provides isopsoralens with high photobinding affinity and conditions for using isopsoralens to allow for high photobinding. High photobinding is defined here as photobinding to nucleic acid that results in significantly higher levels of addition than reported for the known compound AMDMIP.

Baccichetti et al. and Dall'Acqua et al. previously reported the nucleic acid binding characterization of AMDMIP. Baccichetti et al., U.S. Pat. No. 4,312,883; Dall'Acqua et al., J. Med. Chem. 24:178 (1981). These workers reported, while AMDMIP has a high dark binding affinity for DNA, photobinding with AMDMIP results in low levels of addition to nucleic acid. In fact, AMDMIP was found to photobind to DNA less than the parent compound, DMIP. (No RNA binding data for AMDMIP was provided).

The present invention provides photobinding methods for i) known isopsoralens, and ii) new isopsoralens. With respect to methods for known isopsoralens, the present invention provides methods for photobinding of AMDMIP that allow for photobinding of AMDMIP to DNA at a level greater than 1 photobound AMDMIP per 15 base pairs, and to RNA at a level greater than 1 photobound AMDMIP per 20 RNA bases. With respect to photobinding methods for new isopsoralens, the present invention provides photobinding methods for new compound AMIP that allow for photobinding at a level greater than 1 photobound AMIP per 15 base pairs of DNA and a level greater than 1 photobound AMIP per 20 bases of RNA.

While not limited to any particular theory, the photobinding methods of the present invention take into consideration two concepts as they relate to photobinding capacity: a) nucleic acid base pair/compound ratio, and b) isopsoralen structure.

a) Nucleic Acid Base Pair/Compound Ratio

Dall'Acqua et al. compared AMDMIP photobinding with the photobinding of the parent compound, DMIP. The parent compound (as well as other compounds) was tested at concentrations at or near its solubility limit (i.e., DMIP was tested at 10.1 $\mu$g/ml; DMIP's maximum aqueous solubility, as reported by Dall'Acqua et al., is 8 $\mu$g/ml). For comparative purposes, AMDMIP was tested in this concentration range as well (specifically, at 13.1 $\mu$g/ml). Given this concentration range, both DMIP and AMDMIP photobinding was determined at a DNA base pair:isopsoralen ratio of 24.3 to 1 ($1.14 \times 10^{-3}$M DNA:$4.7 \times 10^{-5}$M isopsoralen). With this ratio, photobinding of AMDMIP resulted in 1 photobound AMDMIP per 151 DNA base pairs, which was lower photobinding than that observed for the parent compound, DMIP. Dall'Acqua et al. J. Med. Chem. 24:178 (1981). Thus, where concentrations of DMIP and AMDMIP were approximately equal, DMIP was reported as the better photobinder.

The photobinding methods of the present invention take into consideration the nucleic acid base pair/compound ratio. The photobinding methods of the present invention involve carrying out the photobinding step under conditions where the isopsoralen concentration is increased relative to the concentration of nucleic acid base pairs. Importantly, increasing the isopsoralen concentration takes advantage of the solubility of the isopsoralen; with isopsoralens which have high aqueous solubility, higher concentrations are possible to obtain.

By increasing the concentration of AMDMIP relative to nucleic acid, the present invention takes into consideration the much better solubility of AMDMIP as compared with the parent compound, DMIP. While DMIP is reported to be a better intrinsic photobinder than AMDMIP, the level of addition to nucleic acid is governed by the photobinding compound concentration (relative to nucleic acid) which is (with the concentration of nucleic acid constant) governed by solubility of the photobinding compound. Thus, while DMIP is a better intrinsic photobinder, the poor solubility of DMIP results in a relatively low level of addition (adducts per base pair) to nucleic acid.

By taking advantage of the higher solubility of AMDMIP, higher concentrations of AMDMIP can be used, thus providing a higher ratio of photobinding compound to nucleic acid base pairs prior to irradiation. While AMDMIP is reported to be a less efficient photobinder relative to DMIP, the present invention contemplates increasing the concentration of AMDMIP so that a high level of photoaddition to nucleic acid is achieved, i.e. high photobinding.

The nucleic acid base pair/compound ratio of the photobinding methods of the present invention is preferably less than 3:1. With this ratio, the methods of the present invention allow for photobinding of AMDMIP to DNA at a level greater than 1 photobound AMDMIP per 15 base pairs, and to RNA at a level greater than of 1 photobound AMDMIP per 20 RNA bases.

b) Isopsoralen Structure

While the present invention takes into consideration the nucleic acid base pair/compound ratio, the methods of the present invention further consider isopsoralen structure. Inspection of the molecular structure of AMDMIP (FIG. 2) shows two methyl groups at the 4 and 5' carbons and the aminomethyl moiety at the 4' carbon. It is known that methylation improves the ability of a psoralen or isopsoralen to photobind to nucleic acid. It has been reported that the trialkyl isopsoralens, particularly trimethyl, are better DNA photobinding ligands than the corresponding dialkyl compounds, and analogously, the dialkyl compounds are better photobinders than the monoalkyl analogs. Guiotto et al., J. Med. Chem. 27:959 (1984). In particular, methyl groups at the 4, 4', 5, 5' and 6 positions of the isopsoralen system increase photobinding activity.

Psoralens which contain aminoalkyl moieties at the 4', 5, 5', or 8 positions are charged and show enhanced dark binding and enhanced photoreactivity relative to the uncharged analogs. In particular, the 4' and 5' aminoalyl-trimethylpsoralens show enhances photobinding to nucleic acid. S. Isaacs et al., Biochemistry 16:1058 (1977). I. Willie and J. M. Menter, Nat. Cancer Inst. Monograph 66 (1985).

While not limited to any particular theory, the methods of the present invention take into consideration these structural relationships which suggest that the position of the aminomethyl moiety in AMDMIP may not be optimum for high photobinding activity. The 4'-aminomethyl moiety, through association with external phosphate groups, could be skewing the intercalated complex such that the critical alignment between the 4', 5'and/or 3,4 double bonds and the 5, 6 pyrimidine double bond is disfavored, resulting in a significant reduction in the quantum efficiency of 2+2 photocycloaddition to form the cyclobutane ring.

The present invention provides new compounds where the aminomethyl moiety is at the 5-position (e.g. AMIP). It was hoped that such compounds of the present invention might promote a different and potentially more favorable double bond geometry, resulting in higher photobinding than AMDMIP provides. While it was not predictable that this new geometry could overcome the disadvantage of a compound having no additional methyl groups present on the ring system, the new compounds of the present invention display high photobinding. In this regard, while the known compound AMDMIP has the highest $K_a$ (DNA association constant) of all reported isopsoralens, and new compound AMIP of the present invention has a Ka which is only 28% as strong. AMIP can provide 43% of the modification density provided by AMDMIP. Since i) solubility of the two compounds is essentially the same, and ii) testing was performed (photobinding) at the same concentration, it appears that placing the aminomethyl moiety at the 5 position rather than at the 4' position changes photobinding, relative to dark binding; AMIP is the better photobinder per isopsoralen molecule, even through AMDMIP give the higher number of isopsoralens bound.

3) Labelling Nucleic Acid

As noted, one utility of the compounds is their ability to bind to nucleic acids (RNA and DNA). Furthermore, because the compounds bind nucleic acids, they also bind nucleic acid target sequences. While target sequences are normally present in a mixture of nucleic acids, they may be purified to homogeneity and reacted with photoreactive compounds of the present invention.

While unlabelled compounds bind to nucleic acids, labelled compounds are particularly useful for assessing the level of binding to nucleic acids because, as noted above, labels facilitate detection of the compound as well as the detection of molecules bound to the compound, such as nucleic acids and nucleic acid target sequences. In this manner it is also easier to separate unbound from bound reactants (e.g. unbound isopsoralen from bound isopsoralen). Furthermore, when there is binding, the separation and isolation of bound reactants allows for a yield of substantially pure bound product.

The present invention contemplates binding of the above-named compounds to all types of nucleic acids under a wide variety of conditions and thereby labelling nucleic acids. Of course, the degree of binding will vary according to the particular compound, the particular nucleic acid, and the conditions used. The particular advantage of using isopsoralens such as those of the present invention is that labelling can be carried out without interfering with subsequent hybridization.

The present invention contemplates labelling of nucleic acid and nucleic acid target sequences by 1) labelled compounds synthesized by methods of the present invention and 2) labelled compounds of the present invention synthesized by methods of the present invention.

In one embodiment, the present invention contemplates using BIOMIP and BIODMIP to provide an appended biotin on nucleic acid target, and then using that labelled nucleic acid in a subsequent detection step. For example, the present invention contemplates mixing BIOMIP or BIODMIP with the total DNA extracted from a blood sample suspected of harboring a virus. Irradiation of the mixture causes the BIOMIP or BIODMIP to photobind to the nucleic acid. The present invention contemplates that the next step of the method involves use of nucleic acid probes specific (i.e. complementary) for the viral nucleic acid sequences. These probes are added to the BIOMIP(or BIODMIP)-treated nucleic acid. It is contemplated that the probes are introduced on a solid support such as polystyrene beads. After hybridization and washing, the solid support (containing the probe/target-biotin complex) is treated with a signal development system (e.g. an avidin-HRP complex) for detection of binding.

In a strictly analogous manner, the new compounds FLUORMIP and FLUORDMIP may be used to provide labelled nucleic acid. With these compounds, the nucleic acid can be detected by fluorescence techniques.

The photochemical labelling methods of the present invention have advantages over other nucleic acid labelling techniques. First, as mentioned above, labelling with isopsoralens does not interfere with subsequent hybridization. Second, photochemical labelling allows for labelling of an entire nucleic acid target sequence. This is in contrast to enzymatic labelling methods such as the BIO-UTP system. P. R. Langer et al., Proc. Nat. Acad. Sci. U.S.A 78:6633 (1981). Furthermore, enzymatic labelling (e.g. nick translating) usually results in labelled products that are only about 200 base pairs in length. Finally, labelling nucleic acid with isopsoralens offers the additional advantages of repeatability and low cost.

It is not intended that the labelling methods of the present invention be limited by the nature of the nucleic acid. In one embodiment, the present invention contemplates that nucleic acid is selected from the group human genomic DNA and human RNA. In another embodiment, the present invention contemplates that the nucleic acid sequences are selected from the group consisting of sequences of viral DNA and sequences of viral RNA. In still a further embodiment, the present invention contemplates that the nucleic acid is selected from the group consisting of viral, bacterial, fungal, mycoplasma and protozoan nucleic acid.

IV. CAPTURE OF NUCLEIC ACIDS

The present invention contemplates that the compounds of the present invention be used to label and capture nucleic acid and nucleic acid sequences. In one embodiment, probe DNA is reacted with a cleavable biotin-isopsoralen, such as DITHIOMIP and DITHIODMIP, to yield biotinylated (probe) DNA. This biotin-isopsoralen/nucleic acid complex is then hybridized to target DNA in a mixture of DNA. After hybridization, the biotin-probe-target complex is passed through an avidin-agarose column. The avidinbiotin-probe-target complex is retained on the column, while non-hybridized (non-target) DNA is washed through. Following the wash, the probe-target DNA hybrid is recovered by cleaving the biotin from the isopsoralen via reduction of the disulfide bond of DITHIOMIP or DITHIODMIP. Reduction is readily accomplished with reagents such as dithiothreitol or sodium borohydride.

The present invention also contemplates capture with non-cleavable biotin-isopsoralen such as BIOMIP and BIODMIP. In one embodiment, the probe DNA is reacted with BIOMIP or BIODMIP. The subsequent hybridization, capture and wash steps are the same as described for the cleavable compound. However, following the wash, the present invention contemplates that either the entire probe-target complex is removed from the avidin column by the addition of a reagent that breaks up the biotin-avidin interaction (e.g. 8M guanidinium chloride), or alternatively, the captured target sequence is specifically released from the probe-target complex by denaturation of the hybridized nucleic acid. This latter procedure leaves the probe bound to the column and washes the target off the column. In one embodiment, this step is accomplished by elution with a solution that provides denaturing conditions within the column matrix (e.g. 60% formamide).

V. INHIBITING TEMPLATE-DEPENDENT ENZYMATIC SYNTHESIS

Enzymatic synthesis that involves nucleic acid, either solely as a template (e.g. translation involves the use of nucleic acid as a template to make polypeptides) or as both a template and a product (replication and transcription use nucleic acid as a template to produce nucleic acid) is hereinafter referred to as "template-dependent enzymatic synthesis."

In the case of replication, nucleic acid polymerases replicate a nucleic acid molecule ("template") to yield a complementary ("daughter") nucleic acid molecule. For example, DNA polymerase I, isolated from E. Coli, catalyzes the addition of deoxyribonucleoside triphosphates to the 3' end of a short segment of DNA ("primer") hybridized to a template strand to yield a daughter of the template, starting from a mixture of precursor nucleotides (dATP, dGTP, dCTP, and dTTP). This 5' to 3' template-dependent enzymatic synthesis is also called "primer extension." The reaction will not take place in the absence of template. The reaction can be measured if one or more of the precursor nucleotides are labelled (usually they are radiolabelled with $^{32}P$).

There are a number of known methods of DNA modification that block template-dependent enzymatic synthesis. For example E. coli polymerase I terminates copying single stranded DNA one nucleotide before encountering DNA lesions such as pyrimidine dimers induced by ultraviolet light, P. D. Moore et al., Proc. Natl. Acad. Sci. 78:110 (1981), carcinogen adducts, P. D. Moore et al., Proc. Natl. Acad. Sci. 79:7166 (1982), and proflavin-mediated guanine residue photooxidation, J. G. Piette and P. D. Moore, Photochem. Photobiol. 35:705 (1982).

C. M. Ou et al., Biochemistry 17:1047 (1978) investigated whether DNA replication by DNA polymerase I from *E. coli* B could be inhibited by covalently bound 8-methoxypsoralen (8-MOP) or by 5,7-dimethoxycoumarin (DMC). 8-MOP is a psoralen and was used to crosslink the DNA. DMC is a coumarin derivative that lacks the furyl carbon-carbon double bond necessary for photoaddition to pyrimidine bases of DNA; DMC cannot form crosslinks. It was found that the crosslinked DNA (8-MOP-modified) lost 97% of its template activity for the enzyme used. The DMC-modified (uncrosslinked) DNA lost only 50% of its template activity. It was proposed that the crosslinking of DNA was responsible for the difference in inhibition of template activity.

J. G. Piette and J. E. Hearst, Proc. Natl. Acad. Sci. 80:5540 (1983) reported that *E. Coli* polymerase I, when nick-translating a double-stranded template, is not inhibited by covalently bound psoralen [4'-hydroxymethyl-4,5',8-trimethylpsoralen (HMT)] monoadducts or isopsoralen (5-methylisopsoralen) monoadducts. The enzyme is, however, effectively blocked by psoralen crosslinks.

J. G. Piette and J. E. Hearst, Int. J. Radiat. Biol. 48:381 (1985) later reported that *E. Coli* polymerase I, when carrying out template-dependent enzymatic synthesis on a single-stranded template (single-stranded bacteriophage DNA), was inhibited by HMT monoadducts. It was concluded that DNA structure (single-stranded versus double-stranded) must account for the different results.

G. Ericson and P. Wollenzien, Analytical Biochem. 174:215 (1988) examined psoralen crosslinks on RNA and their ability to block reverse transcriptase. They reported that a psoralen crosslink is an absolute stop for avian myeloblastosis virus reverse transcriptase. Psoralen monoaddcuts showed little inhibition of the enzyme.

These experiments showed that blocking of enzymatic synthesis of nucleic acids could be accomplished with psoralen crosslinks and, in some cases, inhibition could be achieved with psoralens monoadducts. Importantly, the one attempt to block enzymatic synthesis with an isopsoralen showed no inhibition.

The present invention provides the surprising result that template-dependent enzymatic synthesis of nucleic acid can be effectively inhibited with one or more "inhibition agents" wherein the inhibition agents are compounds selected from the group consisting of isopsoralens and photoproduct. As noted earlier, isopsoralens cannot form crosslinks. ("Photoproduct" has been extensively defined and discussed above.)

The present invention contemplates inhibiting template-dependent enzymatic synthesis by A) Site-Specific Covalent Addition, B) Random Covalent Addition, and C) Photoproduct Addition, and reveals D) Compound/Enzyme Specificity.

A. Site-Specific Addition

The present invention contemplates inhibiting of template-dependent elongation by site-specific binding of new and known isopsoralens to nucleic acid. In one embodiment, the method of the present invention for the construction of specifically placed isopsoralen adducts begins with two short oligonucleotides that are complementary to each other, but that differ in length. These oligonucleotides, along with an isopsoralen are placed together under conditions where the oligonucleotides are base paired as a double stranded molecule. This non-covalent complex is irradiated to cause addition of the isopsoralen (320–400 nm) or psoralen (>380 nm) to the oligonucleotides. Following irradiation, monoadducted oligonucleotides are isolated by HPLC or denaturing polyacrylamide gel electrophoresis (PAGE). Because of the differential length of the original short oligonucleotides, monoadducted oligonucleotides specific to each strand are isolated. The present invention contemplates further that the short monoadducted oligonucleotides may be appended to longer oligonucleotides through the use of a ligation reaction and a complementary splint molecule (the longer, ligated molecules are purified by PAGE).

Such specifically constructed monoadducted oligonucleotides are useful to determine the diferential site-specifically of photoreactive compounds. The present invention contemplates the use of different compounds for different site-specifities. For example, AMIP has a different site-specifically from AMDMIP.

B. Random Addition

The present invention also contemplates randomly adding isopsoralens to produce covalent complexes of isopsoralen and nucleic acid. By random it is not meant that the particular isopsoralen will not display preferential placement. By random it is meant that the level of addition (one, two or three adducts, etc.) is not limited to one adduct per strand; the compound has access to a larger number of sites. The present invention further contemplates mixing isopsoralens to create a "cocktail" for random addition. Randomly added cocktails can be used where multiple adducts per strand are desired and where preferential placement is sought. The present invention contemplates that consideration be given to the nature of the nucleic acid (A:T rich, A:T poor, etc.) in selecting both single mixtures and cocktails for random addition.

C. Photoproduct Addition

Previous work towards the blocking of replication of nucleic acids with furocoumarins has historically proceeded by a method having the temporal steps: 1) providing a specific psoralen derivative, 2) providing a particular nucleic acid or nucleic acid target sequence(s), 3) mixing the psoralen with the nucleic acid in the presence of activating wavelengths of electromagnetic radiation. In one embodiment, the present invention contemplates a radical departure from this historical approach to blocking. In one embodiment of the sub-method of the present invention, the temporal sequence is the following: 1) providing furocoumarin derivative(s), 2) exposing the furocoumarin derivative (s) to activating wavelengths of electromagnetic radiation, 3) providing a particular nucleic acid or nucleic acid target sequence(s), 4) mixing the irradiated furocoumarin derivative(s) with the nucleic acid. In this embodiment, the furocoumarin is irradiated *prior* to mixing with nucleic acid. The experimental investigation of this novel temporal sequence has established that furocoumarin photoproduct exists and that photoproduct can inhibit template-dependent enzymatic synthesis, e.g. primer extension.

In one embodiment, the present invention contemplates using AMDMIP photoproduct and AMIP photoproduct ("a photoproduct cocktail") to inhibit polymerase activity. While not limited to any particular molecular mechanism for inhibition, it is contemplated that inhibition is specifically due to the interaction of photoproduct with nucleic acid. In one embodiment, the method of the present invention comprises: a) providing pre-irradiated AMIP and AMDMIP; b) providing one or more nucleic acid target sequences; and c) adding the pre-irradiated AMIP and AMDMIP to the one or more nucleic acid sequences, so that the one or more sequences cannot be extended by polymerase. Again, while not limited to any particular molecular mechanism, it is contemplated that photoproduct is formed which undergoes subsequent thermal addition to the nucleic acid. It is believed that the photoproduct:nucleic acid complex cannot serve as a template for polymerase.

Advantages of photoproduct inhibiting methods of the present invention include the ability to pre-form the inhibition agent in the absence of target. The photoproduct can then be provided at the appropriate point in the process (i.e., when a polymerase inhibiting moiety is required to be added to the nucleic acid or nucleic acid sequence). This pre-irradiation is contemplated particularly where thermally sensitive reagents are used for inhibition. For example, compounds which are thermally sensitive would not be suitable for some types of template-dependent enzymatic synthesis. Such compounds would lose their utility due to thermal decomposition prior to photoactivation. With the novel temporal sequence of the method of photoproduct inhibition of the present invention, the need for thermal stability is obviated since photoproduct can be pre-formed and added at the conclusion of thermal cycling.

D. Compound/Enzyme Specificity

The present invention provides results that suggest there is some compound/enzyme specificity, e.g. some isopsoralens inhibit particular polymerases better than other isopsoralens. For example, MIP and AMIP adducts will inhibit primer extension by Taq polymerase, T4 polymerase and reverse transcriptase. MIP and AMIP adducts, however, do not show the same level of inhibition of primer extension by *E. Coli* polymerase or Klenow fragment. By contrast, AMDMIP adducts show the same level of inhibition of primer extension by all of these enzymes.

VI. STERILIZATION

The present invention contemplates a method of sterilization that is useful for, among other uses, solving the carryover problem associated with amplification of nucleic acid. The overall approach of the method involves rendering nucleic acid after amplification substantially unamplifiable (hence "Post-Amplification Sterilization"), before a carry-over event can occur.

Post-amplification sterilization is designed to control carryover. It is desirable to concurrently run reagent controls to assure that carryover is absent in the first place.

It was noted earlier that target sequences are "targets" in the sense that they are sought to be sorted out from other nucleic acid. Amplification techniques have been designed primarily for this sorting out. "Amplification" is a special case of replication involving template specificity. It is to be contrasted with non-specific template replication (i.e. replication that is template-dependent but not dependent on a specific template). Template specificity is here distinguished from fidelity of replication (i.e. synthesis of the proper polynucleotide sequence) and nucleotide (ribo- or deoxyribo-) specificity.

Template specificity is achieved in most amplification techniques by the choice of enzyme. Amplification enzymes are enzymes that, under conditions they are used, will process only specific sequences of nucleic acid in a heterogenous mixture of nucleic acid. For example, in the case of $Q\beta$ replicase, MDV-1 RNA is the specific template for the replicase. D. L. Kacian et al., Proc. Nat. Acad. Sci USA 69:3038 (1972). Other nucleic acid will not be replicated by this amplification enzyme. Similarly, in the case of T7 RNA polymerase, this amplification enzyme has a stringent specificity for its own promoters. M. Chamberlin et al., Nature 228:227 (1970). In the case of T4 DNA ligase, the enzyme will not ligate the two oligonucleotides where there is a mismatch between the oligonucleotide substrate and the template at the ligation junction. D. Y. Wu and R. B. Wallace, Genomics 4:560 (1989). Finally, Taq polymerase, by virtue of its ability to function at high temperature, is found to display high specificity for the sequences bounded and thus defined by the primers;

the high temperature results in thermodynamic conditions that favor primer hybridization with the target sequences and not hybridization with non-target sequences. PCR Technology, H. A. Erlich (ed.) (Stockton Press 1989).

Enzymes such as *E. coli* DNA polymerase I and Klenow are not specific enzymes. Indeed, within their range of activity (temperature, pH, etc.), they are promiscuous; they will elongate any nucleic acid having short double-stranded segments exposing a 3' hydroxyl residue and a protruding 5' template. This, of course, is not to say that these enzymes cannot be used in an amplification protocol. For example, these enzymes can be used with homogeneous nucleic acid to produce specific target.

It is not intended that the sterilization method of the present invention be limited by the nature of the particular amplification system producing the nucleic acid to be sterilized. Some amplification techniques take the approach of amplifying and then detecting target; others detect target and then amplify probe. Regardless of the approach, amplified nucleic acid can carryover into a new reaction and be subsequently amplified. The present invention contemplates sterilizing this amplified nucleic acid before it can carryover.

A. Sterilization In General

Something is "sterilized" when it is rendered incapable of replication. While the term "sterilization" has typically been applied only in the context of living organisms, it is here meant to be applied to in vitro amplification protocols of polynucleotides where a template polynucleotide functions in the nature of a germination seed for its further propagation.

Sterilization "sensitivity" is an operationally defined term. It is defined only in the context of a "sterilization method" and the particular detection method that is used to measure templates (or organisms). Sterilization sensitivity is the number of germination seeds (e.g., viable bacterial cells or polynucleotide templates) that result in a measurable signal in some sterilization method and defined detection assay.

To appreciate that a "sterilization method" may or may not achieve "sterilization," it is useful to consider a specific example. A bacterial culture is said to be sterilized if an aliquot of the culture, when transferred to a fresh culture plate and permitted to grow, is undetectable after a certain time period. The time period and the growth conditions (e.g. temperature) define an "amplification factor". This amplification factor along with the limitations of the detection method (e.g. visual inspection of the culture plate for the appearance of a bacterial colony) define the sensitivity of the sterilization method. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the "sterilization method" appears to be completely effective (and above which "sterilization" is, in fact, only partially effective). This interplay between the amplification factor of an assay and the threshold that the detection method defines, can be illustrated. Referring now to Table 4, bacterial cells are applied to a plate under two different sets of conditions: in one case, the growth conditions and time are such that an overall amplification of $10^4$ has occurred; in the other case, the growth conditions and time are such that an overall amplification of $10^8$ has occurred.

TABLE 4

| AMPLIFICATION FACTOR | # OF VIABLE BACTERIAL CELLS APPLIED TO A PLATE | | | | |
|---|---|---|---|---|---|
| | 1 | 10 | 100 | 1000 | |
| $10^4$ | $10^4$ | $10^5$ | $10^6$ | $10^7$ | # of Bacterial cells after Amplification |
| | − | − | + | ++ | Detection (+/−) |
| $10^8$ | $10^8$ | $10^9$ | $10^{10}$ | $10^{11}$ | # of Bacterial cells after Amplification |
| | ++ | +++ | +++ | ++++ | Detection (+/−) |

The detection method is arbitarily chosen to be visual inspection. The detectable signal will be proportional to the number of bacterial cells actually present after amplification. For calculation purposes, the detection threshold is taken to be $10^6$ cells; if fewer than $10^6$ cells are present after amplification, no cell colonies are visually detectable and the sterilization method will appear effective. Given the amplification factor of $10^4$ and a detection threshold of $10^6$, the sterilization sensitivity limit would be 100 bacterial cells; if less than 100 viable bacterial cells were present in the original aliquot of the bacterial culture after the sterilization method is performed, the culture would still appear to be sterilized. Alternatively, if the time and growth conditions permitted an amplification of $10^8$, then the sterilization sensitivity limit (assuming the same detection threshhold) would be 1 bacterial cell. Under the latter conditions, the sterilization method must be sufficiently stringent that all bacterial cells are, in fact, incapable of replication for sterilization to appear complete (i.e. the sterilization method would need to cause sterilization, not just substantial sterilization).

B. Sterilization of Potential Carryover

The same considerations of detection threshold and amplification factor are present when determining the sensitivity limit of a sterilization method for nucleic acid. Again, by "sterilization" it is meant that the nucleic acid is rendered incapable of replication, and specifically, unamplifiable.

The post-amplification sterilization method of the present invention renders nucleic acid substantially unamplifiable. In one embodiment, the post-amplification sterilization method renders amplified nucleic acid unamplifiable but detectable. In still another embodiment, the post-amplification sterilization method of the present invention contemplates that the number of carryover molecules of amplifiable nucleic acid that has occurred is small enough that, in a subsequent amplification, any amplified product reflects the presence of true target in the sample. In a preferred embodiment, the post-amplification sterilization method of the present invention renders amplified segments of a target sequence substantially unamplifiable but detectable prior to a carryover event.

It is not intended that the post-amplification sterilization method of the present invention be limited by the nature of the nucleic acid; it is contemplated that &he post-amplification sterilization method render all forms of nucleic acid (whether DNA, mRNA, etc.) substantially unamplifiable.

"Template" encompasses both the situation where the nucleic acid contains one or more segments of one or more target sequences, and the situation where the nucleic acid contains no target sequence (and, therefore, no segments of target sequences). "Template" also encompasses both the situation where the nucleic acid contains one or more replicatable probes, and the situation where the nucleic acid contains no replicatable probes. Where template is used for amplification and amplification is carried out, there is "amplification product." Just as "template" encompasses the situation where no target or probe is present, "amplification product" encompasses the situation where no amplified target or probe is present.

The present invention provides "sterilizing compounds" and methods for using "sterilizing compounds." "Sterilizing compounds" are defined such that, when used to treat nucleic acid according to the sterilization method of the present invention, the nucleic acid is rendered substantially unamplifiable, i.e. substantially sterilized. The preferred sterilizing compounds of the present invention are activation compounds.

While it is not intended that the present invention be limited to any theory by which nucleic acid is rendered substantially unamplifiable by the methods and compounds, it is expected that sterilization occurs by either 1) modification of nucleic acid, or 2) inhibition of the amplification enzyme itself. Again, while not limited to any mechanism, it is expected that, if modification of nucleic acid occurs with sterilizing compounds, it probably occurs because the compounds react with amplified nucleic acid to create sufficient adducts per base (i.e. sufficient "modification density") such that statistically all strands are prevented from either 1) subsequent use of the denatured nucleic acid in single stranded form as template for amplification or 2) dissociation of the double stranded form of the nucleic acid into single strands, thereby preventing it from acting as a template for subsequent amplification. On the other hand, it is expected that, if direct inhibition of the amplification enzyme occurs, it probably occurs because the sterilizing compound acts via 1) hydrophobic and hydrophylic interactions, or 2) steric hindrance.

In the case of sterilizing compounds modifying nucleic acid, it is preferred that interaction of the nucleic acid (whether DNA, mRNA, etc.) with the sterilizing compound causes the amplification enzyme to differentiate between actual target sequences and carryover nucleic acid, such that, should amplified nucleic acid be carried over into a subsequent amplification, it will not be amplified.

C. Selective Sterilization

It is further contemplated that the sterilization method of the present is useful in conjunction with amplification, without regard to the carryover problem. In one embodiment, it is contemplated that sterilization is performed in a selective manner so that with respect to a mixture of nucleic acid, nucleic acid desired to be rendered unamplifiable is rendered substantially unamplifiable, but nucleic acid desired to remain amplifiable (hereinafter "sheltered nucleic acid") remains amplifiable. The present invention contemplates three general approaches to this selective sterilization (and consequent selective amplification).

First, the present invention contemplates taking advantage of the site-specificity of activation compounds, and in particular, photoreactive activation compounds. In this approach, an activation compound is selected that has a known site-specificity (or site preference) for nucleic acid (e.g. TpA site-specificity). It is preferred that the site-specificity is selected with the knowledge of the sequence of the sheltered nucleic acid. In this manner, a site-specificity can be chosen where the activation compound will bind at non-sterilizing modification densities to the sheltered nucleic acid (or not bind at all) but will bind at sterilizing modification densities to the remaining nucleic acid.

Second, the present invention contemplates taking advantage of the unique secondary and tertiary structural requirements of some activation compounds for binding with nucleic acid. In this case, the sheltered nucleic acid must have different secondary or tertiary structure than the remaining nucleic acid. An activation compound requiring secondary or tertiary structure that is lacking in the sheltered nucleic acid is selected and added to the nucleic acid mixture. The activation compound binds at non-sterilizing modification densities with the sheltered nucleic acid and sterilizing modification densities with the remaining nucleic acid.

Finally, the present invention contemplates multiple sterilizations in a multiple amplification protocol. Multiple amplifications systems have been suggested where a first amplification is carried out by a first polymerase, followed by a second amplification with a second polymerase. For example, the first amplification can be used to introduce promotor sites for the enzyme of the second amplification. Mullis et al., Cold Springs Harbor Symposia, Vol. L1, p. 263 (1986). G. J. Murakawa et al., DNA 7:287 (1988). In the sterilization approach to these multiple amplification systems, the present invention takes advantage of the unique polymerase specificities of activation compounds, and in particular photoreactive activation compounds. A first activation compound is selected that, when bound to nucleic acid, will inhibit amplification by the first polymerase in the first amplification, but that will not inhibit the second polymerase in the second amplification. Post-amplification sterilization is carried out after the first amplification with this first activation compound. Amplified nucleic acid treated in this manner will not be amplified by the first polymerase but can be amplified by the second polymerase. Post-amplification sterilization can later performed after the second amplification with a second activation compound that, when bound to nucleic acid, will inhibit amplification with the second polymerase.

D. Selecting Activation Compounds for Sterilization

As noted above, the preferred sterilizing compounds of the present invention are activation compounds. FIG. 3 outlines the methods by which activation compounds can be screened for use as sterilizing compounds. Four "Sterilization Modes" are shown along with the temporal points where potential reactants of each Mode are added to the amplification system (the amplification system is contemplated to encompass all amplification methods, e.g. target-amplifying or probe-amplifying).

The Sterilization Modes consist of the following temporal steps:

Mode I: Add activation compound then amplify sample, followed by activation ("triggering") of the activation compound Mode II: Amplify sample then add activation compound, followed by activation ("triggering") of the activation compound Mode III: Add pre-activated ("triggered") activation compound then amplify sample Mode IV: Amplify sample then add pre-activated ("triggered") activation compound In the general case, an activation compound is "triggered" to an active form. This form provides the sterilizing activity to the system. The type of triggering required depends on the properties of the sterilizing compound. For example, thermally reactive compounds are triggered by providing the correct temperature while photoreactive compounds are triggered by providing the appropriate activating wavelengths of electromagnetic radiation. Thoughtful consideration of FIG. 3 allows any activation compound to be analyzed as a potential sterilizing compound and defines its appropriate Mode of application (if any).

A new compound ("X") can be evaluated as a potential sterilizing compound. X is initially evaluated in Step A of Mode I. In Step A, X is added to the sample during the sample preparation step prior to amplification. The amplification process is performed and the yield of the amplified product compared to an identical sample amplified without X. If the amplification yield is similar in both samples, the sterilization activity of X is evaluated in Step B of Mode I. In Step B, the appropriate "trigger" is pulled to activate X after amplification has occurred. For example, if X is a thermal reagent, the appropriate temperature is provided to generate the activated form of the compound (X* = generically activated X). The sterilization effect of X* on the amplified products is then determined by reamplification of the amplified products after treatment. If an acceptable level of sterilization is realized, a separate evaluation is performed to determine the effect of the modification provided by X* on subsequent detection of the modified target molecules. In this manner, both the effectiveness of X as a Mode I sterilization reagent and the compatibility of the modified amplified target with subsequent detection formats is evaluated.

Alternatively, X may inhibit the amplification process in Mode I, Step A. In this event, X cannot be effectively used in Mode I; X is thereafter evaluated as a Mode II sterilization reagent. In Mode II, the temporal order of amplification, compound addition and triggering are changed relative to Mode I. X is added following amplification in Mode II, thereby avoiding the amplification inhibition detected in Mode I. In this fashion, the sterilization effect of X* on the amplified products can be determined independent of the negative effect of X on amplification. Evaluation of the Mode II sterilization activity is done in the same fashion as for Mode I, Step B.

The two additional methods which use X for sterilization are Modes III and IV. In both these Modes, X is triggered to provide X* prior to addition to the sample. X* is then added to the system either before (Mode III) or after (Mode IV) amplification.

In Mode III, X* may be provided then added to the sample prior to amplification. In the case where X is a photoreactive compound, X* is the resultant product of the exposure of photoreactive compound to activating wavelengths of electromagnetic radiation. If amplification is inhibited with this resultant product, it may reasonably be suspected that exposure of X to activating wavelengths of electromagnetic radiation results in photoproduct.

In Mode IV, X* is provided then added to the system following amplification, thereby avoiding any issue of compatability with the amplification process. X*, whether a thermally activated or photoactivated, when provided and used according to Mode IV, can provide effective sterilization via more than one mechanism. X* may react with amplified target, non-nucleic acid components of the system, or both.

Table 5 summarizes the above.

As noted in FIG. 3, the choice of the appropriate activation compound for post-amplification sterilization also depends in part on the detection method employed. If the detection procedure involves a hybridization step with the amplified nucleic acid sequences, it is desired that the amplified sequences be both available and hybridizable, i.e. they should not be irreversibly double stranded. If the detection procedure need not involve hybridization (e.g., incorporation of labelled nucleic acid precursors or the use of biotinylated primers, which are subsequently detected), the amplified sequence can normally remain double stranded. With the preferred method of sterilization, it is desired that the modification caused by the inactivation procedure not interfere with subsequent detection steps. In the case of post-amplification modifications to amplified target sequences, it is preferred that there be no impact on hybridization to or detection of the amplified segment of the target molecule.

TABLE 5

EVALUATION OF POTENTIAL STERILIZATION REAGENTS

| Mode/Step | Result* | Interpretation/Next Step |
|---|---|---|
| I/A | + ampl | Compound is compatible with amplication/Evaluate in Mode I, Step B |
| I/A | − ampl | Compound is incompatible with amplication/Evaluate in Mode II, Steps A and B |
| I/A + B | + ster | Compound is a useful sterilization reagent in Mode I/Evaluate detection |
| I/A + B | − ster | Compound is ineffective as a sterilization reagent in Mode I/Evaluate in Modes II, III and IV |
| II | + ster | Compound is useful for sterilization in Mode II/Evaluate detection |
| II | − ster | Compound is ineffective as a sterilization reagent in Mode II/Evaluate in Modes III and IV |
| III | − ampl | Compound may be useful in Mode IV. |
| III | + ampl | Compound is compatible with amplification but not useful for sterilization by definition. |
| IV | +ster | Compound is a useful sterilization reagent in Mode IV/Evaluate detection |
| IV | −ster | Compound is an ineffective as a sterilization reagent in Mode IV. |

*+/− ampl = amplifiation inhibited/amplifiation not inhibited
+/− ster = sterilization effective/sterilization ineffective Environmental factors are important considerations—particularly during sample preparation. The preferred compound will not require special handling due to toxicity or sensitivity to the normal laboratory/clinical environment, including the normal incandescent or fluorescent lighting found in such environments. Compounds which are toxic to the user and/or sensitive to room light will require a special environment for use. Special environments make the assay inherently more cumbersome and complex and correspondingly more subject to error. The supporting instrumentation for such assays likewise becomes more complicated.

Because it is desired that amplified nucleic acid not be exposed to the environment until they are sterilized, a preferred embodiment of the present invention contemplates the use of photoreactive compounds for sterilization. As noted earlier, "photoreactive compounds" are defined as compounds that undergo chemical change in response to appropriate wavelengths of electromagnetic radiation. Photoreactive compounds possess the advantage of allowing inactivation without opening the reaction vessel (when appropriate reaction vessels are used). Furthermore, because it is desired that the modification of the amplified nucleic acid not interfere with subsequent steps, the present invention contemplates the use of photoreactive compounds that do not interfere with detection.

In the preferred embodiment, the invention contemplates amplifying and sterilizing in a closed system, i.e. the amplified nucleic acid is not exposed to the environment until modified. In one embodiment, the present invention contemplates having the photoreactive compound present in the reaction mixture during amplification. In this manner, the reaction vessel need not be opened to introduce the sterilizing compound.

The use of photoreactive compounds in closed containers requires that sufficient light of appropriate wavelength(s) be passed through the vessel. Thus, a light instrument must be used in conjunction with the present invention to irradiate the sample. As noted above ("II. PHOTOACTIVATION DEVICES"), instruments with these features are contemplated by the present invention.

In general, the sterilization method of the present invention is a method for treating nucleic acid comprising: a) providing in any order: i) nucleic acid, ii) amplification reagents, iii) one or more amplification enzymes, iv) one or more sterilizing compounds, and v) means for containing a reaction, as reaction components; b) adding to said reaction containing means, in any order, said nucleic acid and said amplification reagents, to make a reaction mixture; and c) adding to said reaction mixture, without specifying temporal order, i) said one or more amplification enzymes, and ii) said one or more sterilizing compounds.

In a preferred embodiment, sterilization comprises the sequential steps: a) providing, in any order, i) one or more photoreactive compounds, ii) nucleic acid, iii) amplification reagents, iv) one or more amplification enzymes, and v) means for containing a reaction; b) adding to the reaction containing means, in any order, one or more photoreactive compounds, nucleic acid, and amplification reagents, to make a reaction mixture; adding said one or more amplification enzymes to said reaction mixture; and d) treating said mixture with appropriate wavelengths of electromagnetic radiation so that said photoreactive compounds are photoactivated.

"Amplification reagents" are defined as those reagents (primers, deoxyribonucleoside triphosphates, etc.) needed for amplification except for nucleic acid and the amplification enzyme. In one embodiment, the means for containing is a reaction vessel (test tube, microwell, etc.).

In another embodiment, sterilization comprises the sequential steps: a) providing, in any order, i) one or more photoreactive compounds, ii) nucleic acid, iii) amplification reagents, iv) one or more amplification enzymes, and v) means for containing a reaction; b) adding to said reaction containing means, said nucleic acid and said amplification reagents, followed by one or more amplification enzymes, to make a reaction mixture; c) adding said one or more photoreactive compounds to said reaction mixture; d) treating said mixture with appropriate wavelengths of electromagnetic radiation so that said photoreactive compounds are photoactivated.

While the various embodiments illustrate that the mixing of photoreactive compound(s), amplification reagents, nucleic acid, and amplification enzyme(s) can be in any order, it is preferred that photoreactive compound(s) be added prior to initiation of amplification (note: the adding of amplification enzyme(s) to the reaction mixture containing amplification reagents and nucleic acid will initiate amplification). The method of the present invention may have the additional step of detecting amplified nucleic acid.

In one embodiment, the photoreactive compound is selected from the group consisting of psoralens and isopsoralens. The preferred photoreactive compounds are isopsoralens. In one embodiment, a cocktail of isopsoralens is used. In another embodiment, the isopsoralen(s) is selected from the group consisting of 5-methylisopsoralen, 5-bromomethylisopsoralen, 5-chloromethylisopsoralen, 5-hydroxymethylisopsoralen, 5-formylisopsoralen, 5-iodomethylisopsoralen, 5-hexamethylenetetraminomethylisopsoralen, 5-aminomethylisopsoralen, 5-N-(N,N'-dimethyl-1,6-hexanediamine)-methylisopsoralen, 5-N-[N,N'-dimethyl-(6-[biotinamido]-hexanoate)-1,6-hexanediamine])-methylisopsoralen, 5-N-[N,N'-dimethyl-N'-(2-{biotinamido}-ethyl-1,3-dithiopropionate)-1,6-hexanediamin]-methylisopsoralen, 5-N-[N,N'-dimethyl-N'-(carboxy-fluorescein ester)-1,6-hexanediamine)-methylisopsoralen, and their radiolabelled derivatives. In still another embodiment, the isopsoralen is selected from the group consisting of 4,5'-dimethylisopsoralen, 4'-chloromethyl-4,5'-dimethylisopsoralen, 4'-bromomethyl-4,5'-dimethylisopsoralen, 4'-hydroxymethyl-4,5'-dimethylisopsoralen, 4'-formyl-4,5'-dimethylisopsoralen, 4'-phthalimidomethyl-4,5'-dimethylisopsoralen, 4'-aminomethyl-4,5'-dimethylisopsoralen, 4'-iodomethyl-4,5'-dimethylisopsoralen, 4'-N-(N,N'-dimethyl-1,6-hexanediamine)-methyl-4,5'-dimethylisopsoralen, 4'-N-[N,N'-dimethyl-N'-(6-{biotinamido}-hexanoate)-1,6-hexanediamine]-methyl-4,5'-dimethylisopsoralen, 4'-N-[N,N'-dimethyl-N'-(2-{biotinamido}-ethyl-1,3-dithiopropionate)-1,6-hexanediamine]-methyl-4,5'-dimethylisopsoralen, 4'-N-[N,N'-dimethyl-N'-(6-carboxyfluorescein ester)-1,6-hexanediamine)-methyl-4,5'-dimethylisopsoralen, and their radiolabelled derivatives.

While the preferred compound for controlling carry-over according to the methods of the present invention is an isopsoralen, the present invention contemplates sterilization with psoralens as well. In one embodiment, the linear furocoumarin 4'-aminomethyl-4,5', 8-trimethylpsoralen (AMT) is used as a post-amplification sterilization reagent.

The present invention contemplates using photoproduct for sterilization. In this embodiment, sterilization comprises the sequential steps: a) providing, in any order, i) photoproduct, ii) nucleic acid, iii) amplification reagents, iv) one or more amplification enzymes, and v) a means for containing a reaction; b) adding to said reaction containing means, in any order, said nucleic acid and said amplification reagents, to make a reaction mixture; c) adding said one or more amplification enzymes to said reaction mixture; and d) adding said photoproduct to said reaction mixture.

In this embodiment, photoproduct is created prior to amplification but introduced after amplification. In another embodiment, photoproduct is made after and introduced after amplification. Photoproduct is made, therefore, at any time prior to mixing with the amplified nucleic acid. However, in both embodiments, photoproduct is not present in the reaction mixture during amplification.

Photoproduct can be both provided and added manually or by an automated system. For example, it is contemplated that photoproduct be made in and introduced from a compartment in a reaction vessel. The compartment is separated from the remaining vessel by a barrier (e.g. a membrane) that is removable in a controlled manner. In the removable barrier approach, photoproduct is made by exposing the entire reaction vessel [with the compartment containing photoreactive compound(s)] to the appropriate wavelength(s) of electromagnetic radiation. When photoproduct is to be added, the barrier is then removed and the newly formed photoproduct added to the amplified product.

In another embodiment, photoproduct is made separately in a first reaction vessel and then injected into a second reaction vessel containing nucleic acid without opening the second reaction vessel. Injection is by a small needle; the needle can be permanently fixed in the side of the vessel if desired.

In still another embodiment, photoproduct is made in a first reaction vessel and pipetted into a second reaction vessel containing nucleic acid. While other arrangements are possible, it is preferred that the pipetting be performed in an automated manner in the housing of a machine large enough to contain the first reaction vessel and the second reaction vessel. The housing serves to contain any carryover while the reaction vessels are open.

The sterilization method utilizing photoproduct may comprise additional steps such as a detection step. In one embodiment, the detection step involves detection of amplified target(s). In another embodiment, the detection step involves detection of amplified probe(s).

E. Polymerase Chain Reaction

In one embodiment, the present invention contemplates controlling the carryover associated with PCR. This embodiment is broadly referred to as "Post-Amplification Sterilization of Target from PCR" or "PAST PCR." For purposes here, a "target sequence" is further defined as the region of nucleic acid bounded by the primers used for PCR. A "segment" is defined as a region of nucleic acid within the target sequence. As noted above, the present invention contemplates sterilization whether or not the sample prepared for amplification contains a segment of a target sequence that can be amplified. Whether or not their is a segment of a target sequence that can be amplified, there is "PCR product." For definitional purposes, "PCR product" refers to the resultant mixture of compounds after two or more cycles of the PCR steps of denaturation, annealing and extension are complete. "PCR product" encompasses both the case where there has been amplification of one or more segments of one or more target sequences, and the case where there has been no amplification.

Figure 4:
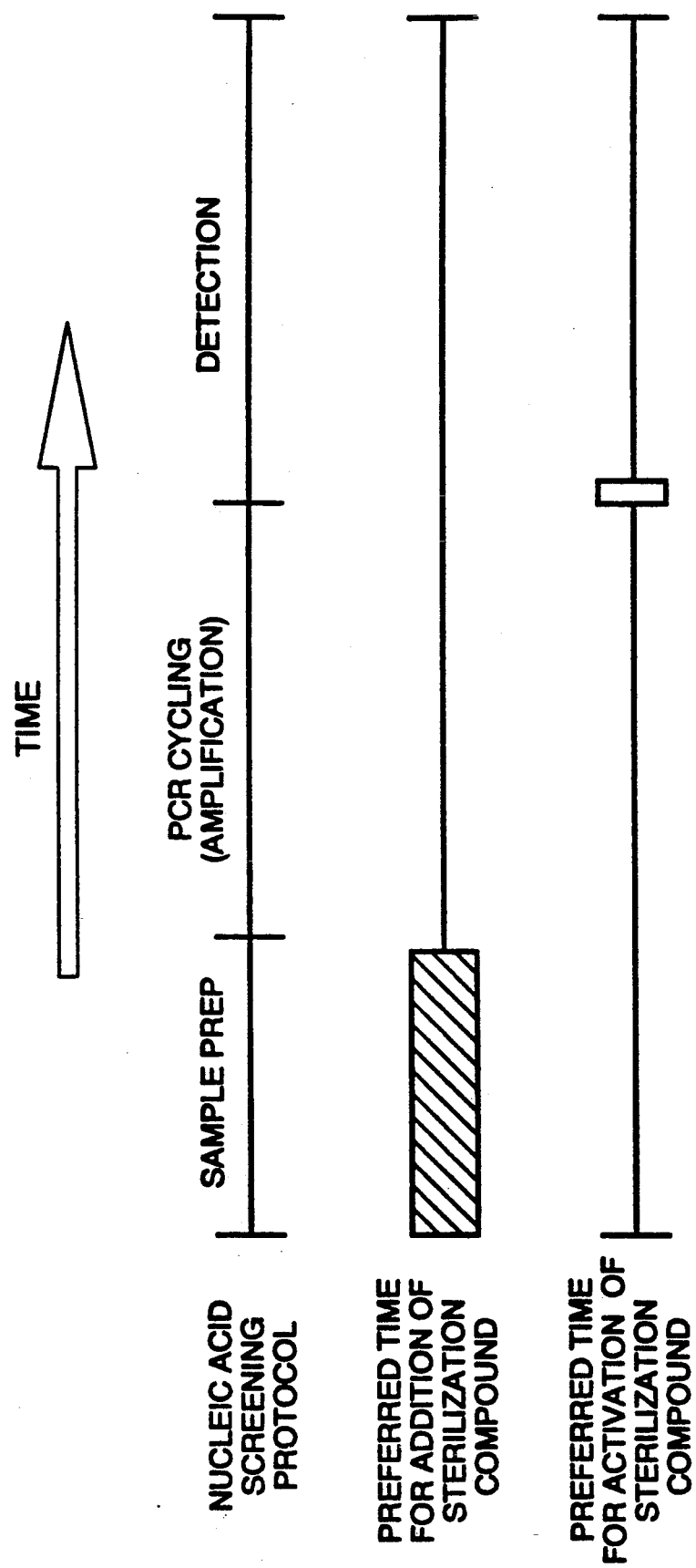
FIG. 4 schematically shows the steps involved in amplifying nucleic acid according to one particular amplification system.

A general nucleic acid screening protocol involving PCR amplification is schematically illustrated in FIG. 4. The steps are broadly characterized as 1) sample preparation, 2) amplification, and 3) detection. The lower time lines of FIG. 4 schematically illustrate the temporal sequence for a) the addition of sterilizing compound(s), and b) the activation of sterilizing compound(s) according to a preferred embodiment of the method of the present invention.

Amplification cycling requires "PCR reagents." "PCR reagents" are here defined as all reagents necessary to carry out amplification except polymerase and template. PCR reagents normally include nucleic acid precursors (dCTP, dTTP, etc.) and primers in buffer. See K. B. Mullis et al., U.S. Pat. Nos. 4,683,195 and 4,683,202, both of which are hereby incorporated by reference.

PCR is a polynucleotide amplification protocol. The amplification factor that is observed is related to the number (n) of cycles of PCR that have occurred and the efficiency of replication at each cycle (E), which in turn is a function of the priming and extension efficiencies during each cycle. Amplification has been observed to follow the form $E^n$, until high concentrations of PCR product are made. At these high concentrations (approximately $10^{-8}$ M/l) the efficiency of replication falls off drastically. This is probably due to the displacement of the short oligonucleotide primers by the longer complementary strands of PCR product. At concentrations in excess of $10^{-8}$M, the kinetics of the two complementary PCR amplified product strands of finding each other during the priming reactions become sufficiently fast that they will occur before or concomitantly with the extension step of the PCR procedure. This ultimately leads to a reduced priming efficiency, and therefore, a reduced cycle efficiency. Continued cycles of PCR lead to declining increases of PCR product molecules. PCR product eventually reaches a plateau concentration.

Table 6 illustrates the relationship of PCR cycle number to the number of PCR product strands that are made as a function of a wide range of starting target molecules (initial copy number). The efficiency of amplification was taken to be 1.85 per cycle, a value measured while using methods of the present invention for the HIV system with the SK38/SK39 primers. Included in Table 6 is the PCR product concentration that is observed if the PCR reaction were to take place in 100 ul volume. The gray area indicates conditions that give rise to PCR products that are in excess of $10^{-8}$ M/l. In these gray regions, PCR product would be expected to be approaching the plateau stage. Also shown in Table 6 is a signal (CPM) for a hybridization assay that is used to detect the presence of PCR product. This signal is calculated on the basis of having a 10% hybridization efficiency of a $^{32}$P labelled probe (3000 Ci/mM) to a 20 µl aliquot of the 100 µl PCR reaction mix.

TABLE 6

| Cycle | Amplification Factor $(1.85)^n$ | INITIAL COPY NUMBER | | | | | | | |
|---|---|---|---|---|---|---|---|---|---|
| | | 1 | 10 | $10^2$ | $10^3$ | $10^4$ | $10^5$ | $3 \times 10^{5*}$ | |
| 20 | $2.20 \times 10^5$ | $2.2 \times 10^5$ | $2.2 \times 10^6$ | $2.2 \times 10^7$ | $2.2 \times 10^8$ | $2.2 \times 10^9$ | $2.2 \times 10^{10}$ | $6.6 \times 10^{10}$ | PCR product molecules |
| | | $3.6 \times 10^{-15}$ | $3.6 \times 10^{-14}$ | $3.6 \times 10^{-13}$ | $3.6 \times 10^{-12}$ | $3.6 \times 10^{-11}$ | $3.6 \times 10^{-10}$ | $1.0 \times 10^{-9}$ | PCR Product (M/l) |
| | | 0 | 0 | 2.4 | 24 | 240 | 2,400 | 7,100 | CPM's |
| 25 | $4.78 \times 10^6$ | $4.8 \times 10^6$ | $4.8 \times 10^7$ | $4.8 \times 10^8$ | $4.8 \times 10^9$ | $4.8 \times 10^{10}$ | $4.8 \times 10^{11}$ | $1.4 \times 10^{12}$ | |
| | | $7.9 \times 10^{-14}$ | $7.9 \times 10^{-13}$ | $7.9 \times 10^{-12}$ | $7.9 \times 10^{-11}$ | $7.9 \times 10^{-10}$ | $7.9 \times 10^{-9}$ | $2.4 \times 10^{-8}$ | |
| | | 0 | 5 | 52 | 520 | 5,200 | $5.2 \times 10^4$ | $1.5 \times 10^5$ | |
| 30 | $1.03 \times 10^8$ | $1.0 \times 10^8$ | $1.0 \times 10^9$ | $1.0 \times 10^{10}$ | $1.0 \times 10^{11}$ | $1.0 \times 10^{12}$ | | | |
| | | $1.7 \times 10^{-12}$ | $1.7 \times 10^{-11}$ | $1.7 \times 10^{-10}$ | $1.7 \times 10^{-9}$ | $1.7 \times 10^{-8}$ | | | |
| | | 11 | 110 | 1,100 | $1.1 \times 10^4$ | $1.1 \times 10^5$ | | | |
| 35 | $2.24 \times 10^9$ | $2.2 \times 10^9$ | $2.2 \times 10^{10}$ | $2.2 \times 10^{11}$ | $2.2 \times 10^{12}$ | | | | |
| | | $3.6 \times 10^{-11}$ | $3.6 \times 10^{-10}$ | $3.6 \times 10^{-9}$ | $3.6 \times 10^{-8}$ | | | | |
| | | 240 | 2,400 | $2.4 \times 10^4$ | $2.4 \times 10^5$ | | | | |
| 40 | $4.86 \times 10^{10}$ | $4.9 \times 10^{10}$ | $4.9 \times 10^{11}$ | $4.9 \times 10^{12}$ | | | | | |
| | | $8.0 \times 10^{-10}$ | $8.0 \times 10^{-9}$ | $8.0 \times 10^{-8}$ | | | | | |
| | | 5,200 | $5.2 \times 10^4$ | $5.2 \times 10^5$ | | | | | |

*1 µg genomic DNA

While not limited to any particular theory, the present invention contemplates that, when an adduct is present on a PCR target sequence within the segment of the target sequence bounded by the primer sequences, the extension step of the PCR process will result in a truncated, complementary strand that is incapable of being replicated in subsequent cycles of the PCR process. As discussed above ("V. INHIBITING TEMPLATE-DEPENDENT ENZYMATIC SYNTHESIS") isopsoralens attached to a DNA polymer represent a stop for Taq polymerase extension reactions. In one embodiment, the present invention contemplates that such isopsoralens are effective in rendering a fraction of the starting target molecules incapable of amplification by the PCR process with Taq polymerase. Importantly, the sterilization protocol will be incomplete if some of the target molecules escape modification by the photochemical modification process. This process is, by its nature, a statistical process. This process can be characterized by measuring an average number (a) of adducts per DNA strand. Not all of the strands will have a adducts per strand. If the addition reaction is governed by Poisson statistics, the fraction of molecules that contain n modifications in a large population of molecules that have an average of a modifications is given by $f_a(n)$ (see Table 7). A fraction of molecules, $f_a(0)$, will contain no modifications and are therefore considered non-sterilized. Table 7 evaluates the non-sterilized fraction of DNA strands that are expected if an average of a modifications per strand exists.

TABLE 7

POISSON STATISTICS APPLIED TO STERILIZATION
$f_a(n) = [_an_c - a]/n!$

| a | $f_a(0)$ | $N = 10^6$, $f_a(0) = e^{-a}$ $Nf_a(0)$ |
|---|---|---|
| 3 | 0.050 | $5.0 \times 10^4$ |
| 4 | 0.018 | $1.8 \times 10^4$ |
| 5 | 0.007 | $6.7 \times 10^3$ |
| 6 | 0.0025 | $2.5 \times 10^3$ |
| 7 | 0.0009 | $9.1 \times 10^2$ |
| 8 | 0.0003 | $3.3 \times 10^2$ |
| 9 | 0.00012 | $1.2 \times 10^2$ |
| 10 | 0.000045 | 45.0 |
| 11 | 0.000017 | 17.0 |
| 12 | 0.0000061 | 6.1 |

TABLE 7-continued

POISSON STATISTICS APPLIED TO STERILIZATION
$f_a(n) = [_an_c - a]/n!$

| a | $f_a(0)$ | $N = 10^6$, $f_a(0) = e^{-a}$ $Nf_a(0)$ |
|---|---|---|
| 13 | 0.0000023 | 2.2 |
| 14 | 0.00000083 | .8 |
| 15 | 0.00000030 | .3 |
| 16 | 0.00000011 | .1 |
| 17 | 0.00000004 | 0.04 | a = Average number of adducts per strand
$f_a(0)$ = Fraction of strands with zero adducts when the average number of adducts per strand is a
$Nf_a(0)$ = The number of non-sterilized molecules, calculated for a total of $10^6$ molecules ($N = 10^6$)

Although the fraction of molecules with no modifications is small for all values of a, the expected number of non-sterilized molecules is large when sterilization is applied to a large number of molecules (N). For example, if carryover consisted of $10^6$ product strands, Table 7 shows that $2.5 \times 10^3$ non-sterilized target molecules are expected if there is an average of 6 effective adducts per strand of PCR product. Effective adducts are those adducts that occur in the segment of a target molecule that is bounded by the primer sequences. For the HIV system this corresponds to 6 adducts in the 56 base long segment between the primer sequences on the 115-mer target molecule. This level of effective adducts corresponds to an average strand modification density of 1 adduct per 9.3 bases.

Ideally, one would like to be able to sterilize a PCR reaction mixture such that a major spill of the reaction would not lead to a carryover problem. A 100 µl PCR sample mixture with PCR product at a plateau concentration of $1 \times 10^{-8}$M contains $6 \times 10^{11}$ complementary PCR product strands. Sterilization of this sample to a level where the expected number of non-sterilizing target molecules is less than one requires that $f_a(0) * 6 \times 10^{11}$ be less than one (here "sterilized target molecule" means a target molecule that contains at least one adduct). By extending the data in Table 7 and assuming a reaction volume of 100 ul, the statistical view of sterilization predicts that 28 adducts per strand of PCR product is sufficient to achieve this level of sterilization. If the number of target strands made by the PCR procedure are increased or reduced, the average number of adducts per strand required to achieve this level of sterilization will change accordingly. For the HIV 115-mer system that has reached plateau concentrations of product ($6 \times 10^{11}$ molecules), this level of sterilization occurs (28 average effective adducts per strand) when the average modification density is increased to 1 adduct per 2 bases.

Alterations of the modification density can be expected through the use of different photoreactive compounds, or the use of the same photoreactive compound at different concentrations. In particular, the modification density is expected to increase through the use of the same photochemical agent at higher concentrations, and attaching the photochemical agent by exposure to actinic light from a device whose optical properties enhance covalent binding.

For a fixed modification density there is another method of improving the sterilization sensitivity limit. The important statistical parameter for sterilization sensitivity is the average number of adducts per PCR strand. By choosing PCR primers judiciously, the length of the PCR products can be varied, and therefore, the average number of adducts per stand can be varied. Table 8 illustrates this effect for two different modification densities. In Case A, a modification density of 1 adduct per 5 bases is assumed. Under these conditions a PCR product oligonucleotide 200 bases in length should have approximately 30 effective adducts per strand. At this level of modification, less than one PCR product molecule in a 100 µl PCR reaction tube would be expected to have no adducts per strand, and therefore, essentially all of the molecules in the reaction tube would be expected to be sterilized. Case B in Table 8 considers the situation in which the modification density is reduced to 1 adduct per 9 bases. Under these conditions, the same level of sterilization requires that the PCR product be at least 300 bases in length for a sufficient number of effective adducts to be present on each strand.

TABLE 8

EXPECTED NUMBER OF
NON-STERILIZED PCR MOLECULES
AS A FUNCTION OF PCR PRODUCT LENGTH

| Lenth of PCR Product | *Average effective Adducts/Strand | Non-Sterilized Molecules per $6 \times 10^{11}$ Starting Molecules |
|---|---|---|
| CASE A: (1 adduct per 5 bases) | | |
| 100 | 10 | $2.7 \times 10^7$ |
| 150 | 20 | $1.2 \times 10^3$ |
| 200 | 30 | <1 |
| 250 | 40 | <<1 |
| 300 | 50 | <<1 |
| CASE B: (1 adduct per 9 bases) | | |
| 100 | 5.5 | $2.4 \times 10^9$ |
| 150 | 11.1 | $9.1 \times 10^6$ |
| 200 | 16.6 | $3.7 \times 10^4$ |
| 250 | 22.2 | 137 |
| 300 | 27.7 | <1 |

*Assumes that to be effective, the adducts must be in the segment of the PCR product that is bounded by the primers. For calculation purposes, the primer lengths were taken to be 25 bases each.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); gm (grams); mg (milligrams); µg (micrograms); L (liters); ml (milliliters); µl (microliters); cm (centimeters); mm (millimeters); µm (micrometers); nm (nanometers); °C. (degrees Centigrade); Ci (Curies); mp (melting point); m/e (ion mass); MW (molecular weight); OD (optical density); EDTA (ethylenediamine-tetracetic acid); 1×TE (buffer: 10 mM Tris/1 mM EDTA, pH 7.5); 1×Taq (buffer: 50 mM KCl, 2.5 mM MgCl$_2$, 10 mM Tris, pH 8.5, 200 µg/ml gelatin); C/M (chloroform / methanol); C/E/T (chloroform/ethanol/triethylamine); C/B/A/F (chloroform/n-butanol/acetone/formic acid); DMF (N,N-dimethylformamide); PAGE (polyacrylamide gel electrophoresis); UV (ultraviolet); V (volts); W (watts); mA (milliamps); bp (base pair); CPM (counts per minute); DPM (disintegrations per minute); TLC (Thin Layer Chromatography); HPLC (High Pressure Liquid Chromatography); FABMS (Fast Atom Bombardment Mass Spectrometry - spectra obtained on a Kratos MS50 instrument - Kratos Analytical, Manchester, England); EIMS (Electron Impact Mass Spectrometry - spectra obtained on an AEI MS-12 Mass Spectrometer-Associated Electric Industries, Manchester, England); NMR (Nuclear Magnetic Resonance; spectra obtained at room temperature on either a 200 MHz or 250 MHz Fourier Transform Spectrometer); Aldrich (Aldrich Chemical Co., Milwaukee, Wis.); Baker (J. T. Baker, Jackson, Tenn.); Beckman (Beckman Instruments, San Ramon, Calif.); BRL (Bethesda Research Laboratories, Gaithersburg, Md.); Cyro (Cyro Industries, Wood Cliff Lake, N.J.); DNEN (Dupont-New England Nuclear, Wilmington, Del. 19805); Gelman (Gelman Sciences, Ann Arbor, Mich.); Eastman (Eastman Kodak, Rochester, N.Y.); Eastman TLC Plates (#13181 TLC plates with fluorescent indicator, Eastman); EM (EM Science, Cherry Hill, N.J.); Lawrence (Lawrence Berkeley Laboratory, Berkeley, Calif.); Mallinckrodt (Mallinckrodt, St. Louis, Mo.); Pierce (Pierce Chemical Co., Rockford, Ill.); Polycast (Polycast Technology Corp., Stamford, Conn.); Rohm and Haas (Rohm and Hass Co., Los Angeles, Calif.); Sigma (Sigma Chemical Co., St. Louis, Mo.); Spectrum (Spectrum Medical Industries, Los Angeles, Calif.).

To better characterize the devices of the present invention, a customized light instrument (hereinafter referred to as "the PTI device") was constructed from commerically available parts (at a cost of approximately $10,000 00) to serve as a control. The device is a modified version of a described device. G. D. Cimino et al., Biochemistry 25, 3013 (1986). Some machining was necessary to retrofit some of the commercial parts and to make specialized adapters and holders.

A 500 watt Hg/Xe arc lamp (Model A5000, Photon Technology International) positioned at the focal point of an elliptical mirror in a commercial lamp housing provides the light for the PTI device. The output from the lamp housing passes into an adaptor tube which provides physical support for additional optical accessories and prevents harmful stray UV radiation from emanating into the lab. A mirror deflects the optical beam in the adaptor tube so that it passes through the other optical components.

Two water-cooled, liquid filters are used. These filters have been selected to provide wavelengths of electromagnetic radiation that are appropriate for furocoumarin photochemistry. (Other photoreactive compounds may have wavelength requirements which are quite different from the furocoumarins.) The first filter is fitted with suprasil windows, filled with $H_2O$, and is used to filter out infrared radiation (IR). Exclusion of IR is required to prevent undesired heating of the sample chamber during irradiation, since addition of furocoumarins to nucleic acid is reduced at elevated temperatures. The second liquid filter provides a window of 320-400 nm light for use with furocoumarin photochemical reactions. This particular wavelength window (320-400 nm) excludes both shorter and longer wavelengths which are inappropriate for furocoumarin photochemistry. For example, furocoumarin:nucleic acid complexes undergo photochemical reversal at wavelengths below 313 nm. Exclusion of these wavelengths is necessary for irreversible photobinding of the furocoumarins to occur. This filter (9 cm in length) is fitted with 0.6 cm pyrex windows and filled with an aqueous solution of 0.85% cobaltous nitrate, 2% sodium chloride. An optical diffuser between the the first filter and the second filter provides even illumination over the entire width of the light beam. This diffuser consists of a ground suprasil plate (0.6 cm) fitted into a lens holder.

Light exiting from the first filter passes through an iris so that beam intensity can be controlled. Two lenses focus the beam within the sample holder by first passing the beam through a shutter system, then through the exit of the adaptor tube and finally across a second mirror. The shutter system consists of a rotary solenoid attached to a metal blade which passes between the exit hole of the adaptor tube and a similar hole in a second aluminum plate. This second plate resides adjacent to the exit port of the adaptor tube and also serves as a mount for the solenoid. The power to the solenoid is controlled by a relay which is run off a timer. The sample holder is composed of rectangular brass and can be irradiated either through the side or from the top. It has been machined with passages for the flow of liquids. Thermoregulation of a sample is achieved by connecting this holder to a thermoregulated circulating water bath. The sample holder also contains passages that allow the flow of gasses over the surfaces of the sample vessels (i.e. cuvette faces, etc.) to prevent condensation of water on these surfaces while irradiating at low temperatures. The orifice for the sample vessel in the sample holder is 1 inch by 1 inch by 2.5 inches. A brass adaptor, with slots for the passage of light, permits standard cuvettes to be used, as well as 13 mm test tubes and Eppendorf tubes. The base of the sample holder is hollow so that a bar magnet attached to a small motor can be inserted beneath the sample vessel and function as a magnetic stirrer. Alternatively, the holder can be placed on top of a laboratory stir plate to achieve stirring capabilities. With this irradiation device, the light beam is approximately 0.8 cm diameter at the focal point and it has an intensity of 340 mW/cm², as measured with a Model J-221 UV meter (UV Products, San Gabriel, Calif.).

The PTI device allows for comparisons of the performance characteristics of the devices of the present invention against the performance characteristics of the more expensive PTI device. The performance characteristics examined in some of the examples below include: A) Thermal Stability, B) Spectral Output, C) Irradiation Intensity, D) Irradiation Uniformity, and E) Photoactivation Efficiency.

Unless otherwise noted, all sample solutions prepared for irradiation were contained in Eppendorph tubes and irradiated through the sides of the tubes (CE-I, CE-II and CE-III) or through the top of the tubes (PTI). Eppendorph tubes have a transmittance I0 of only 8 to 15% for wavelengths in the range of 300 nm to 400 nm (data not shown). Therefore, approximately 90% of the actinic light is lost by the use of these sample vessels. Although Eppendorph tubes are the most convenient sample vessels for biochemical and molecular biological procedures, other types of irradiation vessels having better transmission characteristics are comtemplated (e.g. quartz, pyrex, polycarbonate etc.)

Concentrations for photoproduct are given in terms of the amount of unirradiated starting material, where subsequent irradiation is performed in the absence of nucleic acid. For example, if 50 µg/ml of unirradiated starting material is subsequently irradiated in the absence of DNA, the concentration of resulting photoproduct is given as 50 µg/ml.

The starting compound (unirradiated compound) for photoproduct is sometimes indicated when photoproduct is referred to. For example, the photoproduct produced following irradiation of AMDMIP is referred to as AMDMIP photoproduct.

Where polyacrylamide gel electrophoresis (PAGE) is used, denaturing (7 or 8M urea) polyacrylamide gels (28 cm × 35 cm × 0.4mm) were poured and pre-electrophoresed for 30 to 60 minutes at 2000 Volts, 50 Watts, 25 milliamps. 12% gels were used for oligonucleotides between 40 and 200 base pairs in length; 8% gels were used for longer sequences. Depending on the length of DNA to be analyzed, samples were loaded in either 8M urea, containing 0.025% tracking dyes (bromphenol blue and xylene cyanol), or in 80% formamide, 10% glycerol, 0.025% tracking dyes, then electrophoresed for 2-4 hours at 2000 Volts, 50 Watts, 25 milliamps. Following PAGE, individual bands were, in most cases, visualized by autoradiography. Autoradiography involved exposure overnight at −70° C. to Kodak XAR-5 films with an intensifying screen. In some cases, the visualized bands were cut from the gel and collected for scintillation counting. Scintillation counting involved the use of a scintillation fluid and a commercial scintillation counter (Searle Analytic 92, Model #000 006893).

Generally, PCR was carried out using 175-200 µM dNTPs (deoxyribonucleoside 5'-triphosphates) and 0.5 to 1.0 µM primers. 5 Units/ 100 µl of Taq polymerase was used. PCR reactions were overlaid with 30-100 µl light mineral oil. A typical PCR cycle for HIV amplification using a Perkin-Elmer Cetus DNA Thermal Cycler (Part No. N8010150) was: denaturation at 93° C. for 30 seconds; annealing at 55° C. for 30 seconds; and extension at 72° C. for 1 minute. PCR cycles were normally carried out in this manner for 30 cycles followed by 7 minutes at 72° C.

In many cases, PCR was carried out on an HIV system. This system provides a 115-mer product designated HRI 46:
5'-ATAATCCACCTATCCCAGTAG-
GAGAAATTTATAAAAGATGGATAATCCT
GGGATTAAATAAAATAGTAAGAATG-
TATAGCCCTACCAGCATTCTGGACATAA
GACAAGGACCAAA -3'
and its complement, designated HRI 47:
3'-TATTAGGTGGATAGGGTCATCCTCTT-
TAAATATTTTCTACCTATTAGGA

CCCTAATTTATTTTATCATTCT-
TACATATCGGGATGGTCGTAAGACCT-
GTATT CTGTTCCTGGTTT-5'.

These sequences were used by C. Y. Ou et al., Science 39:295 (1988).

In many of the examples below, compounds are referred to by their abbreviation (see Tables 2 and 3) and/or number (see FIGS. 1 and 2). For example, "(MIP,3)" indicates the compound is 5-Methylisopsoralen (Table 2) and compound 3 in FIG. 1.

EXAMPLE 1

Synthesis of 5-Methylisopsoralen (MIP,3)

Method 1 (three steps)

Step 1: 5-methylresorcinol monohydrate (284 gm, 2.0 mol; Aldrich) was thoroughly mixed with malic acid (280 gm, 2.10 mol; Aldrich) and then placed in a reaction flask containing sulfuric acid (600 ml) and a trace of sodium bisulfite (1.0 gm; Aldrich). The reaction mixture was heated to 90° C. while being mechanically stirred until evolution of carbon dioxide subsided (about 5 hours). The resulting reddish-orange solution was poured into sufficient ice (with vigorous stirring) to make up 1 liter. The receiving flask was maintained at 0° C. by external cooling until the addition of the reaction mixture was complete. The resulting light-orange product that precipitated was collected by suction filtration then washed thoroughly with water. The crude product was air dried on the filter; then recrystallized twice from tetramethylene glycol (1800 ml) to give pure 7-hydroxy-5-methylcoumarin (H5MC,1) as product (220 gm, 62% yield; mp 252°-255° C.).

Step 2: H5MC (177 gm, 1.0 mol), bromoacetaldehyde diethylacetal (207 gm, 1.05 mol, Aldrich), potassium carbonate (100 gm) and freshly distilled dimethylformamide (125 ml) were mixed in a 3 neck reaction flask fitted with a mechanical stirrer and argon line. The reaction was heated and stirred at 100° C. for 43 hours after which all the starting material had been converted to a high Rf TLC spot (Eastman TLC Plates; developed with C/M 98:2; detection with 260 nm ultraviolet light). Unreacted acetal and solvent were removed by distillation under reduced pressure. Water (1500 ml) was added to the residue followed by extraction with chloroform (1000 ml). The chloroform was then repeatedly washed with 1N sodium hydroxide until colorless. Evaporation of the solvent gave the product, the diethoxyethyl ether of 7-hydroxy-5-methylcoumarin (DEMC,2) as an oil (217 gm; 82.4% yield).

Step 3: Glacial acetic acid (310 ml) and zinc chloride (98 gm, 0.72 mol) were placed in a flask fitted with an internal thermometer then heated to between 100° and 114° C. DEMC (50 gm, 0.17 mol) was added to the hot solution and stirred vigorously at temperature for 17 minutes. The hot solution was then poured onto a mixture of ice (1000 ml) and CHCl₃ (500 ml) with vigorous stirring, which was continued until all the ice had dissolved. The CHCl₃ layer was then separated (emulsion) followed by repeated washing with water (500 ml portions). Washing was continued until the pH of the water was neutral. Finally, the CHCl₃ layer was washed with saturated NaCl (500 ml), dried (MgSO₄), and the solvent removed by distillation. The crude dark product (7.7 gm) (mixture of 5-methylisopsoralen and 5-methylpsoralen) was dissolved in a small volume of chloroform, washed with 1N NaOH (to remove phenols), washed with water then brine, then chromatographed on a flash column (EM silica gel, 200-400 mesh), eluting with ethyl acetate/hexanes 70:30 to give the pure product, 5-methylisopsoralen (MIP) (4.7 gm, 13.8%; mp 189.5°-191.5° C.). NMR (CDCl₃) d 2.59 (3 H, s), 6.37 (1 H, d), 7.05 (1 H, d), 7.23 (1 H, s), 7.59 (1 H, d), 7.96 (1 H, d).

EXAMPLE 2

Synthesis of MIP

Method 2 (two steps)

Step 1: H5MC was made from 5-methylresorcinol hydrate as described in Step 1 of Method 1 (Example 1).

Step 2 H5MC (1.76 gm, 10 mmol) and chloroethylene carbonate (6.13 gm, 50 mmol, Aldrich) were heated between 150°-165° C. for 1.5 hours. Following this period, the dark reaction mixture was poured onto ice. This was extracted with chloroform, the chloroform washed with base (0.5N NaOH), water and then dried (Na₂SO₄). Removal of the solvent under reduced pressure gave a brownish syrup (0.7 gm), from which pure product, MIP, was isolated by flash chromatography (EM silica gel, 200-400 mesh), eluted with C/M 98:2. The yield of MIP by this second method was 270 mg (13.5%).

EXAMPLE 3

Radiolabelled MIP Synthesis

Step 1: MIP (58 mg; 0.29 mmol), 10% palladium on charcoal (29 mg, Aldrich), and glacial acetic acid (7.0 ml) were placed in a small round bottom flask, attached to a vacuum line, frozen with liquid nitrogen, and then the reaction vessel was evacuated. Carrier free tritium gas (Lawrence; 60 Ci/mmol) was added to slightly below 1 atmosphere, and the round bottomed flask was warmed briefly in a 60° C. water bath to redissolve the MIP. The heterogeneous mixture was stirred at room temperature for 1 hour after which approximately 0.31 mmol tritium gas had been consumed. The mixture was frozen, the tritium gas evacuated, methanol (10 ml) added, and the slurry centrifuged to remove the catalyst. The supernatant was decanted, frozen and then lyophilized. Following lyophilization, TLC (chroloform) of the residue revealed unreacted strting material, a low Rf blue fluorescent spot corresponding to [4',5'-³H₂]-4'5'-dihydro-5-MIP and a high Rf nonfluorescent spot corresponding to [3,4,4',5'-³H₄-3,4,4',5'-tetrahydro-5-MIP. [4',5'-³H₂]-4'5'-dihydro-5-MIP was isolated by column chromatography on a 0.5×8-inch silica column (60-200 mesh, Baker) eluted with CH₂Cl₂. The recovery was 30-40 mg. This compound was used in Step 2 directly for the preparation of labelled MIP.

Step 2: [4',5'-³H₂]-4'5'-dihydro-5-MIP of Step 1(30-40 mg), 10% palladium on charcoal (32 mg, Aldrich) and diphenylether (5.0 ml, Aldrich) were placed in a small round bottom flask with attached argon line then refluxed for 28 hours. Following this period, TLC (CH₂Cl₂) indicated that most of the starting material had been converted to [4',5'-³H₂]-5-MIP (as determined by co-chromatography with authentic MIP). The product was purified by chromatogrphy on 2 silica columns (60-200 mesh, Baker, eluted with CH₂Cl₂). The fractions containing the purified product were combined, the solvent evaporated under reduced pressure, and the residue dissolved in absolute ethanol.

The specific activity of the compound was established by measuring the optical density of the stock solution to determine its concentration, then counting appropriate aliquots of the stock. In this manner, the specific activity of tritiated [4',5'-$^3$H$_2$]-5-MIP ("tritiated MIP") product was determined to be 7.4 Ci/mmol.

The radiochemical purity was determined by HPLC. Approximately 10$^6$ CPM of tritiated MIP was mixed with 10 ug unlabelled MIP in 50 ul of ethanol (100%). The sample was injected on a C18 octadecasilyl reverse phase chromatography column (Beckman) and eluted with a water/methanol gradient as follows: 0-10 minutes, 100% H$_2$O; 10-70 minutes, 100% H$_2$O-100% CH$_3$OH; 70-80 minutes, 100% CH$_3$OH. Eighty 1.0 ml fractions were collected and 40 ul of each fraction counted. Greater than 99% of the radioactivity co-chromatographed with the optical peak corresponding to tritiated MIP.

EXAMPLE 4

Halomethylisopsoralen Synthesis

This example involves the synthesis of a halomethylisopsoralen, in this case 5-bromomethylisopsoralen (BMIP,5) from MIP. MIP (1.80 gm, 9 mmol) was dissolved CCl$_4$ (193 ml) at reflux. N-bromosuccinimide (1 65 gm, 9 mmol, Aldrich) and dibenzoylperoxide (0.22 gm, 0.9 mmol, Aldrich) were added to the boiling solution and the mixture refluxed for four hours while being monitored by TLC (Eastman TLC Plates; developed with C/M 98:2; detection with 260 nm ultraviolet light). Following this period, the boiling mixture was filtered hot and the filtrate set aside to cool then held at 0° C. for 24 hrs. The resulting crystals (light yellow needles) were collected by filtration, dissolved in CHCl$_3$ (140 ml) then washed with water (140 ml×4). The CHCl$_3$ solution was dried (anhydrous MgSO$_4$) then concentrated by rotary evaporation under reduced pressure to provide the product, BMIP, as yellow crystals (1.75 gm, 68.7%, m.p. 201°-204° C. with decomposition). NMR (CDCl3) d 8.06 (d, H-4), 7.64 (d, H-5'), 7.41 (s, H-6), 7.05 (m, H-4'), 6.43 (d, H-3), 4.72 (s, CH$_2$Br).

EXAMPLE 5

Synthesis of 5-Aminomethylisopsoralen (AMIP, 10)

Method 1 (four steps)

Step 1: The first step of the first method of the present invention for synthesizing AMIP from XMIP involves the synthesis of 5-Hydroxymethylisopsoralen (HMIP,6). XMIP is chosen to be BMIP for purposes of this step.

BMIP (0.2 gms, 0.71 mmol) was refluxed in distilled water (20 ml) while being monitored by TLC (Eastman TLC Plates; developed with C/M 98:2, detection with 260 nm ultraviolet light). After 3 hours, no starting material remained and a new low Rf spot had appeared. Upon cooling of the reaction mixture, the product, HMIP, precipitated as very light yellow needles and was collected by suction filtration (0.15 gms; 96.8%; m.p. 184°-187° C.).

Step 2: The second step of the first method of the present invention for synthesis of AMIP involves synthesis of XMIP from HMIP. XMIP is chosen to be 5-chloromethylisopsoralen (CMIP,5) for purposes of this step.

HMIP (858 mg, 4.0 mmol; obtained from combining numerous runs of Step 1) is dissolved in freshly distilled chloroform (60 ml, dried over 4A molecular sieves). Thionyl chloride (1.49 gm, 12.6 mmol, Aldrich) is added followed by stirring at room temperature. Additional portions of thionyl chloride are added after 1 hour (990 mg, 8.4 mmole) and 16 hr (990 mg, 8.4 mmol). After a total of 25 hr, no starting material remains (TLC, CH$_2$Cl$_2$) and a new high Rf spot appears. The new spot co-chromatographs on TLC with authentic CMIP using several different solvent systems (CH$_2$Cl$_2$; CHCl$_3$; EtOAc:Hexanes 1:3).

Step 3: The third step of the first method of the present invention for synthesizing AMIP involves the synthesis of 5-hexamethylenetetraminomethylisopsoralen (HMTAMIP,9) from XMIP (in this case, CMIP).

The product of Step 2, CMIP, is brought up in 30 ml sieve dried chloroform and hexamethylenetetramine (680 mg, 4.9 mmol) is added. The mixture is stirred at 55° C. for 43 hours, after which an additional portion of hexamethylenetetramine (680 mg, 4.9 mmol) is added. The mixture continues to be stirred at 55° C. for another 48 hours, after which HCl (0.1N, 60 ml) and chloroform (30 ml) are added. The chloroform is then removed and the aqueous phase washed three more times with chloroform (30 ml). The aqueous phase is evaporated under reduced pressure to yield the solid product, HMTAMIP. The product is characterized by TLC, co-chromatographing on TLC with authentic HMTAMIP in several different solvent systems (C/M 98:2; C/M 95:5; C/M 90:10).

Step 4: The next step involves the synthesis of AMIP from HMTAMIP. The solid of Step 3 was suspended in 12 ml ethanol:concentrated HCl (3:1) at room temperature for 72 hours and then concentrated in vacuo. The residue was added to dilute NaOH, extracted with CHCl$_3$ and washed with water. The CHCl$_3$ extract was then further extracted with HCl (0.1N). The aqueous phase was then separated, adjusted to pH 12-13 with NaOH, and extracted with CHCl$_3$. The CHCl$_3$ extract was washed with water, dried (MgSO$_4$) and the solvent removed under reduced pressure to provide the product as the free base, which was converted to the hydrochloride salt with HCl gas (310 mg, 31% yield, based on HMIP). Mass spectrum m/e (relative intensity) 215 (M+, 100%).

EXAMPLE 6

Synthesis of AMIP: Method 2 (five steps)

Step 1: The first step of the second method, synthesis of HMIP from XMIP, is identical to the first step of the first method, since XMIP has been chosen to be BMIP in both cases. The first step proceeds, therefore, according to Step 1 of EXAMPLE 5.

Step 2: The second step of the second method of the present invention for synthesis of AMIP, synthesis of XMIP from HMIP, is the same as the second step of the first method since XMIP has been chosen to be CMIP in both examples. Thus, the second step proceeds as in Step 2 of EXAMPLE 5.

Step 3: The third step of the second method of the present invention for synthesizing AMIP involves the synthesis of 5-iodomethylisopsoralen (IMIP,8) from XMIP (in this case CMIP).

CMIP (577 mg; 2.25 mmol), sodium iodide (1.77 gm, 11.53 mmol; Baker; dried overnight at 120° C.) and acetone (25 ml, Mallinckrodt) are refluxed for 48 hours. Following this period, the reaction mixture is filtered to remove the inorganic salts (mixed NaCl and NaI), the filtrate evaporated under reduced pressure, the residual crude product dissolved in chloroform, loaded on a ½"×20" silica gel column (60-200 mesh, Baker), and eluted with the same solvent. The fractions containing the product, IMIP, are identified by TLC, combined, and the solvent removed under reduced pressure (489 mg; 66.7%).

Step 4: The next step involves the synthesis of HMTAMIP from IMIP. IMIP (489 mg; 1.5 mmol) and hexamethylenetetramine (360 mg; 2.6 mmol) are refluxed in dry CHCl₃ until all the starting IMIP is consumed, as shown by TLC. The resulting precipitate is collected by suction filtration, suspended in dilute acid (0.1N HCl), washed several times with an equivalent volume of CHCl₃, then recovered from the aqueous phase by evaporation. The product, HMTAMIP, is characterized by comparative TLC in several different solvent systems (C/M 98:2; C/M 95:5; C/M 90:10).

Step 5: The final step of this second method involves the synthesis of AMIP from HMTAMIP. This was carried out in the manner described in Step 4 of EXAMPLE 5.

EXAMPLE 7

Synthesis of AMIP: Method 3 (two steps)

In the two step method, XMIP may again be CMIP or BMIP. For this example, the two step method proceeds according to the following scheme:

BMIP→HMTAMIP→AMIP

Step 1: The first step of the second method of the present invention for synthesizing AMIP involves the synthesis of HMTAMIP from XMIP (in this case, BMIP).

BMIP (540 mg, 2.5 mmol) and hexamethylenetetramine (610 mg, 4.4 mmol) were refluxed in dry CHCl₃ for 40 hours. The resulting precipitate was collected by suction filtration and used directly for Step 2.

Step 2: The next step involves the synthesis of AMIP from HMTAMIP. The solid of Step 1 was suspended in 12 ml ethanol:concentrated HCl (3:1) at room temperature for 72 hours and then concentrated in vacuo. The step then proceeds as in Step 4 of Example 5.

EXAMPLE 8

Radiolabelled AMIP Synthesis

As noted above, the present invention provides twelve methods for producing radiolabelled AMIP from MIP. Where the method relies on tritiated MIP, the method proceeds initially according to the steps of EXAMPLE 3 to make tritiated MIP, and then continues according to the steps of EXAMPLE 7. In this example, however, tritiated MIP is not used. For this example, the method proceeds according to the following scheme (nine steps):

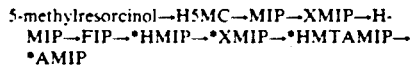

5-methylresorcinol→H5MC→MIP→XMIP→H-MIP→FIP→*HMIP→*XMIP→*HMTAMIP→*AMIP where * indicates a labelled compound.

Steps 1-2: MIP was synthesized via H5MC from 5-methylresorcinol according to the two step method described in EXAMPLE 2, above.

Step 3: For this example, the first XMIP was chosen to be BMIP (later, XMIP is radiolabelled CMIP; see reactions of Step 7 below). BMIP was synthesized from MIP according to the method described in EXAMPLE 4, above.

Step 4: HMIP was synthesized from BMIP according to the method described in Step 1 of method 1 of EXAMPLE 5.

Step 5: New compound 5-Formylisopsoralen (FIP,7) was synthesized from HMIP. 3,5-Dimethylpyrazole (180 mg; 1.9 mmol; Aldrich) was added to a suspension of chromium trioxide (Aldrich; 190 mg; 1.9 mmol) in methylene chloride (6 ml) and the mixture stirred for 15 minutes under argon at room temperature. HMIP from Step 4 (150 mg; 0.69 mmol) was added in one portion and the reaction mixture stirred at room temperature for 2.5 hours, after which TLC (CHCl₃) indicated the reaction was complete. The solvent was removed under reduced pressure and the residue dissolved in a small volume of CHCl₃, loaded on a silica gel column (Baker; 60-200 mesh) and then eluted with CHCl₃. The fractions containing product were combined and the solvent removed to provide the aldehyde (120 mg; 81% yield). Further purification was accomplished by recrystallization from 95% EtOH giving yellow needles.

Step 6: Tritiated HMIP was synthesized from FIP. FIP (71 mg; 0.35 mmol) from Step 5 and ³H₄-sodium borohydride (DNEN; 1.8 mg; 0.0476 mmol) were mixed in 95% ethanol (10 ml) then stirred at room temperature for one hour. After this period, TLC showed all the formyl compound had been reduced to 5-(hydroxy-[³H]-methyl)isopsoralen ("³H-HMIP"). The solvent was removed under reduced pressure, methanol added (10 ml) and then evaporated. This was repeated a total of four times. The residual solid was then dissolved in 3 ml C/M (99:1) and loaded on a 1 cm×30 cm silica gel column (Baker; 60-200 mesh) then eluted with the same solvent mix. The product fractions were combined and the solvent evaporated to provide the labelled alcohol, ³H-HMIP (yield not determined).

Step 7: The ³H-HMIP of Step 6 was used directly for conversion to the chloromethyl derivative, 5-(chloro-[³H]-methyl)isopsoralen ("³H-CMIP"). ³H-HMIP from Step 6 was dissolved in 10 ml chloroform (dried over 4A molecular sieves), then thionyl chloride (248 mg; 2.1 mmol; Aldrich) was added. The reaction mix was stirred under argon at room temperature. Another 165 mg (1.4 mmol) portion of thionyl chloride was added after one hour. This was left stirring for another 16 hours at which point a third portion of thionyl chloride (165 mg; 1.4 mmol) was added. The reaction was evaporated under reduced pressure after another five hours to give the product, ³H-CMIP (yield not determined).

Step 8: The product of Step 7 was brought up in 5 ml chloroform (sieve dried) and hexamethylene tetramine (85 mg; 0.61 mmol; Aldrich) was added. This was stirred at 55° C. for 43 hours, at which point another portion of hexamethylene tetramine (95 mg; 0.68 mmol) was added. Heating was continued for another 48 hours, after which HCl (0.1N; 10 ml) chloroform (5 ml) were added. The chloroform was removed and the aqueous washed three more times with chloroform (5 ml). The aqueous phase was then evaporated under reduced pressure and the solid product, 5-(Hexamethyltetramino-[³H]-methyl)isopsoralen ("³H-HMTAMIP"), was brought up in 12 ml ethanol:concentrated HCl (3:1) for the next reaction.

Step 9: ³H-HMTAMIP from Step 8 was stirred at room temperature in the ethanol:HCl mixture. An additional 2 ml of concentrated HCl was added and the mixture stirred at 40° C. for 15 hours. Following this period, the pH was adjusted to 7 with NaOH and the solution evaporated under reduced pressure. The solid was brought up in 10 ml of 0.1M NaOH and extracted three times with chloroform (5 ml). The chloroform washes were combined and washed twice with water (10 ml). The chloroform was then extracted with HCl (0.1N; 10 ml) and the acidic aqueous phase then was washed three times with chloroform (5 ml). The aqueous was evaporated under reduced pressure and the solid dissolved in ethanol (10 ml). Aliquots of this solution were removed and counted, while the concentration of the stock was determined by UV absorption. The product, 5-(Aminomethyl-[$^3$H]-methyl)isopsoralen ("$^3$H-AMIP"), was determined to be 347 ug/ml and the specific activity $3.1 \times 10^5$ CPM/ug (117 Ci/mol). Overall recovery was 1.6 mCi, 3.47 mg, 0.14 mmol (72% yield based on $^3$H$_4$-NaBH$_4$).

EXAMPLE 9

BIOMIP Synthesis

The BIOMIP synthesis method for the following example proceeds according to the scheme:

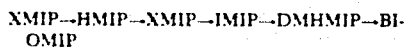

Again, XMIP can be either CMIP or BMIP. For this example, XMIP is CMIP and BMIP, respectively.

Step 1: MIP is reacted to form XMIP. In this step, XMIP is CMIP. MIP (1.80 gm, 9 mmol) is dissolved in CCl$_4$ at reflux. N-chlorosuccinimide (1.20 gm, 9 mmol, Aldrich) and dibenzoylperoxide (0.22 gm, 0.9 mmol, Aldrich) are added and the mixture boiled until no starting material remains (as determined by TLC). Following this period, the boiling mixture is filtered (hot) and the filtrate set aside at 0° C. The resulting precipitate is collected by suction filtration, dissolved in CHCl$_3$, washed with water, dried (anhydrous MgSO$_4$) and concentrated by rotary evaporation under reduced pressure to provide the product, CMIP.

Step 2: HMIP is then synthesized from XMIP (in this case, CMIP). CMIP (233 mg, 1.0 mmol) is refluxed in distilled water (50 ml) while being monitored by TLC (Eastman TLC Plates; developed with chloroform, detection with 260 nm ultraviolet light). After 2 hours, no starting material remains and a new low Rf spot appears. Upon cooling of the reaction mixture, the product, HMIP, precipitates as white needles and is collected by suction filtration.

Step 3: XMIP is then synthesized from HMIP. In this case, XMIP is BMIP. HMIP (270 mg; 1.25 mmol) is dissolved in freshly distilled chloroform (20 ml, dried over 4A molecular sieves). Thionyl bromide (384 mg; 3.0 mmol; Aldrich) is added followed by stirring at room temperature. Additional portions of thionyl bromide are added after 1.5 hours (126 mg, 1.0 mmol) and 3.0 hours (126 mg; 1.0 mmol). After a total of 6.5 hours, no starting material remains (Eastman TLC Plates; CH$_2$Cl$_2$) and a new high Rf spot appears. The solvent is removed under reduced pressure and the residue dissolved in a small volume of CH$_2$Cl$_2$, loaded on a ¼"×20" silica gel column (Baker, 60-200 mesh), and eluted with the same solvent. The fractions containing the product are identified by TLC, combined, and the solvent removed under reduced pressure.

Step 4: IMIP is then synthesized from BMIP via the Finkelstein reaction. In a small round-bottomed flask fitted with a reflux condenser and argon line, a mixture of BMIP (279 mg; 1 0 mmol), sodium iodide (767 mg; 5.15 mmol; Baker; dried overnight at 120° C.) and methyl ethyl ketone (10 ml, Mallinckrodt) are refluxed for 48 hours. Following this period, the reaction mixture is filtered to remove the inorganic salts (mixed NaI and NaBr), the filtrate evaporated under reduced pressure, the residual crude product dissolved in chloroform, loaded on a ¼"×20" silica gel column (60-200 mesh, Baker), and eluted with the same solvent. The fractions containing the product, IMIP, are identified by TLC, combined, and the solvent removed under reduced pressure.

Step 6: 5-N-(N,N'-Dimethyl-1,6-hexanediamine)-methylisopsoralen (DMHMIP,11) is then synthesized from IMIP. IMIP (935 mg; 2.85 mmol; obtained from combining product from numerous runs of Step 5) and freshly distilled N,N'-dimethyl-1,6-hexanediamine (4.1 gm; 28.5 mmol; Aldrich) are refluxed in dry toluene (45 ml) under argon while being monitored by TLC. After a short period no starting material remains and a new, low Rf spot appears. The solvent is removed under reduced pressure and the solid residue dissolved in HCl (1.0N; 60 ml), washed with chloroform (3×25 ml), the acidic aqueous phase made basic with 1.0N NaOH (pH 12), the basic aqueous phase extracted with chloroform (3×50 ml), the chloroform extract washed with water (2×40 ml), saturated sodium chloride (1×40 ml) and finally dried (MgSO$_4$). The solvent is removed under reduced pressure, the residue dissolved in a small volume of C/E/T (9:1:0.25), loaded on a 0.5"×12" silica gel column (60-200 mesh, Baker) and eluted with C/E/T. The fractions containing the pure product, DMHMIP, are identified by TLC, combined and evaporated to provide the product.

Step 7: 5-N-[N,N'-Dimethyl-(6-[biotinamido]-hexanoate)-1,6-hexanediamine])methylisopsoralen (BIOMIP,12a) was made from DMHMIP. DMHMIP (630 mg; 1.8 mmol), biotin-amidocaproate N-hydroxysuccinimide ester (Pierce; 100 mg; 0.22 mol), and DMF (2.7 ml, freshly distilled onto 4A sieves) were placed in a 10 ml round bottomed flask with attached argon line. The reaction was magnetically stirred at room temperature while being monitored by TLC (C/E/T; 9:1:0.25; the product ran as a high Rf spot relative to starting material). After the reaction was complete, the solvent was removed under vacuum and the residue dissolved in a small volume of CH$_2$Cl$_2$:CH$_3$OH (10:1), loaded on a silica gel column (60-200 mesh; 0.5"×20"), and eluted with the same solvent. The product was isolated, the elution solvent removed, and the free amine dissolved in 10 ml ethanol. HCl gas was bubbled through the solution, followed by argon. The ethanol was removed to give the product, BIOMIP (HCl salt) (190 mg; 14.7% yield; FABMS m/e 682 (MH+, 25%)).

EXAMPLE 10

BIOMIP Synthesis

The synthesis method for the following example proceeds according to the scheme:

In this example, XMIP is BMIP.

Step 1: BMIP (400 mg; 1.43 mmol), freshly distilled N,N'-dimethyl-1,6-hexanediamine (3.1 gm; 21.5 mmol; Aldrich) was refluxed in dry toluene (45 ml) under argon while being monitored by TLC. After 1.5 hours, no starting material remained and a new, low Rf spot appeared. The solvent was removed under reduced pressure and the solid residue dissolved in 1.0N HCl (60 ml), washed with chloroform (3×25 ml), the acidic aqueous phase made basic with 1.0N NaOH (pH 12), the basic aqueous phase extracted with chloroform (3×50 ml), the chloroform extract washed with water (2×40 ml), saturated sodium chloride (1×40 ml) and finally dried (MgSO₄). The solvent was removed under reduced pressure, the residue dissolved in a small volume of C/E/T (9:1:0.25), loaded on a 0.5"×12" silica gel column (Baker, 60-200 mesh) then eluted with C/E/T. The fractions containing the pure product were identified by TLC, combined and evaporated to provide the product, DMHMIP, as a viscous oil which solidified upon standing (300 mg; 61% yield).

Step 2: BIOMIP (HCl salt) was then synthesized from DMHMIP as in Step 7 of Example 9.

EXAMPLE 11

Tritiated BIOMIP Synthesis

The present invention also provides methods for synthesizing labelled BIOMIP. One method involves radiolabelling BIOMIP according to the following scheme:

In this example, ³H-XMIP is ³H-CMIP.

Step 1: ³H-CMIP from Step 7 of Example 8 (24 mg, 0.1 mmol) and freshly distilled N, N'-dimethyl-1,6-hexanediamine (0.47 gm; 0.32 mmol) is refluxed in dry toluene (5 ml) under argon while being monitored by TLC. After several hours, no starting material remains and a new, low R$_f$ spot appears. The solvent is removed under reduced pressure and the solid residue dissolved in HCL (1 0N), extracted with chloroform, the acidic aqueous phase separated and made basic with NaOH (1.0N), the basic aqueous phase is extracted with chloroform, the chloroform extract washed with water, saturated sodium chloride then dried (MgSO₄). The solvent is removed under reduced pressure, the residue dissolved in a small volume of C/E/T 9:1:0.25, loaded on a 0.5"×4" silica gel column (60-200 mesh; Baker) and eluted with C/E/T. The fractions containing the pure product are identified by TLC, combined and evaporated to provide the product. The product is further characterized by UV and TLC (co-chromatography with authentic material in several different solvent systems). The 5-N-(N, N'-dimethyl-1, 6-hexanediamine)-[³H]-methylisopsoralen (³H-DMHMIP) so prepared is used directly in Step 2 for the preparation of [³H]-BIOMIP (and other compounds).

Step 2: ³H-DMHMIP (17.5 mg; 0.05 mmol), biotinamidocaproate N-hydroxysuccinimide ester (25 mg; 0.055 mmole; Pierce), and DMF (1.8 ml, freshly distilled onto 4A sieves) are placed in a 5 ml round bottomed flask with attached argon line. The reaction is magnetically stirred at room temperature while being monitored by TLC (C/E/T; 9:1:0.25; the product runs as a high Rf spot relative to starting material). After the reaction is complete, the solvent is removed under vacuum and the residue dissolved in a small volume of CH₂Cl₂:CH₃OH 10:1, loaded on a silica gel column (60-200 mesh, 0.5"×5"), and eluted with the same solvent. The product is isolated as the free base, the elution solvent removed, then dissolved in absolute ethanol. HCl gas is bubbled through the solution, followed by argon. The ethanol is removed to give 5-N-[N, N'-dimethyl-N'-{6-biotinamido}-hexanoate)-1,6-hexanediamine]-³H]-methylisopsoralen (³H-BIOMIP) as the monohydrochloride salt.

EXAMPLE 12

DITHIOMIP Synthesis

The present invention provides methods for synthesizing DITHIOMIP. For this example, the synthesis proceeds according to the following scheme:

XMIP→DMHMIP→DITHIOMIP where XMIP is BMIP.

Step 1: DMHMIP is synthesized from BMIP according to the method described in Step 1 of EXAMPLE 10.

Step 2: DMHMIP from Step 1 (41 mg; 1.20 mmol, 1.0 eq) and sulfosuccinimidyl-2-(biotinamido)-ethyl-1,3-dithiopropionate (102 mg; 0.168 mmol; 1.40 eq) is dissolved in freshly distilled DMF (3.0 ml) in a small, dry round bottomed flask with attached argon line then stirred at room temperature for 5 hours. After this period, the DMF is removed under reduced pressure and the residue suspended in NaOH (1.0N), extracted with chloroform/isopropanol 3:1, and the organic extract washed with water (10 ml×2) then dried (MgSO₄), filtered and evaporated under reduced pressure to give the crude product. This is dissolved in ethanol and HCl gas is bubbled through the solution. The ethanol is removed to give the product, 5-N-[N,N'-dimethyl-N'-(2-{biotinamido}-ethyl-1,3-dithiopropionate)-1,6-hexanediamine]-methyl-isopsoralen (DITHIOMIP,12b) (HCl salt). This is dissolved in ethanol and further characterized by sample treatment with sodium borohydride (Aldrich) or mercaptoethanol (Aldrich). The product of these reactions is compared to untreated material to verify cleavage occurred as expected.

EXAMPLE 13

³H-DITHIOMIP Synthesis

The present invention provides methods for synthesizing ³H-DITHIOMIP. For this example, the synthesis proceeds according to the following scheme:

In this example, ³H-XMIP is ³H-CMIP.

Step 1: ³H-DMHMIP is prepared as described in Step 1 of Example 11.

Step 2: ³H-DMHMIP (24 mg, 0.07 mmol, 1.0eq) and sulfosuccinimidyl-2-(biotinamido)-ethyl-1,3-dithiopropionate (60 mg; 0.10 mmol, 1.4 eq) is dissolved in freshly distilled DMF (1.5 ml) in a small, dry round bottomed flask with attached argon line then stirred at room temperature for 5 hr. After this period, the DMF is removed under reduced pressure and the residue suspended in 0.1N NaOH (5 ml), extracted with chloroform/isopropanol 3:1 (3×5 ml), and the organic extract washed with water (5 ml×2) then dried (MgSO₄), filtered and stripped to give the product, ³H-DITHIOMIP. The product is then characterized by ultraviolet absorption (comparison with authentic material) and TLC (co-chromatography with authentic material in several different solvent systems). Radiochemical purity is determined by HPLC. Approximately 10⁶ CPM of tritiated ³H-DITHIOMIP is mixed with 10 ug of unlabeled DITHIOMIP in 50 ul ethanol (100%). The sample is injected on a C18 octadecylsilyl reverse phase chromatography column (Beckman) and eluted with an acetonitrile/ammonium acetate (0.1M, pH 7) gradient, as follows: 0-10 minutes, 100% ammonium acetate; 10-70 minutes, 100% ammonium acetate→100% acetonitrile; 70-80 minutes, 100% acetonitrile. Eighty 1.0 ml fractions are collected and 40 ul of each fraction is then counted. The product is further characterized by dissolving a sample in ethanol and treating with either sodium borohydride (Aldrich) or mercaptoethanol (Aldrich). The product of these reactions is compared to untreated material to verify cleavage occurs as expected.

EXAMPLE 14

FLUORMIP Synthesis

The present invention also contemplates methods for synthesizing FLUORMIP. For this example, the synthesis proceeds according to the following scheme:

where XMIP is BMIP.

Step 1: DMHMIP is synthesized from BMIP according to the method described in Step 1 of EXAMPLE 10.

Step 2: DMHMIP from Step 1 (13.7 mg, 0.04 mmol, 1.0 eq) in DMF (Mallinckrodt; 1.0 ml distilled onto 4 Å sieves), and 6-carboxyfluorescein-N-hydroxysuccinimide ester (Pierce; 20.7 mg, 0.044 mmol, 1.1 eq) in DMF (1.0 ml) are mixed in a 5 ml round bottomed flask with attached argon line. The reaction mix is stirred several hours at room temperature. After this period, the majority of the DMHMIP is consumed as indicated by TLC (C/B/A/F; 4:1:1:1). The solvent is removed with gentle heating (<50°) under reduced pressure. The residue is dissolved in HCL (0.1N) and extracted with chloroform/isopropanol 3:1. The organic extract is then reduced in volume, loaded onto a glass backed preparative silica gel TLC plate (20 cm × 20 cm × 2 mm; Baker), and eluted with C/B/A/F. The major low Rf band is scraped from the plate, eluted with C/M (90:10), the silica removed by filtration and the solvent evaporated under reduced pressure. The product is dissolved in a small volume of ethanol and HCl gas bubbled through the solution. The ethanol is then evaporated to provide 5-N-[N,N'-dimethyl-N'-(carboxyfluoresceinester)-1,6-hexanediamine)-methylisopsoralen (FLUORMIP, 12c) as the monohydrochloride salt.

EXAMPLE 15

3H-FLUORMIP Synthesis

The present invention also contemplates methods for synthesizing 3H-FLUORMIP. For this example, the synthesis proceeds according to the following scheme:

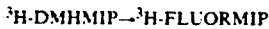

3H-DMHMIP from Step 1 of Example 11 (2.5 mg; 0.007 mmol; 117 Ci/mmol; 1.0 eq) in DMF (Mallinckrodt; 1.0 ml distilled onto 4 Å sieves) and 6-carboxyfluorescein-N-hydroxy-succinimide ester (3.7 mg; 0.008 mmol; 1.1 eq; Pierce) in DMF (1.0 ml) are mixed in a 5 ml round bottomed flask with attached argon line. The reaction mix is stirred several hours at room temperature. After this period, the majority of the 3H-DMHMIP is consumed as indicated by TLC (C/B/A/F; 4:1:1:1). The DMF is removed with gentle heating (<50°) under reduced pressure. The crude product is dissolved in HCL (0.1N; 3 ml) and extracted with chloroform/isopropanol 3:1 (3 ml×3). The organic extract is then reduced to 2 ml, loaded onto a glass backed preparative silica gel TLC plate (20 cm×20 cm×2 mm; Baker), and eluted with C/B/A/F. The major low Rf band is scraped from the plate and eluted with methanol. The silica is removed by filtration and the solvent evaporated under reduced pressure. The product is dissolved in a small volume of ethanol and HCl gas bubbled through the solution. The ethanol is then evaporated to provide 3H-FLUORMIP as the monohydrochloride salt. The product is characterized by ultraviolet absorption (comparison with authentic material) and TLC (co-chromatography with authentic meterial in several different solvent systems). The specific activity is determined by determining the optical density of an ethanolic stock of the compound and scintillation counting of aliquots of this solution (117 Ci/mmol). Radiochemical purity is determined by HPLC. Approximately $10^6$ CPM of 3H-FLUORMIP is mixed with 10 μg of unlabelled FLUORMIP in 50 μl ethanol (100%). The sample is injected on a C18 octadecasilyl reverse phase chromatography column (Beckman) and eluted with acetonitrile/ammonium acetate (0.1M; pH 7) gradient, as follows: 0-10 minutes, 100% ammonium acetate; 10-70 minutes, 100% ammonium acetate→100% acetonitrile; 70-80 minutes, 100% acetonitrile. Eighty 1.0 ml fractions are collected and 40 μl of each fraction is then counted.

EXAMPLE 16

DMIP Synthesis

This example describes the method of the present invention for synthesizing DMIP. From resorcinol, the method proceeds in four steps according to the following scheme:

Step 1: Resorcinol (110 gm; 1.0 mol, Aldrich) is mixed with ethylacetoacetate (130 gm, 1.0 mol, Aldrich) and placed in a dropping funnel. This mixture is added dropwise to a chilled (10° C.) solution of sulfuric acid (1000 ml) in a three necked flask fitted with a mechanical stirrer and internal thermometer. The rate of addition is such that the internal temperature does not exceed 10° C. The solution is stirred for 12 hours then slowly poured onto 2 kg of ice and 3 liters of water. Following vigorous stirring, the precipitate is collected by suction filtration, washed with water, dissolved in 5% aqueous NaOH (1500 ml), then reprecipitated by addition of dilute sulfuric acid (650 ml) with vigorous stirring. The product, 7-Hydroxy-4-methylcoumarin (H4MC,13), is collected by filtration, washed with water, then allowed to air dry (145 gm; 41% yield; mp 185° C.).

Step 2: H4MC (145 gm; 0.82 mol; Aldrich) was treated with 2,3-dichloro-1-propene (107.8 gm; 0.97 mol; Aldrich) in DMF (1178 ml; Mallinckrodt)/toluene (931 ml; Mallickrodt) in the presence of potassium carbonate (154 gm; 1.12 mol; Baker) and a catalytic amount of potassium iodide (7.1 gm; 0.05 mmol; Baker). The mixture was heated to 95° C. with stirring for 12 hour, after which TLC indicated no starting material remained. The solvent was removed under reduced pressure and the residual paste extracted with hot chloroform. The chloroform was washed with water, saturated NaCl, dried (MgSO$_4$) then the solvent removed under reduced pressure. The residual solid was dissolved in absolute ethanol at reflux (1200 ml) and set aside. The resulting crystals were collected by suction filtration, washed with cold ethanol and vacuum dried to provide 7-($\beta$-chloroallyloxy)-4-methylcoumarin (CAMC,14) (143.5 gm, 70% yield). NMR (CDCl3) d 7.5 (1H, d), 6.8-6.9 (2H, m), 6.2 (1H, d), 5.5-5.6 (2H, M), 4.2 (2H, m), 2.4 (3H,M).

Step 3: Rearrangement of CAMC was accomplished in high yield by refluxing the allyl ether from Step 2 (143.5 gm; 0.55 mole) in a mixture of p-diisopropylbenzene (Aldrich, 1000 ml) and butyric anhydride (96 ml, 92.8 gm; 0.59 mol, Aldrich) under argon for 18 hours. The cooled reaction mixture was diluted with chloroform, washed with water and then saturated sodium bicarbonate, dried (MgSO$_4$) then evaporated under reduced pressure. Following recrystallization from ethanol, 79.9 grams of mixed 6 and 8-($\beta$-chloroallyl)-7-butyroxy-4-methylcoumarin (BCAMC,15) were obtained. HPLC analysis (Beckman; C18-ODS reverse phase column, isocratic elution with 60% CH$_3$OH/40% H$_2$O) showed the mixture to contain 85.7% of the desired 8-substituted isomer, of which a sample was purified by column chromatography (60-200 mesh silica gel, elution with CH$_2$Cl$_2$). The structures of the two isomers were confirmed by NMR. NMR (CDCl3) d 7.56 (1H, d), 7.11 (1H, d), 6.26 (1h, d), 5.05-5.19 (2H, m), 3.84 (2H, m), 2.55-2.62 (2H, m), 2.43 (3H, d), 1.78-1.82 (2H, m), 1.01-1.09 (3H, t).

Step 4: Ring closure was achieved by treatment of 20 grams of the mixed isomers with 70% sulfuric acid at 5° C., precipitating the product by addition of the reaction mixture to a 50:50 mixture of water and ice (3000 ml). Following extraction with chloroform, 12.5 grams (94%) of the mixed isomeric products 4,5'-dimethylisopsoralen (DMIP, 16) and 4,5'-dimethylpsoralen were obtained. Purification of the desired 4,5'-dimethylisopsoralen was accomplished by repeated recrystallization from ethanol (to give approximately 85% yield of pure DMIP).

EXAMPLE 17

Radiolabelled DMIP Synthesis

Step 1: DMIP (21.4 mg, 0.1 mmol), 10% palladium on charcoal (15 mg, Aldrich) and glacial acetic acid (Mallinkrodt, 2 ml) are placed in a 25 ml round bottom flask and stirred with tritium gas (Lawrence; 150 Ci) until no more tritium is absorbed. The catalyst is removed by centrifugation, followed by evaporation of the supernatant under vacuum. The residual solid is dissolved in methylene chloride (1 ml), loaded on a ½" by 5" silica gel column (60-200 mesh, Baker), and eluted with methylene chloride. Column fractions containing the non-fluorescent [3,4,4',5'-$^3$H$_4$]-tetrahydro-4,5'-dimethylisopsoralen ($^3$H-THDMIP,17) are identified by TLC, combined, and the solvent removed under reduced pressure. This material is further characterized by comparison with authentic unlabelled compound (UV; co-chromatography on TLC in CHCl3; C/M 98:2). 2.45 Ci of material was recovered, corresponding to a preliminary specific activity of 24.5 Ci/mmol. This material was then used in Step 2 for the preparation of tritiated DMIP.

Step 2: $^3$H-THDMIP, prepared as described above, is placed in a 25 ml round bottomed flask along with diphenyl ether (5 ml) and 10% palladium on charcoal (30 mg; Aldrich). A nitrogen bubbler is attached and the mixture refluxed for 24-36 hours. After cooling to room temperature, absolute ethanol is added (5 ml) and the catalyst removed by centrifugation. The supernatant is partially evaporated, loaded on a ½" by 5" silica gel column (Baker, 60-200 mesh), and eluted with methylene chloride. The fractions containing the product are combined, the solvent volume reduced and the chromatography repeated on a ½"×10" column as above. Column fractions containing the product are combined and the solvent removed. The (3,4'-[$^3$H$_2$])-4,5'-dimethylisopsoralen ($^3$H-DMIP) so obtained is stored in ethanol to inhibit radiolysis.

The specific activity of the $^3$H-DMIP is established by measuring the optical density of the stock solution to determine its concentration, then counting appropriate aliquots of the stock.

The radiochemical purity is determined by HPLC. Approximately 10$^6$ CPM of $^3$H-DMIP is mixed with 10 ug unlabelled DMIP in 50 ul of ethanol (100%). The sample is injected on a C18 octadecasilyl reverse phase chromatography column (Beckman) and eluted with a water/methanol gradient as follows: 0-10 minutes, 100% H$_2$O; 10-70 minutes, 100% H$_2$O→100% CH$_3$OH; 70-80 minutes, 100% CH$_3$OH. Eighty 1.0 ml fractions are collected and 40 ul of each fraction counted. Greater than 99% of the radioactivity co-chromatographs with the optical peak corresponding to $^3$H-DMIP.

EXAMPLE 18

CMDMIP Synthesis

4'-Chloromethyl-4,5'-dimethylisopsoralen (CMDMIP,18) was prepared from DMIP as follows: DMIP (11.9 gm; 55.6 mmol) was dissolved in acetic acid (600 ml) then chloromethyl methylether (46 ml; 48.7 gm; 600 mmol) added. The homogeneous solution remained at room temperature for 16 hours, after which a second portion of chloromethyl methylether (46 ml; 48.7 gm; 600 mmol) was added. The solution was left at room temperature another 53 hours after which crystals began to form. The reaction flask was cooled at 0° C. for 78 hours, resulting in the formation of a large mass of white precipitate, which was collected by suction filtration then dried on the filter. The yield was 10.9 gm (74.7%). The NMR spectra of the product, CMDMIP, was consistent with that described by Dall'Acqua et al., J. Med. Chem 24, 178 (1981).

EXAMPLE 19

Radiolabelled CMDMIP Synthesis

The present invention also contemplates labelled CMDMIP. The present example describes one method of the present invention involving four steps:

Step 1: 4'-Hydroxymethyl-4,5'-dimethylisopsoralen (HMDMIP,19) was prepared from CMDMIP. CMDMIP (1.0 gm; 3.8 mmol) was placed in a 250 ml round bottomed flask and refluxed with water for four hours. TLC (C/M 95:5) showed that all the starting material had been converted to a single low Rf spot after this time. The reaction mixture was cooled to 0° C. for 2 hours and then the product collected by suction filtration.

Step 2: New compound 4'-Formyl-4,5'-dimethylisopsoralen (FDMIP,20) was prepared from HMDMIP by a novel synthesis method of the present invention. 3,5-Dimethylpyrazole (830 mg, 8.7 mmol, Aldrich) was added to suspension of chromium trioxide (874 mg, 8.8 mmol) in methylene chloride (25 ml) and the mixture stirred for 30 min under argon at room temperature. HMDMIP from Step 1 (800 mg; 3.3 mmol) was added in one portion and the reaction mixture stirred at room temperature for 2.5 hours. TLC showed the reaction was over after 3 hours ($CHCl_3$). The solvent was removed under reduced pressure and the residue dissolved in a small volume of $CHCl_3$ loaded on a silica gel column (60–200 mesh, Baker) then eluted with $CH_2Cl_2$. The fractions containing product were determined by TLC, combined and the solvent removed to provide FDMIP (647 mg, 81%). Further purification was accomplished by recrystallization from 95% EtOH giving yellow needles.

Step 3: 4'-(hydroxy-[$^3$H]-methyl)-4,5'-dimethylisopsoralen ($^3$H-HMDMIP) was prepared from FDMIP. The FDMIP of Step 2 (18 mg; 0.0743 mmol) and sodium-[$^3$H]-borohydride (DNEN, 1.8 mg, 0.0476 mmol; 60 Ci/mmol) were stirred in 95% ethanol (8 ml) at room temperature for 5 hours. After this period, TLC showed the FDMIP (Rf 0.7) had been completely reduced to $^3$H-HMDMIP (Rf 0.15). The solvent was removed by lyophilization and the residual solid dissolved in C/M (99:1, 1 ml), loaded on a 1 cm×30 cm chromatography column (60–200 mesh silica gel; Baker) and eluted with C/M (99:1). The fractions which contained $^3$H-HMDMIP were identified by TLC, combined and evaporated. The product was used directly in Step 4 for the preparation of 4'-([$^3$H]-Chloromethyl-4,5'-dimethylisopsoralen ($^3$H-CMDMIP).

Step 4: $^3$H-CMDMIP was prepared from $^3$H-HMDMIP with thoinyl chloride. (Alternatively, 4'-([$^3$H]-Bromomethyl)-4,5'-dimethylisopsoralen ($^3$H-BMDMIP) can be prepared from $^3$H-HMDMIP using thionyl bromide. $^3$H-BMDMIP is preferred due to its higher reactivity in $S_N2$ displacement reactions, such as BMDMIP→HDAMDMIP and BMDMIP→PHIMDMIP; accordingly, thionyl bromide is the reagent of choice to provide XMDMIP where X=Br). $^3$H-HMDMIP, prepared as described in Step 3, was placed in a small round bottomed flask and dissolved in freshly distilled chloroform (5 ml, dried over 4A molecular sieves). Thionyl chloride (41 mg; 0.35 mmol; Aldrich) was added and the yellow solution stirred for one hour. TLC ($CH_2Cl_2$) indicated all the starting alcohol had been converted to the product following this period. The solvent was removed under reduced pressure, benzene added (5 ml) and then evaporated under reduced pressure (twice). The white solid residue was used directly for the preparation of additional labelled compounds.

EXAMPLE 20

AMDMIP Synthesis

This example describes the synthesis of AMDMIP from DMIP according to the following scheme:

DMIP→PHIMDMIP→AMDMIP

Step 1: DMIP (51 gm, 0.41 mole) is dissolved with heat in $CH_2Cl_2$ then cooled to room temperature. N-Hydroxymethylphthalimide (59.5 gm; 0.34 mol) is added and the mixture cooled to 8° C. A mixture of $CF_3SO_3H$ (19.8 ml; 33.6 gm; 0.22 mol) and $CF_3COOH$ (280 ml; 189 gm; 1.66 mol) is added from a dropping funnel over a period of 40–50 min. during which the temperature of the reaction mix is maintained between 8° C.–12° C. by external cooling. Following the addition, the reaction flask is brought to room temperature then refluxed until all the starting material is consumed (TLC; $CH_2Cl_2$). After the reaction is complete, one of two procedures is employed for work-up. In the first, the solvent is removed under reduced pressure, the residual yellow solid dissolved in chloroform, the chloroform washed with water, 0.3 M NaOH, water, then dried ($MgSO_4$). The product is isolated by column chromatography (60–200 mesh silica gel, Baker). Alternatively, the reaction mixture is reduced to half volume, then the crude product is precipitated by the addition of methanol, followed by filtration. The precipitate is washed with methanol then recrystallized from ethanol:chloroform (1:1), providing 4'-phthalimido-4,5'-dimethylisopsoralen (PHIMDMIP, 21).

Step 2: PHIMDMIP (40 gm; 0.11 mol) is dissolved in 95% ethanol (1800 ml) followed by the addition of hydrazine hydrate (15 ml; 85% in water; Aldrich). The solution is heated (60° C.) with stirring for 17 hours after which additional hydrazine (15 ml) is added. After another 4 hours, TLC (C/M 98:2) indicated all the starting material is consumed. The solvent is evaporated under reduced pressure and the residual solid dissolved in a mixture of chloroform (500 ml) and 0 1M NaOH (500 ml). The chloroform is separated and the basic aqueous phase extracted twice more with chloroform (250 ml). The combined chloroform extracts is washed twice with water (500 ml), then back-extracted with 0.1M HCl (3×250 ml) to form the protonated amine. The chloroform is removed and the acidic aqueous phase washed three more times with chloroform (250 ml). The acidic aqueous phase is then made basic with NaOH (1.0N) and extracted three times with chloroform. The chloroform extracts are combined, washed with water, dried ($MgSO_4$), then evaporated under reduced pressure and the residual solid dissolved in 1000 ml ethanol. HCL gas is passed through the chilled ethanol solution to provide the hydrochloride salt of 4'-aminomethyl-4,5'-dimethylisopsoralen (AMDMIP,22), which is filtered, washed with ethanol, then dried under vacuum (23 gm; 75% yield). All analytical data (NMR, elemental analysis) is checked to be consistent with published results.

EXAMPLE 21

Radiolabelled AMDMIP Synthesis

The present invention also contemplates labelled PHIMDMIP and labelled AMDMIP. One method of the present invention involves the scheme:

$^3$H-CMDMIP→3H-PHIMDMIP→$^3$H-AMDMIP

Step 1: $^3$H-CMDMIP, prepared as described above, was dissolved in 2 ml freshly distilled DMF in the presence of 4A molecular sieves. Potassium phthalimide (43 mg, 0.23 mmol) was added and the mixture heated to 40° C. and stirred for 42 hours. Following this period, the solvent was removed and the residual solid dissolved in chloroform: methanol 98:2 (1 ml), loaded on a 1 cm×20 cm silica gel column (60–200 mesh) then eluted with C/M 98:2. The fractions containing product were identified by TLC ($CH_2Cl_2$), combined and evaporated under reduced pressure. The solid residue, 4'-(phthalimido-[³H]-methyl)-4,5'-dimethylisopsoralen (³H-PHIMDMIP), was used directly for the preparation of tritiated AMDMIP.

Step 2: ³H-PHIMDMIP, prepared as described above, was dissolved in 95% ethanol (3 ml). Hydrazine hydrate (5 mg, 0.1 mmol) was added and the solution heated (60° C.) and stirred for 17 hr after which additional hydrazine (0.04 mmol) was added. After another 4 hr, TLC indicated all the starting material had been consumed. The solvent was evaporated under reduced pressure and the residual solid dissolved in a mixture of chloroform (5 ml) and NaOH (0.1N; 5 ml). The chloroform was separated and the basic aqueous phase extracted twice more with chloroform (5 ml). The combined chloroform extracts were washed twice with water (10 ml then back-extracted with HCl (0.1N; 10 ml) to form the protonated amine. The chloroform was removed and the acidic aqueous phase washed three more times with chloroform (5 ml). The aqueous phase was then evaporated under reduced pressure and the residual solid dissolved in ethanol (10 ml). An appropriate dilution of the stock solution was made, counted, and the concentration determined by optical density. Overall recovery of the product was 4.57 mg (16.8% based on ³H-CMDMIP). The specific activity was $2.2 \times 10^5$ CPM/μg (93 mCi/mmol).

EXAMPLE 22

BIODMIP Synthesis

This example describes one method of the present invention for the synthesis of BIODMIP according to the following scheme:

CMDMIP→HDAMDMIP→BIODMIP

Step 1: CMDMIP (250 mg, 0.9 mmole, 1.0 eq), N,N'-dimethyl-1,6-hexane-diamine (1.83 gm; 12.7 mmol; 14.0 eq; Aldrich) and toluene (28 ml, freshly distilled onto 4A sieves) were placed in a 50 ml round bottomed flask with attached reflux condensor and argon line. The reaction mix was brought to reflux with a heating mantle while being magnetically stirred. TLC after 1 hour (benzene/methanol 1:1) found approximately 80% of the starting material converted to a single low Rf spot. The total reflux time was 17 hours after which essentially no starting material remained. The toluene was removed under reduced pressure on the rotovap and the residual yellowish oil dissolved in a small volume of chloroform. This solution was loaded on a small (0.5"×5") chromatography column (60-200 mesh silica gel; Baker) then eluted with 95% ethanol:concentrated NH₄OH (4:1), collecting 15 1-ml fractions. Fractions containing product were identified by TLC, combined, the solvent removed under reduced pressure, and the residue reloaded on a second silica column (0.5"×20") and re-eluted with C/E/T (9:1:0.25). This solvent system effected separation of the product from unreacted N,N'dimethyl-1,6-hexanediamine. This separation was confirmed by development of the TLC plate with iodine or ninhydrin (0.5% in ethanol) following elution. Fractions containing purified product were combined and the solvent removed under reduced pressure and the residual oil placed under high vacuum to constant weight. The yield of 4'-N-(N,N'-dimethyl-1,6-hexanediamine)-methyl-4,5'-dimethylisopsoralen (HDAMDMIP, 24) was approximately 50%. Mass spectrum m/e (relative abundance) 370, (M+, 1.09); absorption spectra maxima (nm): 252, 303.

Step 2: HDAMDMIP (18.4 mg, 0.5 mmole, 1.0 eq), biotinamidocaproate N-hydroxysuccinimide ester (45.5 mg; 0.10 mmol; 2.0 eq; Pierce), and DMF (1.5 ml, freshly distilled onto 4A sieves) were placed in a 10 ml round bottomed flask with attached argon line. The reaction was magnetically stirred at room temperature. TLC after 1 hour (C/E/T 9:1:0.25) showed a high Rf product spot. After 5 hr reaction time, another 20 mg of biotin starting material was added and the reaction was continued for another hour. The solvent was removed under vacuum and the residue dissolved in a total of 10 ml chloroform:isopropanol 3:1 and transferred to a separatory funnel. HCl (0.1N; 10 ml) was added and the layers mixed thoroughly then allowed to separate. The organic phase was removed and the aqueous phase adjusted to pH 13 then extracted again with chloroform:isopropanol 3:1. The organic extracts were combined and the solvent removed under reduced pressure. The residual solid (39.4 mg) was dissolved in C/F/T, loaded onto a silica gel column (60–200 mesh, 0.5"×20"), and eluted with the same solvent. The product was isolated (as the free amine), the elution solvent removed, and the free amine dissolved in ethanol (10 ml). HCl gas was bubbled through the solution, followed by argon. The ethanol was removed to give 31.7 mg of 4'-N-[N,N'-dimethyl-N'-(6-{biotinamido}-hexanoate-1,6-hexanediamine]-methyl-4,5'-dimethylisopsoralen (BIODMIP, 25a) (HCl salt) (85% yield). FABMS m/e (relative abundance) 710 (MH+, 60%)

EXAMPLE 23

Radiolabelled BIODMIP Synthesis

This example describes the synthesis of radiolabelled HDAMDMIP and BIODMIP from radiolabelled CMDMIP according to the following scheme:

³H-CMDMIP→³H-HDAMDMIP→³H-BIODMIP

Step 1: ³H-CMDMIP (70 mg; 0.27 mmol), prepared as described above, and N,N'-dimethyl-1,6-hexanediamine (500 mg, 3.5 mmole) and freshly distilled toluene (8 ml) were mixed in a 50 ml round bottomed flask. The solution was stirred overnight. TLC (chloroform/benzene/acetone/formic acid 4:1:1:1) showed that product had formed and essentially all the starting material had been consumed. The toluene was removed under reduced pressure and the residual solid was dissolved in 1-2 ml of C/E/T (9:1:0.25). This was loaded onto a silica gel column (0.5"×2", 60–200 mesh, Baker) and eluted with the same solvent. Fractions containing the product (not separated from the hexanediamine) were combined and the solvent removed under reduced pressure. The solid was dissolved in 1-2 ml in the same solvent, loaded onto a larger column (0.5"×20") and eluted with the same solvent. The presence of the hexanediamine compound on TLC was detected by using 1% ninhydrin in ethanol (the solution was sprayed onto the TLC plates and the plates heated at 70°-80°). The column fractions containing pure 4'-N-(N,N'-dimethyl-1,6-hexanediamine)-[³H]-methyl-4,5'-dimethylisopsoralen (³H-HDAMDMIP) were thus identified, combined and the solvent removed under reduced pressure, providing 53.7 mg (58% yield).

Step 2: ³H-HDAMDMIP (2 mg; 0.005 mmol; 1 eq) and biotinamidocaproate N-hydroxysuccinimide ester (6.2 mg; 0.014 mmol; 2.8 eq) and DMF (1.0 ml, over sieves) were mixed in a 10 ml round bottomed flask. The reaction and work-up procedures were identical to the preparation of the unlabelled compound. Recovered 1.8 mg product (47% yield) at a specific activity of $2.6 \times 10^7$ CPM/umol ($3.5 \times 10^4$ CPM/μg).

EXAMPLE 24

DITHIODMIP Synthesis

This example describes one method of the present invention for the synthesis of DITHIODMIP according to the following scheme:

HDAMDMIP→DITHIODMIP

HDAMDMIP (30 mg; 0.80 mmol; 1.0 eq) and sulfosuccinimidyl-2-(biotinamido)-ethyl-1,3-dithiopropionate (68 mg; 0.112 mmol; 1.40 eq) were dissolved in freshly distilled DMF (1.5 ml) in a small, dry round bottomed flask with attached argon line then stirred at room temperature for 3 hr. After this period, the DMF was removed under reduced pressure and the residue suspended in 0.1N NaOH (7 ml), extracted with chloroform/isopropanol 3:1 (20 ml×2), and the organic extract washed with 0.5N HCL (20 ml×2), water (10 ml×2) then dried (MgSO4), filtered and stripped to give the crude product as a yellow oil (5.4 mg). The acidic extract from the organic wash was made basic by the addition of 1.0N NaOH (30 ml) then extracted with chloroform (25 ml×2). The chloroform was dried (Na$_2$SO$_4$), filtered and stripped to give additional product (24 mg). To further characterize the product, 4'-N-[N,N'-dimethyl-N'-(2-{biotinamido}-ethyl-1,3-dithiopropionate)-1,6-hexanediamine]-methyl-4,5'-dimethylisopsoralen (DITHIODMIP, 25b) (free base), small aliquots of the stock (ethanolic solution) were treated with sodium borohydride (Aldrich) or mercaptoethanol (Aldrich), then the product of these reactions compared to untreated material. In both cases the product was cleaved as expected.

EXAMPLE 25

Radiolabelled DITHIODMIP Synthesis

This example describes one embodiment of the method of the present invention for the synthesis of $^3$H-DITHIODMIP according to the following scheme:

$^3$H-CMDMIP→$^3$H-IMDMIP→$^3$H-HDAMDMIP→$^3$H-DITHIODMIP

Step 1: $^3$H-CMDMIP (20 mg; 0.75mmol) prepared as described in Step 4 of Example 19 and sodium iodide (57 mg; 0.38 mmol; dried overnight at 120° C.) and acetone (Mallinckrodt) are refluxed for 48 hours. Following this period, the reaction mixture is filtered to remove the resulting NaCl, the filtrate evaporated under reduced pressure, and the residual crude product dissolved in chloroform, loaded on a ¼×5" silica gel column (60-200 mesh; Baker) then eluted with chloroform. The fractions containing the product, 4'-(iodo-[$^3$H]-methyl)-4,5'-dimethylisopsoralen ($^3$H-IMDMIP, 23), are identified by TLC, combined and solvent removed under reduced pressure. The product is used directly for Step 2.

Step 2: Using the $^3$H-IMDMIP prepared in Step, 1, $^3$-H-HDAMDMIP is prepared. The synthesis and work-up are identical to the procedures described in Step 1 of Example 23 except $^3$H-CMDMIP is replaced by $^3$H-IMDMIP and the reagent concentrations used are reduced by two thirds. The resulting crude $^3$H-HDAMDMIP is further purified by column chromatography as described then used directly for the preparation of $^3$H-DITHIODMIP.

Step 3: Using the $^3$H-HDAMDMIP prepared in Step 3, $^3$H-DITHIODMIP is prepared. $^3$H-HDAMDMIP (5 mg; 0.013 mmol; 1.0 eq) and sulfosuccinimidyl-2-(biotinamido)-ethyl-1,3-dithiopropionate (11 mg; 0.019 mmol; 1.5 eq) is dissolved in freshly distilled DMF (1.5 ml) in a small, dry round bottomed flask with attached argon line then stirred at room temperature for 3 hours. After this period, the DMF is removed under reduced pressure and the residue suspended in NaOH (0. 1N; 3 ml), extracted with chloroform/isopropanol 3:1 (7 ml×2), and the organic extract washed with HCl (0.5N; 7 ml×2), water (5 ml×2) then dried (MgSO4), filtered and stripped to provide the crude product as a yellow oil. The product is characterized by ultraviolet absorption (comparison with authentic material) and TLC (co-chromatography with authentic material is several different solvent systems). Radiochemical purity is determined by HPLC. Approximately $10^6$ CPM of tritiated $^3$H-DITHIODMIP is mixed with 10 μg of unlabelled DITHIODMIP in 50 μl ethanol (100%). The sample is injected on a C18 octadecylsilyl reverse phase chromatography column (Beckman) and eluted with an acetonitrile/ammonium acetate (0.1M; pH 7) gradient, as follows: 0–10 minutes, 100% ammonium acetate; 10–70 minutes, 100% ammonium acetate→100% acetonitrile; 70–80 minutes, 100% acetonitrile. Eighty 1.0 ml fractions are collected and 40 μl of each fraction is then counted. The product is further characterized by dissolving a sample in ethanol treating with either sodium borohydride (Aldrich) or mercaptoethanol (Aldrich). The product of these reactions is compared to untreated material to verify cleavage occurs as expected.

EXAMPLE 26

FLUORDMIP Synthesis

This example describes one method of the present invention for the synthesis of FLUORDMIP according to the following scheme:

CMDMIP→HDAMDMIP→FLUORDMIP

Step 1: HDAMDMIP was prepared from CMDMIP as described in Step 1 of Example 22.

Step 2: HDAMDMIP from Step 1 (10 mg; 0.027 mmol; 1.0 eq) in DMF (1.0 ml, distilled onto 4A sieves; Mallinckrodt) and 6-carboxyfluorescein-N-hydroxysuccinimide ester (15.1 mg; 0.032 mmol; 1.1 eq; Pierce) in DMF (1.0 ml, distilled onto 4A sieves; Mallinckrodt) were mixed in a 5 ml round bottomed flask with attached argon line. The reaction mix was stirred for several hours at room temperature, after which the majority of the starting material had been consumed as indicated by TLC (C/B/A/F - 4:1:1:1). The solvent was removed with gentle heating (<50° C.) under reduced pressure. The residue was dissolved in HCl (5 ml; 0.1N) then extracted with chloroform/isopropyl alcohol (3:1). The organic extract was then reduced in volume, loaded onto a glass backed preparative silica gel TCL plate (20 cm×20 cm×2 mm; Baker) then eluted with C/B/A/F. The major low Rf band was scraped off, eluted with chloroform/isopropanol (3:1), the silica removed by filtration and the solvent evaporated under reduced pressure. The product was dissolved in a small volume of ethanol and HCl gas bubbled through the solution. The ethanol was then evaporated to provide 4'-N-[N,N'-dimethyl-N'-(6-carboxyfluoresceinester)-1,6-hexanediamine)-methyl-4,5'-dimethylisopsoralen (FLUORDMIP, 25c) as the monohydrochloride salt. FABMS (free base) m/e 729,M+; absorption spectrum relative maximum (nm) 447.

EXAMPLE 27

Radiolabelled FLOURDMIP Synthesis

This example describes one embodiment of the method of the present invention for the synthesis of radiolabelled FLUORDMIP according to the following scheme:

FDMIP→$^3$H-HMDMIP→$^3$H-CMDMIP→$^3$H-HDAMDMIP→$^3$H-FLUORDMIP

Step 1: $^3$H-HMDMIP was prepared from FDMIP as described in Step 3 of Example 19.

Step 2: $^3$H-CMDMIP was prepared from $^3$H-HMDMIP as described in Step 4 of Example 19.

Step 3: $^3$H-HDAMDMIP was prepared from $^3$H-CMDMIP as described in Step 1 of Example 23.

Step 4: $^3$H-FLUORDMIP was prepared from $^3$H-HDAMDMIP. $^3$H-HDAMDMIP (3.1 mg; 0.0084 mmol; 1.0 eq) in DMF (1.7 ml, distilled over 4A sieves) and 6-carboxyfluorescein-N-hydroxysuccinimide (4.0 mg; 0.0084 mmol; 1 0 eq) in DMF (1.0 ml) were mixed in a 5 ml round bottomed flask with attached argon line. This mixture was stirred overnight. The work-up was similar to the preparation in Step 2 of Example 26, except the preparative TLC plate was eluted with C/B/A/F (5:1:1:1 ; this solvent gave a slightly higher Rf and better separation of the product). Approximately 2.1 mg product was obtained (a 42% yield) with a specific activity of 93 mCi/mmol.

EXAMPLE 28

Solubility of Photoreactive Compounds

Figure 5:
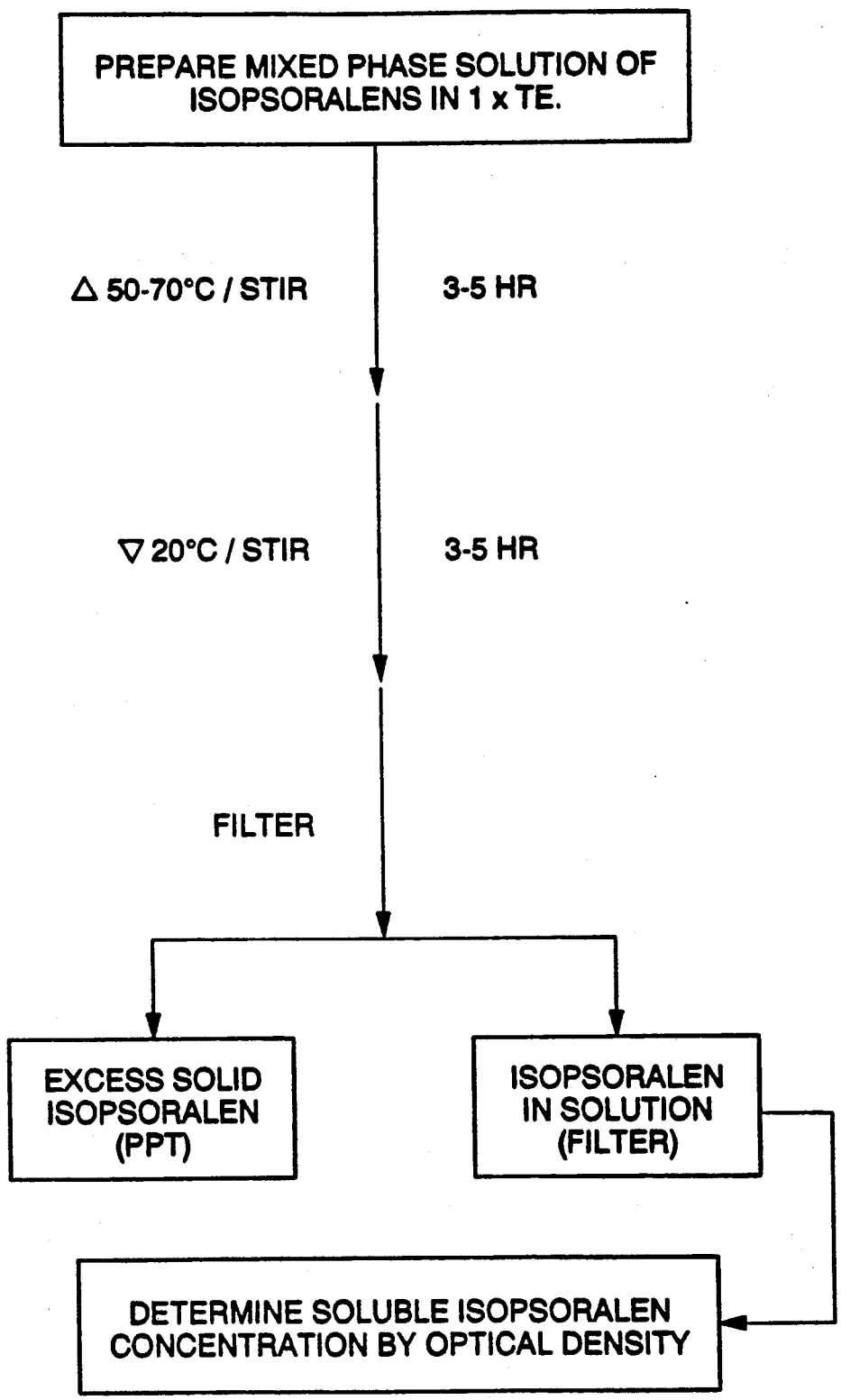
FIG. 5 schematically shows a manner of determining compound solubility.

The solubilities of AMIP, AMDMIP, DMIP, MIP and isopsoralen (IP) were determined experimentally according to the scheme set forth in FIG. 5. To perform the solubility measurement, it was first necessary to establish known optical densities for a 1 μg/ml solution of each compound. These were determined by preparing either ethanolic or aqueous stocks of each compound at known concentrations in 1×TE, then measuring the optical density of each solution. From this information, the absorption of a 1 μg/ml solution was computed. Alternatively, the extinction coefficient may be thus determined and used in the same fashion. In this manner, the following absorption data was collected:

| Compound | Wavelength (nm) | O.D. 1 μg/ml (1 × TE) | Emax |
|---|---|---|---|
| AMIP | 249 | 0.087 | $2.19 \times 10^4$ |
| AMDMIP | 249.5 | 0.082 | $2.29 \times 10^4$ |
| DMIP | 250.5 | 0.102 | $2.18 \times 10^4$ |
| MIP | 249 | 0.092 | $1.97 \times 10^4$ |
| IP | 247 | 0.105 | $1.95 \times 10^4$ |

To determine the solubility of each compound, an excess (2-25 mg) of each (except for AMDMIP; see below) was placed in 1×TE (0.37-2 ml) then heated (50°-70° C.) for several hours. After this, each mixture was stirred for several hours at room temperature in the presence of undissolved solid (this procedure assured that supersaturation did not occur). Following this step, undissolved compound was removed by filtration using a 0.2 u nylon-66 syringe filter (Arco LC13; Gelman). The concentration of the remaining soluble compound was then determined by measuring the optical density of the filtrate and computing the solubility from the known optical density of a 1 μg/ml solution of that compound.

The solubility of the compounds was thus determined to be as follows:

| Compound | Solubility in 1 × TE (μg/ml) |
|---|---|
| AMIP | 21,000 |
| AMDMIP | >22,700* |
| DMIP | nd** |
| MIP | nd |
| IP | 2 |

*The solubility of AMDMIP was a minimum of 22,700 μg/ml, as the initial mix of the compound was entirely soluble in the volume of 1 × TE used
**nd = not detectable (solubility was less than 1 μg/ml)

EXAMPLE 29

Dark Binding of Photoreactive Compounds

Equilibrium Dialysis was used to determine the association ("dark binding") constants of AMIP, AMDMIP and MIP with calf thymus DNA. The tritium labelled isopsoralens were used for the experiment. The method was a modification of that of Isaacs et al. Biochemistry 16, 1058-1066 (1977).

Spectrapor 2 dialysis tubing (Spectrum) was pretreated by boiling in saturated sodium bicarbonate then rinsed thoroughly with double distilled water. Calf thymus DNA (Sigma) was prepared at a concentration of 50 μg/ml in 1×TE. The samples were prepared by placing 1.0 ml of the DNA solution inside the bag and using enough isopsoralen to provide an isopsoralen:DNA base pair ratio of 1:15. The samples were prepared with the tritiated isopsoralen ("Drug") placed either inside or outside of the dialysis bag (each sample was placed in a scintillation vial containing a small magnetic stir bar). The samples were stirred at 4° C. for five days in the dark. After this period the bags were removed, opened, and the radioactivity inside and outside the bag determined by scintillation counting. The concentration of the DNA was determined by measuring optical density at 260 nm. The dissociation constant ($K_a$) was calculated from this information (Table 9). Preparing the samples in duplicate with the isopsoralen both inside and outside the dialysis bag provided a check that the system had come to equilibrium at the end of the dialysis period (the amount of isopsoralen inside and outside the bag at equilibrium should be, and was, the same in both cases).

TABLE 9

| SAMPLE | MASS OF DRUG | LOCATION OF DRUG | VOLUME OF DNA STOCK IN DIALYSIS BAG | VOLUME OF 1 × TE STOCK IN DIALYSIS BAG |
|---|---|---|---|---|
| MIP in | 1.27 ug | inside bag | 1 ml | 10 ml |
| HMT in | 1.43 ug | " | " | " |
| AMIP in | 1.30 ug | " | " | " |
| AMDMIP in | 1.01 ug | " | " | " |
| MIP out | 1.27 ug | outside bag | " | " |
| HMT out | 1.43 ug | " | " | " |
| AMIP out | 1.30 ug | " | " | " |
| AMDMIP out | 1.01 ug | " | " | " |

The association constant, $K_a$ is defined here as $$K_a = \frac{[P\cdot DNA]}{[P][DNA]} \text{ for the reaction } P + DNA = P\cdot DNA$$

where P=free drug in solution, DNA=DNA binding site for the drug, and P:DNA=drug associated with the DNA. The following summarizes the $K_a$ values determined for the compounds:

| Sample | $K_a$ |
|---|---|
| AMIP in | $2.96 \times 10^4$ |
| AMIP out | $2.21 \times 10^4$ |
| AMDMIP in | $7.66 \times 10^4$ |
| AMDMIP out | $1.07 \times 10^5$ |
| MIP in | $9.08 \times 10^3$ |
| MIP out | $2.07 \times 10^3$ |

EXAMPLE 30

Photoactivation Device

One embodiment of the photoactivation device of the present invention is designated "CE-I." CE-I is an irradiation device having the following features: 1) an inexpensive source of electromagnetic radiation, 2) temperature control of the sample, 3) a multisample holder, 4) a multiple sample irradiation format, and 5) a compact design that requires minimal bench space.

Figure 6:
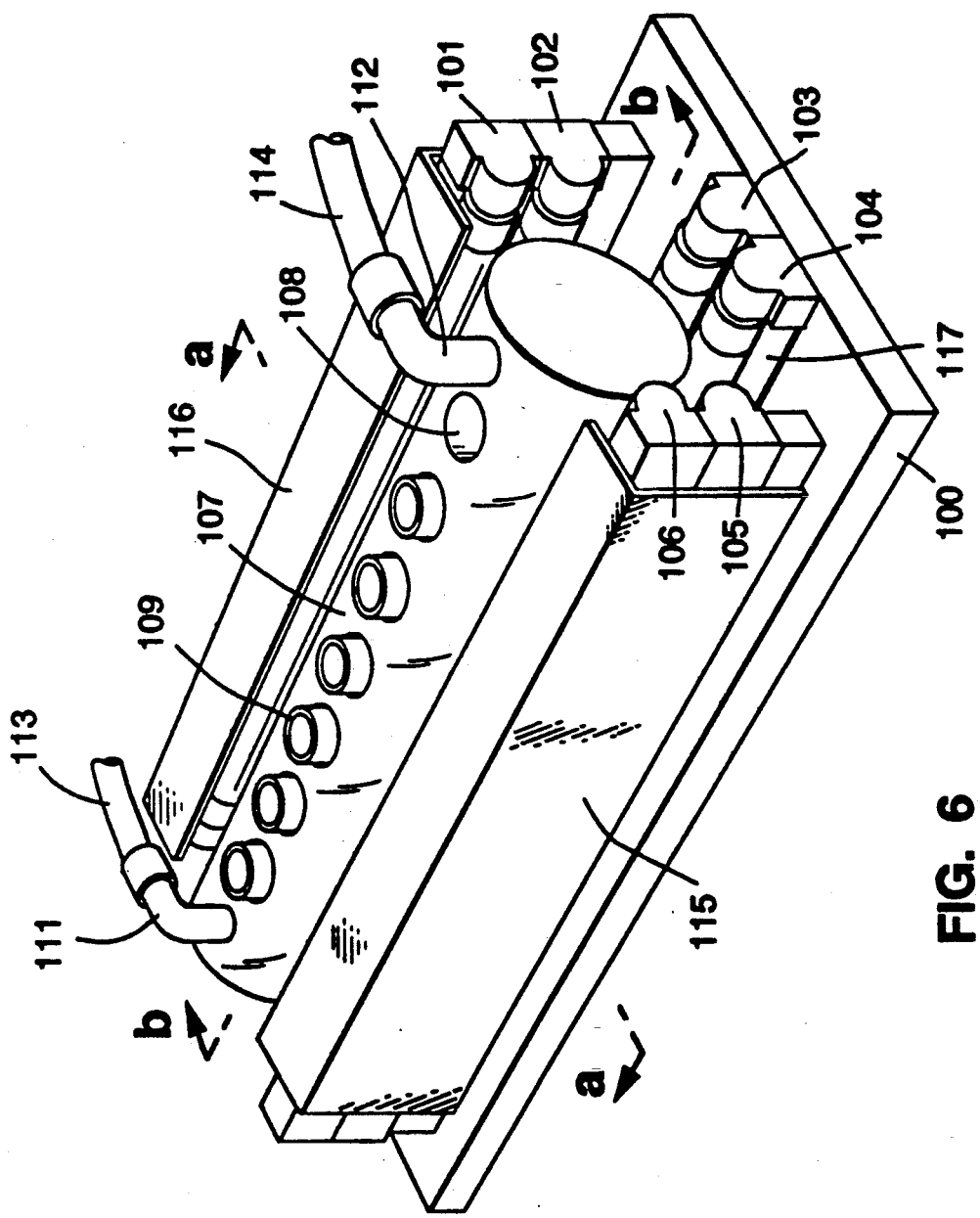
FIG. 6 is a perspective view of an embodiment (CE-I) of the photoactivation device of the present invention.

FIG. 6 is a perspective view of CE-I, integrating the above-named features. The figure shows the bottom platform of a housing (100) with the rest of the housing removed (not shown), having six bulbs (101-106) connectable to a power source (not shown) arranged around a chamber (107) having a plurality of intrusions (108) for supporting a plurality of sample vessels (109). The bulbs serve as a source of electromagnetic radiation and, in one embodiment, ultraviolet radiation. While not limited to the particular bulb type, the embodiment is configured to accept an industry standard, F8T5BL hot cathode dual bipin lamp.

The chamber (107), in addition to holding sample vessels (109), holds temperature control liquid (not shown), thereby serving as a means for controlling the temperature of the sample vessels (109).

Figure 7:
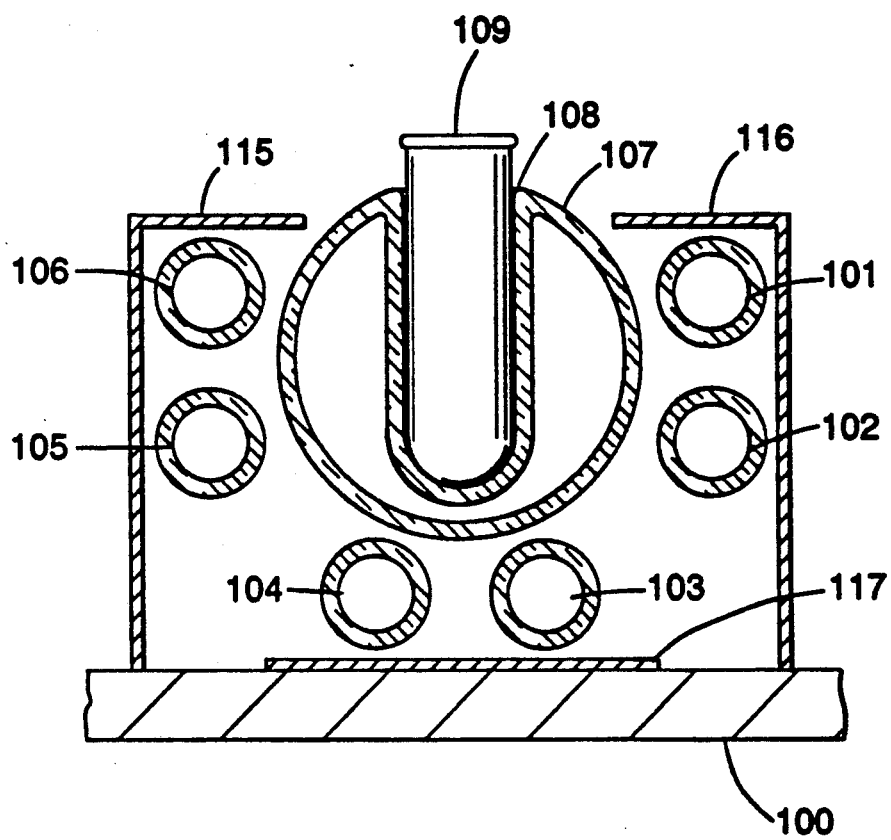
FIG. 7 is a cross-sectional view of CE-I along lines a—a of FIG. 6.

FIG. 7 is a cross-sectional view of CE-I along the lines of a—a of FIG. 6. FIG. 7 shows the arrangement of the sources (101-106) around the chamber (107). FIG. 7 also shows the chamber (107) is punctuated with sample holder intrusions (108) with dimensions designed to accommodate the sample vessels (109).

It is not intended that the present invention be limited by the nature of the material used to form the chamber (107). In one embodiment, it is made of glass. In another embodiment, it is made of plastic. In a preferred embodiment, it is made of UV transmitting acrylic selected from the group of commercial acrylics consisting of ACRYLIC-UVT (Polycast), PLEXIGLAS 11-UVT (Rohm & Haas), PLEXIGLAS G-UVT (Rohm & Haas) and ACRYLITE OP-4 (Cyro).

Similarly, it is not intended that the present invention be limited by the nature of the method used to form the chamber (107). In one embodiment, it is molded as one piece. In another embodiment, it is molded as separate pieces and then assembled.

FIG. 6 shows that the temperature control liquid is introduced via a liquid inlet port (111) and removed via a liquid outlet port (112). It is preferred that the liquid inlet port (111) and the liquid outlet port (112) connect via tubes (113, 114) to a liquid source (not shown). It is further preferred that the liquid source allow for recirculation of the liquid. To improve temperature control, static temperature control liquid (not shown) may be placed in the intrusions (108).

It is not intended that the present invention be limited to any particular temperature control liquid. One inexpensive temperature control liquid contemplated by the invention is water.

Figure 8:
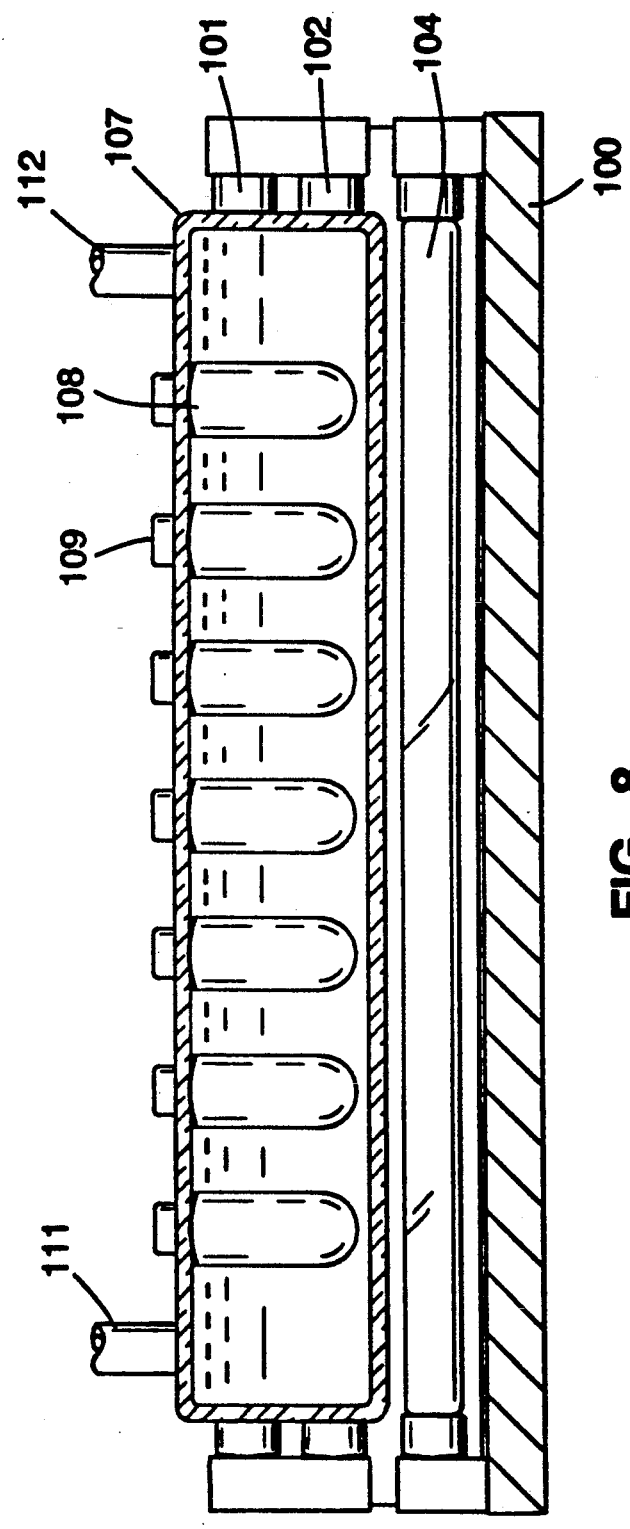
FIG. 8 is a cross-sectional view of CE-I along lines b—b of FIG. 6.

FIG. 8 shows the CE-I embodiment with seven intrusions (108) placed within the boundary defined by the inlet (111) and outlet (112) ports. While the number of intrusions (108) and their placement may be selected to suit the convenience of the user, some configurations may impact irradiation efficiency.

FIGS. 6 and 7 also show an array of reflectors (115, 116, 117). It is preferred that the reflectors are made from UV reflecting metal.

While not limited to any particular dimensions (the drawings are not drawn to scale), it is preferred that the intrusions (108) be approximately 4 cm deep, that the intrusions be spaced approximately 3 cm apart, and the the distance from the top surface of the housing to the opening of the intrusions be approximately 6.5 cm. In such an arrangment, the lower bulbs (103, 104) are preferably 2.3 cm apart when measured from their centers (their centers are preferably 1.2 cm above the housing when measured from the surface of the reflector 117). This allows the lower bulbs (103, 104) to be less than 1.5 cm in distance from the bottom of the reaction vessel (109).

The other bulbs can be viewed as two more sets (101, 102 and 105, 106) (for a total of three, two bulb sets in all). Within a set, it is preferred that the bulbs are 2.3 cm apart when measuring from their centers (their centers are preferably 1.2 cm away from the the surface of the reflectors 115, 116). It is preferred that the reflectors 115 and 116 are approximately 11 cm apart when measuring from their sides.

It is preferred that the relationship of the chamber (107) length ("CL") to the bulb (101-106) length ("BL") and to the reflector (115,116,117) length ("RL") is as follows:

RL>BL>CL

Preferred lengths are RL=29.5 cm, BL=between 26 cm and 29 cm, and CL=approximately 25 cm.

EXAMPLE 31

Photoactivation Device

One embodiment of the photoactivation device of the present invention is designated "CE-II." CE-II is an irradiation device created to serve as a convenient photoactivation device having the following features: 1) an inexpensive source of electromagnetic radiation, 2) temperature control of the sample, 3) a multisample holder, 4) a multiple sample irradiation format, 5) a housing that shields the user from stray electromagnetic radiation, and 6) a compact design that requires minimal bench space.

Figure 9:
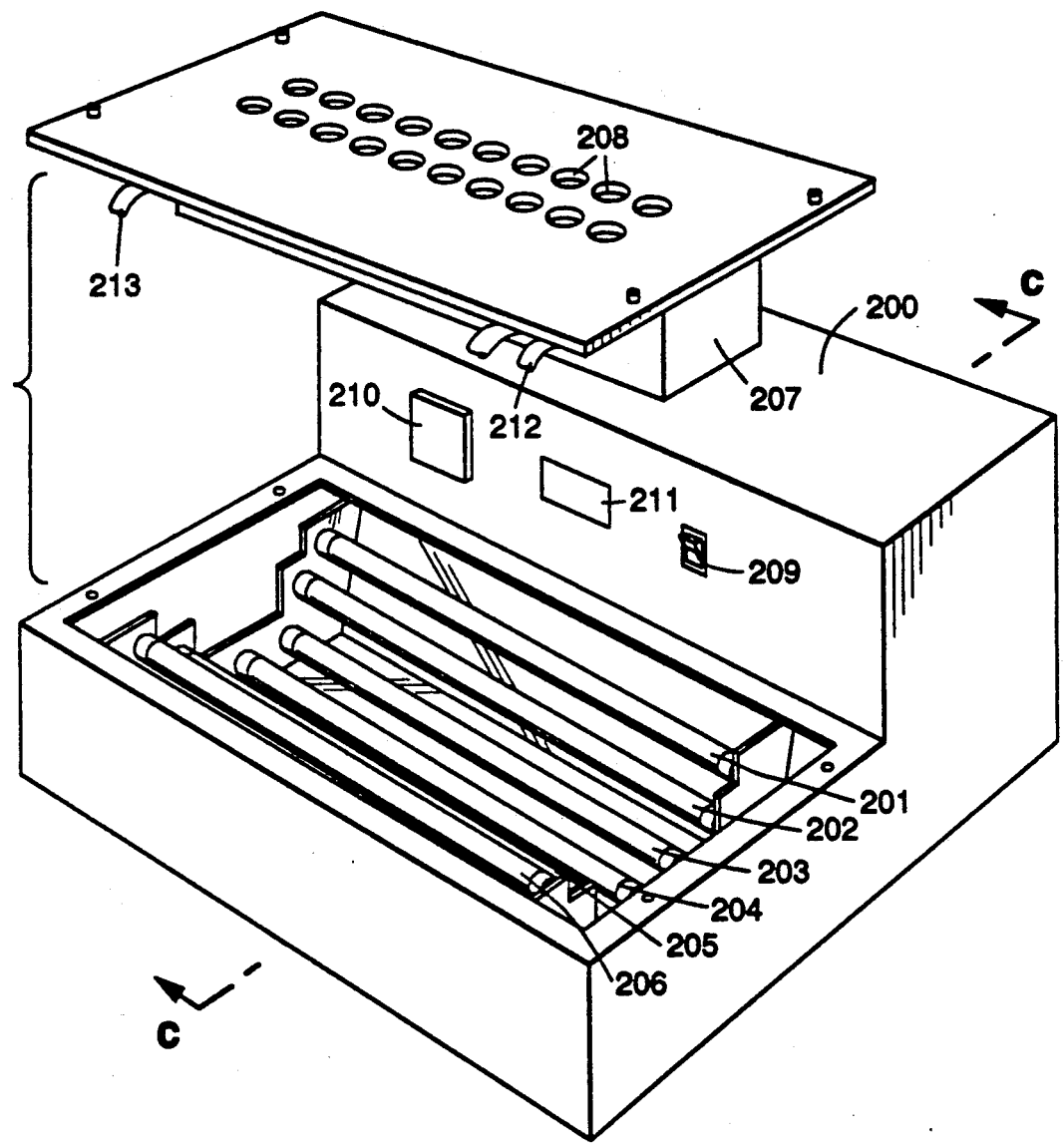
FIG. 9 is a perspective view of an alternative embodiment (CE-II) of the photoactivation device of the present invention.
Figure 10:
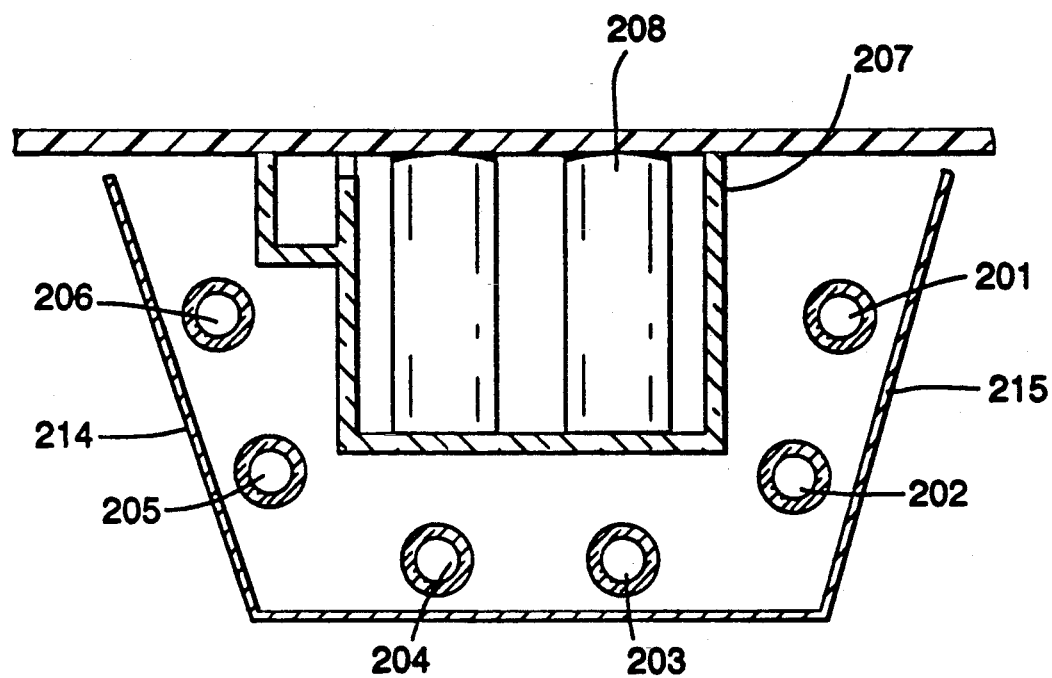
FIG. 10 is a cross-sectional view of CE-II along lines c—c of FIG. 9.

FIG. 9 is a perspective view of CE-II, integrating the above-named features, showing a housing (200) containing six bulbs (201–206) connectable to a power source (not shown) arranged around a detachable chamber (207). FIG. 10 shows that the chamber (207) has a plurality of intrusions (208) for supporting a plurality of sample vessels (not shown).

The bulbs serve as a source of electromagnetic radiation and, in one embodiment, ultraviolet radiation. While not limited to the particular bulb type, the embodiment is configured to accept an industry standard, F8T5BL hot cathode dual bipin lamp.

The housing (200) also serves as a mount for several electronic components. A main power switch (209) controls the input current from the AC power source (not shown). For convenience, this power switch (209) is wired to a count down timer (210) which in turn is wired in parallel to an hour meter (211) and to the coils (not shown) of the source of electromagnetic radiation. The count down timer (210) permits a user to preset the irradiation time to a desired level of sample exposure. The hour meter (211) maintains a record of the total number of radiation hours that are provided by the source of electromagnetic radiation. This feature permits the bulbs (201–206) to be monitored and changed before their output diminishes below a minimum level necessary for rapid photoactivation.

The chamber (207), in addition to holding sample vessels, holds temperature control liquid (not shown), thereby serving as a means for controlling the temperature of the sample vessels.

It is not intended that the present invention be limited by the nature of the material used to form the chamber (207). In one embodiment, it is made of glass. In another embodiment, it is made of plastic. In a preferred embodiment, it is made of UV transmitting acrylic selected from the group of commercial acrylics consisting of ACRYLIC-UVT (Polycast), PLEXIGLAS II-UVT (Rohm & Haas), PLEXIGLAS G-UVT (Rohm & Haas) and ACRYLITE OP-4 (Cyro).

Similarly, it is not intended that the present invention be limited by the nature of the method used to form the chamber (207). In one embodiment, it is molded as one piece. In another embodiment it is molded in separate pieces and then assembled.

FIG. 9 shows that the temperature control liquid is introduced via tubes (212, 212) from a liquid source (not shown) and is circulated via liquid inlet and outlet ports (not shown). It is not intended that the present invention be limited to any particular temperature control liquid. One inexpensive temperature control liquid contemplated by the invention is water.

FIG. 10 shows the positioning of reflectors (214,215). It is preferred that the reflectors be made from UV reflecting metal.

FIG. 9 shows CE-II with twenty intrusions (208) placed within the boundary defined by tubes (212, 213). While the number of intrusions (208) and their placement may be selected to suit the convenience of the user, there can be a significant impact on irradiation efficiency. In this embodiment, the intrusions (208) were aligned in two rows with the intrusion (208) of one row lined up opposite the intrusion (208) of the other row. Performance data obtained subsequent to the design indicated that this arrangement of intrusions (208) may cause the electromagnetic radiation to be partially blocked, i.e. the intrusion (208) of one row is blocking electromagnetic radiation coming from one side of the device so that the intrusion (208) opposite from it in the other row receives less electromagnetic radiation.

FIG. 10 shows the "V-shape" geometry of the bulb (201–206) placement of this embodiment in relation to the chamber (207). The V-shape geometry is, in large part, dictated by the dimension demands placed on the chamber (207) by virtue of the double row arrangment of the intrusions (208). The distance from the center of one intrusion (208) in one row and to the center of the opposite intrusion (208) in the other row is greater than 5.5 cm. This causes the upper level bulbs (201, 206) to be placed almost 13.5 cm apart (measured center to center), the middle level bulbs (202, 205) to be placed almost 11.5 cm apart (measured center to center), and the lower level bulbs (203, 204) to be placed almost 4.0 cm apart (measured center to center).

It is preferred that the relationship of the chamber (207) length ("CL") to the bulb (201–206) length ("BL") and to the reflector (214,215) length ("RL") is as follows:

RL>BL>CL

In this embodimnt, CL=approximately 37 cm.

EXAMPLE 32

Photoactivation Device

A preferred embodiment of the photoactivation device of the present invention is designated "CE-III." CE-III is an irradiation device created to optimize rapid photoactivation having the following features: 1) an inexpensive source of electromagnetic radiation, 2) temperature control of the sample, 3) control of irradiation time, 4) a multisample holder, 5) a multiple sample irradiation format, 6) a housing that shields the user from stray electromagnetic radiation, and 7) a compact design that requires minimal bench space.

Figure 11:
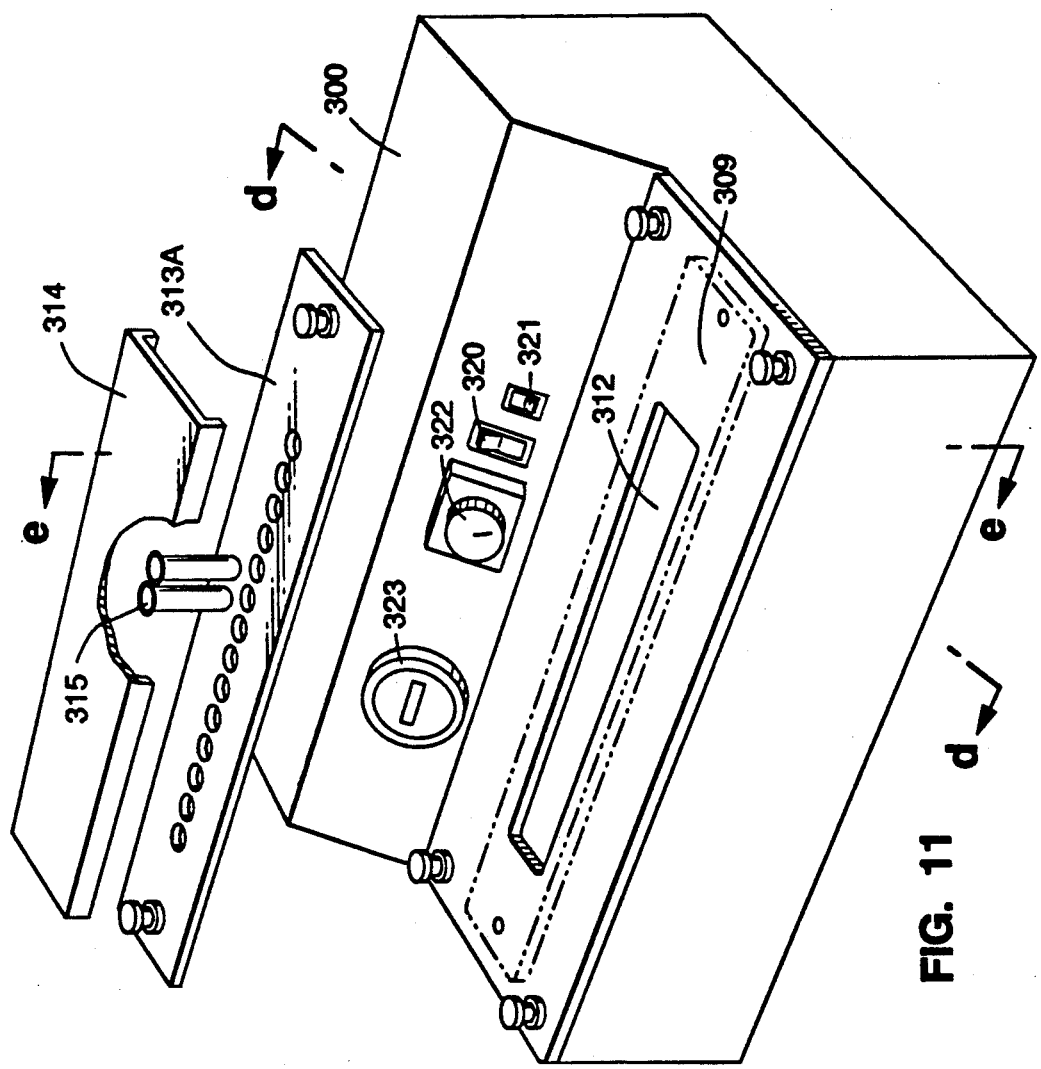
FIG. 11 is a perspective view of yet another alternative embodiment (CE-III) of the photoactivation device of the present invention.
Figure 12:
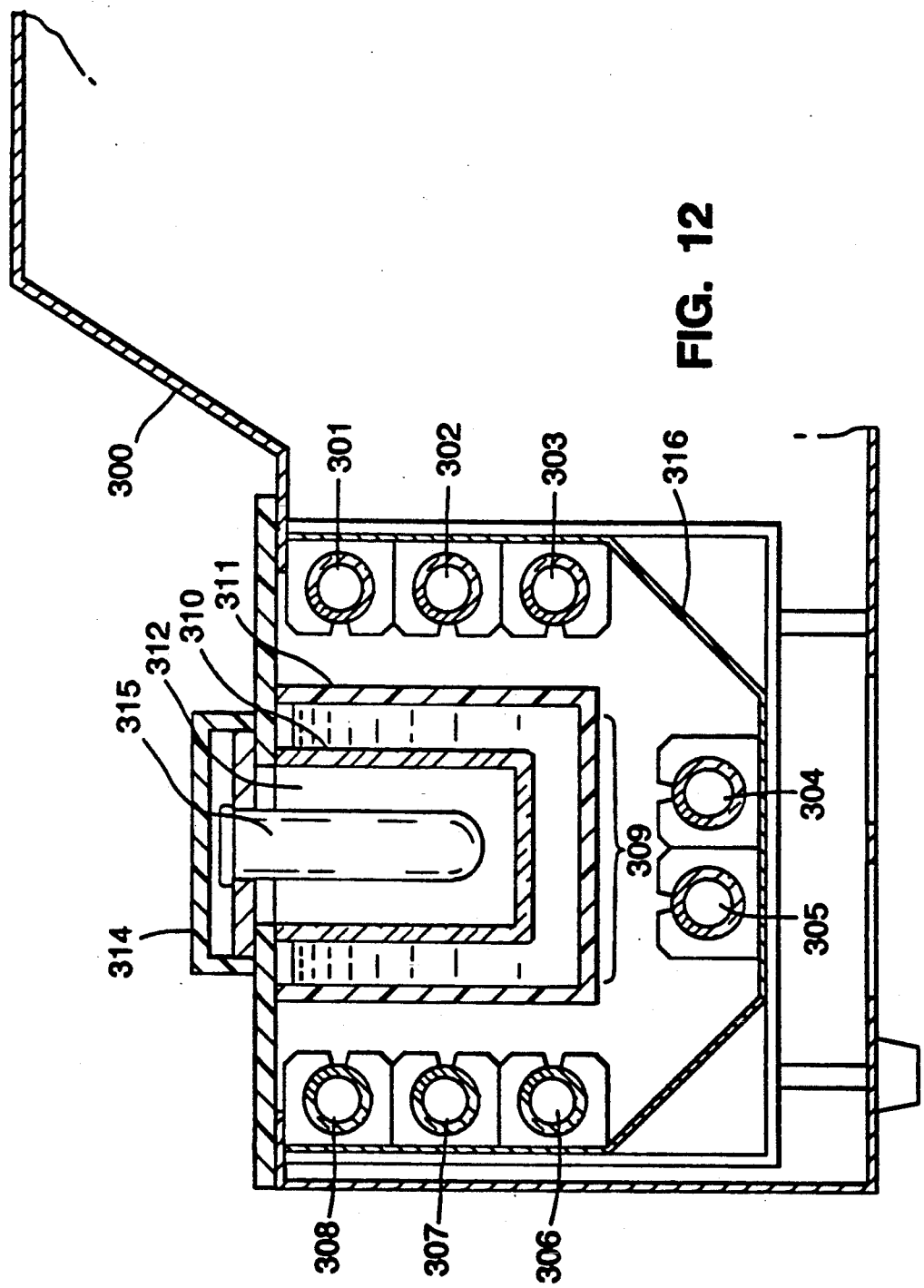
FIG. 12 is a cross-sectional view of CE-III along lines d—d of FIG. 11.
Figure 13:
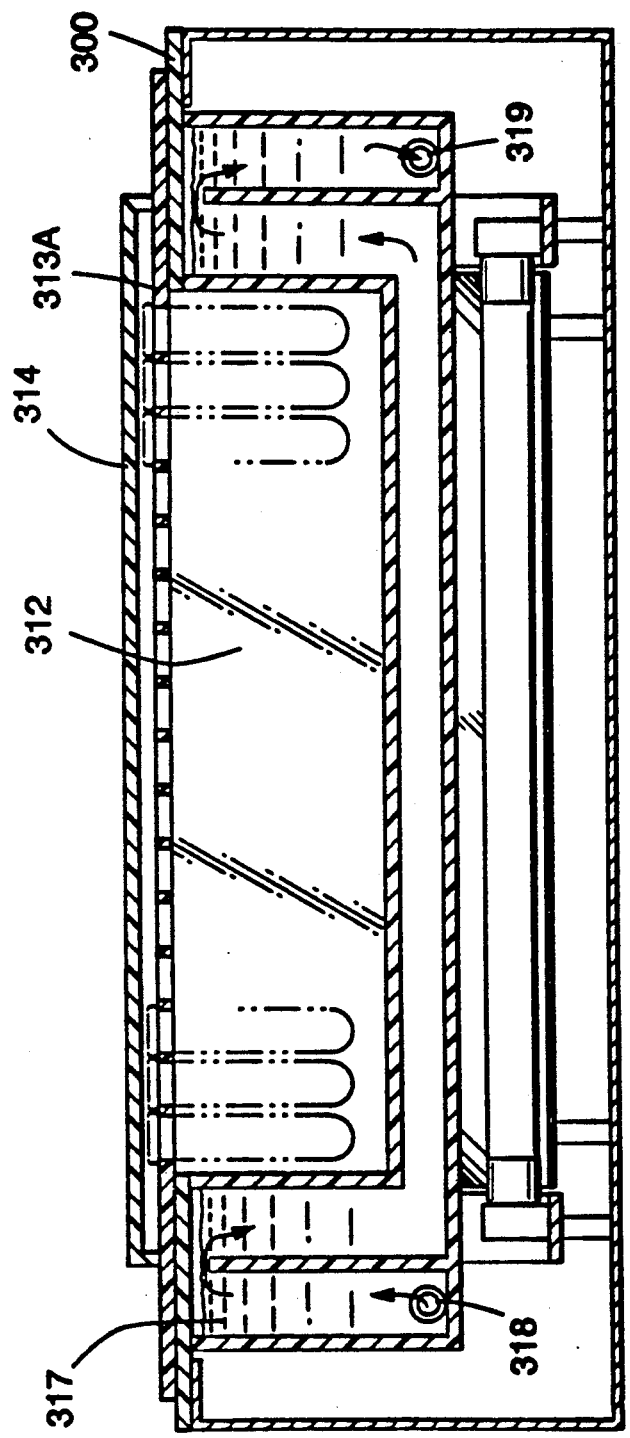
FIG. 13 is a cross-sectional view of CE-III along lines e—e of FIG. 11.

FIGS. 11, 12 and 13 are views of CE-III, integrating the above-named features, showing a housing (300) containing eight bulbs (301–308) connectable to a power source (not shown) arranged around a detachable chamber (309), having interior (310) and exterior walls (311). The interior walls (310) form a trough (312). FIGS. 11 and 13 show one embodiment of an interchangeable, detachable sample rack (313A). The sample rack (313A) is detachably coupled to the housing (300) above the trough (312). Sample vessels (315) fit in the sample rack (313A) and are thereby aligned in the trough (312). A sample overlay (314) extends over and covers the interchangeable sample rack (313A) sealing the unit and shielding the user from electromagnetic radiation when the device is in operation.

Figure 14:
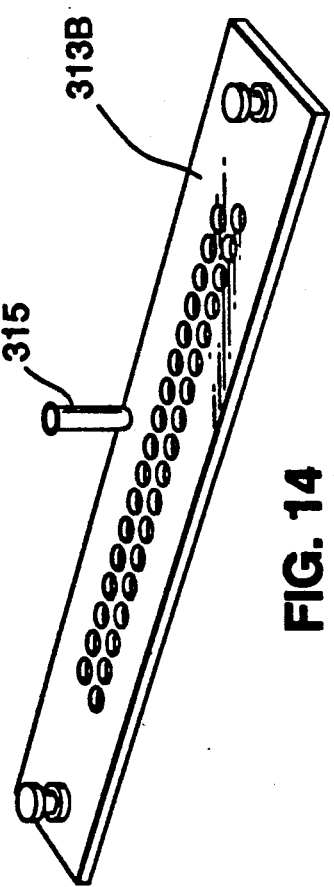
FIG. 14 is a perspective view of a removable sample tray for processing large numbers of samples.

FIG. 14 shows an alternative embodiment of an interchangeable, detachable sample rack (313B). Note that in this embodiment, the placement of sample vessels (315) in two rows is staggered to avoid blocking electromagnetic radiation (compare with CE-II, above).

FIG. 12 shows a unitary reflector (316) extending around all the bulbs (301–308) of the device. It is preferred that the reflector (316) is made of UV reflecting material.

The chamber (309) holds circulating temperature control liquid (317) between the interior (310) and exterior walls (311), thereby serving as a means for controlling the temperature of the sample vessels (315). FIG. 13 shows that the circulating temperature control liquid (317) is introduced from a liquid source (not shown) via a liquid inlet port (318) and removed via a liquid outlet port (319), allowing for recirculation of the liquid. To improve temperature control, static temperature control liquid (not shown) may be placed in the trough. It is not intended that the present invention be limited to any particular temperature control liquid. One inexpensive temperature control liquid contemplated by the invention is water.

It is not intended that the present invention be limited by the nature of the material used to form the chamber (309). In one embodiment, it is made of glass. In another embodiment, it is made of plastic. In a preferred embodiment, it is made of UV transmitting acrylic selected from the group of commercial acrylics consisting of ACRYLIC-UVT (Polycast), PLEXIGLAS 11-UVT (Rohm & Haas), PLEXIGLAS G-UVT (Rohm & Haas) and ACRYLITE OP-4 (Cyro).

Similarly, it is not intended that the present invention be limited by the nature of the method used to form the chamber (309). In one embodiment, it is molded as one piece. In another embodiment it is molded in separate pieces and then assembled.

The housing (300) also serves as a mount for several electronic components. A main power switch (320) controls the input current from the AC power source (not shown). For convenience, this power switch is wired to a timer activation switch (321); in the "ON" position, the timer activation switch (321) provides power to a count down timer (322). The count down timer (322) in turn controls the current to an hour meter (323) and to the coils (not shown) of the source of electromagnetic radiation. The count down timer (322) permits a user to preset the irradiation time to a desired level of sample exposure. The hour meter (323) maintains a record of the total number of radiation hours that are provided by the source of electromagnetic radiation. This feature permits the bulbs (301–308) to be monitored and changed before the output diminishes below a level necessary to achieve rapid photoactivation. In the "OFF" position, timer activation switch (321) is wired such that it bypasses the count down timer (322) and provides continual power to the hour meter (323) and the coils (not shown) of the source of electromagnetic radiation.

FIG. 12 shows the "U-shape" geometry of the bulb (301–308) placement of this embodiment in relation to the chamber (309). (Compare with the V-shape geometry of CE-II.) The U-shape geometry is, in large part, allowed by the smaller dimensions of the chamber (207) by virtue of the trough (312) design.

While not limited by the particular dimensions, the width of the trough (312), when measured by the length of the bottom exterior wall (311) is 6 cm. The upper level bulbs (301, 308) are placed less than 9 cm apart (measured center to center).

Again, it is preferred that the chamber (309) length ("CL"), the bulb (301–308) length ("BL") and the reflector (317) length ("RL") follow the relation ship: $RL > BL > CL$.

EXAMPLE 33

Photoactivation Device: Temperature Control

Temperature changes can have a drastic impact on photoactivation chemistry. It is desired that the devices of the present invention provide temperature control to limit the possibility of uncontrolled changes on photoactivation results.

Figure 15A:
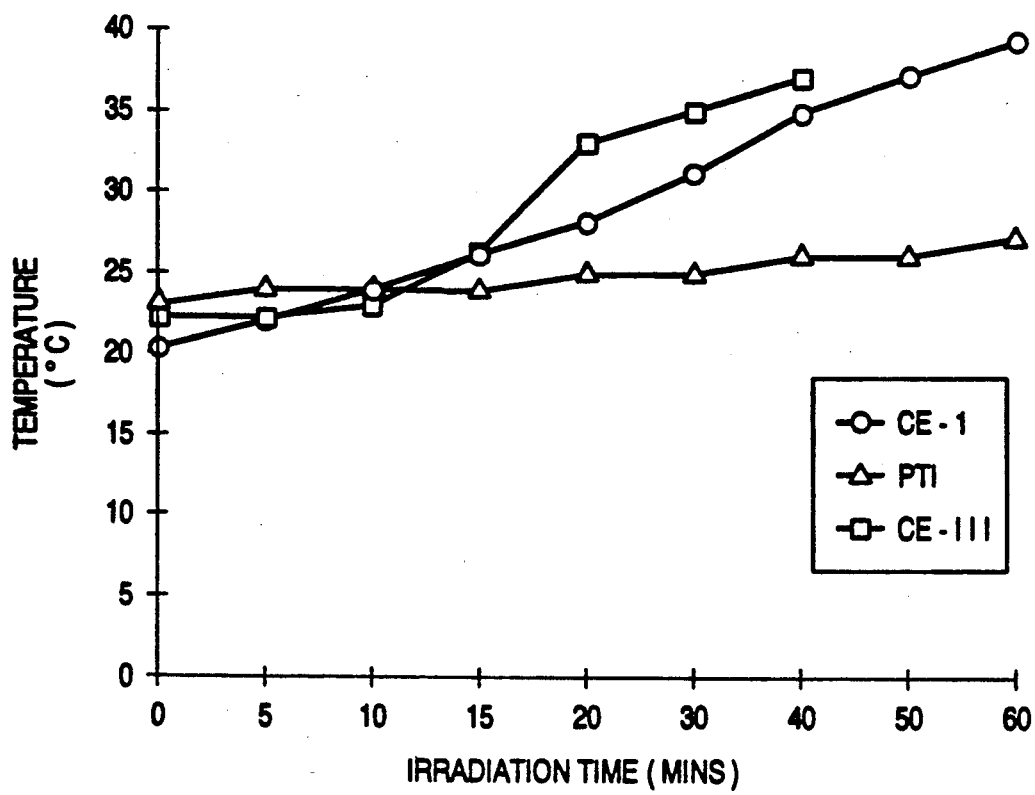
FIG. 15A shows the impact of irradiation time on temperatures of the sample using particular embodiments of the photoactivation device.
Figure 15B:
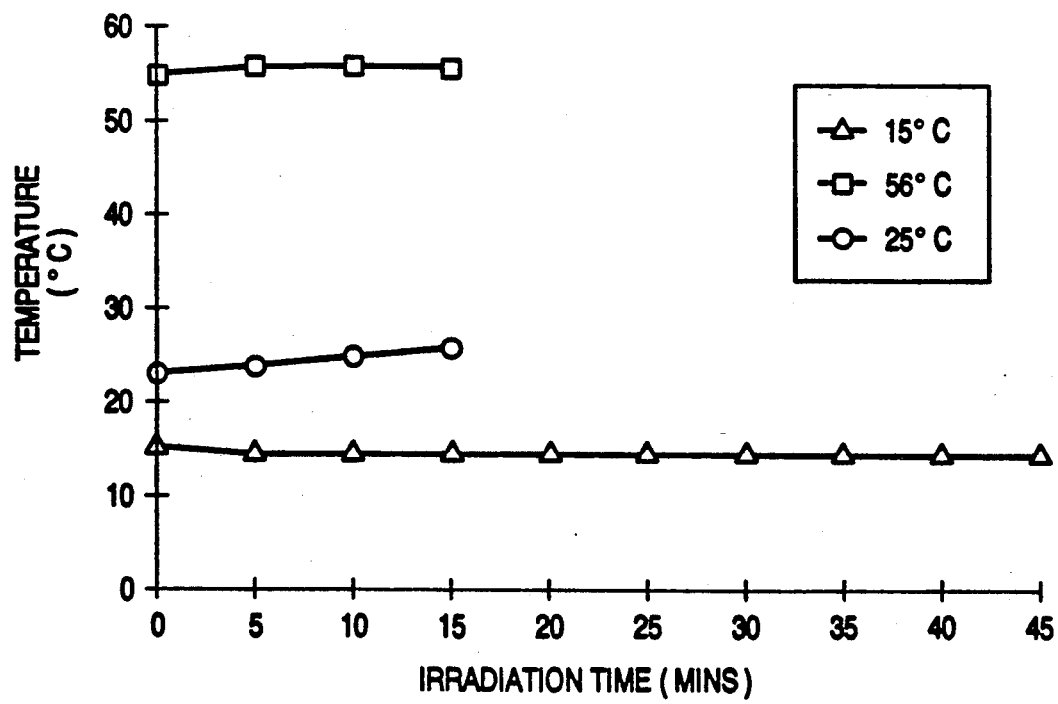
FIG. 15B shows the impact of irradiation time on temperatures of the sampling using three different temperatures.

FIG. 15 illustrates the problem of lack of temperature control for the devices of the present invention. CE-I, CE-III and the PTI device were allowed to irradiate 1.5 ml Eppendorph tubes without using the means for controlling the temperature of the sample vessels of the present invention. The temperature of the temperature control liquid was measured over time. Measurements were conducted with a type T thermocouple immersed into a 0.5 ml Eppendorph tube containing 100 $\mu$l of dH$_2$O. The Eppendorph tube was irradiated in each device. For irradiations with the PTI device, the tube was irradiated from the top down, with the cap closed. Temperature was monitored on an Omega Temperature Controller, Model 148 (Omega Engineering, Inc., Stamford, Conn.).

The results (FIG. 15A) show that the temperature of the sample vessel rapidly increases in temperature without temperature control. By contrast, irradiations with temperature control (FIG. 15B) show a constant temperature.

EXAMPLE 34

Photoactivation Device: Energy Output

Figure 16:
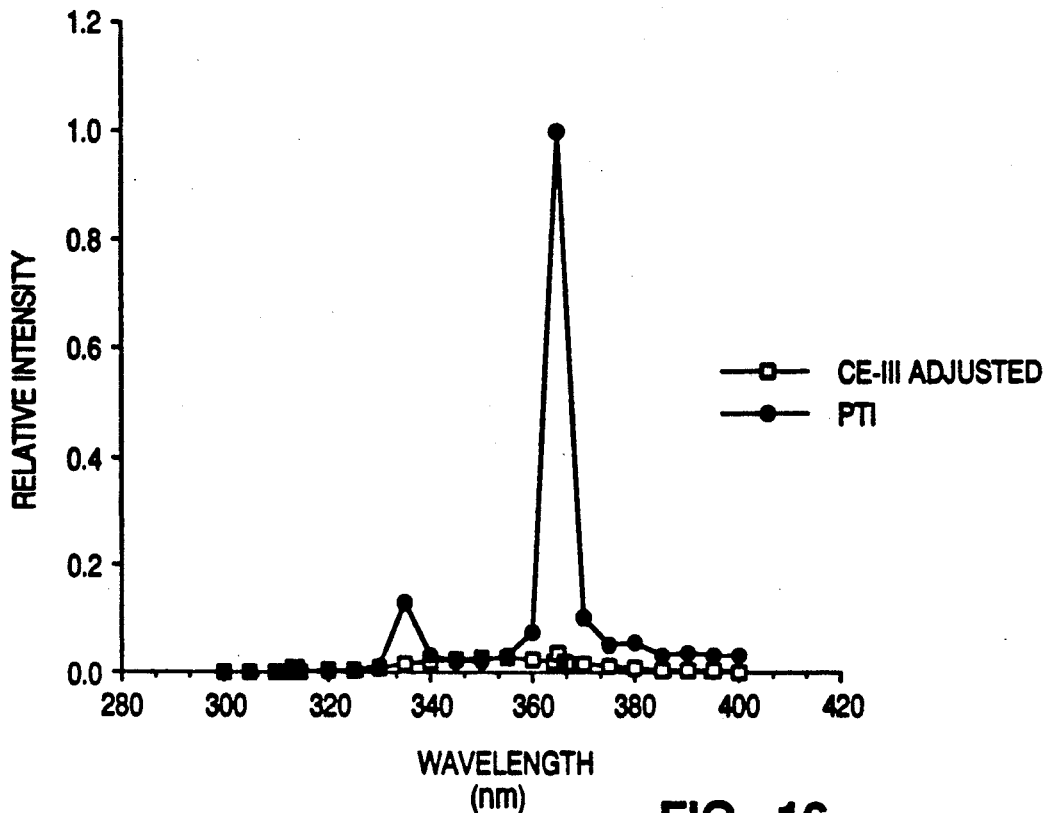
FIG. 16 shows the relative energy output of the alternative embodiments of the device of the present invention.
Figure 17:
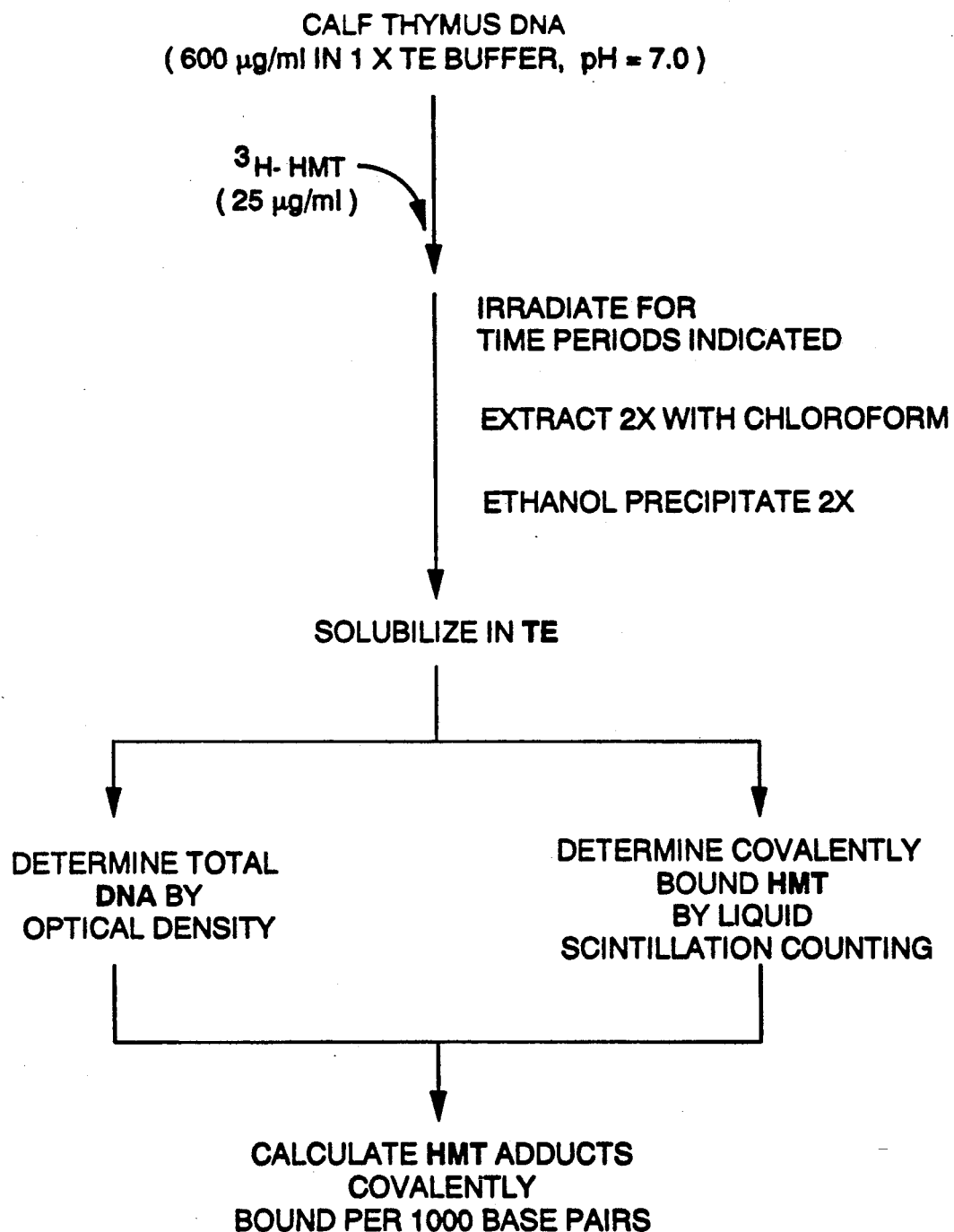
FIG. 17 is a flow chart schematically showing a manner of measuring binding.

This example investigates energy output as it relates to optimum photobinding kinetics. FIG. 16 shows the relative energy output of the devices of the present invention. The PTI device has a tremendously strong intensity relative to CE-III. From the relative intensity output it would appear that the fluorescent source of ultraviolet irradiation is not of sufficient flux for rapid photoactivation. At the very least, a dramatic difference in kinetics of photobinding was expected for the two machines. The impact of this difference on binding was investigated as shown in FIG. 17. $^3$H-HMT was used to measure binding to calf thymus DNA. $^3$H-HMT was mixed with the DNA and irradiated. The product was then extracted with chloroform to separate the unbound $^3$H-HMT. The nucleic acid was then precipitated and solubilized. Bound HMT was determined by scintillation counting along with measuring the optical density of the DNA solution.

Figure 18:
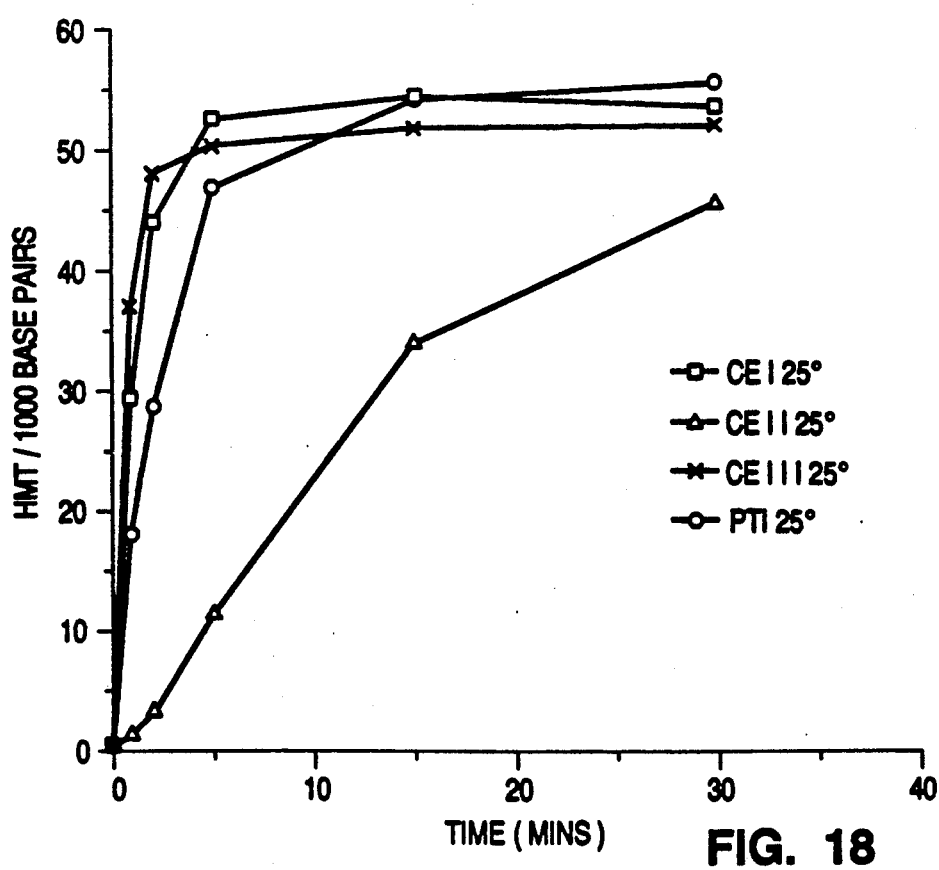
FIG. 18 shows covalent binding according to particular embodiment of the photoactivation device of the present invention.

The results are shown in FIG. 18. Surprisingly, the kinetics of the CE-III device are essentially the same as the costly PTI device. Plateau binding for the CE-III and PTI machines was reached in less than five minutes. Interestingly, CE-II did not reach plateau binding under the conditions of the experiment. (Plateau binding might be reached with the CE-II device in one of two ways: 1) additional radiation time, or 2) use of a sample vessel with better UV transmission properties such as a polycarbonate tube).

EXAMPLE 35

Photoactivation Device: Sample Position

Figure 19:
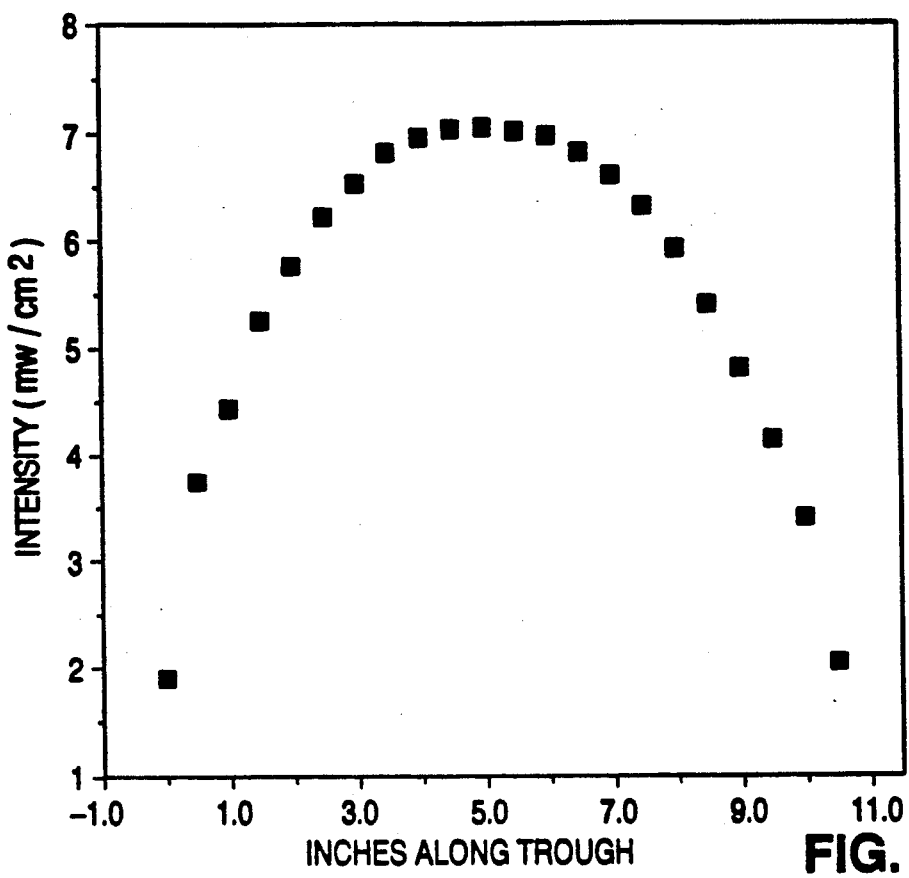
FIG. 19 shows the intensity of the light of one embodiment of the device of the present invention according to sample position.
Figure 20:
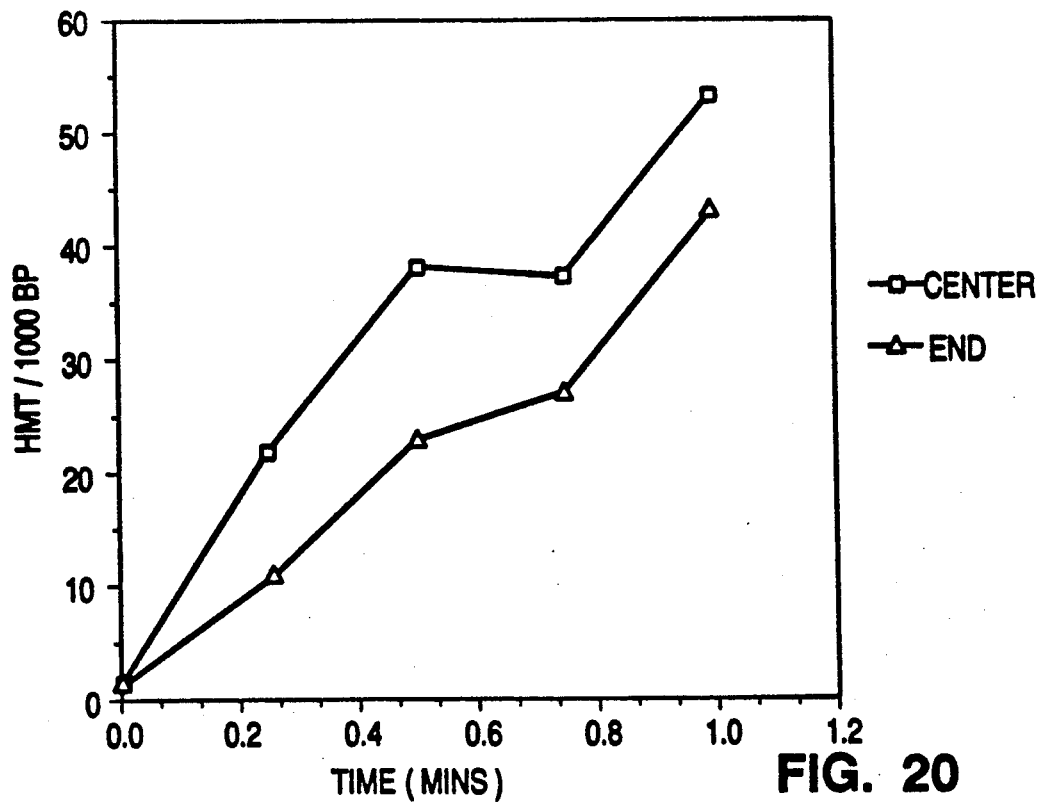
FIG. 20 shows covalent binding according to sample position.

The impact of the small differences in position of samples within the photoactivation device was investigated. FIG. 19 shows the intensity of the light of CE-III at the surface of the trough (FIG. 12, element 312) according to sample position. Samples from the center position and the end position of the sample rack (FIG. 11, element 313A) were examined for photobinding in the manner outlined in FIG. 17. The results are shown in FIG. 20. It is clear that some difference in photoaddition kinetics exists when the irradiation time is below two minutes. This illustrates the importance of plateau binding to nullify such small positional differences (contrast FIG. 20 with FIG. 18).

EXAMPLE 36

Photoactivation Device: Photoproduct

In the first part of this example, the various embodiments of the photoactivation device of the present invention were investigated for their ability to create photoproduct. In the second part, photoproduct is shown to bind to nucleic acid.

Figure 21:
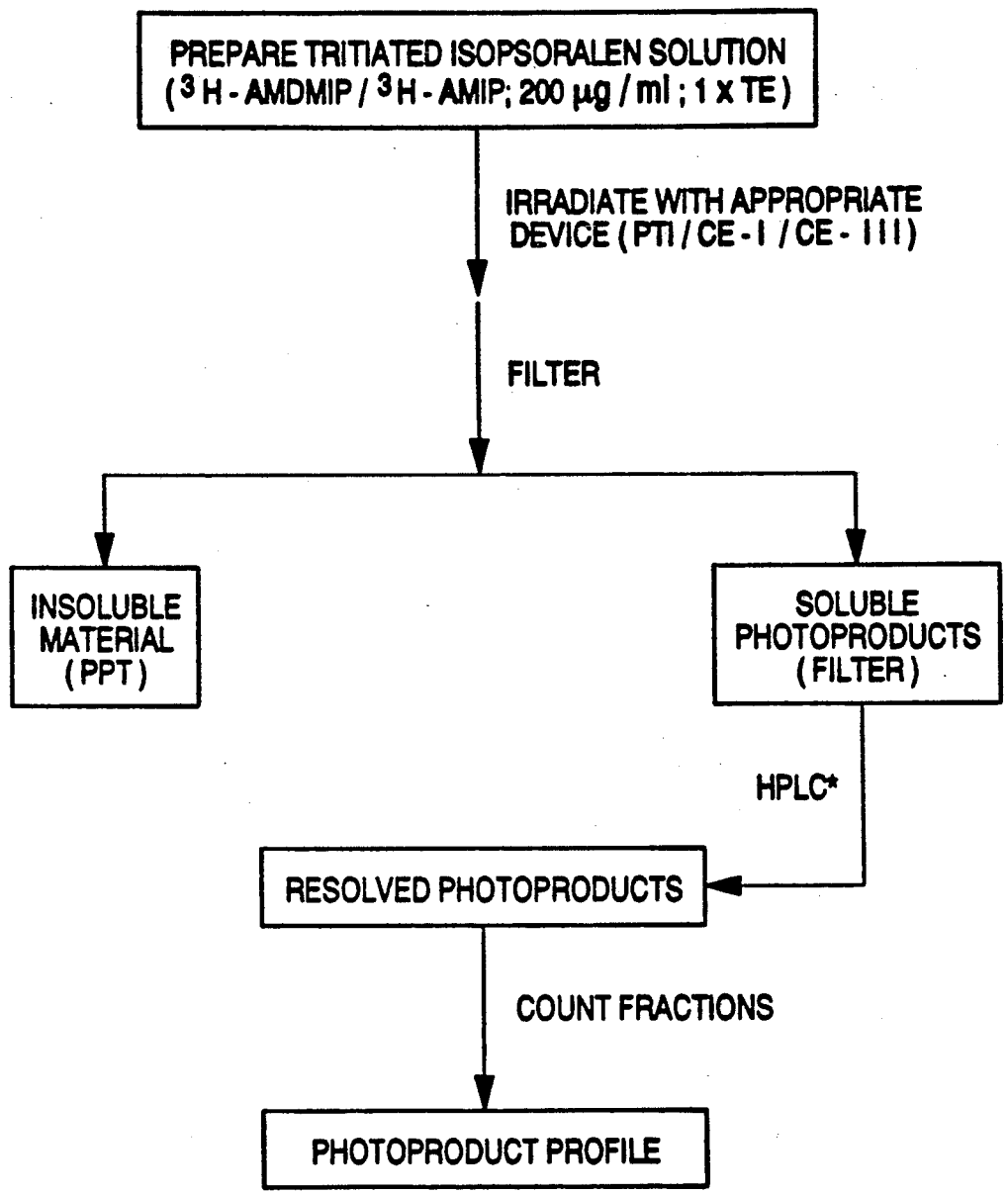
FIG. 21 shows schematically a manner of measuring production of photoproduct.
Figure 22A:
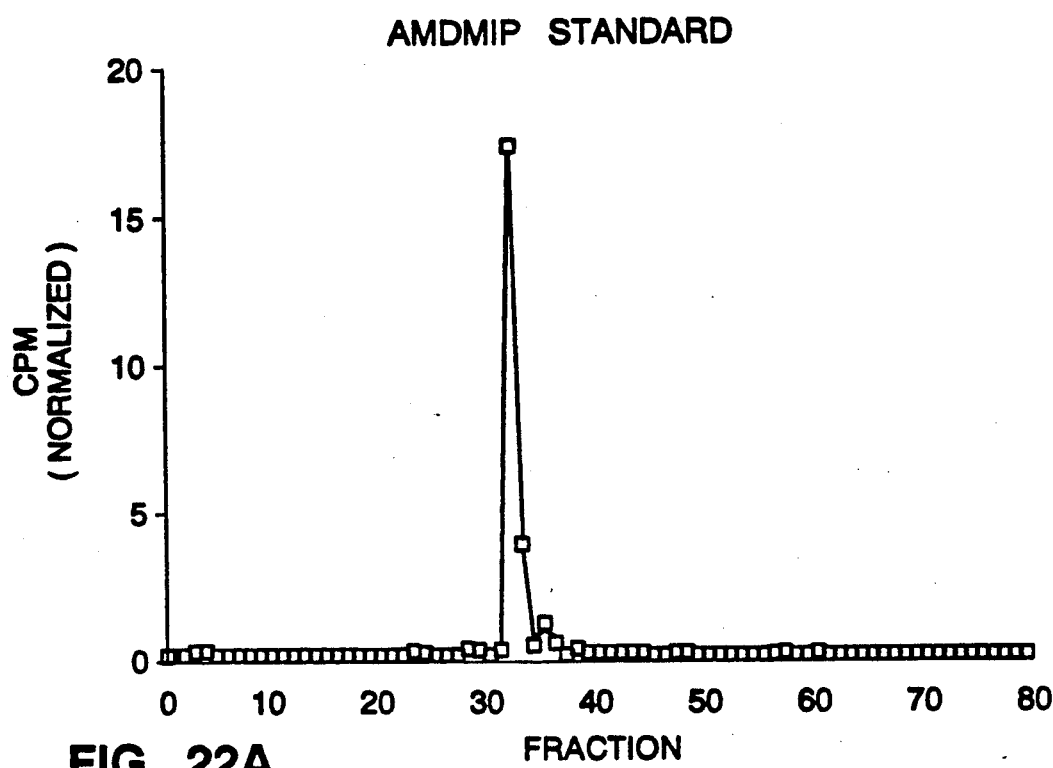
FIG. 22A shows the production of photoproduct over time with no irradiation.
Figure 22B:
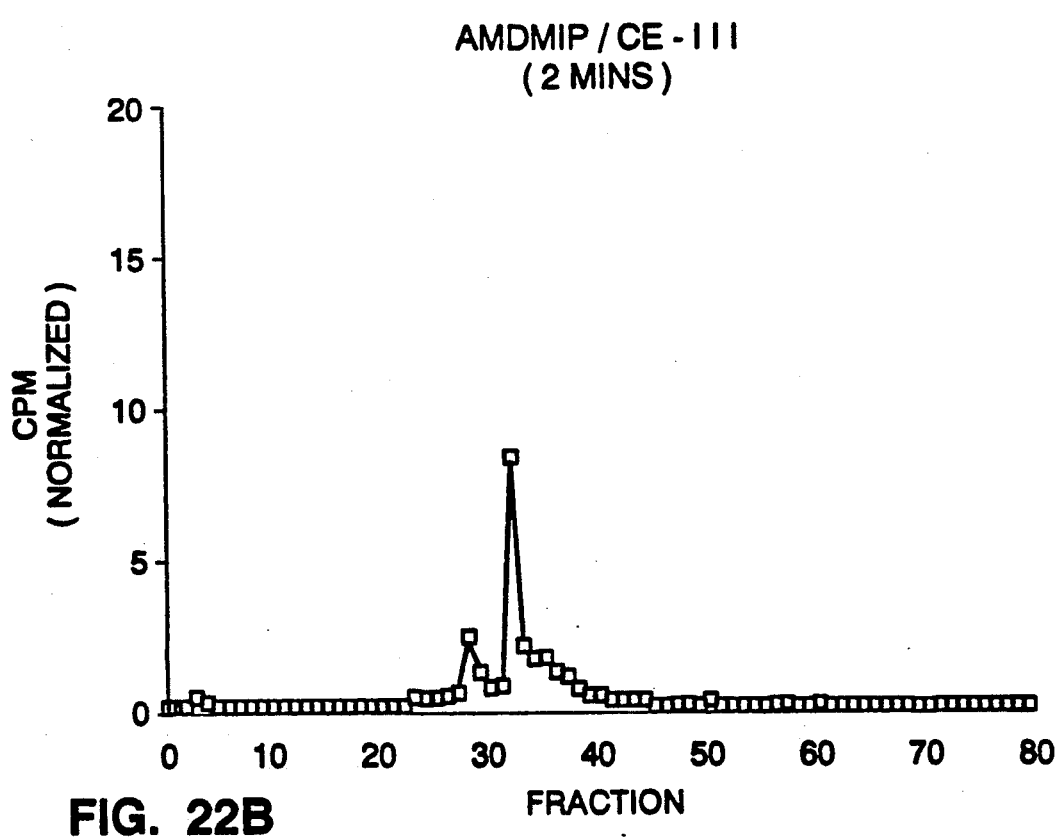
FIG. 22B shows the production of photoproduct over time after 2 mins of irradiation.
Figure 22C:
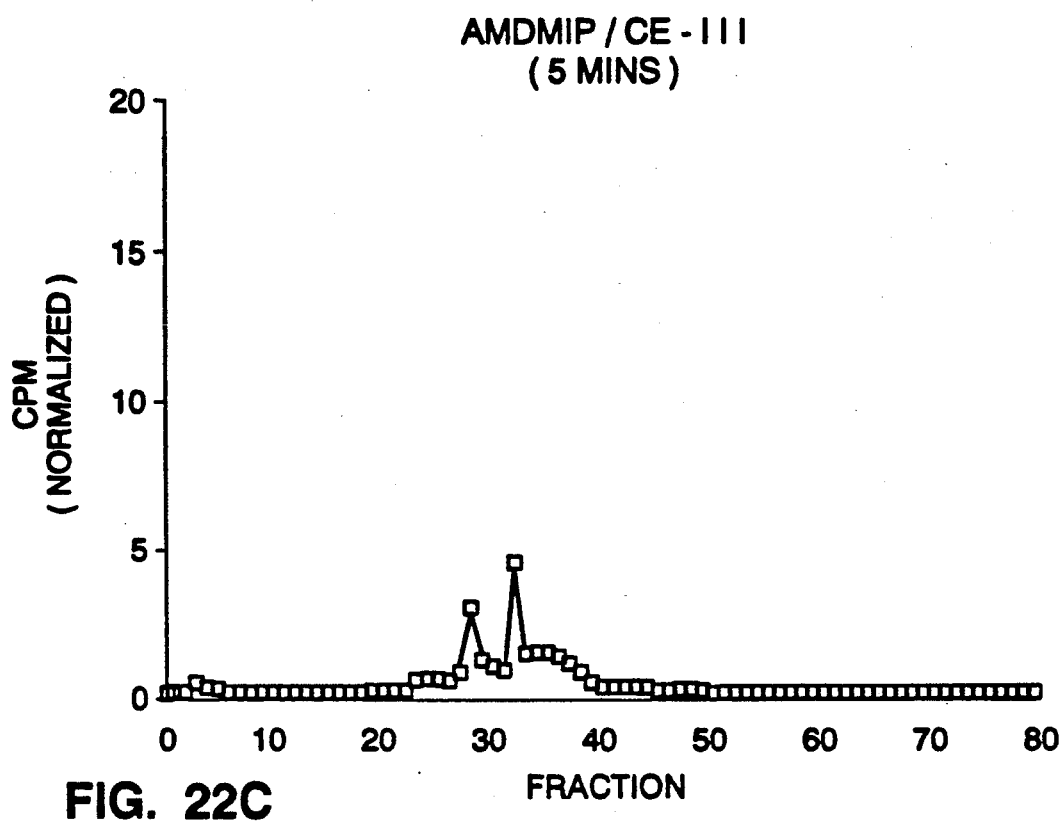
FIG. 22C shows the production of photoproduct over time after 5 mins of irradiation.
Figure 22D:
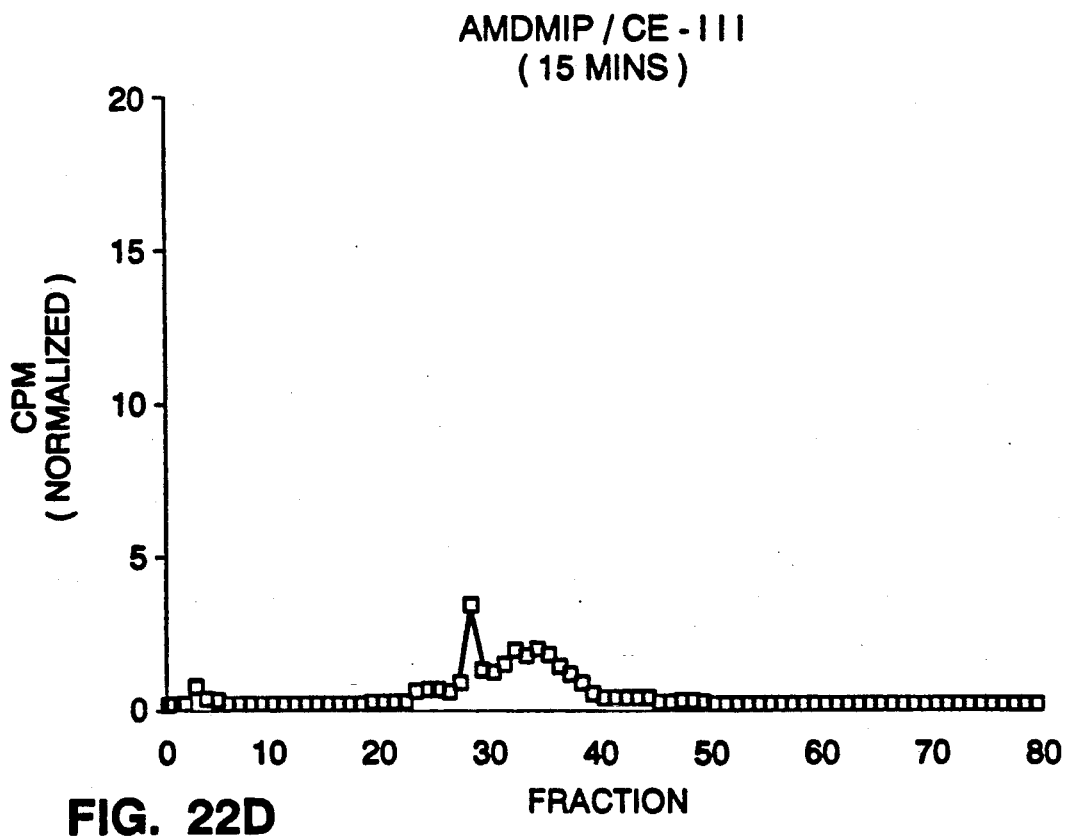
FIG. 22D shows the production of photoproduct over time after 15 mins of irradiation.

FIG. 21 shows schematically the manner in which photoproduct generation was investigated. FIG. 22 shows the production of photoproduct over time on the CE-III device for known compound AMDMIP. While the AMDMIP standard (unirradiated compound) shows a single peak on HPLC (FIG. 22A), AMDMIP photoproduct peaks increase and the AMDMIP peak diminishes from two minutes (FIG. 22B), five minutes (FIG. 22C) and fifteen minutes (FIG. 22D).

Figure 23A:
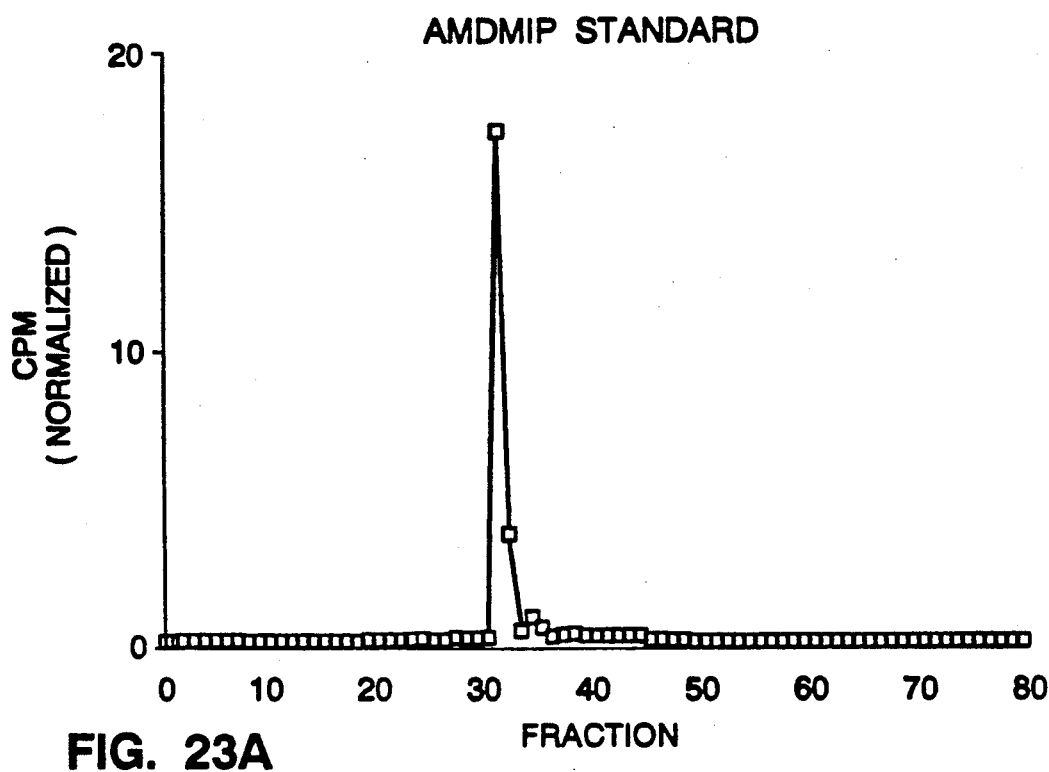
FIG. 23A shows the production of photoproduct over time with no irradiation.
Figure 23B:
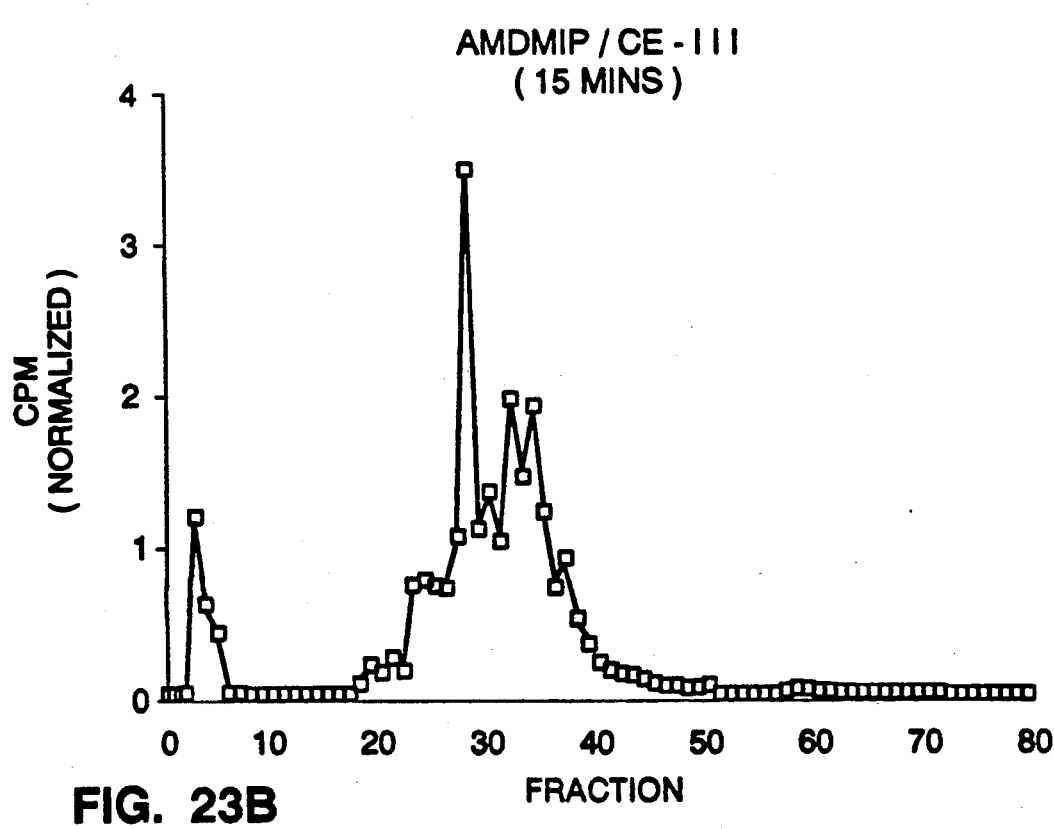
FIG. 23B shows the production of photoproduct over time after 15 mins of irradiation with the CE-III photoactivation device.
Figure 23C:
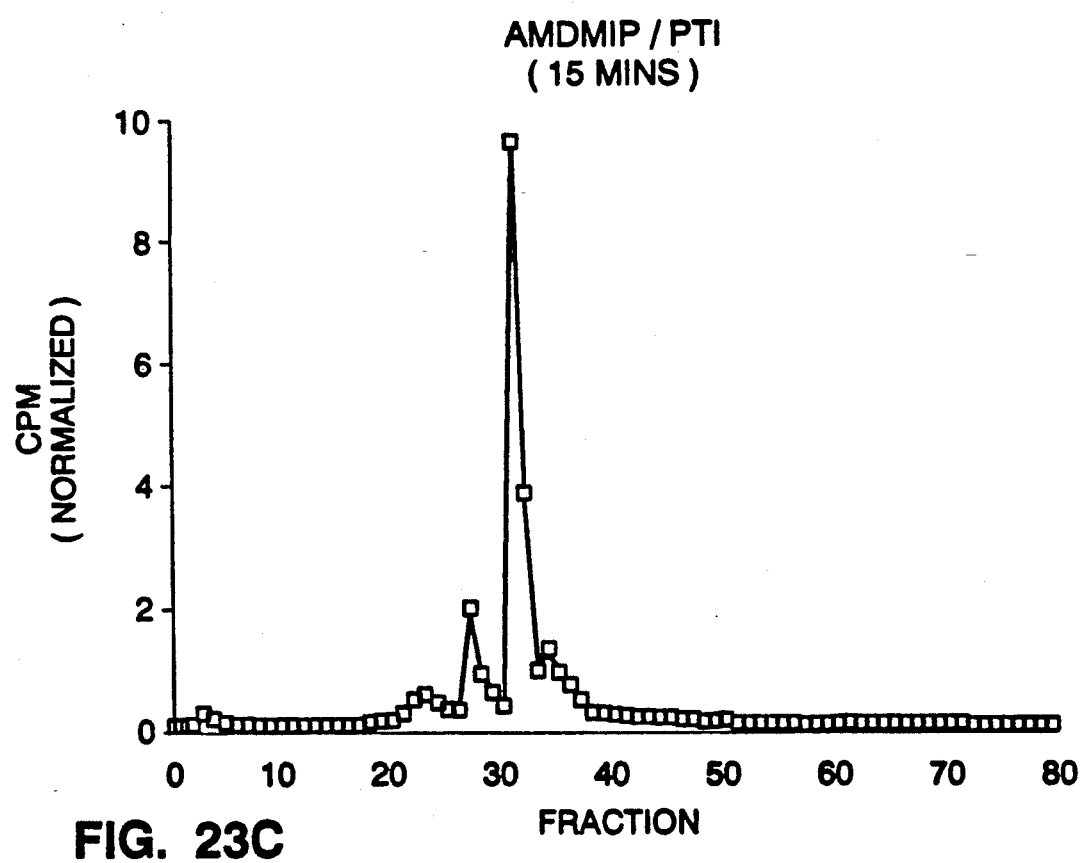
FIG. 23C shows the production of photoproduct over time after 15 mins of irradiation with the PTI photoactivation device.
Figure 24A:
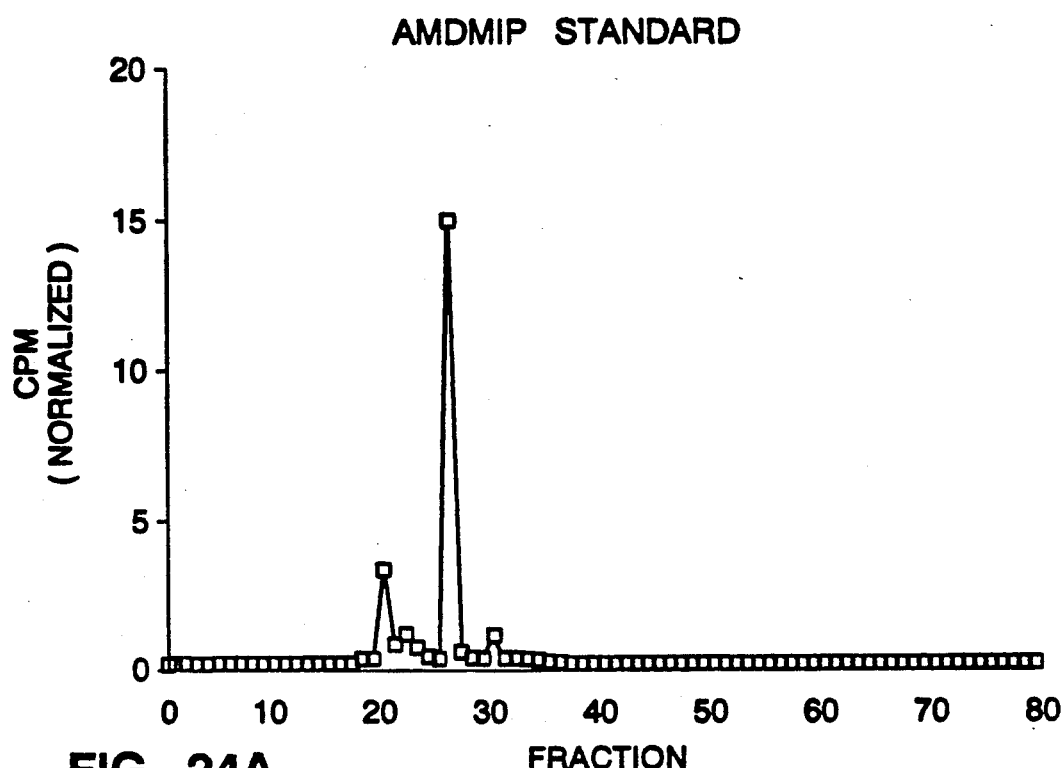
FIG. 24A shows the production of photoproduct from a novel compound of the present invention with no irradiation.
Figure 24B:
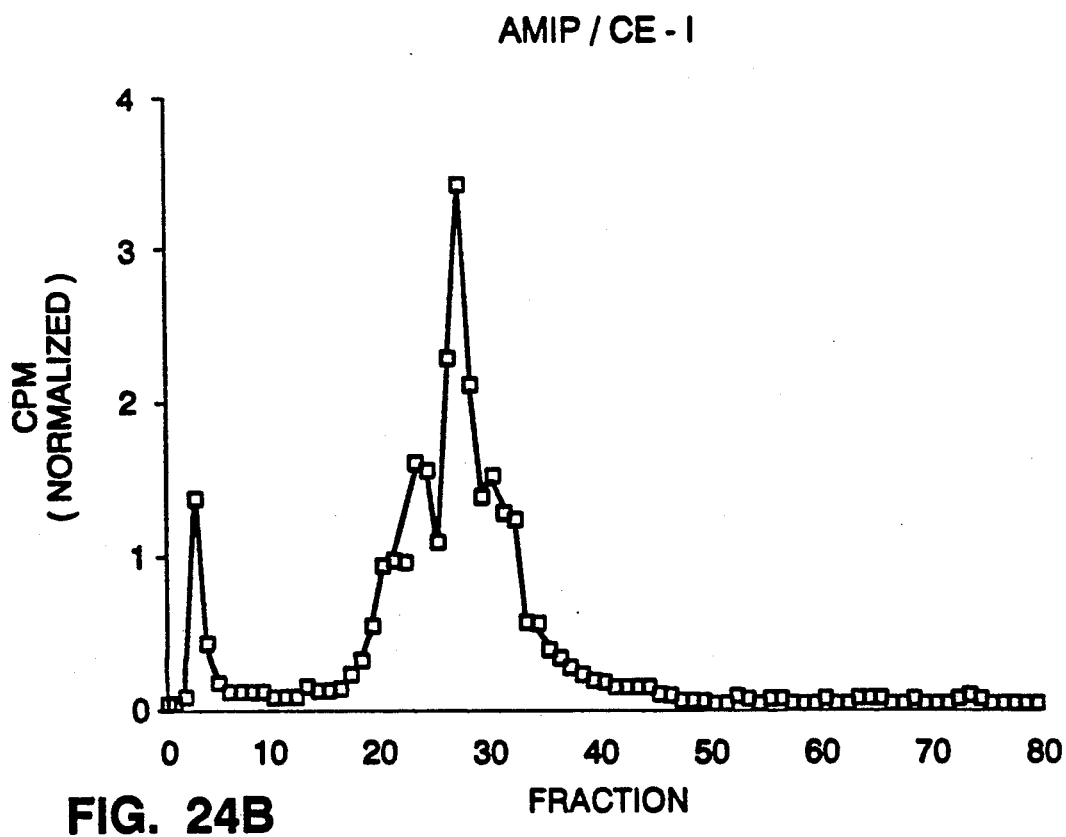
FIG. 24B shows the production of photoproduct from a novel compound of the present invention with irradiation from the CE-I photoactivation device.
Figure 24C:
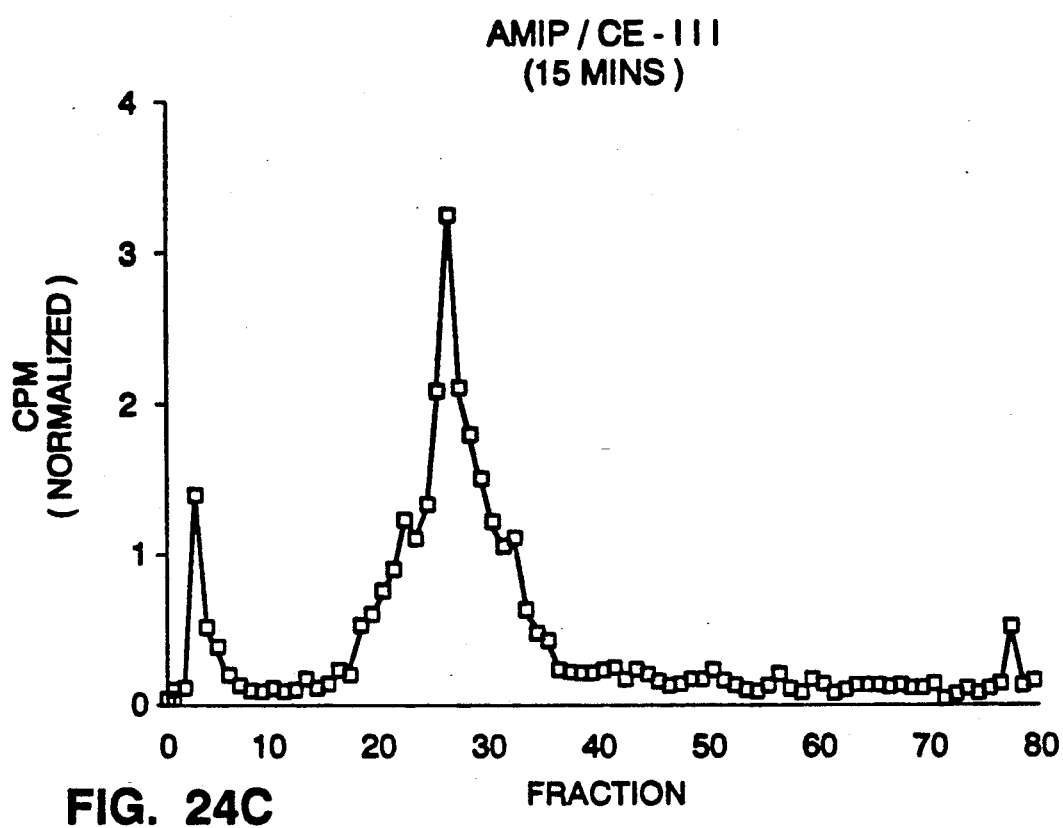
FIG. 24C shows the production of photoproduct from a novel compound of the present invention with irradiation from the CE-III photoactivation device.
Figure 24D:
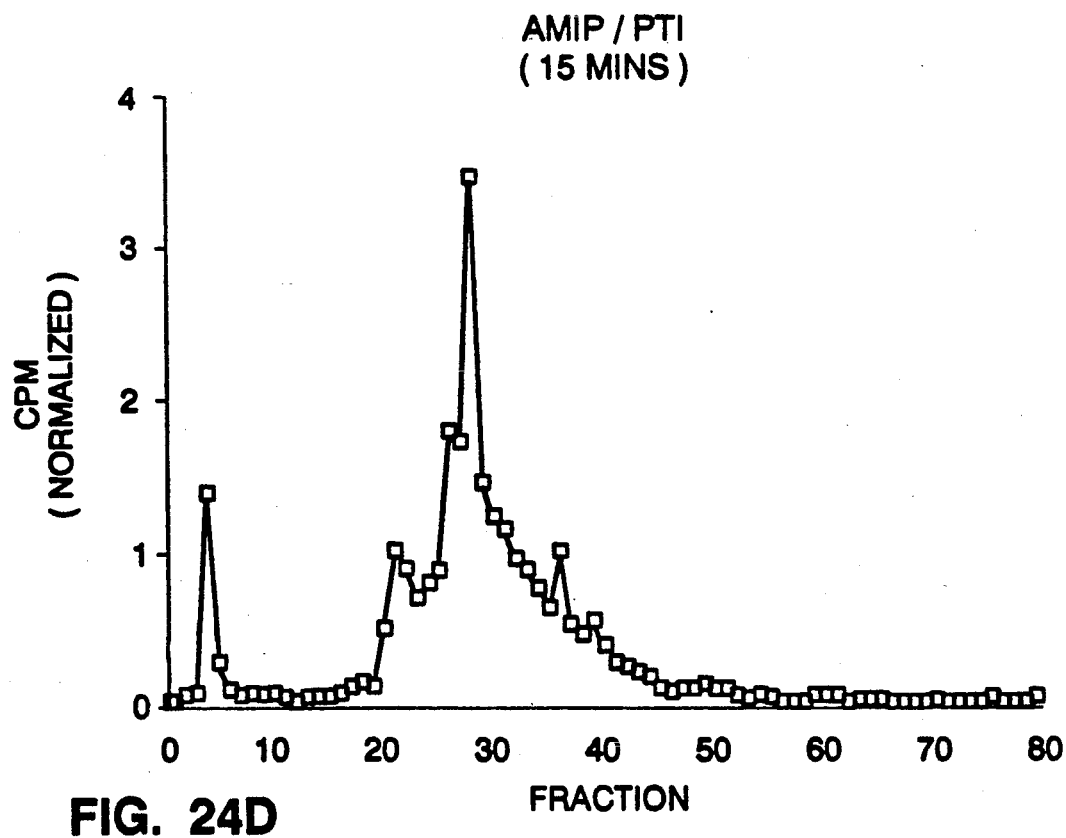
FIG. 24D shows the production of photoproduct from a novel compound of the present invention with irradiation from the PTI photoactivation device.

FIG. 23 shows production of photoproduct according to the photoactivation device used for known compound AMDMIP. Again the AMDMIP standard is a single peak on HPLC (FIG. 23A). By contrast, the fifteen minute irradiation with CE-III shows increase in photoproduct peaks and a decrease in the AMDMIP peak (FIG. 23, compare A to B and note scale change). Irradiation for the same time period, however, on the PTI device shows very little reduction in the AMDMIP peak and very little generation of photoproduct peaks (FIG. 23, compare A to C and note scale change). Clearly, the CE-III device generates more AMDMIP photoproduct than does the PTI device.

FIG. 24 shows production of photoproduct according to the photoactivation device used for novel compound AMIP. The AMIP standard is primarily a single peak on HPLC (FIG. 24A). By contrast, the fifteen minute irradiation with CE-I device shows the appearance of photoproduct peaks and a decrease in AMIP the peak (FIG. 24, compare A to B and note scale change). Similarly, the fifteen minute irradiation with CE-III device shows the appearance of photoproduct peaks and a decrease in the AMIP peak (FIG. 24, compare A to C and note scale change). Interestingly, irradiation of AMIP for the same time period with the PTI device shows approximately the same amount of photoproduct formation as with the CE-I and CE-III devices (FIG. 24, compare D with B and C).

The nucleic acid binding properties of photoproduct were investigated with calf thymus DNA. 200 µg/ml of $^3$H-AMDMIP ($1 \times 10^5$ CPM/ml) in Taq buffer was irradiated at room temperature with either the CE-III device or the PTI device. This irradiation was performed for 15 minutes in the absence of nucleic acid. Following the irradiations, 200 µl of the irradiated solution was mixed with 200 µl of 1000 µg/ml DNA solution in Taq buffer. Several identical samples were prepared in this manner. One set of samples was allowed to react with the DNA for 2 hours at room temperature. The other set of samples was subjected to 30 cycles of heating and cooling by placing the samples in a thermal cycler [Perkin-Elmer Cetus DNA Thermal Cycler (Part No. N8010150); each cycle involved 93° C. for 30 seconds, 55° C. for 30 seconds and 72° C. for 1 minute]. When the DNA reactions were complete, all samples were analyzed for DNA-associated tritium counts (CPM) by following the flow chart outlined in FIG. 17.

The DNA-associated counts are given in terms of adducts per 100 base pairs in Table 10. For calculation purposes, these adducts are reported as if they represented monomers of AMDMIP. Regardless of the accuracy of this approximation, the process of irradiating $^3$H-AMDMIP clearly results in a tritiated product which associates (i.e. binds) with DNA in the absence of subsequent activating wavelengths of electromagnetic radiation. The extent of the association is shown in Table 10 to depend upon the reaction conditions.

Binding is influenced by the photoactivation device used. When $^3$H-AMDMIP irradiated with the CE-III device is compared with $^3$H-AMDMIP irradiated with the PTI device, a significantly greater amount of associated counts is observed. This can be viewed as consistent with the observation (FIG. 23) that more photoproduct is made with CE-III than with the PTI device after the same exposure time. Interestingly, thermal cycling results in a five fold higher association than a 2 hour reaction at room temperature (reqardless of the device used).

As seen by the results with no irradiation, the isolation procedure that was applied to the DNA samples to remove unbound reactants removes most of the non-covalently associated reactants. The increase in counts seen when irradiated AMDMIP reacts with DNA, relative to those counts seen when unirradiated AMDMIP is reacted, is therefore presumed to be due to covalent association of photoproduct with DNA.

TABLE 10

| | Binding of Photoproduct to Nucleic Acid | | |
|---|---|---|---|
| DEVICE | IRRADIATION | DARK REACTION TREATMENT | ADDUCTS PER 1000 BASE PAIRS |
| None | None | Room Temp. | 1.1 |
| None | None | Thermally Cycled | 0.9 |
| CE-II | 15 mins. | Room Temp. | 4.4 |
| CE-III | 15 mins. | Thermally Cycled | 24.3 |
| PTI | 15 mins. | Room Temp. | 1.7 |
| PTI | 15 mins. | Thermally | 5.7 |

TABLE 10-continued

| | Binding of Photoproduct to Nucleic Acid | | |
|---|---|---|---|
| DEVICE | IRRADIATION | DARK REACTION TREATMENT | ADDUCTS PER 1000 BASE PAIRS |
| | | Cycled | |

That is not to say, however, that the counts must be due to covalent interactions. It is possible that photoproduct has a very high non-covalent association with nucleic acid. This association may be high enough that photoproduct is non-covalently associated with DNA even after the rigorous work up.

EXAMPLE 37

Nucleic Acid Binding

Figure 25:
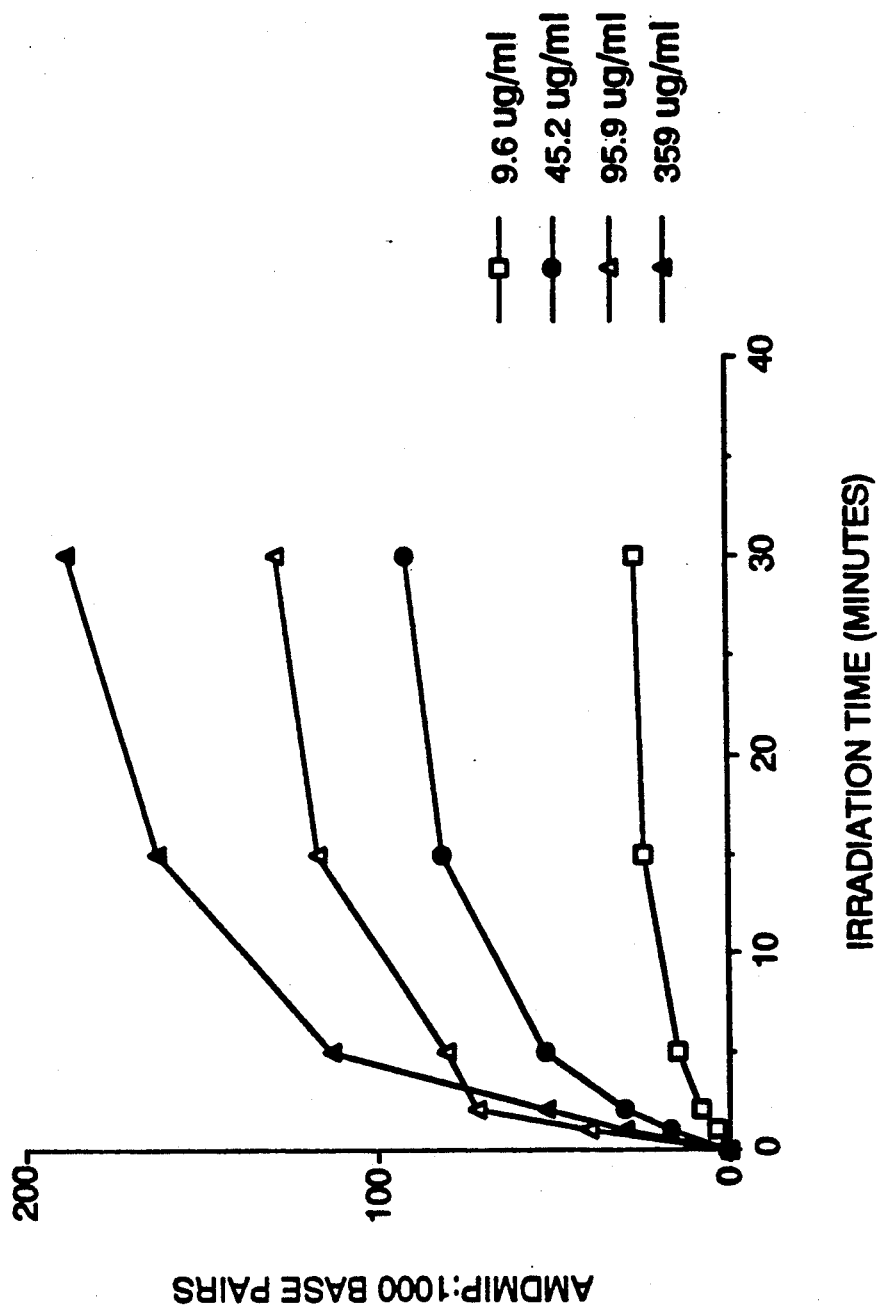
FIG. 25 shows binding as a function of concentration.

It will be desirably in some situations to have precise control of the binding levels of a photoactive compound to nucleic acids. As shown earlier in FIG. 18, binding levels are a function of the irradiation time. Providing that the irradiation time is sufficient to achieve the plateau level, a constant level of binding can be achieved. In addition to light exposure, the concentration of the photoactive compound also affects the ultimate binding levels. As discussed in the introduction, photoactive compounds such as psoralen and isopsoralen undergo competing reactions during exposure to actinic light. They will undergo photodecomposition at the same time as they add to polynucleotides. Although the structural properties of a particular photoactive compound determine the relative rates of photodecomposition to photoaddition reactions, the initial concentration of the compound does affect the plateau level of binding. This example investigates the binding levels as a function of concentration. Following the procedure outlined in FIG. 17, $^3$H-AMDMIP was used at different concentrations to measure binding to calf thymus DNA. The results are shown in FIG. 25. Clearly, the concentration of AMDMIP affects the binding levels achieved with calf thymus DNA. Providing irradiations are of sufficient duration to achieve plateau levels, the concentration dependence can be used to precisely control addition reactions to a desired level of photobinding.

EXAMPLE 38

Nucleic Acid Binding

FIG. 17 can again be referred to as a flow chart schematically showing the manner in which covalent binding was measured for the compounds synthesized by the methods of the present invention. $^3$H-AMIP ($3.1 \times 10^5$ cpm/$\mu$g), $^3$H-AMDMIP ($2.2 \times 10^5$ cpm/$\mu$g), and $^3$H-MIP ($2.1 \times 10^5$ cpm/$\mu$g) were added to 300 $\mu$l of calf thymus DNA (Sigma) in 1×TE buffer. All of the isopsoralen compounds were added at a nominal concentration of 100 $\mu$g/ml. However, actual concentrations obtained empirically (counted after sitting overnight at room temperature) were: $^3$H-AMIP (105 $\mu$g/ml), $^3$H-AMDMIP (115 $\mu$g/ml), and $^3$H-MIP (<10 $\mu$g/ml).

To assess binding, three samples were prepared for each compound; two were irradiated (15 minutes at 25° C. with the CE-I device) while one was unirradiated as a control. Following irradiation, the samples were extracted four times with CHCl$_3$ then precipitated twice. The final pellet was brought up in 1 ml of 1×TE buffer and resuspended by shaking at 40° C. overnight. 50 $\mu$l of each sample was then diluted to 0.5 mls with H$_2$O. The concentration of DNA was determined by UV absorption (A$_{260}$) and the amount of covalently bound isopsoralen ("adduct") was determined by scintillation counting ($3 \times 100$ $\mu$l aliquots). From these numbers, the following binding ratios (adducts: DNA base pair) were determined:

| $^3$H-Compound | Ratio |
|---|---|
| AMIP | 1:16.7 |
| AMDMIP | 1:7.2 |
| MIP | 1:44.2 |

From these ratios it is clear that AMDMIP has the highest binding and MIP has the lowest binding. It is not clear, however, that MIP's low binding ratio is due to low affinity with DNA. Indeed, from the fact that empirically determined concentration of MIP was <10 $\mu$g/ml as opposed to 100 $\mu$g/ml for AMDMIP, it would appear that the low ratio is due primarily to low solubility of MIP.

On the other hand, the fact that the concentrations of AMIP and AMDMIP were approximately the same would suggest that the difference in ratios represents a difference in affinity.

EXAMPLE 39

Nucleic Acid Binding $^3$H-AMIP (0.04 umol) or $^3$H-AMDMIP (0.035 $\mu$mol) were added to 5 $\mu$g (0.1 nmol) each of HRI 46 and HRI 47 (complementary 115-mers) in a total volume of 100 $\mu$l of either standard irradiation buffer (0.1M NaCl, 10 mM Tris pH 7, and I mM EDTA) or 1×Taq buffer (50 mM KCl, 50 mM Tris pH 8.5, 2.5 mM MgCl$_2$, 200 $\mu$g/ml gelatin). To assess binding, three samples were prepared for each compound; one was irradiated for 15 minutes at 25° C. with the CE-I photoactivation device; one was irradiated for 15 minutes at 25° C. with the PTI photoactivation device; one was unirradiated as a control. All the samples were then extracted four times with 100 $\mu$l CHCl$_3$, brought to 0.2M NaCl and 5 mM MgCl$_2$, and precipitated with 250 $\mu$l ethanol at $-20$° C. The pellets were dried, resuspended and reprecipitated. The final pellets were brought up in 0.5 ml H$_2$O. The concentration of DNA was determined by UV absorption (A$_{260}$) and the amount of adduct was determined by scintillation counting ($4 \times 100$ $\mu$l aliquots). Binding was calculated using molecular weights (AMIP*HCl MW=251.5;AMDMIP*HCl MW=279.5; 115-mer complex MW=74800) and concentrations (30 $\mu$g/ml oligo per 1 OD at 260 nm). From these numbers, the following binding ratios (adducts:DNA base pair) were determined:

| $^3$H-Compound | Device | Buffer | Ratio |
|---|---|---|---|
| AMIP | CE-I | NaCl | 1:9.3 |
| AMIP | PTI | NaCl | 1:14.2 |
| AMIP | CE-I | Taq | 1:7.6 |
| AMIP | PTI | Taq | 1:12.5 |

-continued

| ³H-Compound | Device | Buffer | Ratio |
|---|---|---|---|
| AMDMIP | CE-I | NaCl | 1:2.7 |
| AMDMIP | PTI | NaCl | 1:3.9 |
| AMDMIP | CE-I | Taq | 1:2.5 |
| AMDMIP | PTI | Taq | 1:4.2 |

From these ratios it is clear that AMDMIP again has the highest binding. Interestingly, the CE-I device shows better ratios (regardless of the compound used) than the PTI device. Most importantly, the use of discreet viral sequences of DNA results in better binding than calf thymus genomic DNA.

This latter point is probably due to the A:T rich nature of the sequences used. HRI 46 and 47 have almost 60% A:T sequences. Since isopsoralens are thought to intercalate preferentially at these sites, an A:T rich nucleic acid such as used here should show increased binding with these photoreactive compounds.

This increased binding is due to two factors: 1) using a higher isopsoralen concentration relative to nucleic acid and 2) the above-mentioned A:T rich nature of the sequences used. It is expected that increasing the concentration of photoreactive compound (relative to concentration of nucleic acid) will increase binding up to a point. A higher relative concentration of AMIP to DNA was used here as compared to the relative concentration in Example 38, and a corresponding increase in covalent binding was realized (1:9.3 versus 1:16.7).

EXAMPLE 40

Nucleic Acid Binding

BIODMIP (100 μg/ml) was irradiated for 30 minutes at room temperature with the PTI device in 500 μl of 1×TE buffer with 2 μg of Hind-III restriction fragments of lambda DNA. After the first irradiation, the mixture was transferred to a new tube containing 50 μg additional BIODMIP and this was incubated at 37° C. for one hour to dissolve the compound. This was followed by a second 30 minute irradiation at room temperature with the PTI device. It was observed that, under these conditions BIODMIP added to the DNA at a ratio of 1 covalently bound BIODMIP per 20 base pairs.

EXAMPLE 41

Nucleic Acid Binding

This example describes photobinding of ³H-AMIP, ³H-AMDMIP and BIOMIP to RNA. A tRNA stock was prepared at a concentration of 765 μg/ml in 1×TE/10 mM NaCl. Appropriate amounts of each compound were prepared in separate reaction vessels such that upon addition of 200 μl of the tRNA solution (153 μg) the final concentration of each compound was 100 μg/ml. ³H-AMIP and ³H-AMIP were used in the experiment; the BIOMIP used was unlabelled. Each reaction vessel was then irradiated for 30 minutes at 25° C. in the CE-III device. Identical unirradiated reaction mixtures were used as controls for each compound. Following irradiation, each mixture was extracted with CHCl₃ (4×200 μl) then precipitated (X2). The pellets were resuspended in 1×TE and the binding levels determined as follows. For the two labelled compounds (³H-AMDMIP and ³H-AMIP), the nucleic acid concentration was determined optically and radioactivity measured by scintillation counting of aliquots of the stock solutions. Binding of the compounds was then calculated to be as follows:

| Sample | Adducts:RNA Bases |
|---|---|
| AMIP Control | 1:51000 |
| AMIP + hv | 1:18 |
| AMDMIP Control | 1:15000 |
| AMDMIP + hv | 1:18 |

To determine if binding of BIOMIP to tRNA has occurred, it was necessary to use a non-radioactive format which detected the biotin moiety on the compound. A commercial kit ("BluGene"; BRL) was used for this purpose. The kit instructions were followed for detection of both the control DNA (supplied with the kit) and BIOMIP treated tRNA. Samples containing 20, 10, 5, 2 or 0 pg of control DNA and between 1 μg and 10 μg of BIOMIP treated tRNA (+/− light) were spotted onto a dry nitrocellulose membrane then fixed by baking under vacuum at 80° C. for 2 hours. The blot was then developed as specified with the following results. All of the control DNA samples gave the expected color pattern, with even the 2 pg sample visible on the blot. A clear increase in signal was seen for the irradiated samples (1 μg<5 μg<10 μg) while no signal was evident from the unirradiated controls. This demonstrated that BIOMIP had covalently bound to the tRNA.

EXAMPLE 42

Template-Dependent Enzymatic Synthesis

The sequences that are presented in FIG. 26 describe several oligonucleotides that are used in the synthesis of either a normal 71-mer or the identical 71-mer containing a site-specifically placed psoralen or isopsoralen monoadduct. The 71-mer is a sub-sequence of the Human Immunodeficiency Virus (HIV) sequence. (An HIV DNA system is described in a co-pending application, Ser. No. 25,725.) SK-39 is a primer oligonucleotide that is complementary to the 3' end of the 71-mers. This primer oligonucleotide can be extended on the 71-mer template to make a complementary strand of the 71-mer.

Figure 27:
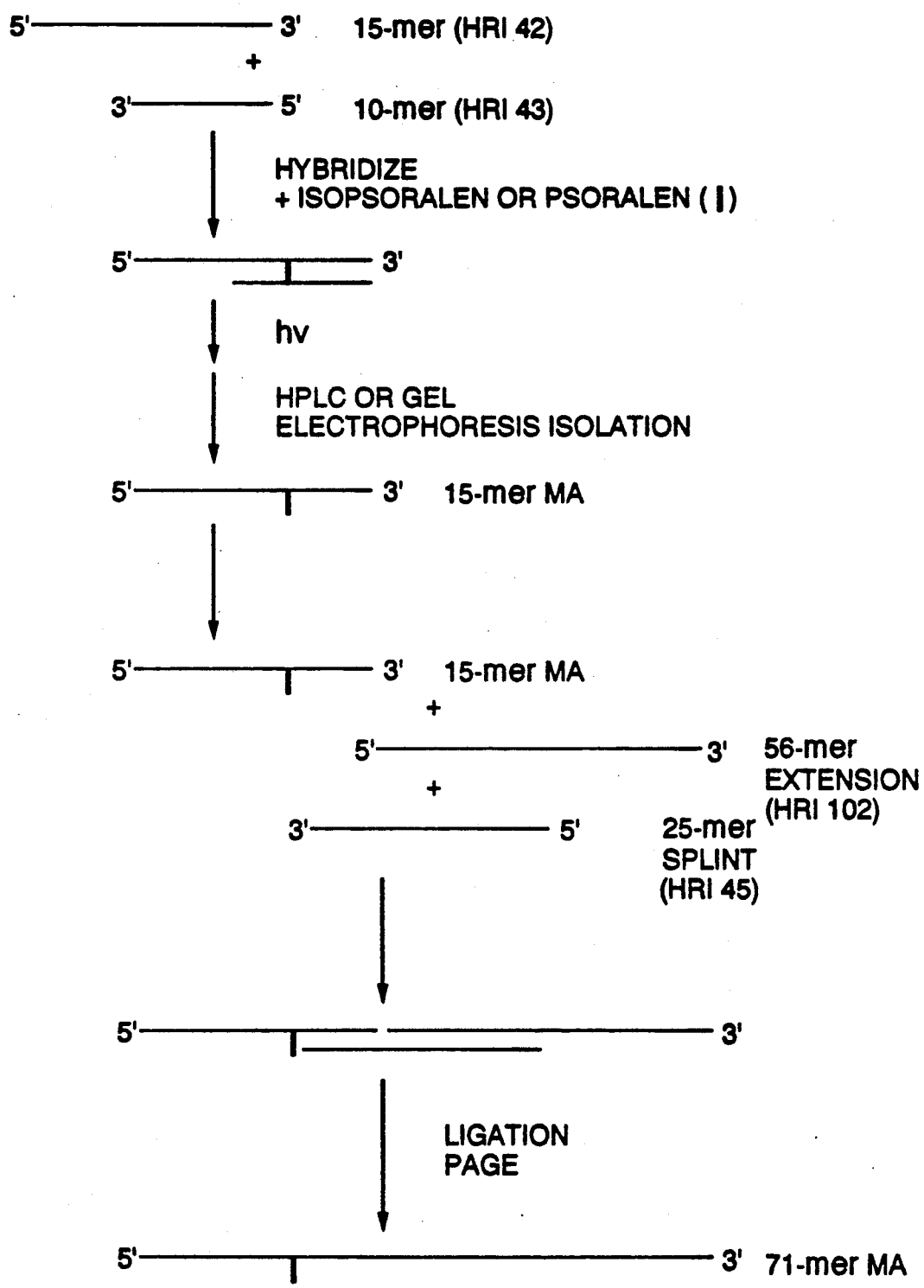
FIG. 27 shows a manner of synthesizing monoadducted templates.

FIG. 27 shows the manner in which the monoadducted template was derived. Preparation of 71-mers which contain site-specific monoadducts involves 1) preparation of different 15-mer monoadducts from the same unmodified 15-mer (HRI-2), and 2) ligation of the different 15-mer monoadducts to the same 56-mer "extender oligonucleotide" (HRI 102) using a 25-mer oligonucleotide (HRI-45) as a splint. The arrows in FIG. 27 indicate the direction of synthesis, while the monoadduct is indicated by a short line that is perpendicular to the oligomer. While each of the 71-mer monoadducts contains the adduct at a base position that is greater than 56 bases from the 5' end, the precise position of the monoadduct is not meant to be indicated.

To prepare the 15-mer adducts, the 15-mer was incubated with a complementary 10-mer along with psoralen or isopsoralen under hybridization conditions. The mixture was then irradiated to provide the monoadducted 15-mer. While the invention is not dependent on knowing the precise mechanism of coupling, it has generally been believed that the 10-mer directs the isopsoralen to a single TpA site within the double-stranded helix formed by the 10-mer/15-mer hybrid. After isolation of an HPLC peak believed to contain the 15-mer with a single psoralen or isopsoralen monoadduct, these 15-mer monoadducts were ligated to a 56-mer extender in order to provide the monoadducted 71-mers for use as polymerase templates. The ligation reaction therefore utilized three oligonucleotides: the particular psoralen or isopsoralen monoadducted 15-mer, the 56-mer extender, and the 25-mer splint. The ligation complex was hybridized together then ligated. The ligated product was then isolated as a single band by denaturing PAGE.

To provide highly purified 71-mers which contain a single monoadduct, it was necessary to provide highly purified 15-mer monoadduct prior to the ligation step. This was accomplished by repurification of the HPLC purified monoadducted 15-mers by PAGE. In this way, essentially all the non-monoadducted 15-mer was removed prior to ligation. Separation of 15-mer monoadduct from unmodified 15-mer was readily accomplished by PAGE (while the same technique is not effective for separation of the corresponding unmodified 71-mer and monoadducted 71-mer sequences). In this manner, exceedingly pure monoadducted 71-mers were produced for the primer extension reactions; monoadducted 71-mers (as well as unmodified 71-mers) are used in template-dependent enzymatic extension experiments in examples 43-47 below.

EXAMPLE 43

Template-Dependent Enzymatic Synthesis

Figure 28:
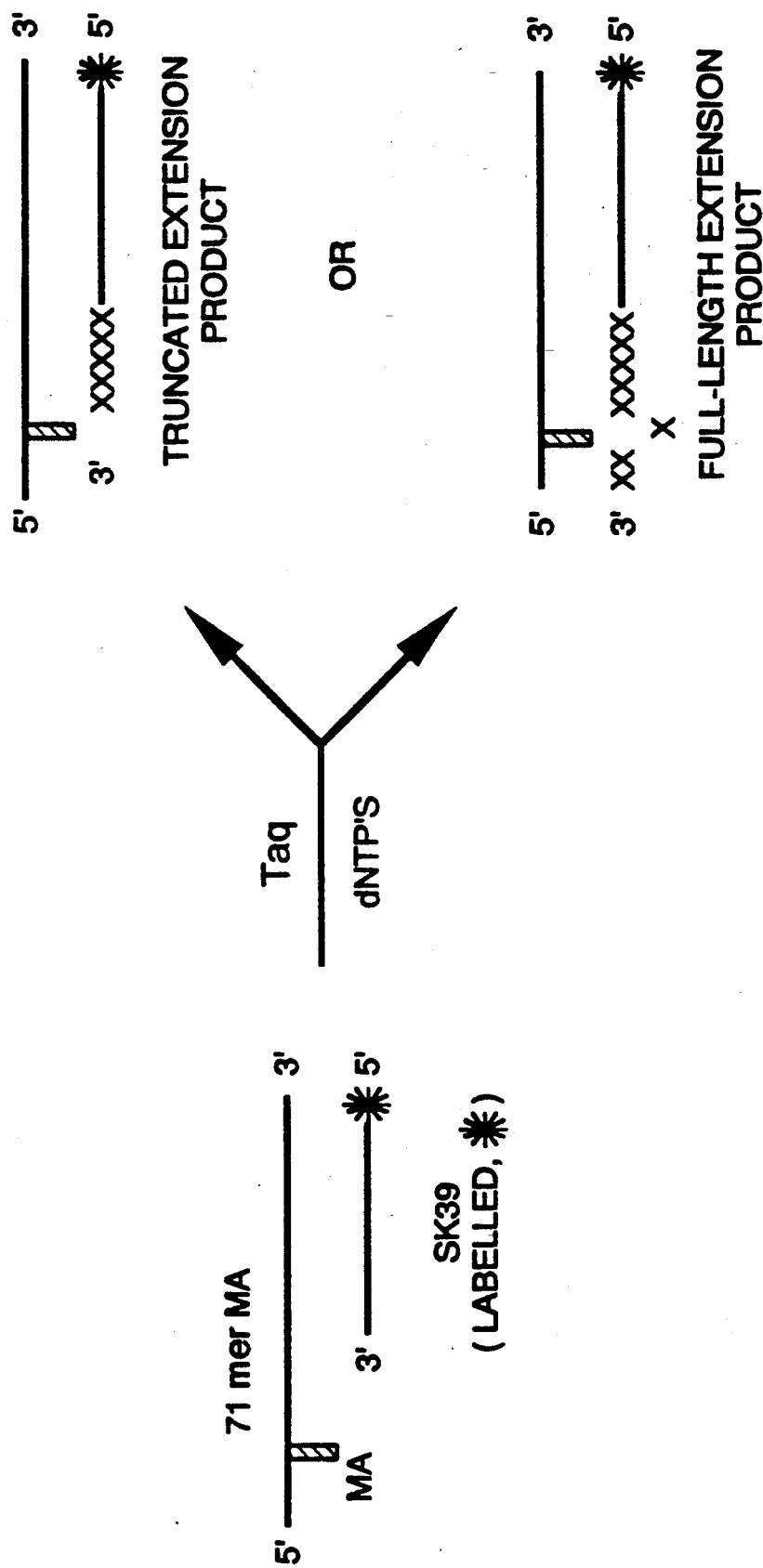
FIG. 28 shows a manner of measuring primer extension.

In this experiment, monoadducted 71-mers (as well as unmodified 71-mers) were used in template-dependent enzymatic extension. AMIP, AMDMIP, and MIP 71-mer monoadducts were made as in Example 42. FIG. 28 shows the manner in which extension is achieved. Note that the 3' end of the 71-mer (HRI 55) is complementary to the primer (SK-39) (see also FIG. 26). Each of the extension experiments were run at 37° C. for 0, 5 or 15 minutes. Each of the reactions were initiated by providing the templates and deoxyribonucleoside 5'-triphosphates (dATP, dGTP, dCTP, and dTTP are collective abbreviated as dNTPs), and by adding the particular polymerase last to start the reaction. For detection, the primer extension reaction utilized 5' $^{32}$P-labelled primer. The reactions were stopped by adding EDTA. Analysis was by denaturing PAGE followed by autoradiography.

Reaction conditions for each of the different polymerases were as follows:

1) *E. Coli* DNA Polymerase: 50 mM Tris Buffer (pH 7.5); 10 mM MgCl$_2$; 1 mM DTT; 50 µg/ml bovine serum albumin (BSA); 100 µM dNTPs; 3 units of polymerase (for 25 µl volume); 1×10$^{-8}$ M primer; 1×10$^{-9}$ M 71-mer;

2) Klenow Polmerase: (same as *E.Coli* except add 3 units of Klenow instead of *E. Coli* polymerase);

3) T4 Polymerase: 50 mM Tris Buffer (pH 8.0); 5 mM MgCl$_2$; 5 mM DTT; 50 mM KCl; 50 µg/ml BSA; 5 units T4 polymerase;

4) Reverse Transcriptase: 50 mM Tris Buffer (pH 8.0); 5 mM MgCl$_2$; 5 mM DTT; 50 mM KCl; 50 µg/ml BSA; 100 µM dNTPs; 20 units of Reverse Transcriptase.

Figure 29:
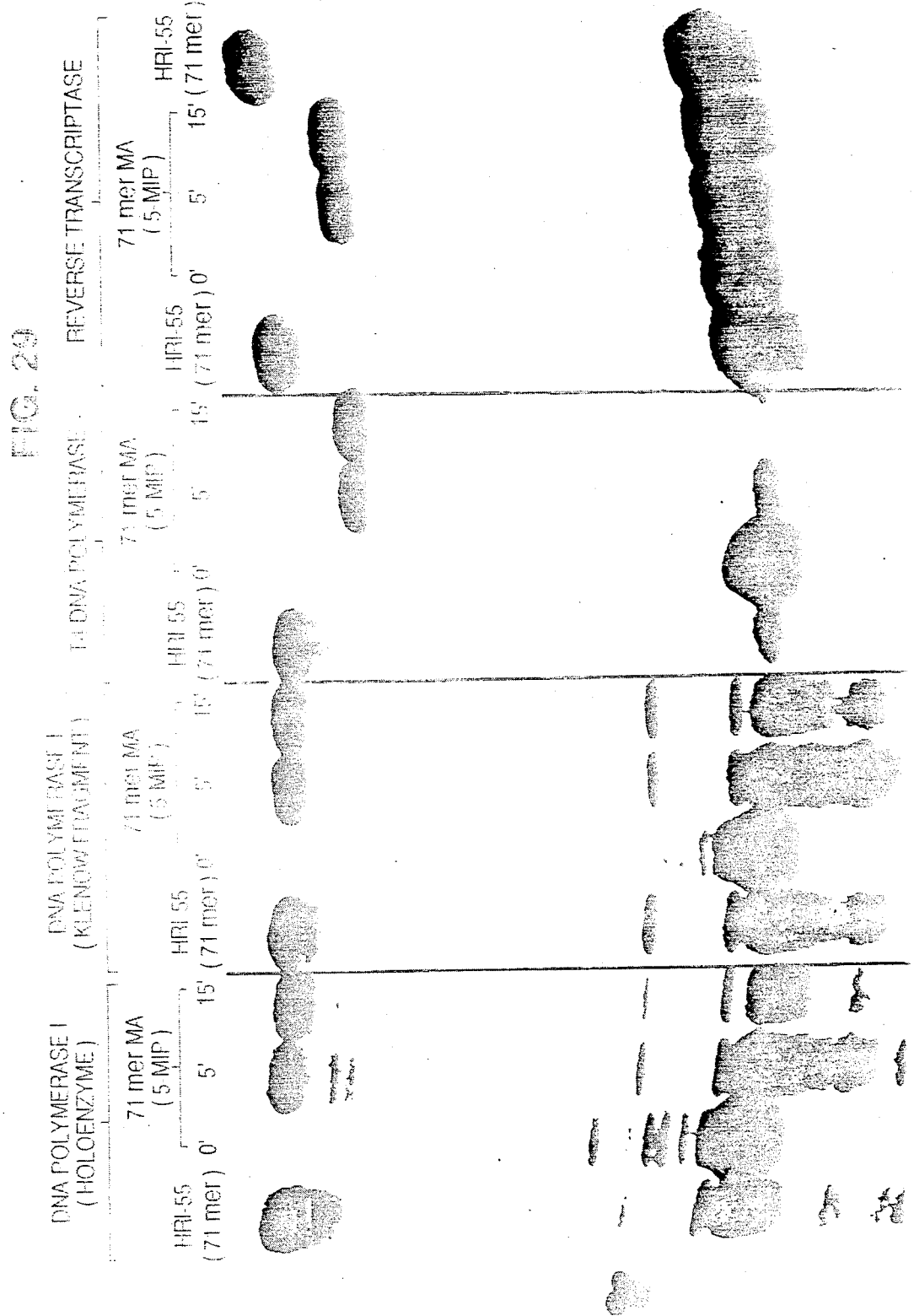
FIG. 29 is an autoradiograph after gel electrophoresis, showing polymerase inhibition results with MIP.
Figure 30:
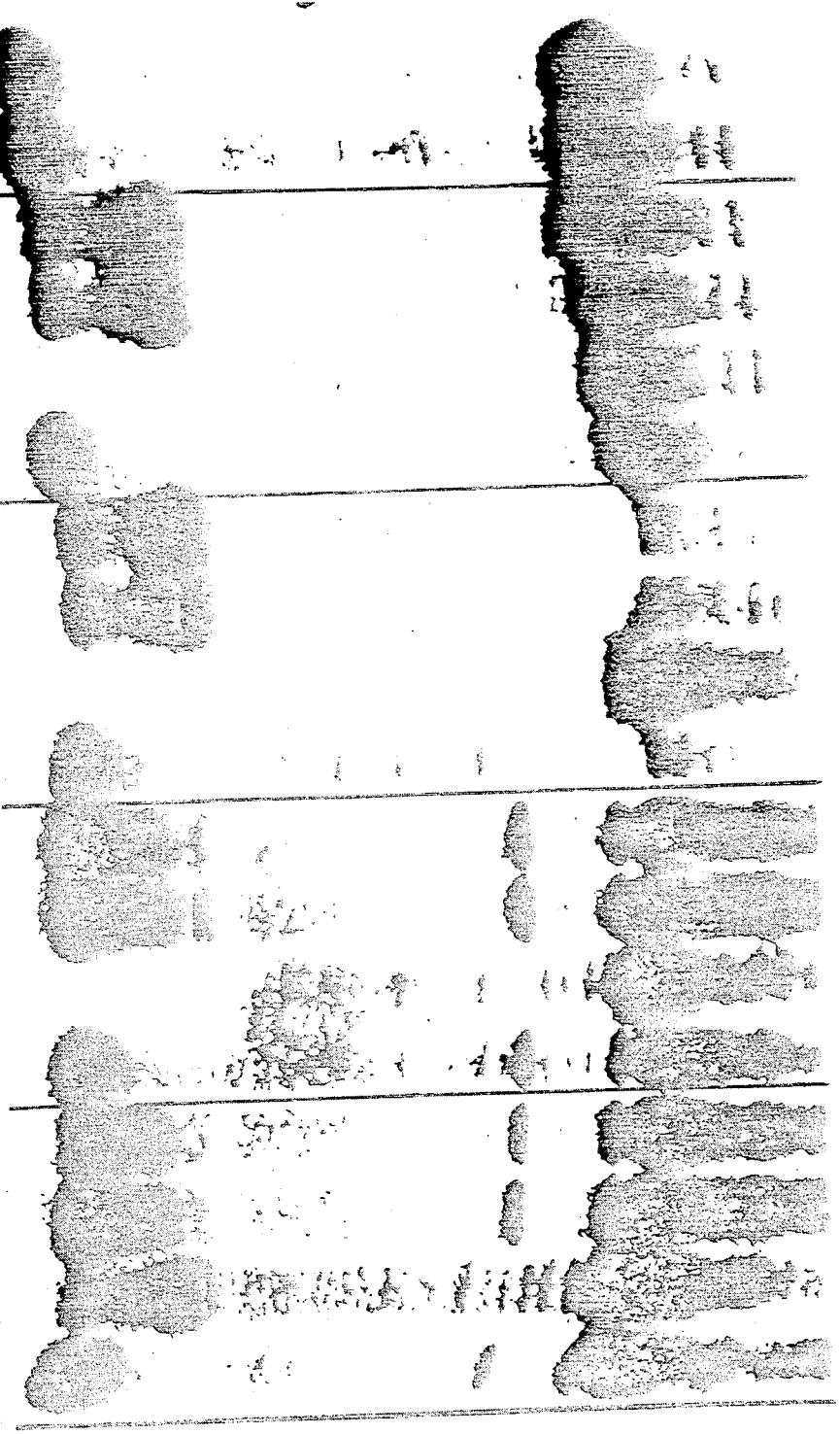
FIG. 30 is an autoradiograph after gel electrophoresis, showing polymerase inhibition results with AMIP.
Figure 31:
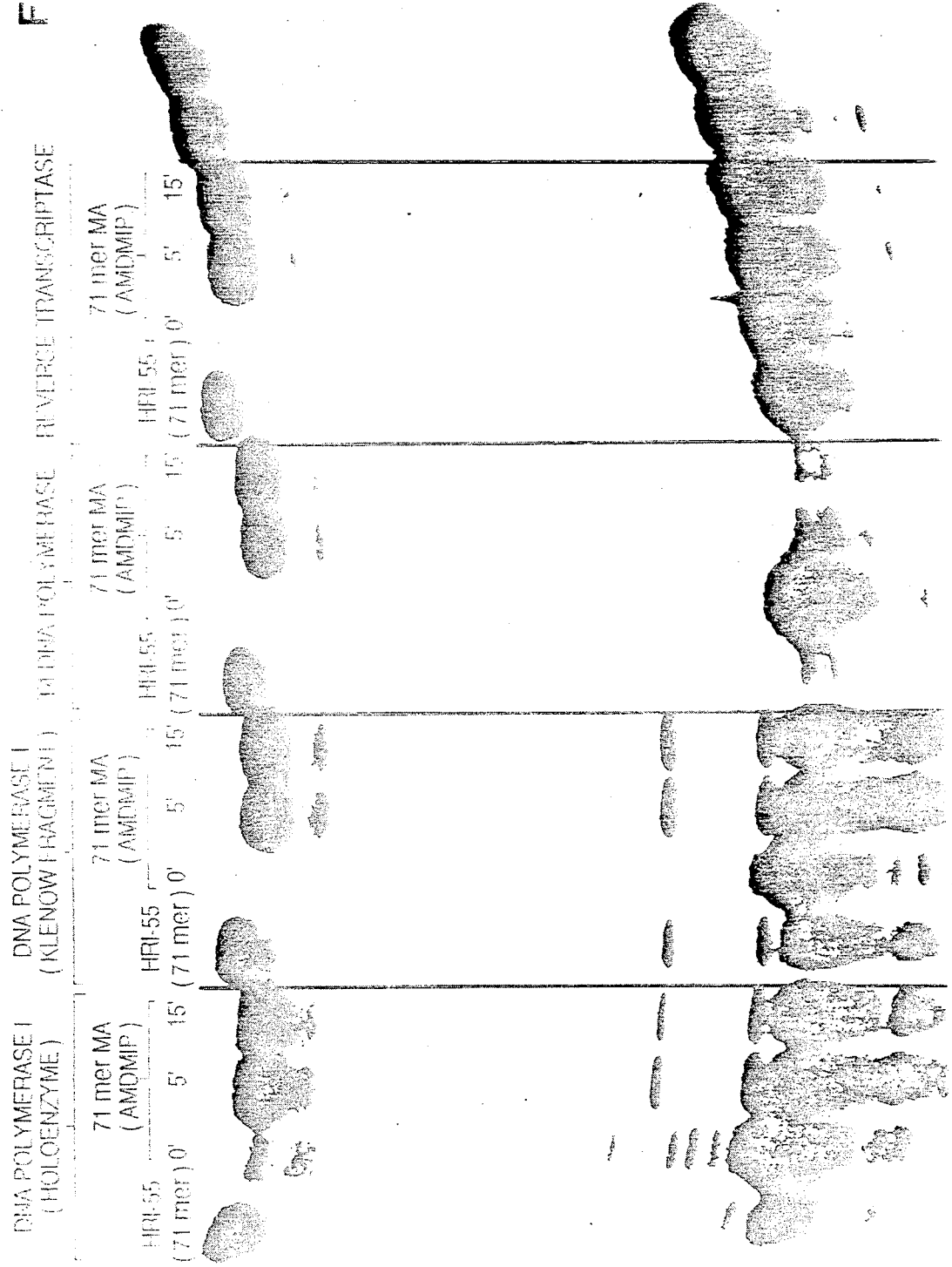
FIG. 31 is an autoradiograph after gel electrophoresis, showing polymerase inhibition results with AMDMIP.

The results with MIP, AMIP, and AMDMIP are shown in FIGS. 29, 30 and 31 respectively. Both MIP and AMIP adducts appear to be complete stops for T4 polymerase and reverse transcriptase, but not complete stops for *E. coli* DNA polymerase and Klenow. AMDMIP adducts appears to be a complete stop for all of the polymerases tested.

EXAMPLE 44

Template-Dependent Enzymatic Synthesis

In this experiment, monoadducted 71-mers (as well as unmodified 71-mers) were used in template-dependent enzymatic extension. AMIP, AMDMIP, and MIP 71-mer monoadducts were made as in Example 42. Extension was carried out as in Example 43 except that in this experiment, Taq I DNA polymerase, a thermostable DNA polymerase isolated from *Thermus acuaticus* (Stratagene, Inc., La Jolla, Calif.) was assessed for its ability to read past isopsoralens.

The reaction mixture was in 80 µl total volume and comprised 1×Taq buffer, 200 µM each of dNTP's, 0.05 units of Taq per µl of reaction volume; 1×10$^{-9}$M in 71-mer MA; 1×10$^{-8}$M in $^{32}$P-labelled SK-39. Each reaction was set up with everything except Taq polymerase. The samples were initially heated to 95° C. for 5 mins, then incubated at 55° C. for 3 mins. The extension reaction was initiated by addition of Taq polymerase. At the indicated time points (0.5, 1.0, 5.0 mins), 20 µl of the reaction mix was removed to a tube containing 1 µl of 0.5M EDTA to stop the reaction. All products were analyzed on a 20% polyacrylamide, 7M urea gel followed by autoradiography.

Figure 32:
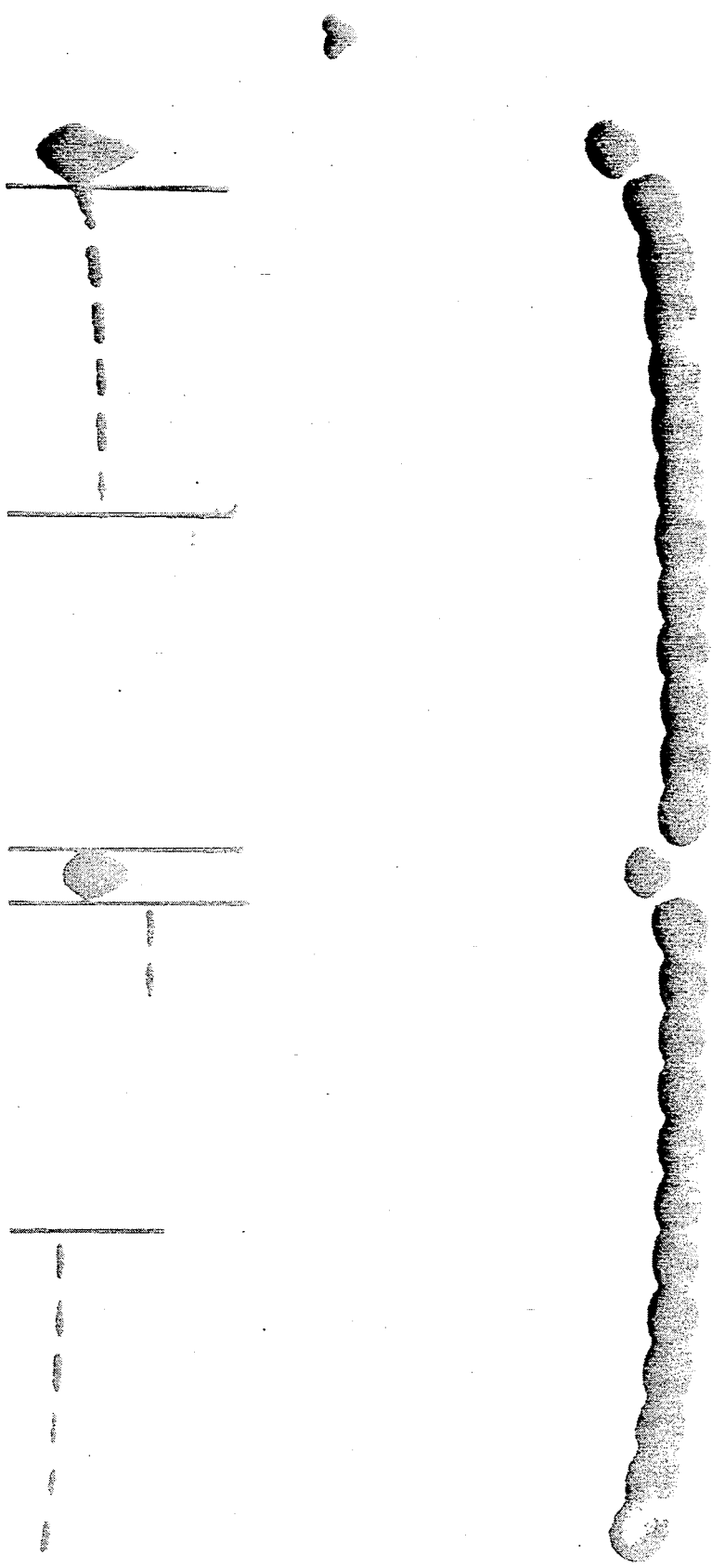
FIG. 32 is an autoradiograph after gel electrophoresis, showing Taq polymerase inhibition results with AMIP, AMDMIP, and MIP 71-mer monoadducts.

The results are shown in FIG. 32. The lanes with the control template (HRI 55) show the position of the full length 71-mer extension product. Each time point was measured in duplicate. The extension reaction appears to be complete at the earliest time point (30 sec). The lanes with the targets containing the isopsoralens (MIP, AMIP, and AMDMIP) indicate stops at positions that are shorter than the full length 71-mer product.

Unexpectedly, each adduct results in a stop at a different position within the sequence of the 71-mer. The MIP stop appears to be at about the position of the TpA sequence in the 10-mer that was used to create the monoadduct. AMIP has multiple stops, at differing positions relative to the MIP stop. AMDMIP has a different stop altogether. The longest extension product with AMIP and the AMDMIP stop indicate that the isopsoralens are probably located on the initial 15-mer outside the region of the 10-mer/15-mer interaction. This shows that the isopsoralens don't necessarily follow the rules reported for psoralen derivatives (i.e. that an intercalation site is required, and further that a TpA site is preferred.)

EXAMPLE 45

Template-Dependent Enzymatic Synthesis

This experiment investigated whether blocking of Taq polymerase by monoadducts is complete or whether monoadducts can be bypassed by the enzyme. In order to view the process of bypass synthesis, it is necessary to cycle the extension reaction of the primer with the 71-mer templates. Cycling in this case consists of mixing the primer with the 71-mer template, adding Taq polymerase and appropriate reagents, extending, heating to induce strand separation, reannealing of the primer to the 71-mer template, extending again, and subsequent stand separation. This process can be repeated as necessary. During this process, only the complement of the 71-mer template is being synthesized. It is accumulating in a linear fashion with the number of thermal cycles (in contrast to PCR where both strands are being synthesized and accumulate geometrically).

The templates and reaction conditions were as in Example 44 above except that three samples were used for each monoadduct and each sample was tested under 5 different conditions:

Samples (1): one sample for each monoadduct was used to carry out extension at 55° C. as in Example 43;

Samples (2): one sample for each monoadduct was used to carry out extension by the following series of steps: denaturing at 95° C.; incubating for 30 seconds at 55° C.; adding Taq polymerase for 3 minutes at 55° C.; cooling the reaction for 1 minute at 7° C.; stopping the reaction with EDTA for one minute at 95° C.:

Samples (3): one sample for each monoadduct was used to carry out extension by repeating the following series of steps nine times: denaturing at 95° C.; incubating for 30 seconds at 55° C.; adding Taq polymerase for 3 minutes at 55° C.; cooling the reaction for 1 minute at 7° C. At the end, the reaction is stopped with EDTA for one minute at 95° C.

Figure 33:
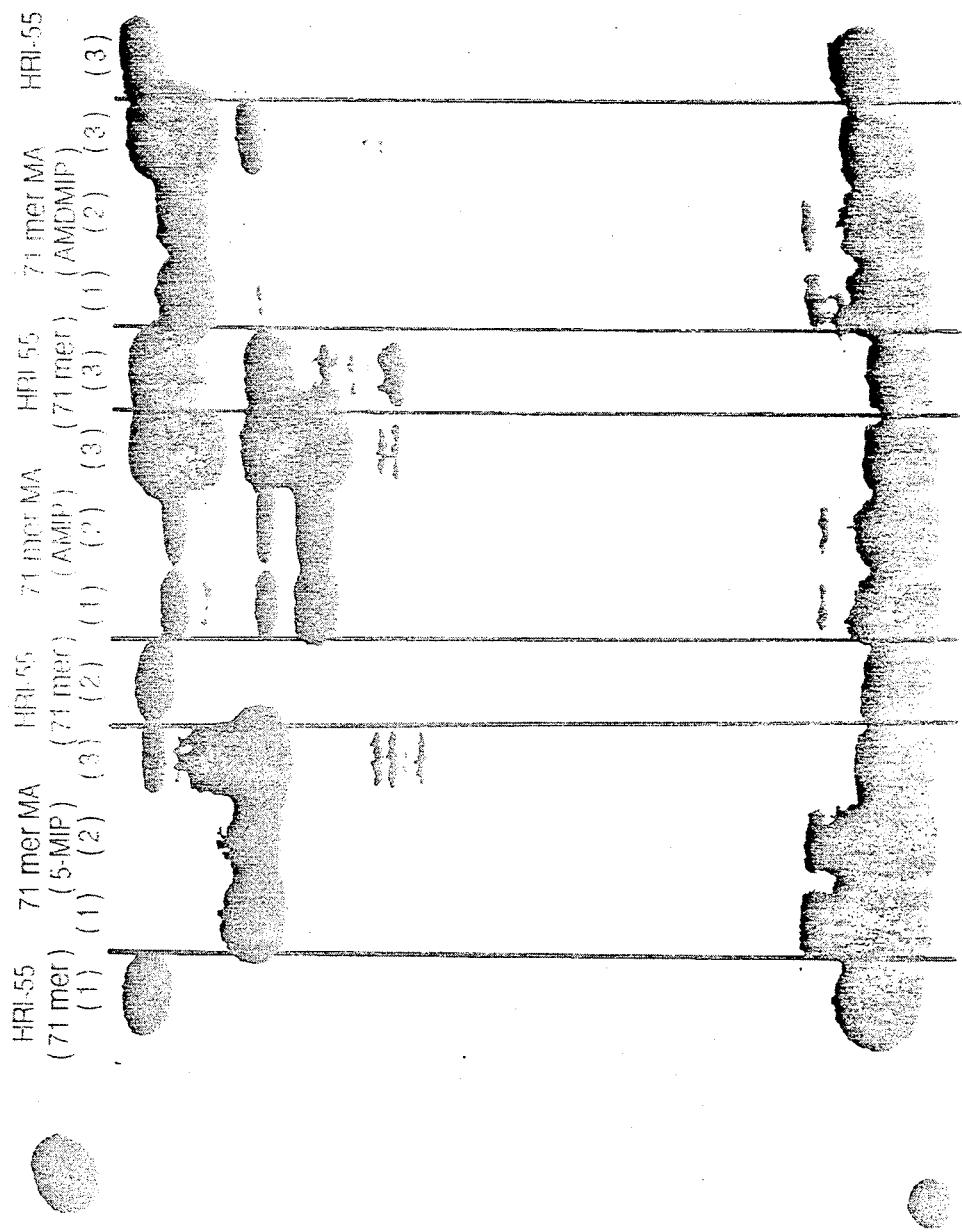
FIG. 33 is an autoradiograph after gel electrophoresis, showing Taq polymerase inhibition results with AMIP, AMDMIP, and MIP 71-mer monoadducts after repeated cycles.

The results are shown in FIG. 33. At either 55° C. or one cycle of extension, there appears to be no read through (i.e. Taq polymerase is completely blocked). After nine cycles there is evidence of full length extension product. It is not clear, however, if these results indicted actual read through or just extension of non-monoadducted 71-mer contaminant.

EXAMPLE 46

Template-Dependent Enzymatic Synthesis

It was investigated whether blocking of Taq polymerase is complete or whether blocking can be overcome. While the results described in Example 45 suggested bypass occurred (since full length extension products were produced after 10 cycles using isopsoralen monoadducted 71-mer template), it was not clear if the result were due to actual bypass of the monoadduct or to extension of non-monoadducted 71-mer that was present as a contaminant. Non-monoadducted 71-mer could have been present due to incomplete separation of 15-mer monoadduct from unmodified 15-mer prior to ligation during the preparation of the 71-mer (see Example 42).

Figure 34:
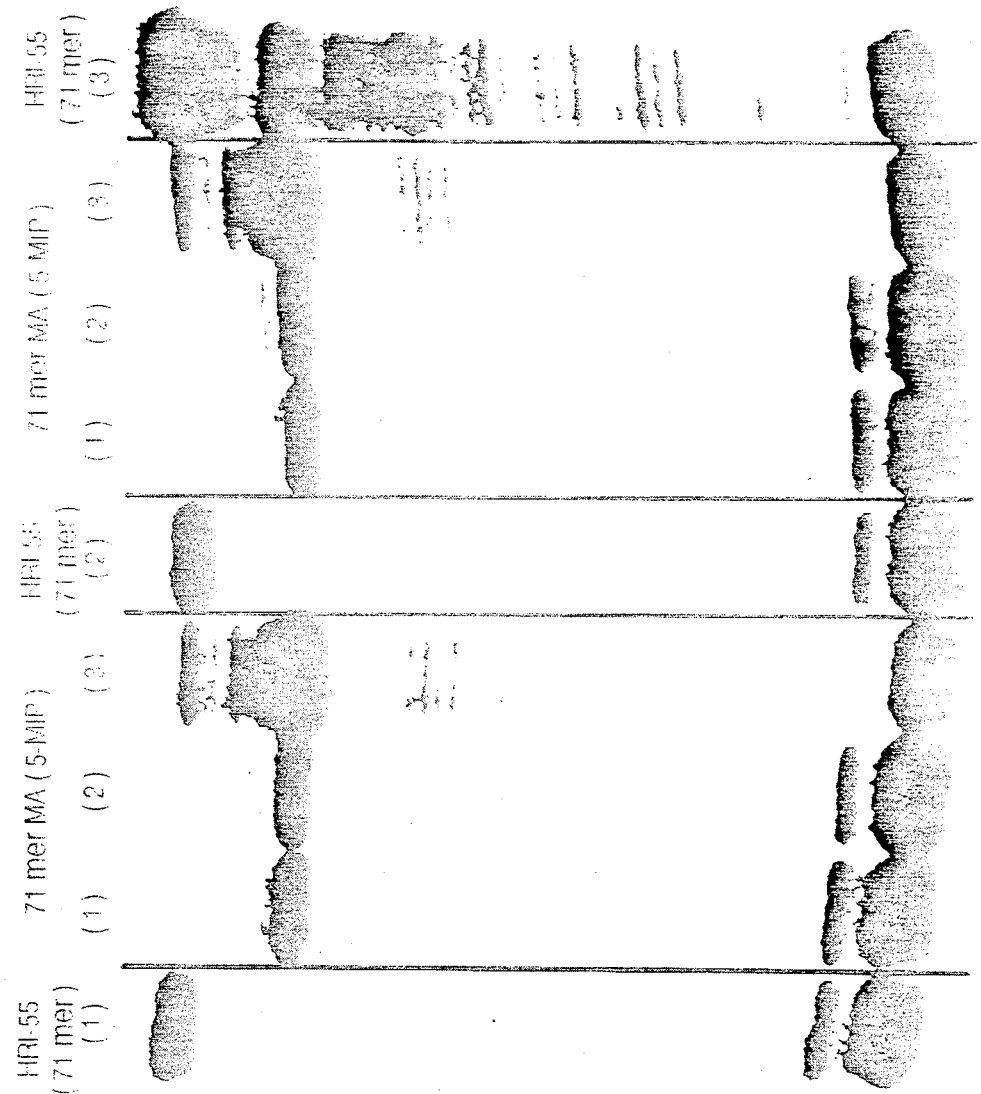
FIG. 34 is an autoradiograph after gel electrophoresis, showing inhibition results of HPLC-repurified 5-MIP monoadduct.

To investigate this question further, a new 5-MIP monoadducted 71-mer was prepared by repurification of the HPLC purified 5-MIP monoadducted 15-mer by PAGE. In this way, more of the non-monoadducted 15-mer was removed prior to ligation. The purified 71-mer was then used as template in an extension experiment as described in Example 45. After 10 cycles, there was still evidence of extension product (FIG. 34). Excision of the band and counting found this full length extension product constituted 2.3% of the total extension products (i.e., 97.7% of the extension products were truncated).

EXAMPLE 47

Template-Dependent Enzymatic Synthesis

From Examples 43, 44 and 45, it is clear that some isopsoralens may be used for polymerase blocking. It is important to note that isopsoralens form monoadducts with double stranded nucleic acid but do not form crosslinks because of their angular structure. Because of this, these isopsoralen-modified single strands remain detectable by hybridization procedures. On the other hand, it may be useful under some circumstances to block replication with psoralens. This experiment examines the ability of HMT to block Taq polymerase on an HIV template.

Figure 35:
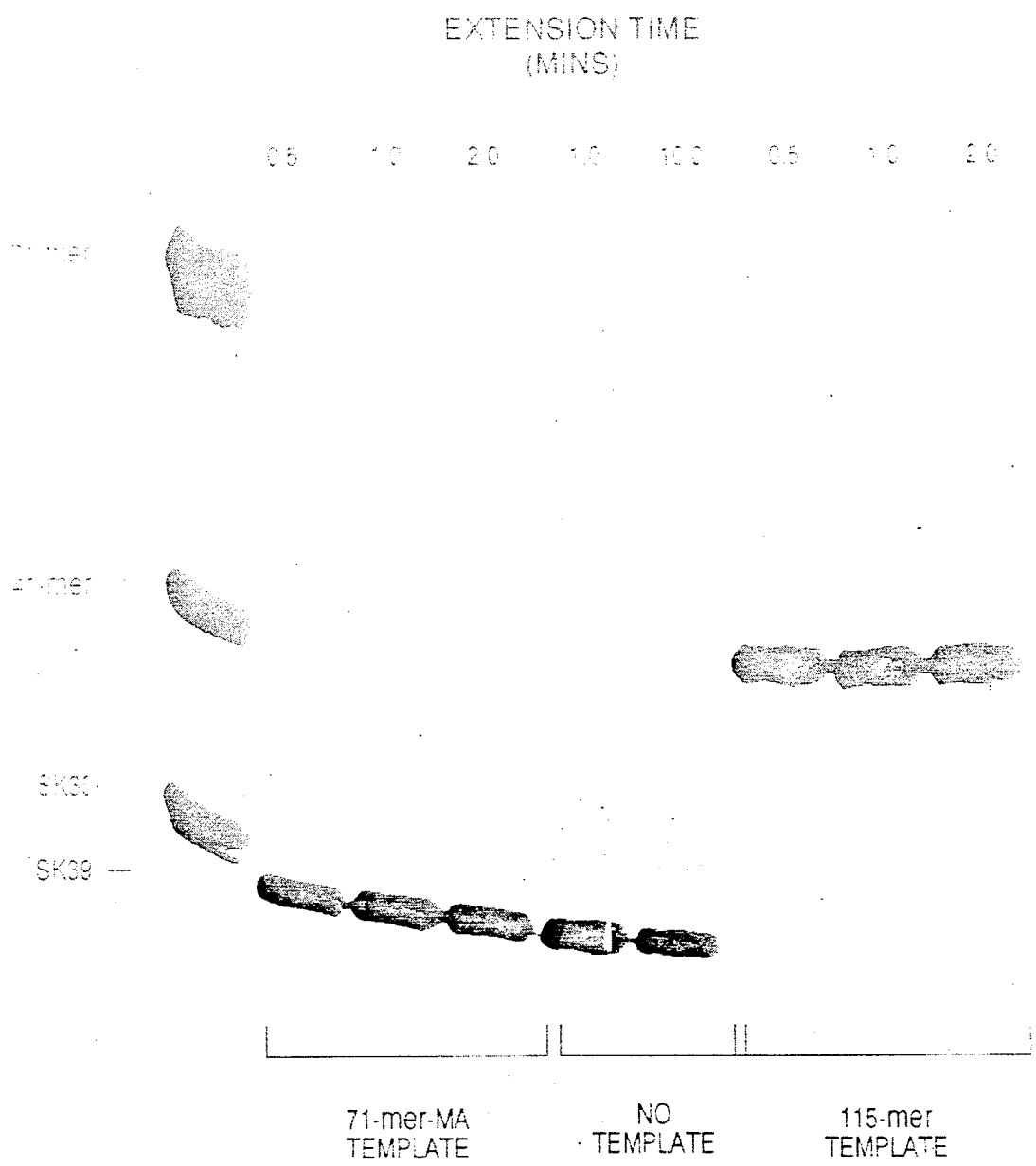
FIG. 35 is an autoradiograph after gel electrophoresis, showing Taq polymerase inhibition results with an HMT 71-mer monoadduct.

Monoadducted 71-mer was constructed as described, but for HMT. Extension was carried out and analyzed as before on PAGE. The results for Taq polymerase are shown in FIG. 35. Clearly, HMT monoadducts stop Taq polymerase. Full length 71-mer is not made and a shorter strand corresponding to the position of the HMT adduct was made.

EXAMPLE 48

Template-Dependent Enzymatic Synthesis

In this experiment, the ability of AMIP, AMDMIP and MIP to block replication of 71-mer is investigated by randomly adding each compound to the 71-mer. Of course, addition may only be random in the sense that one or more adducts may be formed with any one strand of nucleic acid. The actual placement of the isopsoralen may be governed by preferential binding at particular sites (e.g. A:T). In addition to blockage by random adducts, photoproducts of the various isopsoralens may be providing an inhibitory effect. No attempt to separate the effects of photoproduct from the effects of covalent adducts on the 71-mer template was made in this series of experiments.

In these experiments, the 71-mer template ($10^{-9}$M) primed with $^{32}$P-SK-39 ($10^{-8}$) and extended with Taq polymerase in a total volume of 20 μl. The dNTP concentration was 200 μM. In the control samples, the 71-mer, the primer, and the dNTPs were mixed in Taq buffer in a volume of 18 μl. These samples were initially denatured at 95° C. for 5 minutes, followed by equilibration at 55° C. for 3 minutes. Taq enzyme was then added (0.5 units) and the extension reaction was carried out for 5 minutes at 55 C. The reaction was stopped by making the solution 10 mM in EDTA. In another set of samples, the 71-mer in 10 μl was mixed with either AMIP (200 μg/ml), AMDMIP (200 μg/ml), or MIP (60 μg/ml). Half of these samples were irradiated for 15 minutes on the CE-I devices at 25° C. The other half was kept in the dark as controls. These samples were then mixed with the primer and dNTPs as before, and were subjected to the same thermal profile and extension reactions as the samples that were described earlier. The results were examined by PAGE. The extended product bands were identified by autoradiography, excised and counted (data not shown).

The unirradiated controls that contained the isopsoralens resulted in full length extension products; no truncated products were observed. Quantitation of these extension products showed they were equivalent to the amount of extension products seen in the samples that did not contain isopsoralens, which corresponded to about 8% of the primer being extended.

The irradiated samples that contained either AMIP or AMDMIP were not extended at all. The irradiated sample that contained MIP resulted in some full length extension product and a minor truncated product. The amount of full length product with irradiated MIP was half of that observed with the control samples.

EXAMPLE 49

Template-Dependent Enzymatic Synthesis

In this experiment, the ability of two different Phenylazide derivatives (see Table 1), photobiotin (Vector Labs) and monoazide ethidium chloride, to block replication of 71-mer was investigated by randomly adding each compound to the 71-mer. Again, addition may only be random in the sense that one or more adducts may be formed with any one strand of nucleic acid. The actual placement of these compounds may be governed by preferential binding at particular sites (e.g. A:T). In addition to blockage by random adducts, there may be inhibition by photoproducts. As in Example 48, no attempt was made to separate the impact of photoproducts from that of covalent binding of photosensitive compound on the 71-mer.

The two compounds, photobiotin and monoazide ethidium chloride, have different spectral characteristics. To activate these compounds, two different wavelength regions were selected using a single light source (General Electric Sunlamp, Model RSM, 275 watt. The light source was positioned 10 cm above uncapped Eppendorph tubes which contained samples to be irradiated. The samples were kept on ice during irradiation. A pyrex dish was placed between the lamp and the samples.

For samples containing photobiotin, 2.5 cm of water was added to the pyrex dish to help remove some of the infrared radiation. The samples were irradiated for 15 minutes.

For samples containing monoazide ethidium chloride, wavelengths less than 400 nm were filtered out by using 2.5 cm of an aqueous solution of 2.9M $NaNO_2$. Removal of short wavelengths (i.e. wavelengths shorter than 400 nm) is necessary for the use of monoazide ethidium chloride. Irradiation of this compound with shorter wavelengths results in conversion to non-active forms (data not shown). Wavelengths below 400 nm are therefore undesirable for use with this compound.

In this experiment, the 71-mer template ($2 \times 10^{-9}$M) in 10 μl was mixed with either no photoreactive compound, photobiotin ($6 \times 10^{-6}$M), or monoazide ethidium ($1.4 \times 10^{-3}$M). Half of each of these samples were irradiated on ice for 15 minutes with wavelengths appropriate for each specific photoreactive compound. The other half of the samples were kept in the dark as controls. The samples containing no photoreactive compound were exposed with the water filter in place. $^{32}$P-SK-39 primer ($1 \times 10^{-8}$M), dNTPs (200 μM), and additional buffer were added to yield a volume of 18 μl. The samples were then denatured at 95° C. for 5 minutes, and then equilibrated at 55° C. for 3 minutes. Taq polymerase was then added and extension was allowed to proceed for 5 minutes at 55° C. The reactions were stopped by bringing the samples 10 mM in EDTA. The products were examined by PAGE (data not shown). The controls containing no photoreactive compound, no photoreactive compound plus light, and photobiotin (Dark control) all showed similar amounts of full length extension product. No truncated products were observed with these samples. The dark control with monoazide ethidium chloride resulted in inhibition of extension. Photobiotin, by contrast, showed inhibition only after irradiation.

EXAMPLE 50

Template-Dependent Enzymatic Synthesis

This example demonstrates that AMDMIP photoproduct inhibits primer extension. This example also demonstrates that the inhibitory effect of photoproduct is not sufficient to account for all the inhibition seen when a 71-mer target is irradiated in the presence of AMDMIP and subsequently extended.

71-mer was made up in Taq buffer. Samples were prepared as follows: 1) dark control samples were not subjected to activating light; 2) 10 μl samples of the 71-mer ($2 \times 10^{-9}$M) were irradiated in the presence of 200 μg/ml AMDMIP, and 3) 10 μl samples of a 200 μg/ml solution of AMDMIP were irradiated in the absence of the 71-mer target. All irradiations were carried out with the CE-I device at 25° C. After preparing the above samples, unirradiated AMDMIP was added to one set of the dark control samples. Another set of dark controls received irradiated AMDMIP. $^{32}$P-SK-39 primer and dNTPs were then added to all samples and the volume was adjusted to 18 μl. These samples were denatured at 95° C. for 5 minutes, followed by equilibration at 55° C. for 3 minutes. Taq polymerase was then added and the extension reaction was carried out for 5 minutes. The reaction was stopped by bringing the samples to 10 mM in EDTA. The final concentrations of all reagents during the extension reactions were:

| Buffer | 1 × Taq |
|---|---|
| Taq Polymerase | 0.5 units |
| dNTPs | 200 μM |
| $^{32}$P-SK-39 Primer | $1 \times 10^{-8}$ M |
| 71-mer target | $1 \times 10^{-9}$ M |
| AMDMIP | 100 μg/ml |

The results were analyzed by PAGE (data not shown). A visual inspection of the autoradiograph showed that the dark controls yielded full length extension product. 71-mer that was irradiated in the presence of AMDMIP resulted in no extension products at all. The sample that contained AMDMIP photoproduct and unirradiated 71-mer resulted in full length entension product, but at about 10% of the level seen in the dark control samples. The observation that some extension product was made in the presence of photoproduct but not with directly irradiated 71-mer indicates that the effects of photoproduct and covalent addition of AMDMIP to a template oligonucleotide may be synergistic.

EXAMPLE 51

Post-Amplification Sterilization

Figure 36:
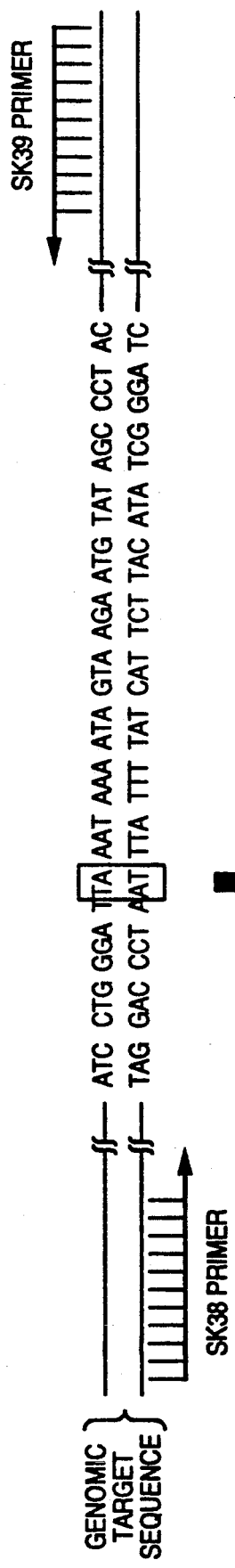
FIG. 36 shows the oligonucleotide system for amplification and subsequent detection of HIV DNA.

FIG. 36 describes a series of oligonucleotides that can be used with the PCR amplification technique. Two primers are described (SK-38 and SK-39) that are complementary to a segment of the HIV genome. Each primer is complementary to sequences at the 5' ends of one of each of two strands of a 115 base pair long segment of the HIV genome. In addition, FIG. 36 describes a crosslinkable probe molecule which is capable of hybridizing and crosslinking to one strand of the 115-mer PCR product. Repeated thermal cycling of SK-38 and SK-39 in the presence of Taq polymerase, appropriate reagents, and a target polynucleotide containing at least the 115-mer segment bounded by SK-38/SK-39, will result in the synthesis of both strands of the 115-mer. Therefore, PCR amplification will occur, with both strands of the 115-mer accumulating geometrically. This is in contrast to the oligonucleotides described in FIG. 26. Only one primer (SK-39) is described in FIG. 26 which is capable hybridizing to the 3' end of the 71-mer target oligonucleotide (HRI-55). The lack of a second primer in the system of oligonucleotides described by FIG. 26 prevents this system from being amplified geometrically. Repeated thermal cycling of HRI-55 and SK-39 in the presence of Taq polymerase and appropriate reagents will result in the linear accumulation of the complement of HRI-55.

The system described in FIG. 36 for the HIV DNA system was used for PCR sterilization. In FIG. 36, the arrows indicate the polymerase extension direction for the primers. The HMT monoadduct on SK-19-MA is shown by (■). A block denotes a natural, conserved 5-TpA-3' crosslinking site in the DNA sequence of HIV.

PCR amplification requires numerous cycles of denaturation and replication. Because denaturation is most conveniently accomplished by heat, the polymerase is ideally thermostable. See K. B. Mullis et al., U.S. Pat. Nos. 4,683,195 and 4,683,202 (incorporated by reference.) Taq I DNA polymerase, a thermostable DNA polymerase isolated from *Thermus aquaticus* (Cetus Corp., Emmeryville, Calif.) was used for all amplifications.

Unless otherwise noted, the PCR amplification procedure follows the broad temporal steps of FIG. 4: 1) template preparation, 2) amplification cycling, and 3) detection.

AMDMIP photoproduct was made by irradiating AMDMIP (using the CE-III device) in 1×Taq buffer (50 mM KCL, 2.5 mM $M_gCl_2$, 10 mM Tris, pH 8.5, 200 $\mu$g/ml gelatin) in a separate vessel for 15 minutes at room temperature (RT). Aliquots of AMDMIP photoproduct and the unirradiated compound were added (by pipetting) at 50, 100, 200 and 300 $\mu$g/ml to 1 $\mu$l aliquots of a $10^6$ dilution of PCR product copies. PCR product was provided by a) preparing template, b) providing template, c) providing PCR reagents, d) providing polymerase, e) mixing PCR reagents, template, and polymerase to initiate PCR, f) cycling to synthesize PCR product.

Step a): Template Preparation. The templates were derived from actual patient samples. Ficoll-Hypaque separated peripheral blood mononuclear cells (PBMCs) are prepared from individuals enrolled in a longitudinal AIDS study. Approximately $1 \times 10^6$ cells are added to 10 ml of RPMI containing 10% fetal calf serum. The cells are pelleted by centrifugation at 200×g for 5 minutes and washed twice with 10 ml PBS. The cell pellet is resuspended in a solution of 50 mM KCl, 10 mM Tris-HCl (pH 8.3), 2.5 mM $MgCl_2$ and subsequently lysed by the addition of 0.5% Tween 20 and 0.5% NP40. Samples are digested with 60 $\mu$g/ml proteinase K (Sigma) for 1 hour at 60° C. Inactivation of the proteinase K is achieved by heating the sample at 95° C. for 10 minutes.

Step b): Providing Template. For the reaction, 10 $\mu$l of template (equivalent to approximately $3 \times 10^4$ cells) is placed in a reaction vessel (0.5 ml Eppendorph tube) for later amplification.

Steps c), d) e) and f). PCR reagents were provided, mixed to a final volume of 20 $\mu$l and cycled as described above.

Figure 37:
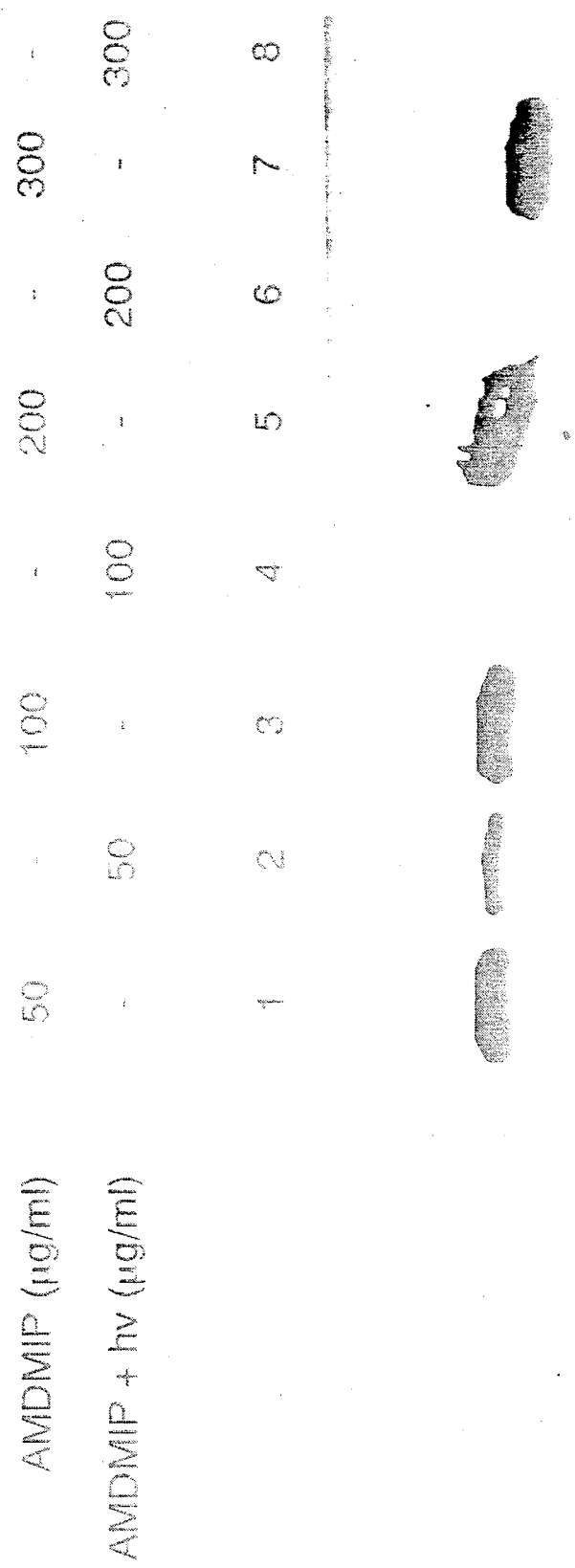
FIG. 37 is an autoradiograph after gel electrophoresis, showing sterilization of PCR with photoproduct.

To evaluate the efficacy of photoproduct as a sterilization reagent, a subsequent polymerase chain reaction was carried out for 30 cycles in the presence of $\alpha$-$^{32}$P-dCTP. PCR reaction products were then visually examined by running them on a 12% acrylamide/8M urea gel followed by autoradiography. The results are shown in FIG. 37. The irradiated compound (i.e. photoproduct) shows complete sterilization (i.e. no PCR product is evident) at concentrations above 50 $\mu$g/ml (Lanes 4,6 and 8); photoproduct shows partial sterilization (i.e. some PCR product is evident) at 50 $\mu$g/ml (Lane 2). The unirradiated compound (i.e. the control) shows no sterilization (Lanes 1,3,5 and 7).

With the concentration spectrum for photoproduct sterilization of PCR broadly defined, an additional experiment was performed to more specifically pinpoint the cutoff for photoproduct sterilization of PCR. Again, AMDMIP photoproduct was made by separately irradiating AMDMIP (with the CE-III device) in 1×Taq buffer for 15 minutes at RT. This time, however, aliquots of AMDMIP photoproduct were added to PCR product to give a concentration range of between 0 25 and 50 $\mu$g/ml.

Again, to evaluate the efficacy of this method of sterilization, a subsequent polymerase chain reaction was carried out for 30 cycles in the presence of $\alpha$-$^{32}$P-dCTP. PCR product was then quantitated by running gels (see above), cutting the bands (detected by autoradiography) and counting the bands on a commercial scintillation counter. The results are plotted on FIG. 38.

Figure 38:
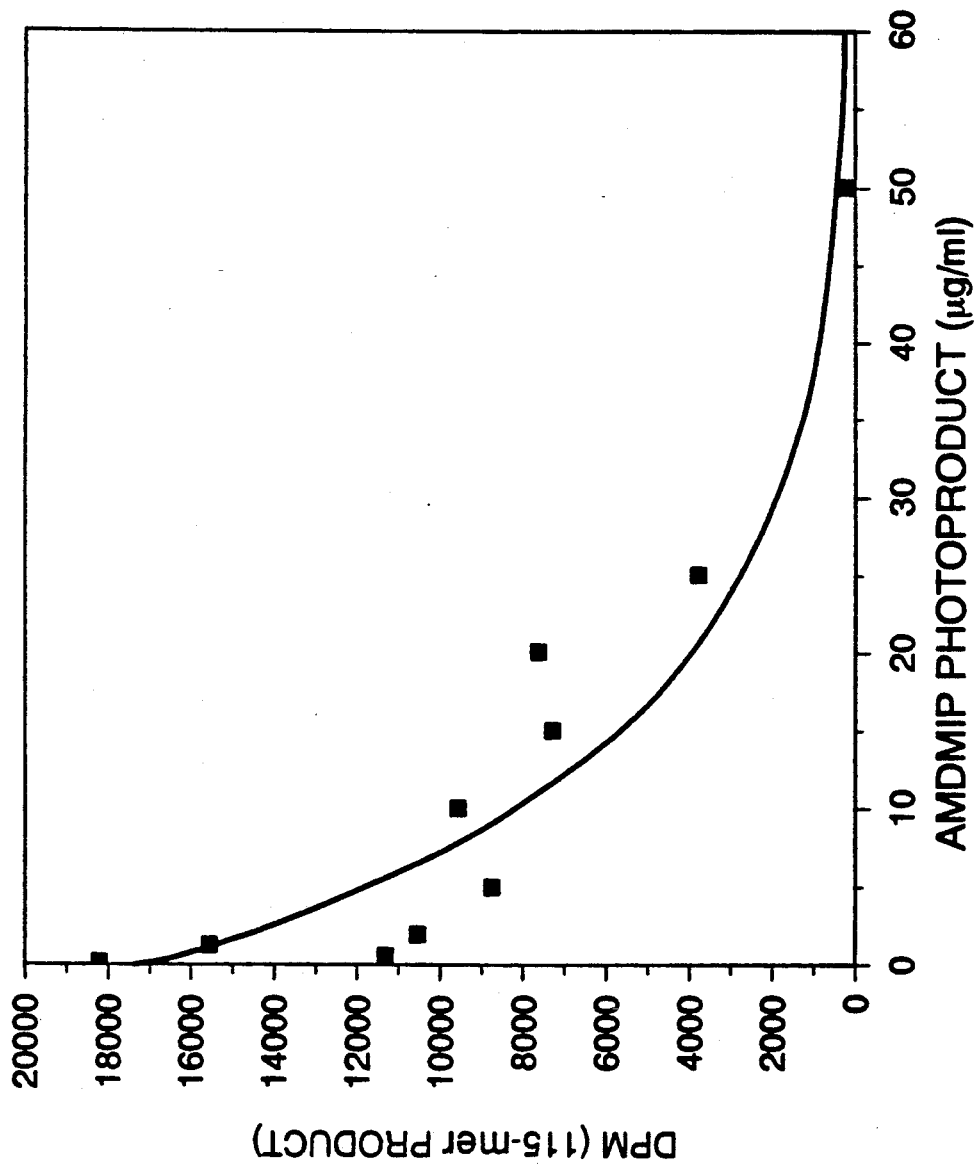
FIG. 38 is a plot of counts (CPM) from bands cut after gel electrophoresis, showing sterilization of PCR according to concentration of photoproduct.

FIG. 38 shows that as little as 5 $\mu$g/ml of photoproduct can result in as much as a 50% reduction in the amount of PCR product (as measured by DPM). On the other hand, very little reduction in PCR product is seen at 0.25 $\mu$g/ml; with concentrations of photoproduct below 0.25 $\mu$g/ml, photoproduct sterilization of PCR is insignificant.

EXAMPLE 52

Post-Amplification Sterilization

It may be desired that photoproduct sterilization of PCR be avoided. Other methods of sterilization—methods that are preferred over photoproduct sterilization—may be employed without interference of photoproduct sterilization by either 1) working with photoreactive compound concentrations that are below that where photoproduct sterilization can occur, or 2) by selecting conditions where less photoproduct is generated.

In this experiment, conditions were selected where less photoproduct was generated. These conditions involve irradiation of AMDMIP with the PTI light source. More intact AMDMIP remains after irradiation with the PTI light source (in contrast with irradiation of AMDMIP with the CE-III device; see FIG. 23).

AMDMIP in 1×Taq buffer was irradiated in the PTI source for 15 minutes at RT. As a control, AMDMIP in 1×Taq buffer was irradiated with the CE-III device for 15 minutes at RT. In both cases, photoproduct was added to 1 $\mu$l aliquots of a $10^6$ dilution of a PCR product mixture to give a final concentration of 100 $\mu$l/ml photoproduct. As a control, unirradiated AMDMIP was added to similar PCR product mixtures at the same concentration as the photoproduct. PCR product was provided as described earlier.

Figure 39:
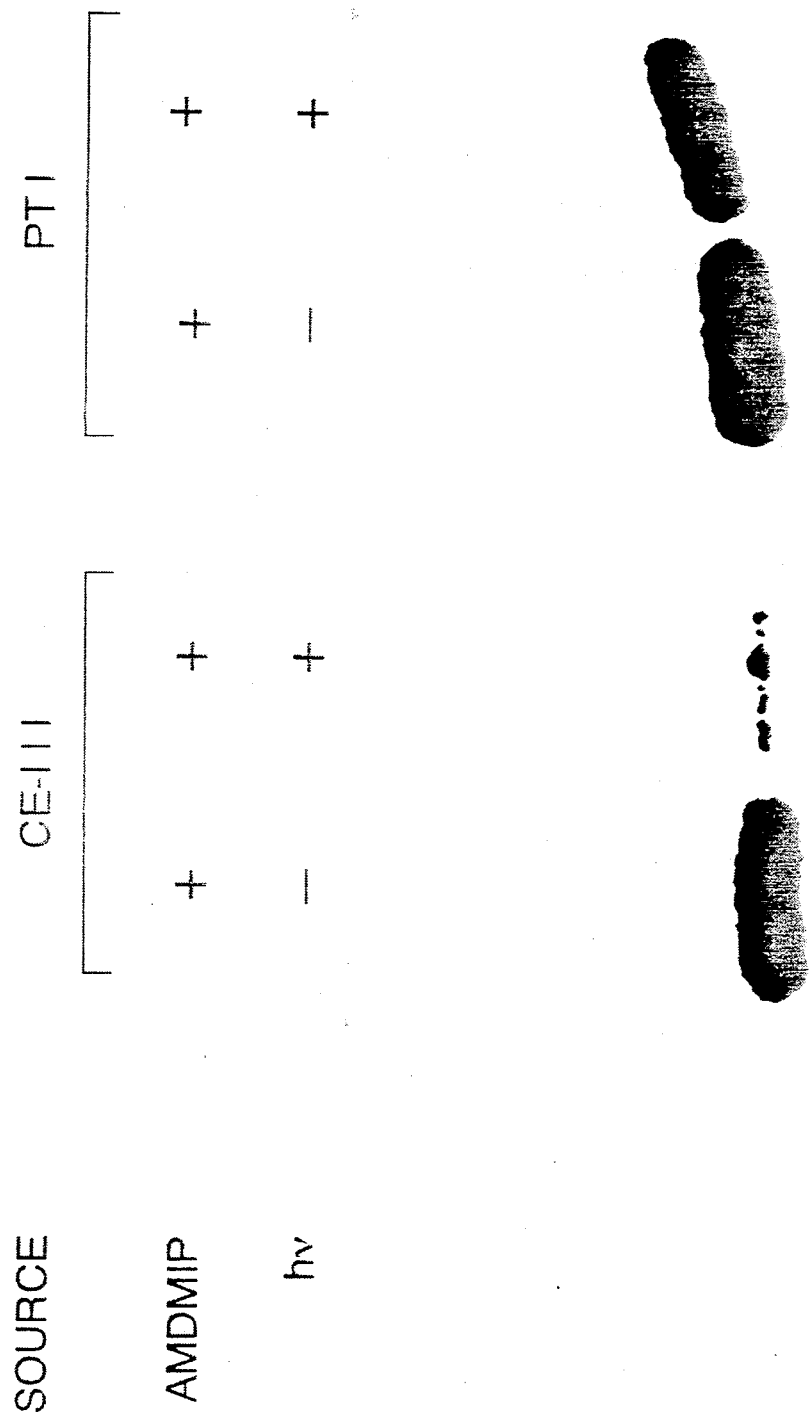
FIGS. 39 is an autoradiograph after gel electrophoresis, showing sterilization of PCR according to the photoactivation device used.

To evaluate the efficacy of this sterilization method, a new PCR reaction was carried out for 30 cycles in the presence of $\alpha$-$^{32}$P-dCTP. PCR product was examined on gels as in Example 51 (FIG. 37) and the gels were subjected to autoradiography. The results are shown in FIG. 39.

In both cases where unirradiated AMDMIP was used (FIG. 39, Lanes 1 and 3) PCR product is clearly evident. Where AMDMIP irradiated in the CE-III device is used, extensive sterilization is observed. By contrast, where AMDMIP irradiated in the PTI device is used, little sterilization is observed. AMDMIP irradiated with the PTI light source shows the same results as unirradiated AMDMIP (control), suggesting that photoproduct is at a concentration below which its effects are seen by the PCR assay.

The dramatic difference in results between the two light sources may be due to the fact that the CE-III source has a shorter wavelength (300 nm cutoff) relative to the PTI source (320 nm cutoff). The absorption spectrum of AMDMIP suggests it would be more reactive with the broader light window provided by the CE-III source.

EXAMPLE 53

Post-Amplification Sterilization

To systematically evaluate the effect of the presence of increasing concentrations of isopsoralen on PCR, AMDMIP (0, 100, 200, 400 µg/ml) was added to $10^7$ copies of HIV 115-mer as template. PCR was then carried out for 30 cycles in the presence of $\alpha$-$^{32}$P-dCTP. The PCR product was run on denaturing polyacrylamide gel and autoradiographed. The bands were thereafter cut and counted. The results were as follows:

| [AMDMIP] | Counts (CPM) |
|---|---|
| 0 | 42200 |
| 100 | 77200 |
| 200 | 77500 |
| 400 | 69400 |

The results show that unirradiated isopsoralen does not cause PCR sterilization. Indeed, with this particular isopsoralen, AMDMIP, there is enhancement of PCR product. Importantly, even high concentrations (400 µg/ml) of AMDMIP show no appreciable impact on amplification.

EXAMPLE 54

Post-Amplification Sterilization

In this embodiment, the method of sterilization comprises: 1) providing PCR reagents, 2) providing template, 3) providing polymerase, 4) mixing PCR reagents, template, and polymerase to initiate PCR, 5) cycling to provide PCR product, 6) providing isopsoralen, 7) adding isopsoralen to PCR product, and 8) irradiating PCR product.

Note that, while the isopsoralen could be introduced to the mixture at any time prior to irradiation (e.g. at the time the template is added in order to avoid opening the reaction vessel again prior to irradiating), in this embodiment, the isopsoralen is added after amplification.

Figure 40:
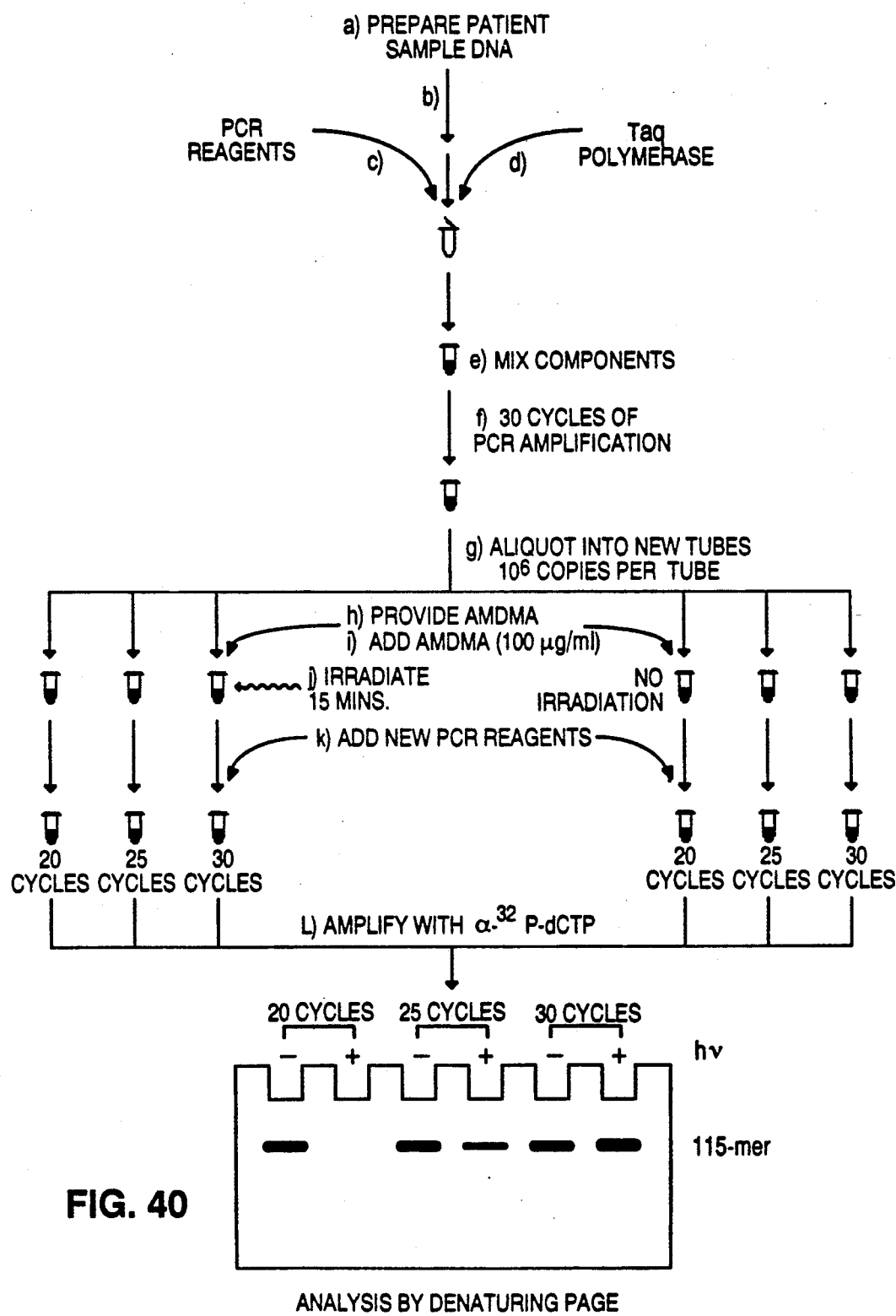
FIG. 40 shows schematically a manner of measuring PCR sterilization according to cycle number.

To demonstrate the effectiveness of the method of the present invention, the sterilized carryover must be shown to be unamplifiable. For the purposes of this determination, the steps of the following experiment include (see FIG. 40): a) preparing template, b) providing template, c) providing PCR reagents, d) providing polymerase, e) mixing PCR reagents, template, and polymerase to initiate PCR, f) cycling to provide PCR product, g) carrying over of PCR product into new tubes, h) providing isopsoralen, i) adding isopsoralen to the carryover, j) irradiating, k) addition of new PCR reagents, and l) subsequent PCR.

Steps a), b), c), d), e), and f). PCR product was provided as described earlier.

Step g) Carrying over of PCR product. Aliquots of PCR product were added into new reaction tubes at $10^6$ copies per tube.

Step h) Providing Isopsoralen. AMDMIP was synthesized as described and diluted.

Step i) Addition of Isopsoralen. AMDMIP (100 µg/ml, approximately $10^{-4}$M) was added reaction vessels containing carryover.

Step j) Irradiation. Irradiation was performed on the PTI device to avoid photoproduct. Three of the new reaction tubes were irradiated while the others were left unirradiated as controls. Irradiation was for 15 minutes at RT as above.

Step k) PCR Reagents and Taq Polymerase Were Added to Appropriate Concentrations. The final volume was increased two fold such that AMDMIP photoproducts were at 50 µg/ml.

Step l) Subsequent PCR. Amplification was performed in closed reaction vessels using primer pair SK-38/39 for 20, 25 or 30 cycles, using the temperature profile for cycling described above in the presence of $\alpha$-$^{32}$P-dCTP.

Figure 41:
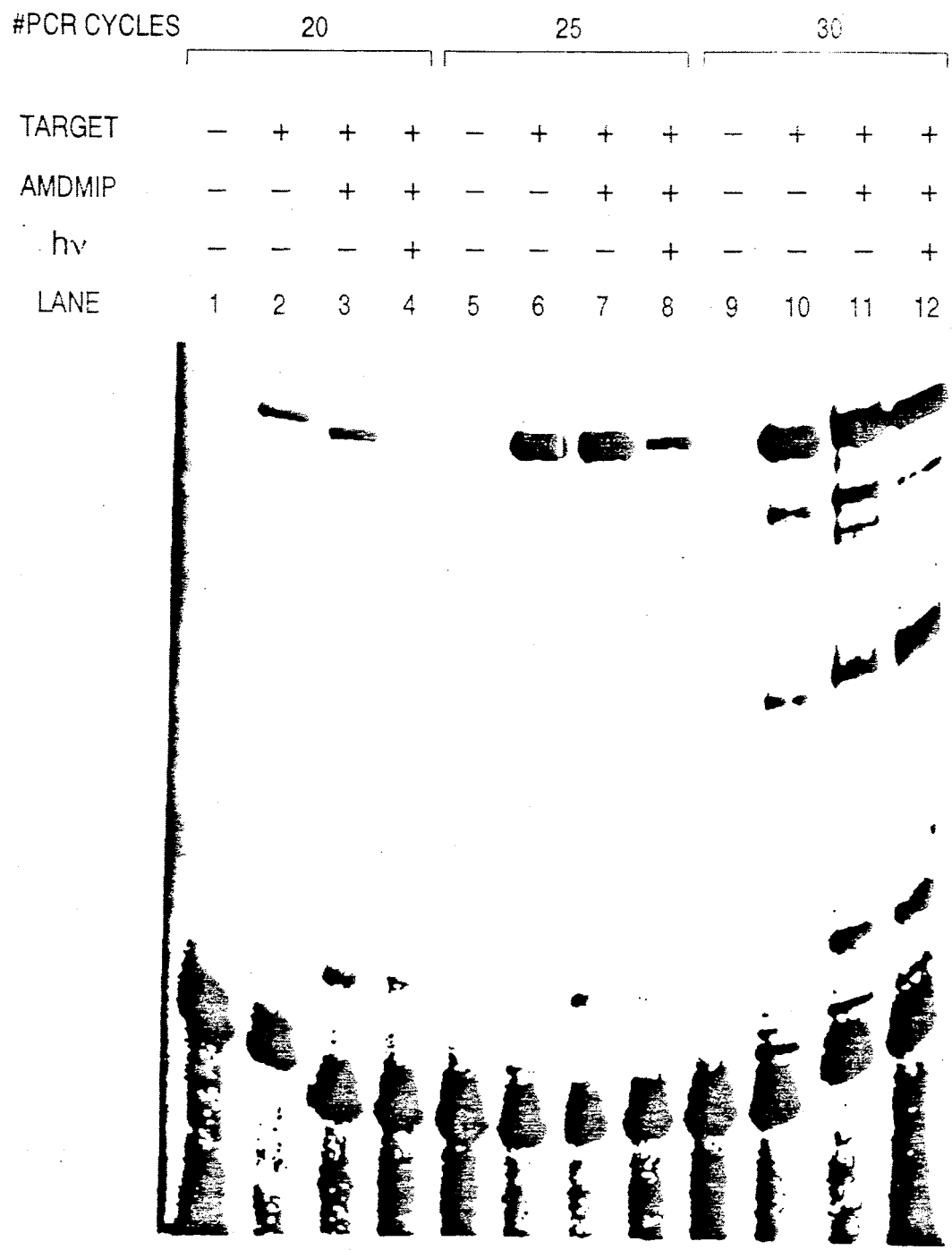
FIG. 41 is an autoradiograph after gel electrophoresis, PCR sterilization according to cycle number.

The results were evaluated by gel electrophoresis and autoradiography (FIG. 41). To the right of the gel lanes, the bands corresponding to starting material and product are indicated. As expected, the control reactions that have no carry-over (Lanes 1, 5, and 9) show no amplified product. On the other hand, the control reactions that contain carryover produced in the first amplification without AMDMIP (Lanes 2, 6, and 10) show amplification. The control reactions that contain carryover produced in the first amplification with AMDMIP, but that were not light-treated (Lanes 3, 7, and 11), also show amplification. Importantly, the reactions that received carryover, AMDMIP and irradiation (Lanes 4, 8 and 12) show isopsoralen sterilization of PCR to a degree that is cycle dependant. With twenty cycles, sterilization appears to be complete (i.e. the twenty-cycle amplification does not provide detectable product). With twenty-five cycles, PCR product is visible (Lane 8), albeit it is reduced relative to controls (Lanes 6 and 7). Finally, with thirty cycles, no significant sterilization is observed; PCR product (Lane 12) is approximately the same relative to controls (Lanes 10 and 11).

On the basis of visual examination of the bands, AMDMIP, when photoactivated in the presence of carryover, appears to be very effective at 20 cycles. However, at thirty cycles, sterilization appears to be overwhelmed. This illustrates the interplay of amplification factor and sterilization sensitivity.

FIG. 41 can be interpreted in terms of Table 6. At 20 cycles of PCR, sterilization appeared to be completely effective (lane 4 compared to lane 3). If 100 CPM is taken to be the threshold for seeing a band on the autoradiograph, then Table 6 shows that the sterilization protocol of this example with AMDMIP left less than $10^4$ target molecules that were capable of being replicated by the PCR procedure. At 25 cycles of PCR, a very measurable band was observed (lane 8), suggesting that at least $10^3$ target molecules retained replicating capabilities. At 30 cycles of PCR it is difficult to distinguish the control signal from the signal obtained with the sterilized sample (lane 11 compared with lane 12). This is consistent with both the control sample and the AMDMIP treated sample reaching the plateau region of the PCR amplification process.

EXAMPLE 55

Post-Amplification Sterilization

To demonstrate the effectiveness of the method of the present invention, the sterilized carryover is again shown to be unamplifiable. In this example, however, isopsoralen is introduced prior to amplification.

Figure 42:
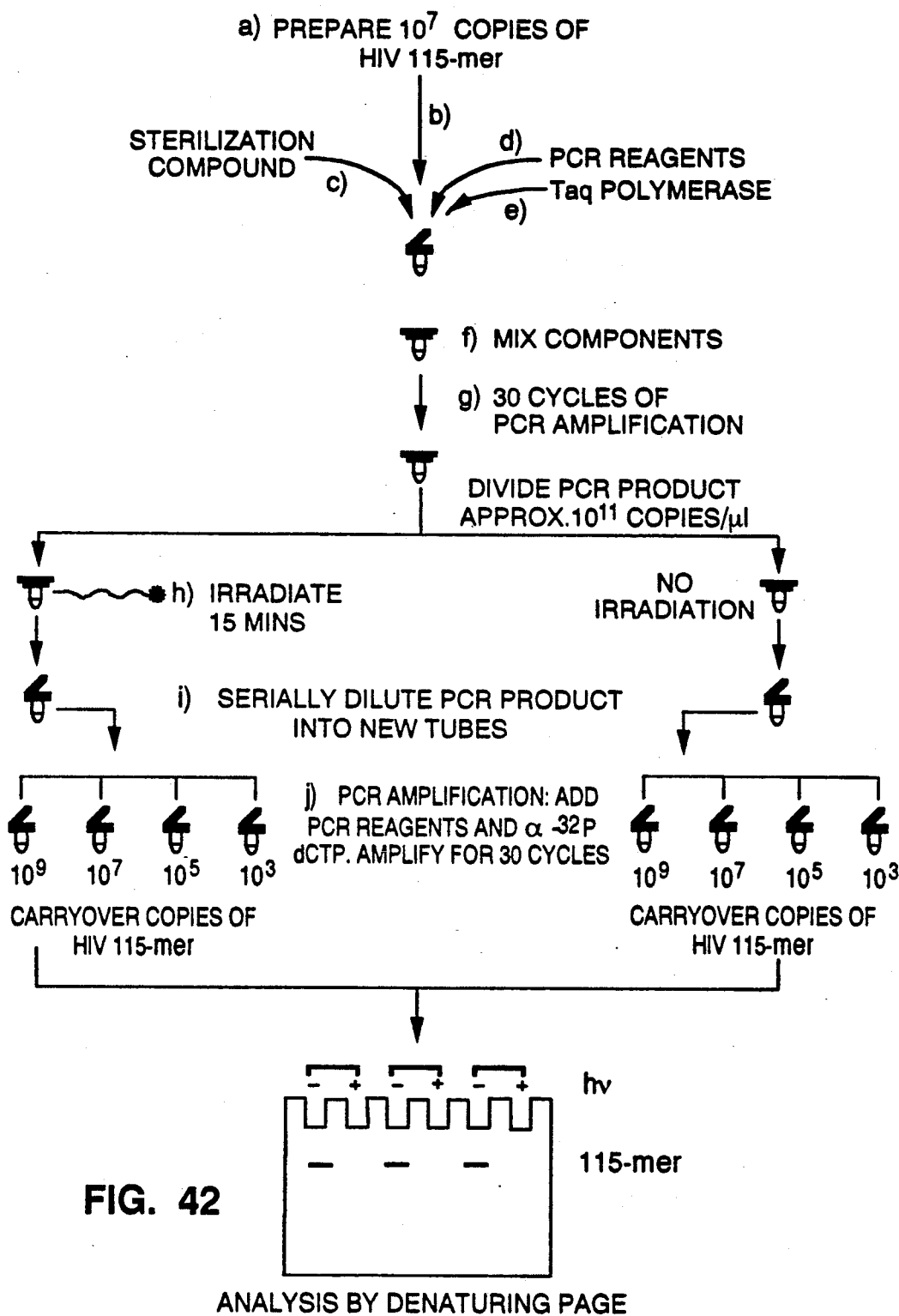
FIG. 42 shows schematically a preferred manner of measuring PCR sterilization.

For the purposes of this determination, the steps of the following experiment include (see FIG. 42): a) preparing template, b) providing template, c) providing isopsoralen, d) providing PCR reagents, e) providing polymerase, f) mixing isopsoralen, PCR reagents, template, and polymerase to initiate PCR, g) cycling to provide PCR product, h) irradiating, i) carrying over of PCR product into new tubes at specific copy numbers, and j) amplifying in a subsequent PCR.

Step a): Template Preparation. HIV 115-mer was used as template.

Step b) Providing Template. For the reaction, template (equivalent to approximately $10^7$ copies) in buffer was provided for the reaction vessel.

Step c) Providing Isopsoralen. AMDMIP (400 μg/ml) was provided as the isopsoralen. This is a higher concentration of AMDMIP than used in the previous example.

Steps d), e), f) and g). PCR reagents and polymerase were provided, mixed and cycled as described above. This time, however, isopsoralen is part of the pre-amplification mixture.

Step h) Irradiation. Irradiation was performed on the CE-III device for 15 minutes at 25° C.

Step i) Carrying over of PCR product. Aliquots of PCR product were added into six new reaction tubes two tubes for each dilution. Dilutions to yield $10^7$, $10^5$ and $10^3$ copies were made. (Note that the dilutions were made from a concentration of approximately $10^{10}$ copies/μl thus, the dilutions produce a concentration of photoproduct that is far too low to consider photoproduct sterilization.)

Step j) Subsequent PCR. New PCR reagents and polymerase were provided and mixed. Amplification was performed in closed reaction vessels using primer pair SK-38/39 for 30 cycles, using the temperature profile for cycling described above in the presence of $\alpha$-$^{32}$P-dCTP.

The results were evaluated by gel electrophoresis and autoradiography (FIG. 43). The control reactions that contained carryover produced in the first amplification with AMDMIP, but that were not light-treated (Lanes 1, 3, and 5) show amplification. Importantly, the reactions that received carryover from the first PCR after irradiation in the presence of AMDMIP (Lanes 2, 4 and 6) show complete, post-amplification sterilization.

EXAMPLE 56

Photobiotin and monoazide ethidium chloride were previously tested for their ability to block template-dependent enzymatic synthesis (see Example 49). The effect of photoproduct (if any) was not investigated at that time.

In this experiment, photobiotin and monoazide ethidium chloride were tested as PCR sterilization reagents. The temporal steps were performed to examine photoproduct effects (if any). Solutions of photobiotin and monoazide ethidium chloride were made up in 1×Taq buffer. Concentrations of photobiotin ranged form $7 \times 10^{-4}$M to $7 \times 10^{-10}$M; concentrations of the monoazide ethidium chloride ranged from $3 \times 10^{-6}$M to $3 \times 10^{-10}$M. The high-end of these concentration series was based on earlier experiments that showed that higher concentrations of these compounds shut down PCR by dark binding. Each compound solution was divided into two parts: One part was irradiated under a GE sunlamp through a pyrex filter (300nm cut-off); the other half was irradiated under a GE sunlamp through a 2.9 M NaNO$_2$ liquid filter (400 nm cut-off). Irradiations were carried out on ice for 15 minutes. After irradiation, aliquots of each tube were carried over into tubes containing PCR reagents and target (HIV 115-mer); PCR was then carried out for 30 cycles in the presence of $\alpha$-$^{32}$P-dCTP. After amplification aliquots were analyzed on 12% acrylamide/8M urea gels.

The results obtained show that monoazide ethidium chloride, when tested in this mode, does not inhibit PCR; 115-mer amplified at the high concentration points. By contrast, when used in this mode, photobiotin shut down PCR at the highest concentration used ($7 \times 10^{-4}$M) (115-mer amplified at all lower concentrations).

Given these results, it is believed that blocking of primer extension seen earlier (Example 49) with the monoazide ethidium chloride was probably due to photobinding and not photoproduct binding. The results seen here with photobiotin, however, suggest that the previous blocking was probably due to photobiotin photoproduct.

EXAMPLE 57

Post-Amplification Sterilization

A PCR sample is prepared for amplification with the following changes. Instead of AMDMIP, AMT is added prior to amplification at a concentration of 100 μg/ml. Instead of primer pair SK-38/39, the biotinylated analogs, in which biotin has been appended to the 5' end of one or both primers via an intervening tetraethylenglycol bridge (ester linkage to the biotin), are used. Following 30 cycles of PCR, the reaction vessel is exposed to 300-400 nm light on the CE-III device. Following irradiation, the PCR reaction vessel is opened and the PCR product removed. Free primer is then removed by spinning the PCR reaction mix through a Centricon 100 (Amicon Division, W R Grace & Co., Danvers, Mass.). The Centricon filters consist of a semipermeable membrane which permits the passage of short oligonucleotides, but not long oligonucleotides. PCR product is differentially retained in the retentate. Several washes are required (these membranes are conveniently mounted in a disposable plastic tube that is spun in a centrifuge for 5 mins at 2000×g). After the final wash, the retentate is immobilized on a nylon membrane or a nitrocellulose membrane by filtration. The filter is then baked under vacuum for 2 hours at 80° C. After immobilization, the PCR product is detected with a commercially available biotin detection systems (BluGene Detection System; catalog #8179 SA; BRL).

Alternatively, detection may be realized by the incorporation of a-$^{32}$P-deoxyribonucleoside triphosphates during the PCR amplification step. The steps here are the same as the first method except for the detection step. Instead of immobilization following the irradiation step, a portion of the sterilized sample is loaded on a 8M urea (denaturing) 11% polyacrylamide gel and electrophoresed for 2-3 hours at 50 watts (25 mA/2000 V) until the marker dye bromphenol blue just runs off the gel. The crosslinked double stranded PCR product is them visualized by autoradiography (XAR-5 X-ray film; Kodak); a typical exposure time is 12-16 hours.

To show that the AMT treated product is sterilized, aliquots of AMT treated PCR reaction mix containing $10^4$ to $10^{10}$ copies of PCR product are carried over into new reaction vessels. PCR reagents are added and the samples reamplified for 30 cycles, and $\alpha$-$^{32}$P-dCTP is present during the amplification. Following PCR, the reamplified samples are analyzed by denaturing PAGE as described above. In all cases, the crosslinked (AMT treated) PCR product does not reamplify.

In a third method, a solution of AMT (100 μg/ml) is prepared and irradiated for 15 minutes on the CE-III device. This solution is then added to a PCR reaction tube which contains target DNA for amplification along with all the reagents necessary for PCR. The mix is then amplified for 30 cycles in the presence of $\alpha$-$^{32}$P-dCTP, then analyzed by PAGE, as above. No reamplification was observed, hence the AMT photoproduct is in itself an effective inhibitor of PCR. The mechanism of photoproduct inhibition is not understood at this time, but is clearly concentration dependent.

EXAMPLE 58

Post-Amplification Sterilization

As discussed generally for sterilization, it is expected that the sensitivity of sterilization will depend upon both the modification density and the length of the PCR target sequences. In this experiment, the effect of modification density and target length on sterilization sensitivity were examined by sterilizing two different length PCR products with either AMIP or AMDMIP. Each isopsoralen was used at two different concentrations for the sterilization procedure to produce differing modification densities on PCR targets.

The two PCR targets used in these experiments were a 115-mer (SK-38/SK-39 HIV system) and a 500-mer. The 500-mer target is obtained from a PCR amplification of a lambda plasmid with primers PCR 01/02. This system is provided by Cetus/Perkin Elmer as a control in their commercial kits of PCR reagents (Catalogue No. N801-0055). For both of these systems equivalent copy numbers of each target were prepared in the following manner: An initial 30 cycle PCR reaction was carried out for each system with the appropriate primers and targets. Aliquots (approximately $10^5$-$10^6$ target copies) of each of these reactions were transferred to a second set of PCR reactions. These second sets of PCR amplifications were carried out in the presence of $\alpha$-$^{32}$P-dCTP, again for 30 cycles. Aliquots of these reactions were removed and counted by liquid scintillation counting. With these numbers, the specific activity of the $\alpha$-$^{32}$P-dCTP, and the sequence of each of the PCR product oligonucleotides (115-mer and 500-mer), the concentrations of each of the two PCR product oligonucleotides in the second set of PCR reaction tubes was determined. Both the 115-mer and the 500-mer concentrations were then adjusted to exactly $1\times 10^{-8}$M by the addition of additional Taq buffer. These stocks of equivalent copy number of PCR products were then used for further investigation. Each of the stock solutions then was subdivided into four reaction tubes. The reaction tubes were adjusted to contain the following: Tube 1, 100 μg/ml AMIP; Tube 2, 400 μg/ml AMIP; Tube 3, 100 μg/ml AMDMIP; and Tube 4, 400 μg/ml AMDMIP. Each of these samples was again split into two portions, one part being irradiated for 15 minutes at room temperature with the CE-III device and the other part kept in the dark. Serial dilutions of the irradiated and the unirradiated targets were then carried out on these samples for 30 cycles in the presence of $\alpha$-$^{32}$P-CTP. Aliquots of these samples were analyzed on denaturing polyacrylamide gels. The PCR product bands were visualized by autoradiography, cut, and counted in a liquid scintillation counter.

Figure 44:
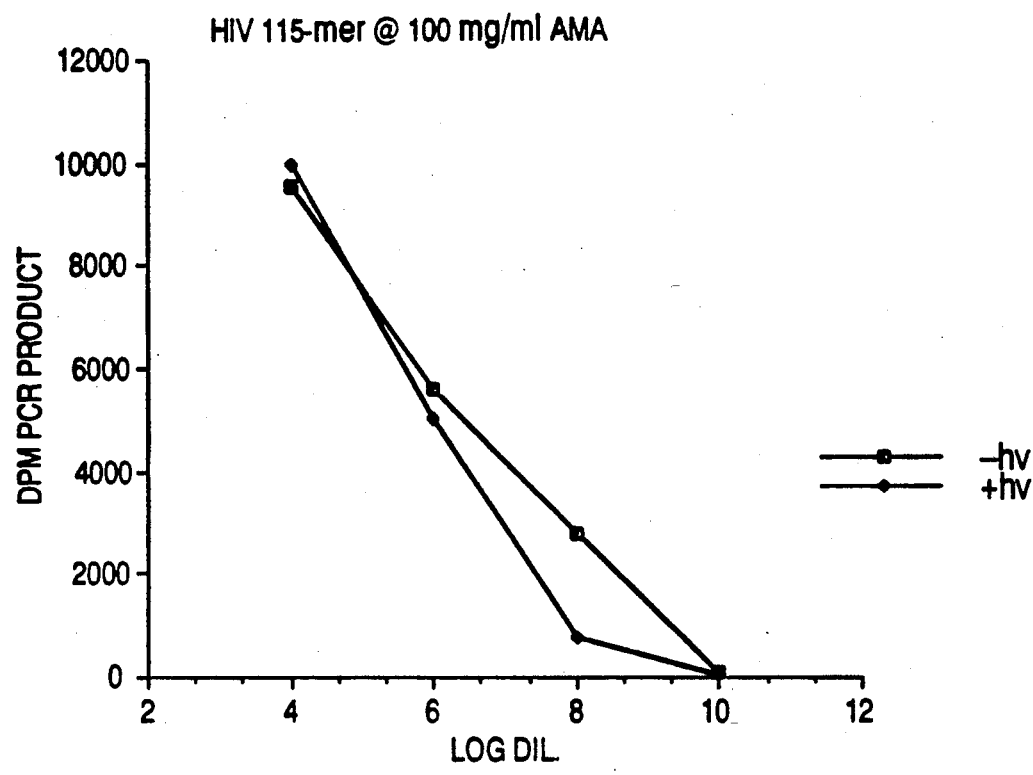
FIGS. 44A, 44B, 44C and 44D show plotted counts of PCR product bands that were visualized by autoradiography, cut, and counted in a liquid scintillation counter, illustrating the effect of modification density and target length on sterilization.
Figure 44:
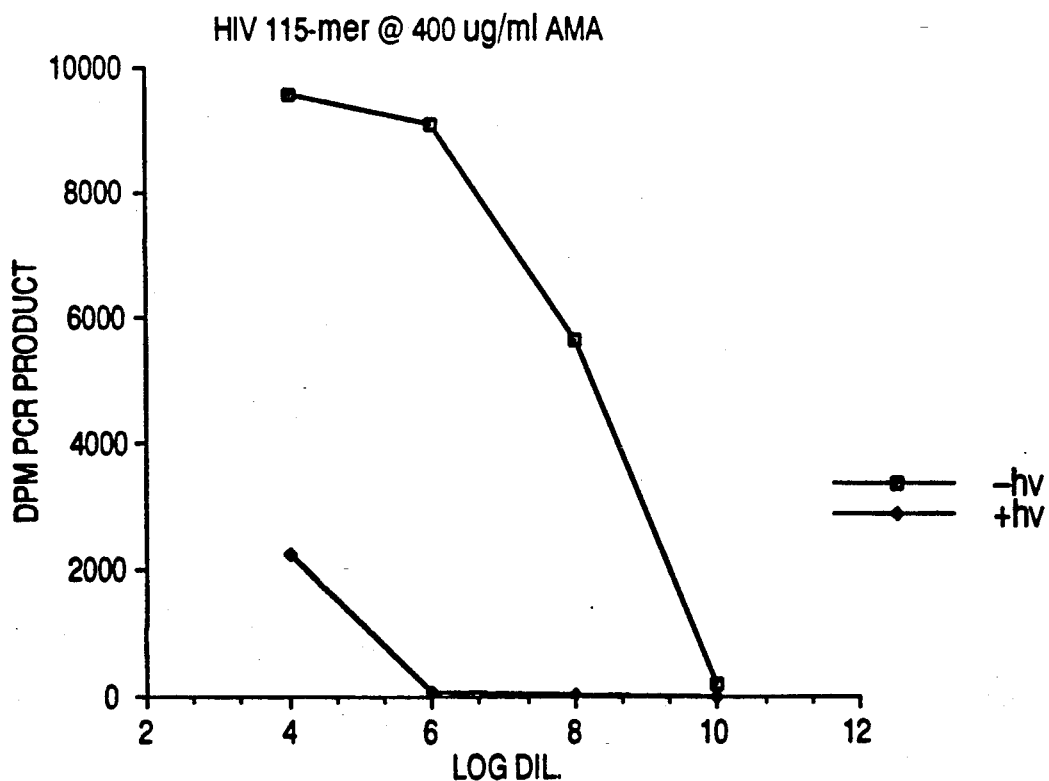

The sterilization effect of 100 μg/ml AMIP on the 115-mer PCR product is illustrated in FIG. 44(A). A $10^8$ fold dilution of the irradiated PCR carryover product, corresponding to 600 carryover molecules, resulted in a diminished PCR signal compared to its unirradiated control after 30 cycles of amplification. At $10^6$ fold or less dilutions of the PCR carryover products, both the irradiated and the unirradiated samples yield similar signals. Apparently at 100 μg/ml, AMIP has an insufficient modification density on the 115-mer to effectively sterilize more than about 10,000 molecules of carryover. When the concentration of AMIP was increased to 400 μg/ml, sterilization sensitivity was improved with the 115-mer target. FIG. 44(B) shows that a carryover of 600,000 molecules of unirradiated PCR product results in a signal which is consistent with the concentration of the PCR product being in the plateau region of PCR amplification. The equivalent amount of irradiated PCR carryover product does not produce a measurable PCR signal at all. 100 fold more of the irradiated PCR carryover product does start to overwhelm this sterilization protocol, indicating that the sterilization sensitivity limit with 400 μg/ml AMIP and the 115-mer PCR product is about $10^6$ carryover molecules.

Figure 44C:
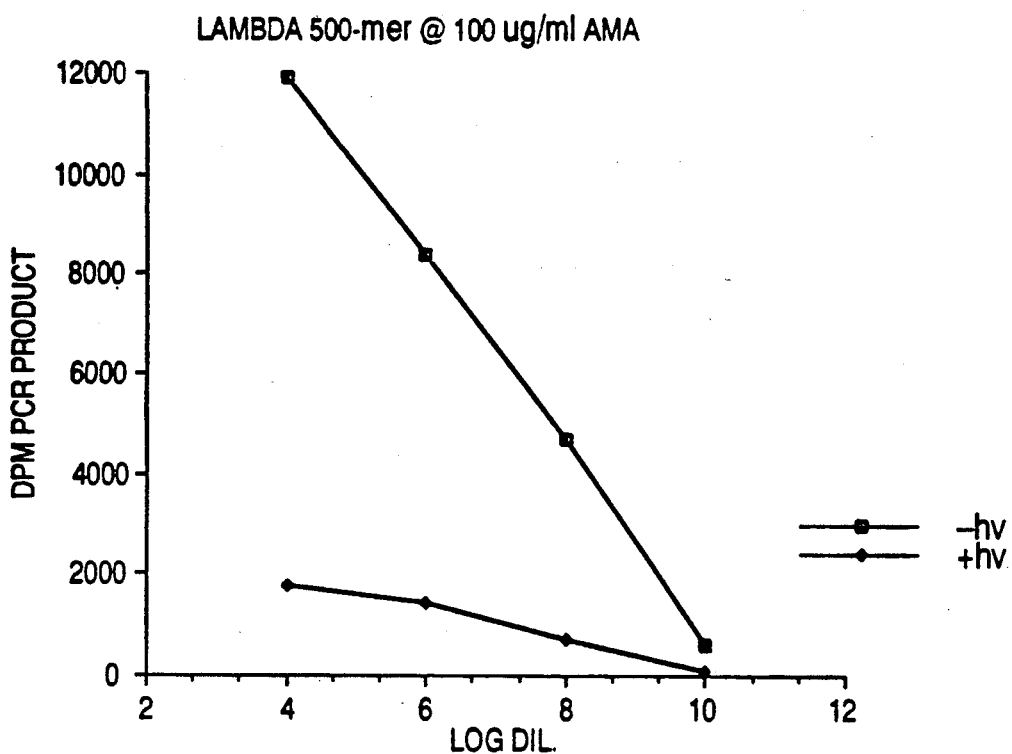
Figure 44:
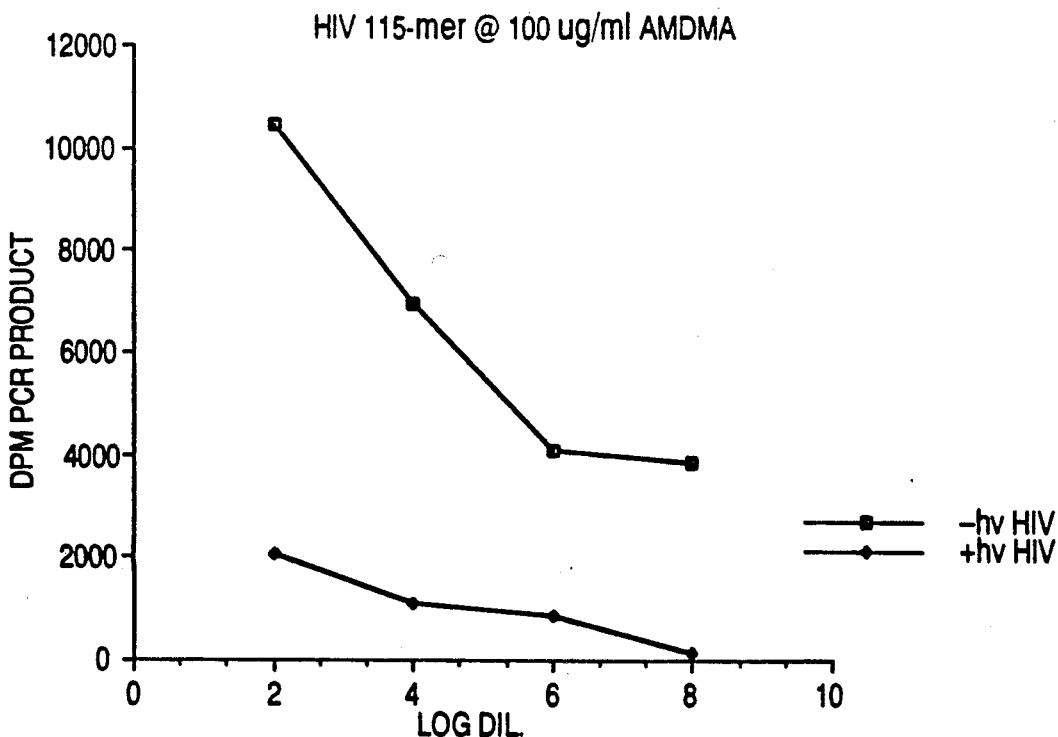

The effect of PCR product length is illustrated by comparing FIG. 44(C) to FIG. 44(A). At 100 μg/ml of AMIP, the 500-mer PCR product is clearly more effectively sterilized than the 115-mer PCR product. At 400 μg/ml AMIP, the irradiated 500-mer was not amplified at all for any of the dilution series up to $6\times 10^9$ molecules of carryover (data not shown). Larger amounts of carryover were not tested. The unirradiated 500-mer with 400 μg/ml AMIP yielded signals comparable to those in FIG. 44(C).

FIG. 44(d) shows that AMDMIP at 100 μg/ml is a better sterilization agent with the 115-mer PCR product than is AMIP at a similar concentration (compare with FIG. 44(A)). When AMDMIP was used at 400 μg/ml, the irradiated carryover series yielded no signal at all up to $6\times 10^9$ molecules of carryover with the 115-mer PCR product. The unirradiated controls yield normal levels of PCR signals from the carryover molecules. When AMDMIP was used with the 500-mer PCR product, both 100 μg/ml and 400 μg/ml concentrations resulted in no signal in the irradiated dilution series. AMDMIP at 100 μg/ml has a high enough modification density on the 500-mer target that there appears to be no non-sterilized 500-mers in $6\times 10^9$ carryover molecules with the $\alpha$-32P assay for PCR product.

EXAMPLE 59

Figure 45:
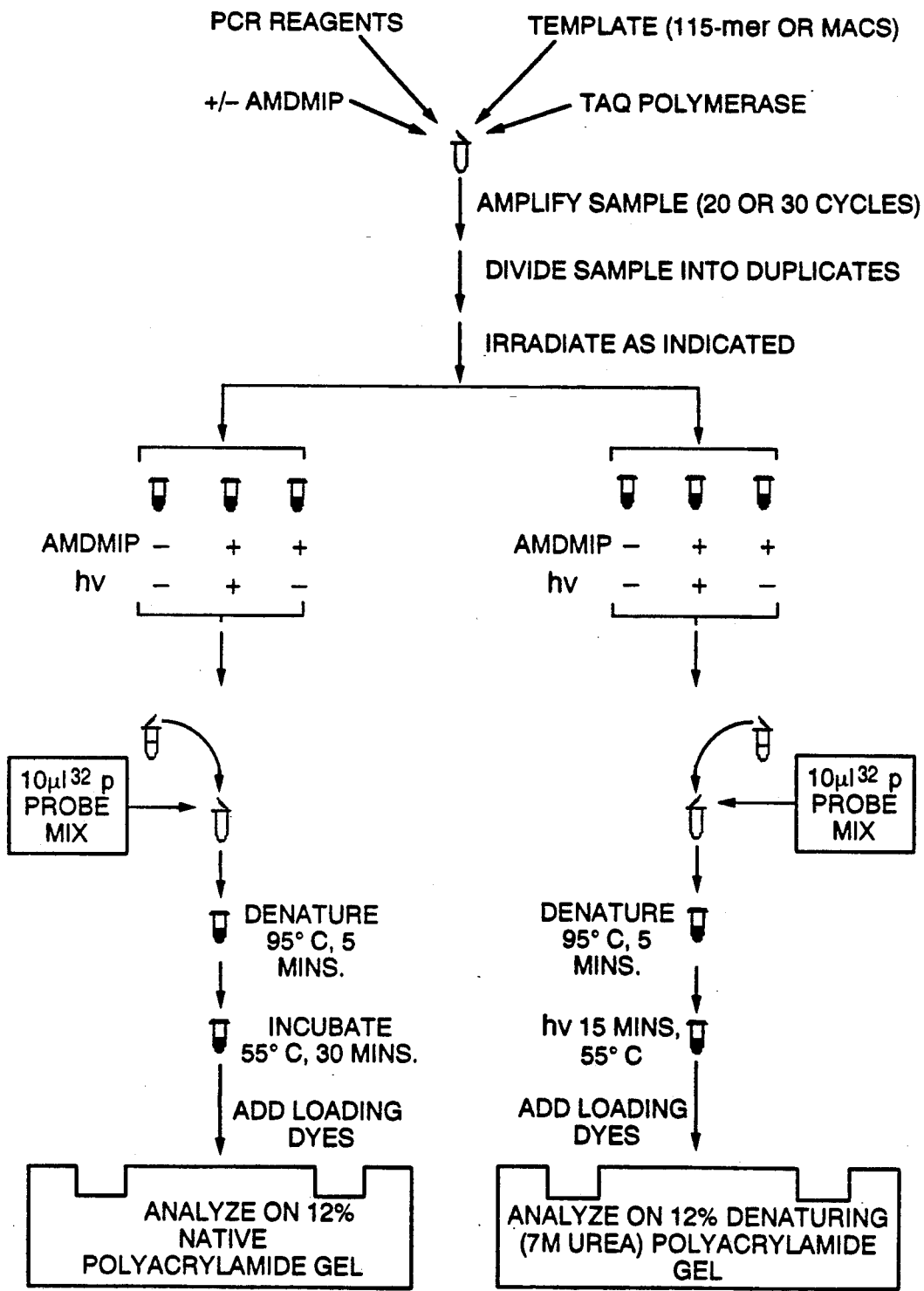
FIG. 45 shows schematically two different hybridization formats: 1) Oligonucleotide Hybridization (OH) and 2) Crosslinkable Oligonucleotide Probe Analysis (COP).

It is believed that isopsoralens form monoadducts with double stranded nucleic acid but do not form crosslinks because of their angular structure. Because of this, these isopsoralen-modified single strands should remain detectable by hybridization procedures. The following experiments demonstrate the particular usefulness of isopsoralens by virtue of their compatibility with two different hybridization formats: 1) Oligonucleotide Hybridization (OH) and 2) Crosslinkable Oligonucleotide Probe Analysis (COP) (FIG. 45). The experiments show that AMDMIP sterilized target molecules remain detectable by both OH and COP procedures. The presence of AMDMIP on the target 115-mer appears not to inhibit probe hybridization and likewise, does not reduce the crosslinkability of these sterilized target molecules, when assayed and examined visually on gels.

Preparation of Samples

The HIV 115-mer system with primers SK-38/SK-39 was used for the experiment (see FIG. 36, "HIV Oligonucleotide System"). Two types of starting template were used: previously amplified 115-mer or genomic DNA, isolated from an individual known to be infected with HIV (MACS sample). For previously amplified 115-mer between $10^5$ and $10^6$ copies were used for starting template. For the genomic (MACS) sample, approximately 1 μg ($3 \times 10^5$ copies) of genomic DNA were used. Two PCR samples were prepared for each type of template then amplification was carried out for either 20 or 30 cycles. One of the two PCR samples contained AMDMIP at 200 μg/ml while the other was AMDMIP free. Following amplification, the AMDMIP containing samples were divided and half were irradiated. Analysis (OH or COP) was then done on the three samples from each set (AMDMIP free, AMDMIP unirradiated, and AMDMIP irradiated) for each cycle number. The AMDMIP free samples served as control, the AMDMIP unirradiated sampes adressed the effect of non-covalently bound AMDMIP on detection, and AMDMIP irradiated samples addressed the effect of covalently bound AMDMIP on detection.

COP and OH assays were performed a follows. 10 μl of the PCR reaction mixture was added to 3.3 μl of "probe mix" [5'-labelled SK-19 (normal or monoadducted) at $10^{-8}$M containing EDTA and an appropriate salt mixture], overlaid with 30-40 μl of light mineral oil, then heated to 95°-100° C. for 5 minutes. For COP, the hybridization mixture as placed in the PTI device at 56.C and irradiated for 15 minutes. Following this, loading dyes (containing urea or formamide) were added, the sample heated to 95°-100° C. for 5 minutes, quick chilled on wet ice, then loaded on a denaturing PAGE gel followed by electrophoresis under denaturing conditions. For OH reactions, the hybridization mixture was incubated at 56° C. for 30 minutes, loading dyes added, and aliquots loaded directly into a native PAGE gel followed by electrophoresis under native conditions.

1. COP Results: The results with COP are shown in FIG. 46. Samples 1-6 contain previously amplified 115-mer that was re-amplified either 20 (samples 1,3,5) or 30 (Samples 2,4,6) cycles then detected by COP. Samples 1 and 2 are controls (without AMDMIP); samples 3 and 4 are (with AMDMIP and with light) sterilized samples; samples 5 & 6 are (with AMDMIP but without light) controls. The bands corresponding to amplified 115-mer crosslinked to labelled 41-mer probe (SK-19 MA) are the upper bands in FIG. 46. Samples 11-16 are the same series except the MACS sample was used as template.

Inspection of FIG. 46 shows that only the samples amplified 30 times generated significant PCR product (band excision allowed the 20 cycle samples to be quantitated; see below). The visual intensity all of the hybrid bands in the 30 cycle series appear to be quite similar. For the 30 cycle series, comparison of the (no compound) control amplification (lanes 2/12) with the test amplification [with AMDMIP and light (lanes 4/14)] with the (no light) control amplification (lanes 6/16) shows little difference in band intensity. Better quantitation was obtained by excising the bands and counting which provided the following numbers:

| Sample | CPM(%) | Sample | CPM(%) |
|--------|--------|--------|--------|
| 1 | 3104(100) | 11 | 878(100) |
| 3 | 1944(62) | 13 | 460(52) |
| 5 | 4480(144) | 15 | 464(53) |
| 2 | 43948(100) | 12 | 53304(100) |
| 4 | 36452(83) | 14 | 41777(78) |
| 6 | 39596(90) | 16 | 35176(66) |

The trends in both the 20 and 30 cycle series were similar. Comparison of the (with AMDMIP and light) samples (3,4,13,14) with the corresponding (without AMDMIP and without light) samples (1,2,11,12) shows the hybridization signal is reduced between 52 and 83%. Comparison with the (with AMDMIP but without light) controls also show a reduction in hybridization signal (except sample 5). It is expected that these (no light) samples are samples which contained AMDMIP but were not sterilize prior to the COP analysis. However, light is added during the COP procedure, and since AMDMIP is present, photoaddition occurs during COP.

Figure 47:
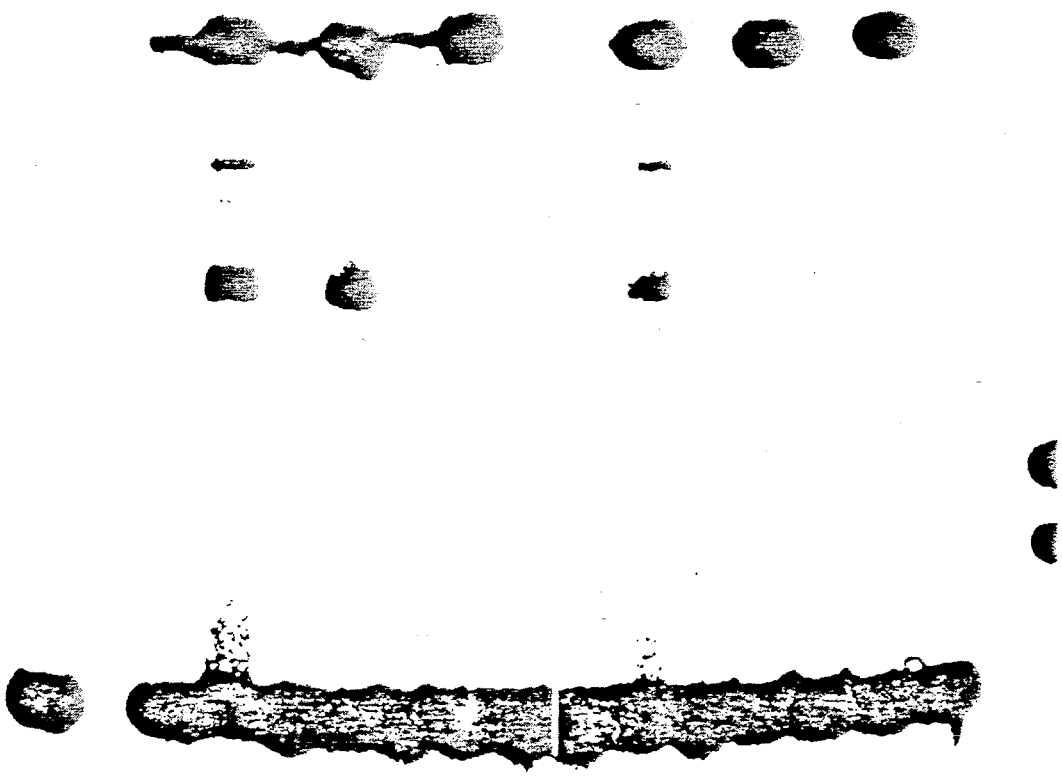
FIG. 47 is an autoradiograph after gel electrophoresis, showing hybridization after sterilization by Oligonucleotide Hybridization (OH).

2. OH Results: The results with OH are shown in FIG. 47. This experiment used the same amplified samples described above; it was identical to the COP experiment except that detection was by OH. Samples 1-6 again contain previously amplified 115-mer that was re-amplified either 20 (samples 1,3,5) or 30 (samples 2,4,6) cycles followed by OH analysis. Samples 1 and 2 are (without compound and without light) controls; samples 3 and 4 are (with AMDMIP and with light) samples; samples 5 and 6 are (with AMDMIP but without light controls. The bands corresponding to amplified 115-mer hyridized to labelled 41-mer probe SK-19) are the upper bands in FIG. 47. Lanes 11-16 are the same series but the MACS sample was used as the template. The sample in the middle is a negative (reagent) control, while "M1" and "M2" are probe alone (as marker).

Visual inspection of FIG. 47 shows that only the samples amplified 30 times provided significant PCR product. In the 30 cycle series, the band intensities all appear to be similar. Comparison of the control amplifications (lanes 2/12) with the test (with AMDMIP and light; lanes 4/14) and the control (with AMDMIP but without light; lanes 6/16) show similar intensity. It was not possible to obtain reliable counts from the bands in this gel (native gels do not tolerate the band excision process), so more quantitative comparisons were not made. Relying on the visual signal of the gels one can conclude that there may be no impact of the photoreactive compound (whether covalently or non-covalently bound to nucleic acid) on subsequent detection of the amplified target. Assuming the quantitation of the OH (if it could be done) shows the same trend as the COP data, there may be a difference of up factor of 2 in hybridization signal caused by the presence of the photoreactive compound.

EXAMPLE 60

Post-Amplification Sterilization

Figure 48:
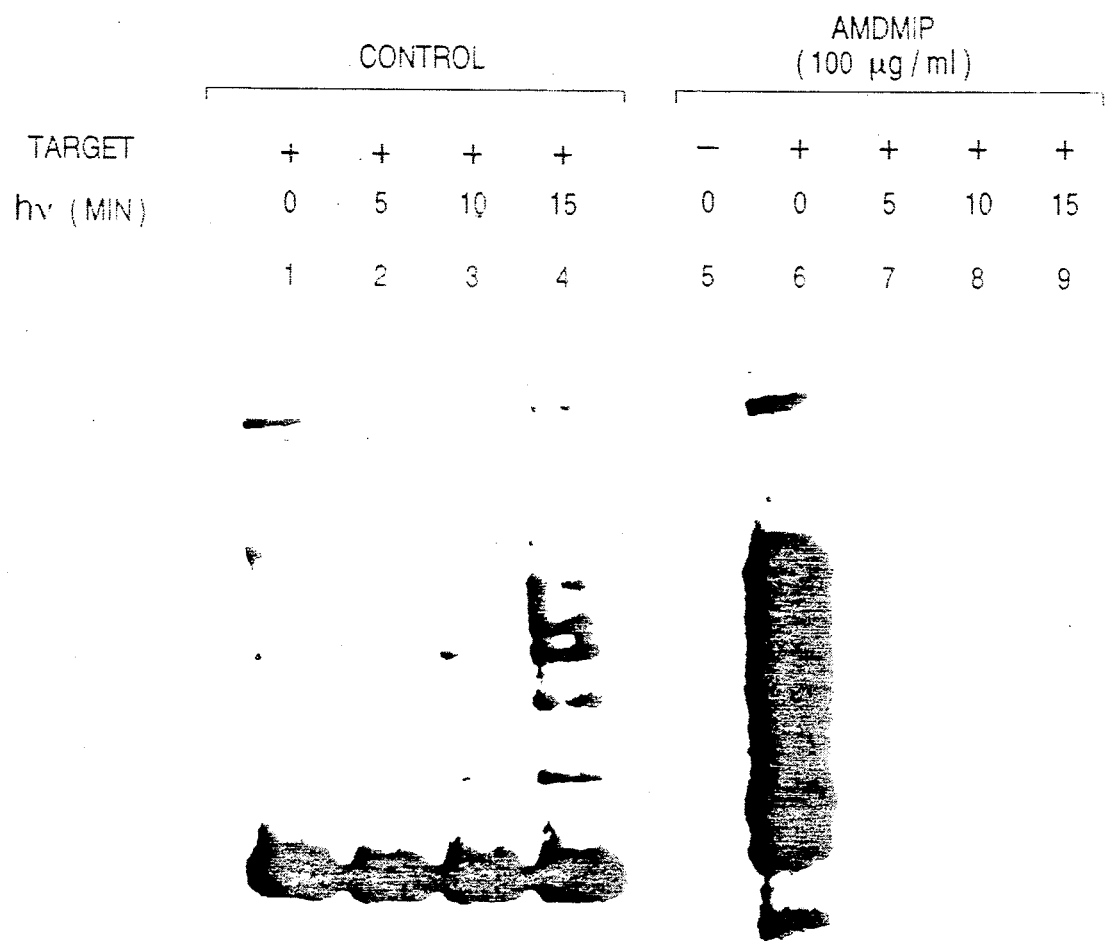
FIG. 48 is an autoradiograph after gel electrophoresis, showing PCR sterilization of an HLA DNA system.

Four samples containing 1 μg of Molt-4 human genomic DNA target were prepared for PCR with primers KM 29 (5'-GGTTGGCCAATCTACTCCCAGG) and HRI-12 (5'-GGCAGTAACGGCAGACTACT). These primers give a 174 bp product within the human beta globin gene. All four samples contained AMDMIP at 100 μg/ml, and were irradiated for 0, 5, 10 or 15 minutes prior to PCR amplification. A duplicate set of control samples were also prepared which did not contain AMDMIP. Amplification were carried out in 1×Taq buffer (50 mM KCl, 10 mM Tris pH 8.5, 2.5 mM MgCl$_2$, 200 μg/ml gelatin), 175 μM each dNTP, 20 μM primer with 2.5 units of Taq polymerase and 100 μg/ml AMDMIP present during amplification. PCR was carried out for 30 cycles; one cycle = 30 sec at 94° C. (denaturing), 30 sec at 55° C. (primer annealing), and 60 sec at 72° C. (extension). $\alpha$-$^{32}$P-dCTP was used as an internal label. After amplification, the samples were analyzed for product by PAGE followed by autoradiography. As shown in FIG. 48, irradiation in the presence of AMDMIP at all time points (Lanes 5-8 are, respectively, 0, 5, 10 and 15 minutes) resulted in no amplification of the sterilized genomic target. Irradiation in the absence of AMDMIP at all time points (Lanes 1-4 are, respectively, 0, 5, 10 and 15 minutes) resulted in amplification of the genomic target.

Note that the concentration of AMDMIP was selected to be 100 μg/ml. This concentration of unirradiated AMDMIP was determined to have no significant impact on amplification (data not shown). Even when the sterilizing compound is the same, it is desirable to determine appropriate concentrations for each particular amplification system (in this example, Globin) and not rely on concentrations determined for other systems (e.g. HIV). In general, results with the present invention indicate that, the longer the length of the amplification product, the lower the concentration of unactivated compound needed to inhibit amplification (data not shown).

EXAMPLE 61

Post-Amplification Sterilization

This example investigated the concentrations at which non-psoralen compounds inhibited PCR in the absence of light. The compounds tested were the following: 1) ethidium bromide (a Phenanthridine, see Table 1), 2) xylene cylanol (an Organic Dye, see Table 1), 3) bromphenol blue (an Organic Dye, see Table 1), 4) coumarin and 5) methylene blue (a Phenazathionium Salt, see Table 1).

Figure 49:
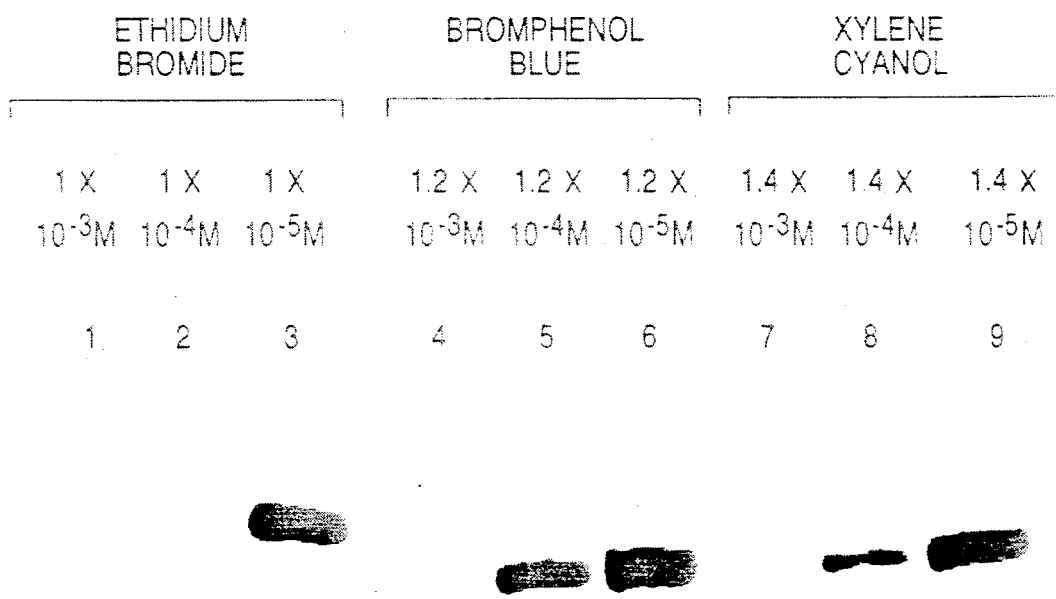
FIG. 49 is an autoradiograph after gel electrophoresis, showing inhibition of PCR with non-furocoumarin compounds.
Figure 1A:
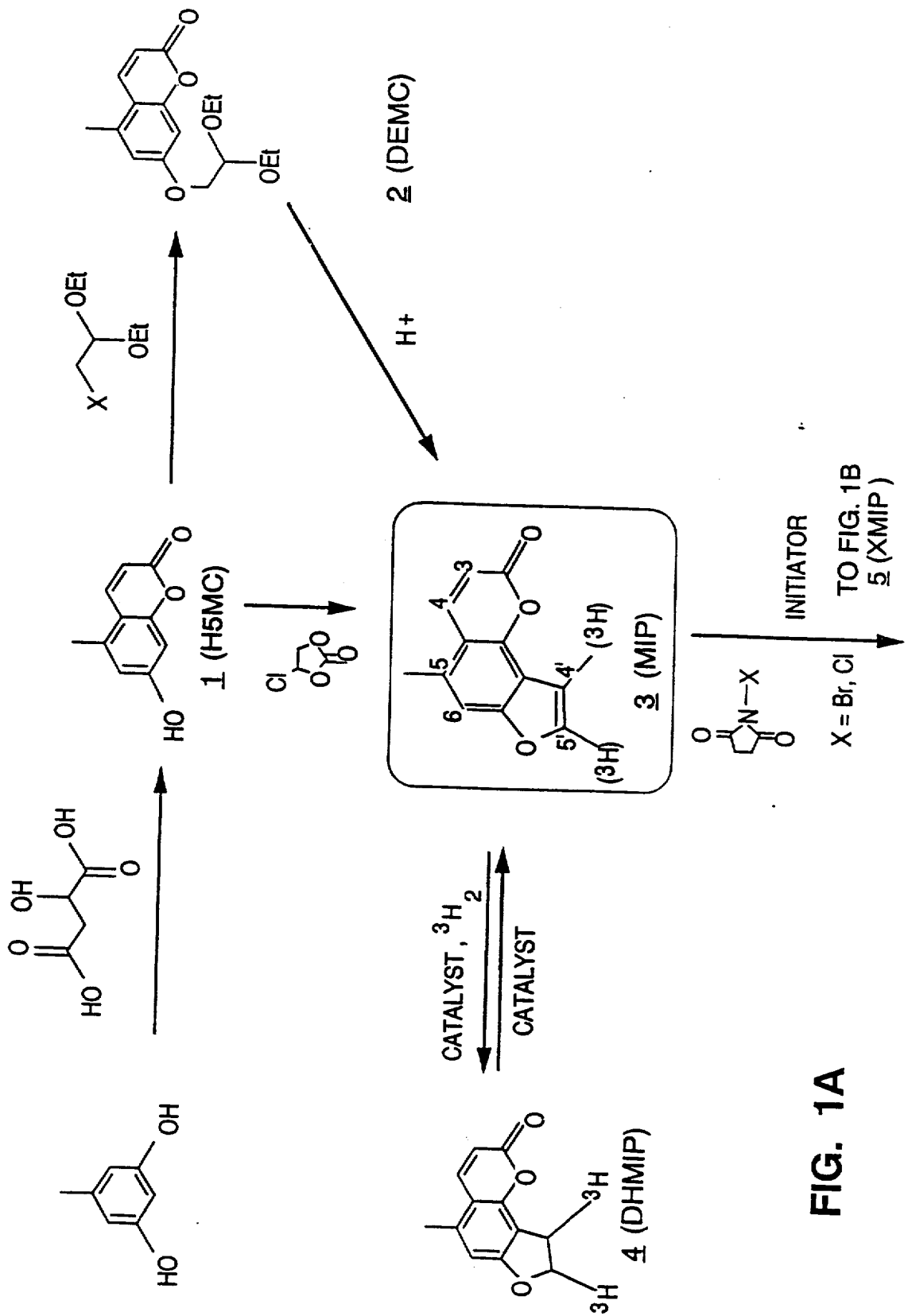
Figure 1B:
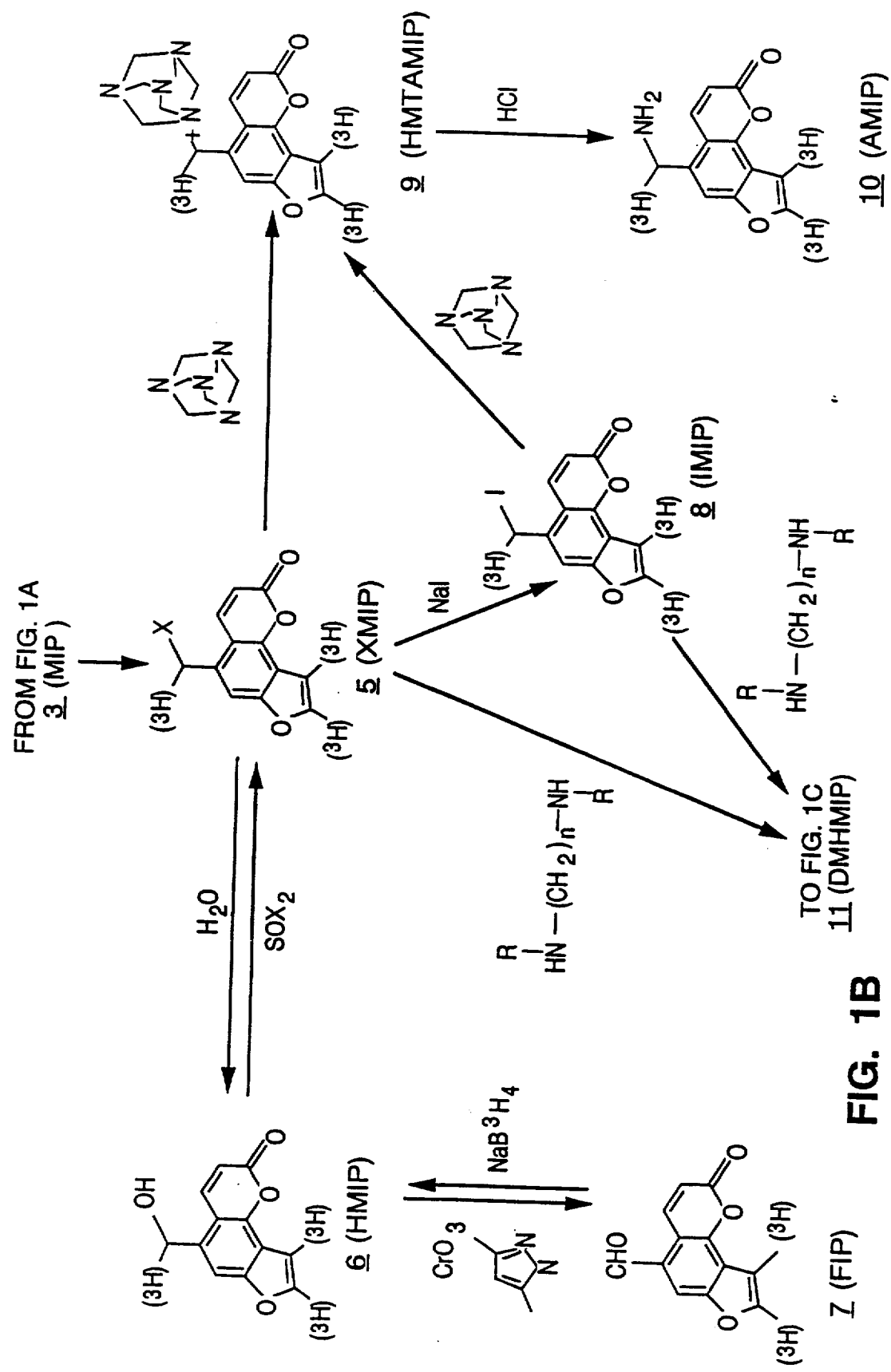
Figure 1C:
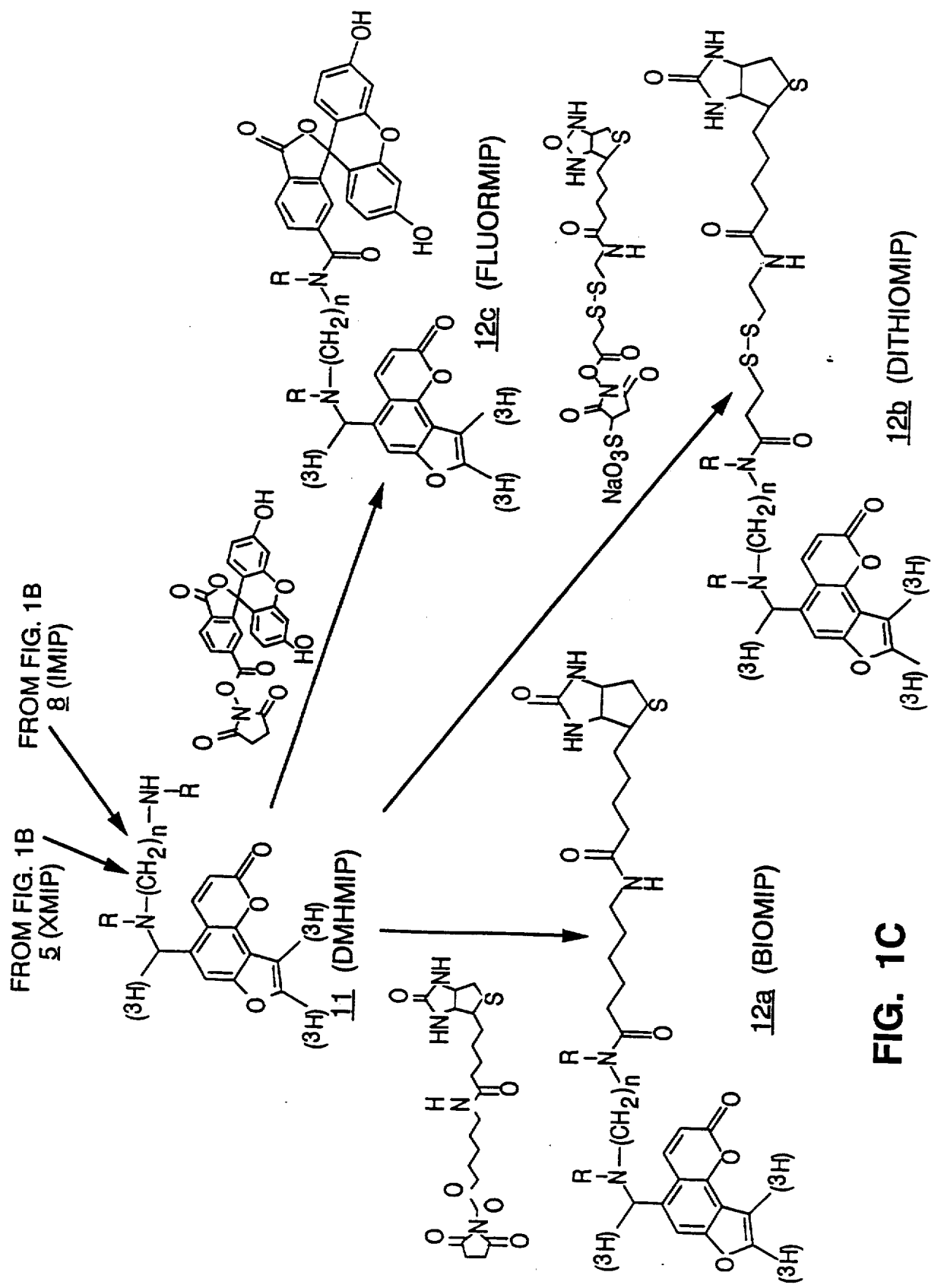
Figure 2B:
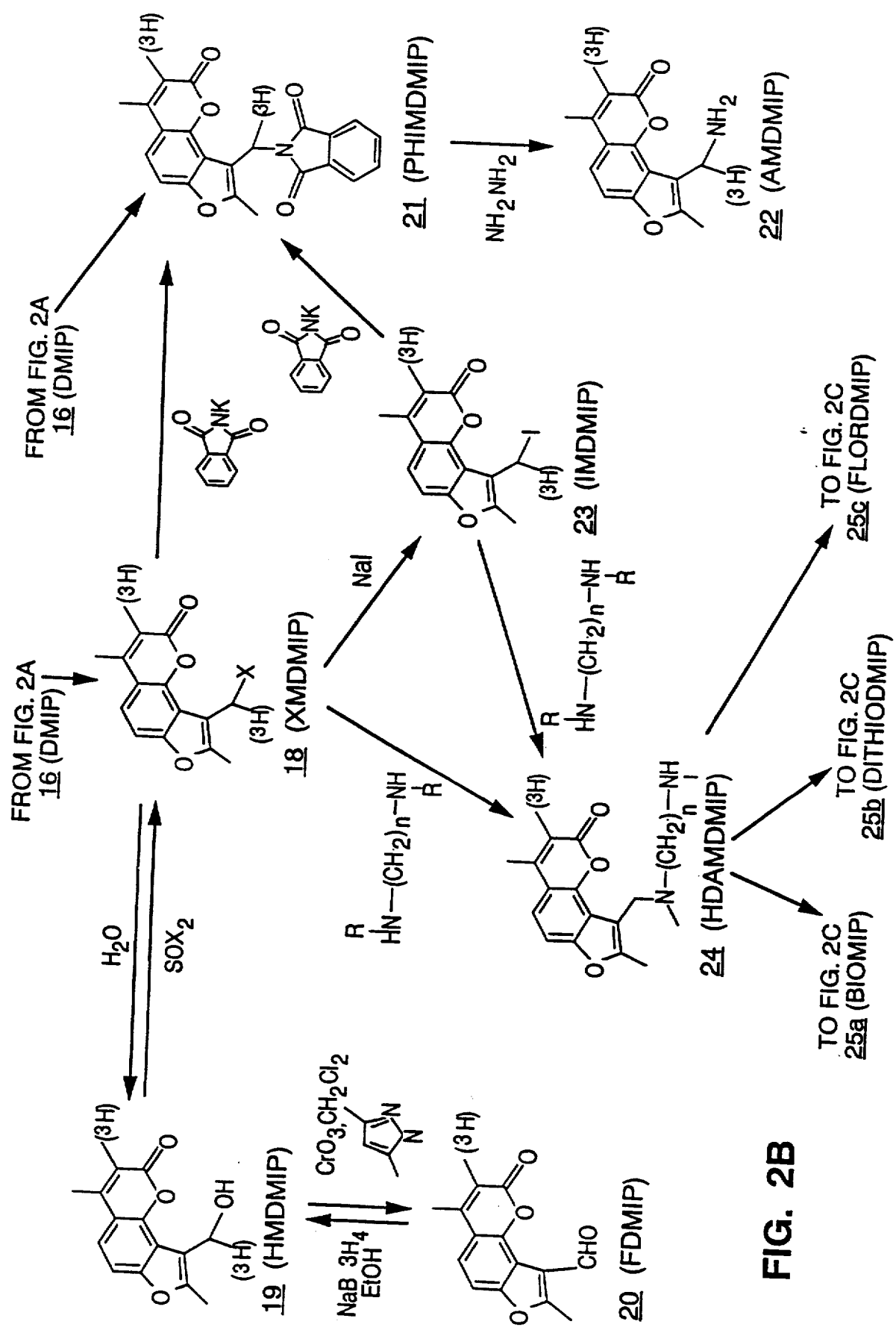
Figure 2C:
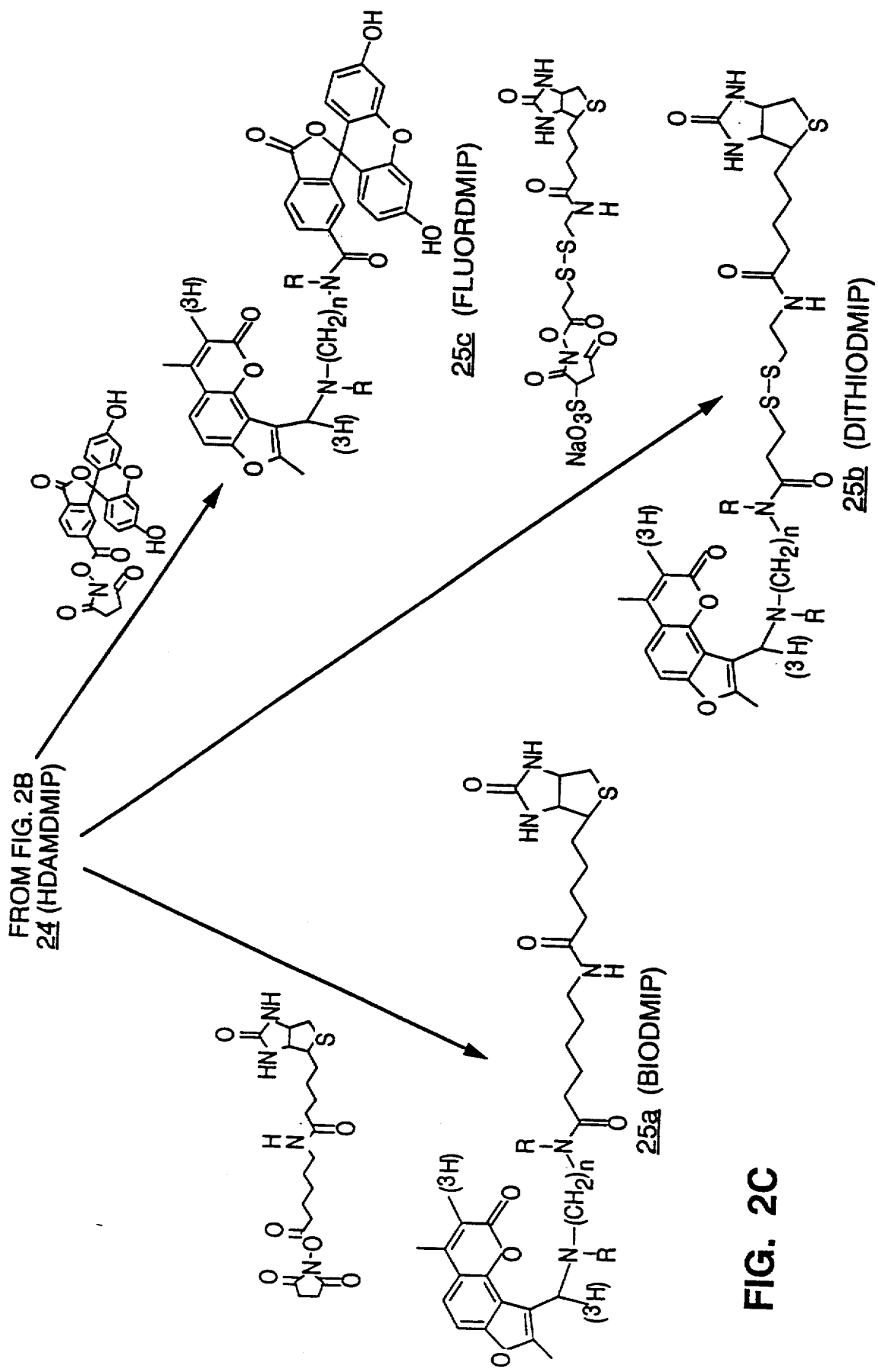
Figure 5:
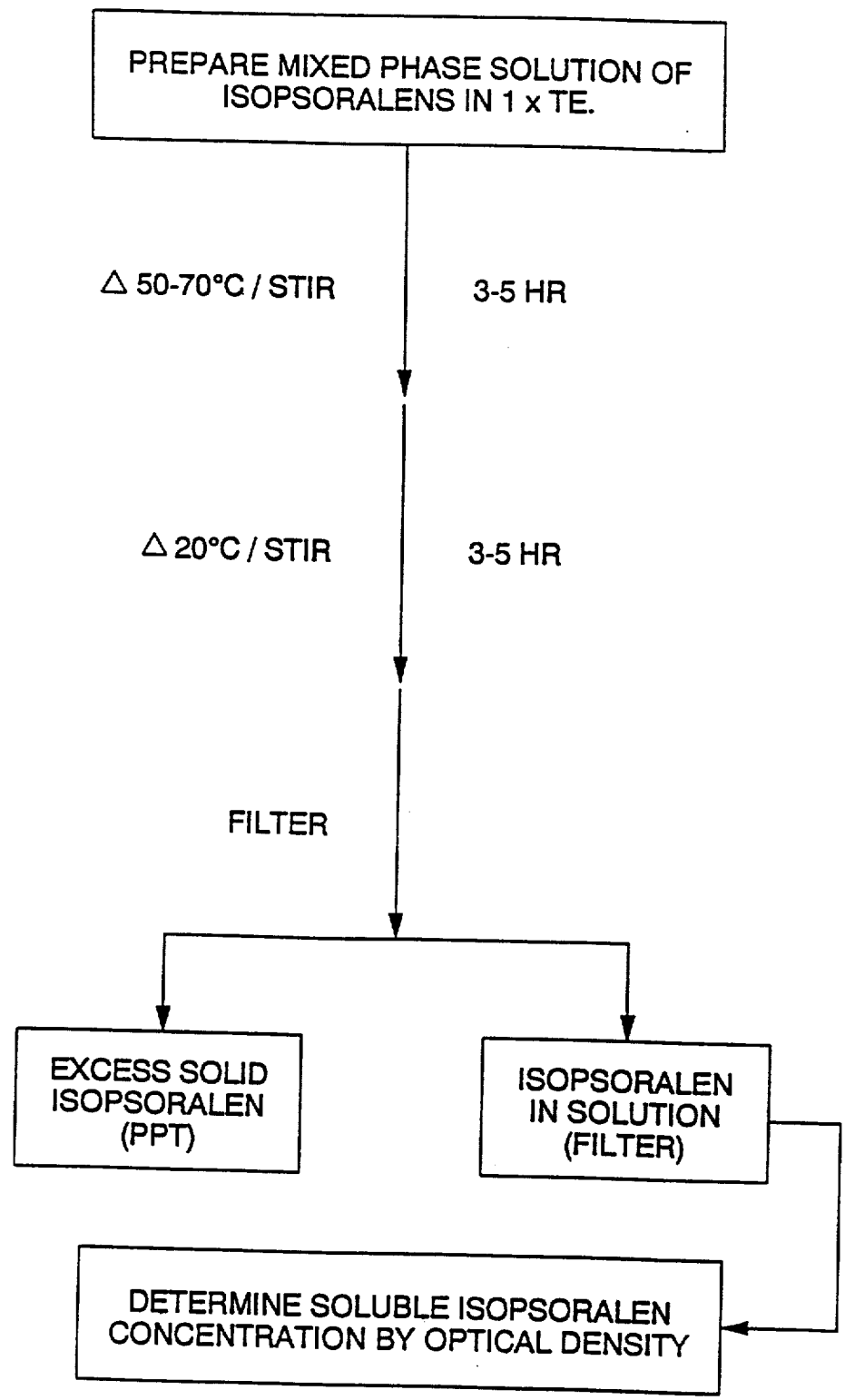
Figure 44:
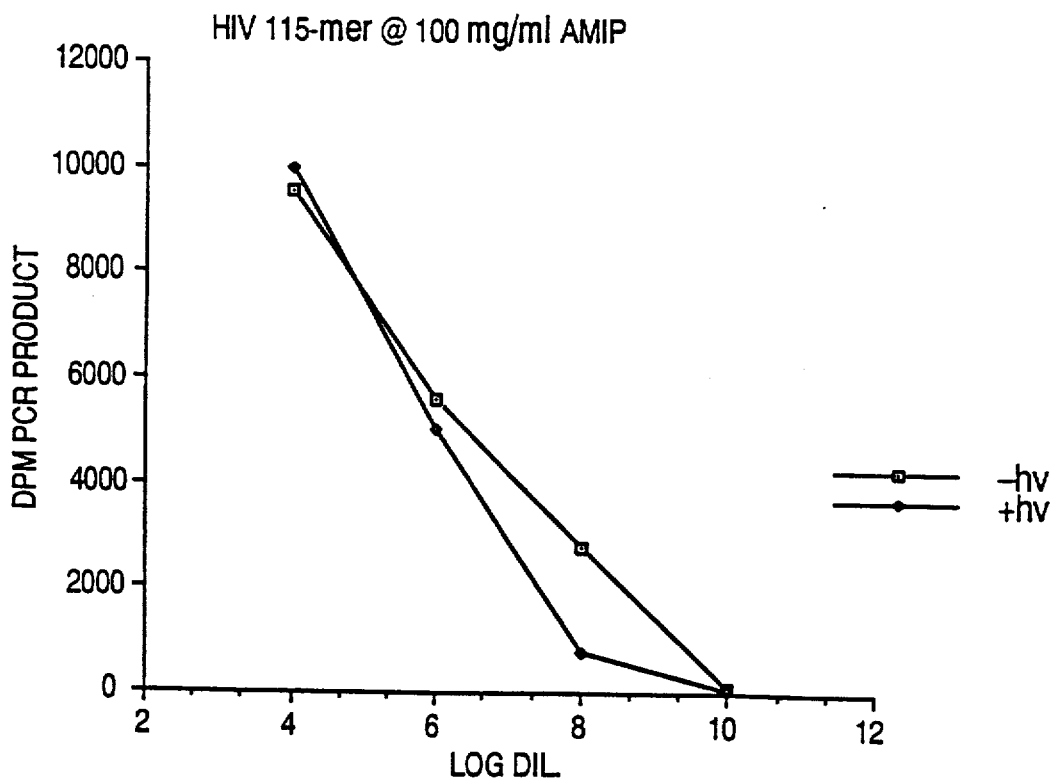
Figure 44:
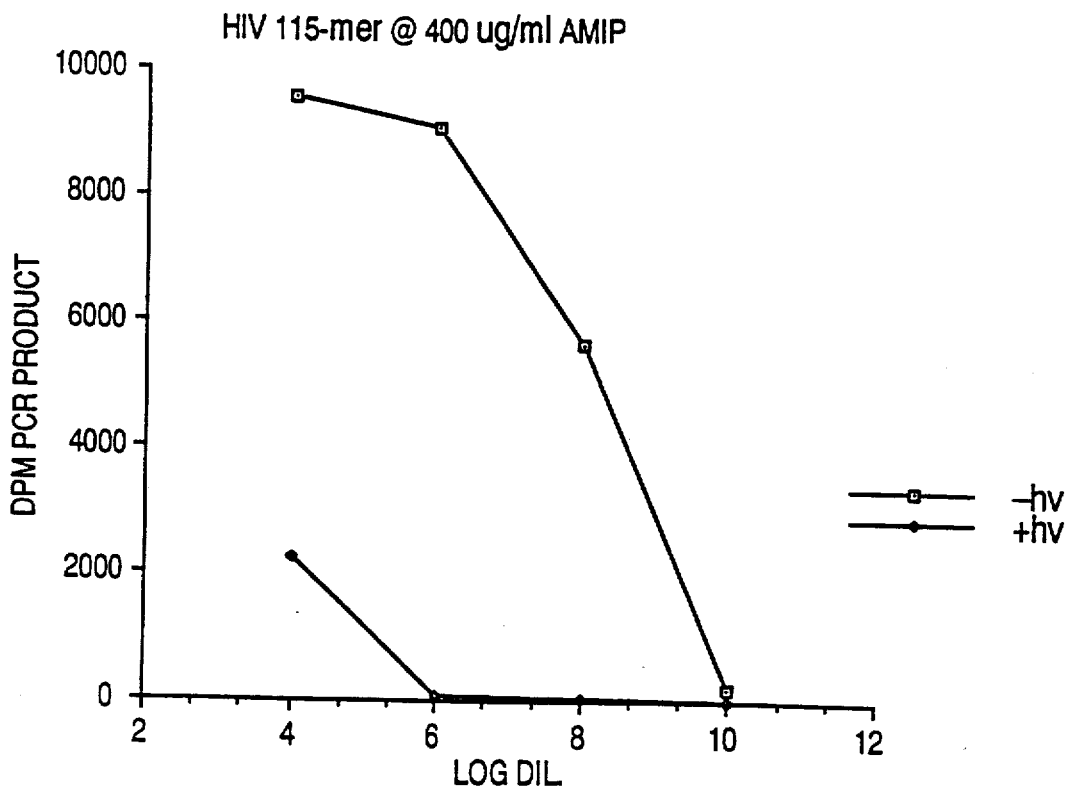
Figure 44C:
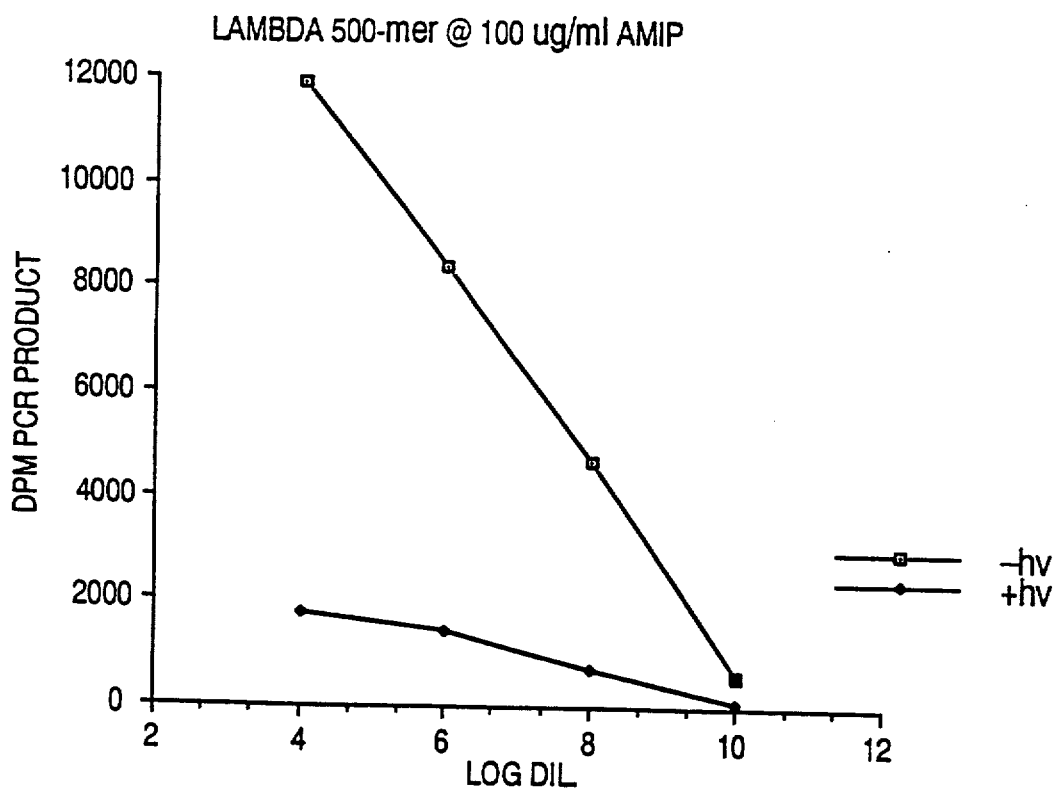
Figure 44:
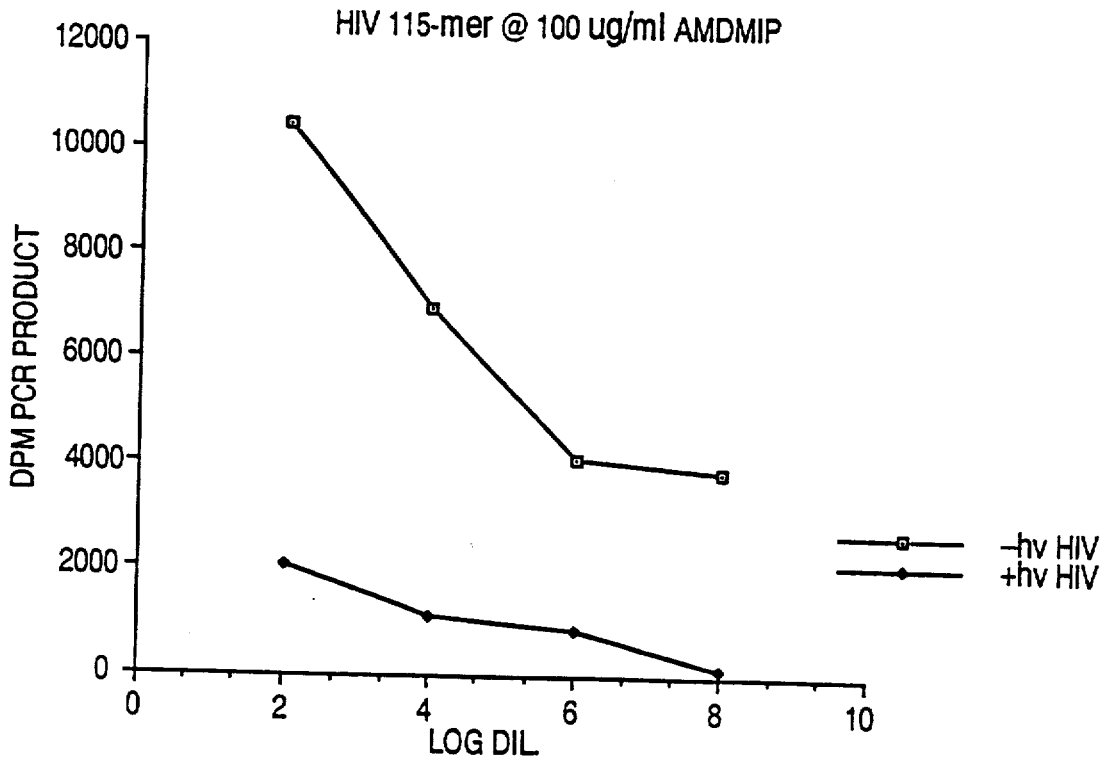
Figure 47:
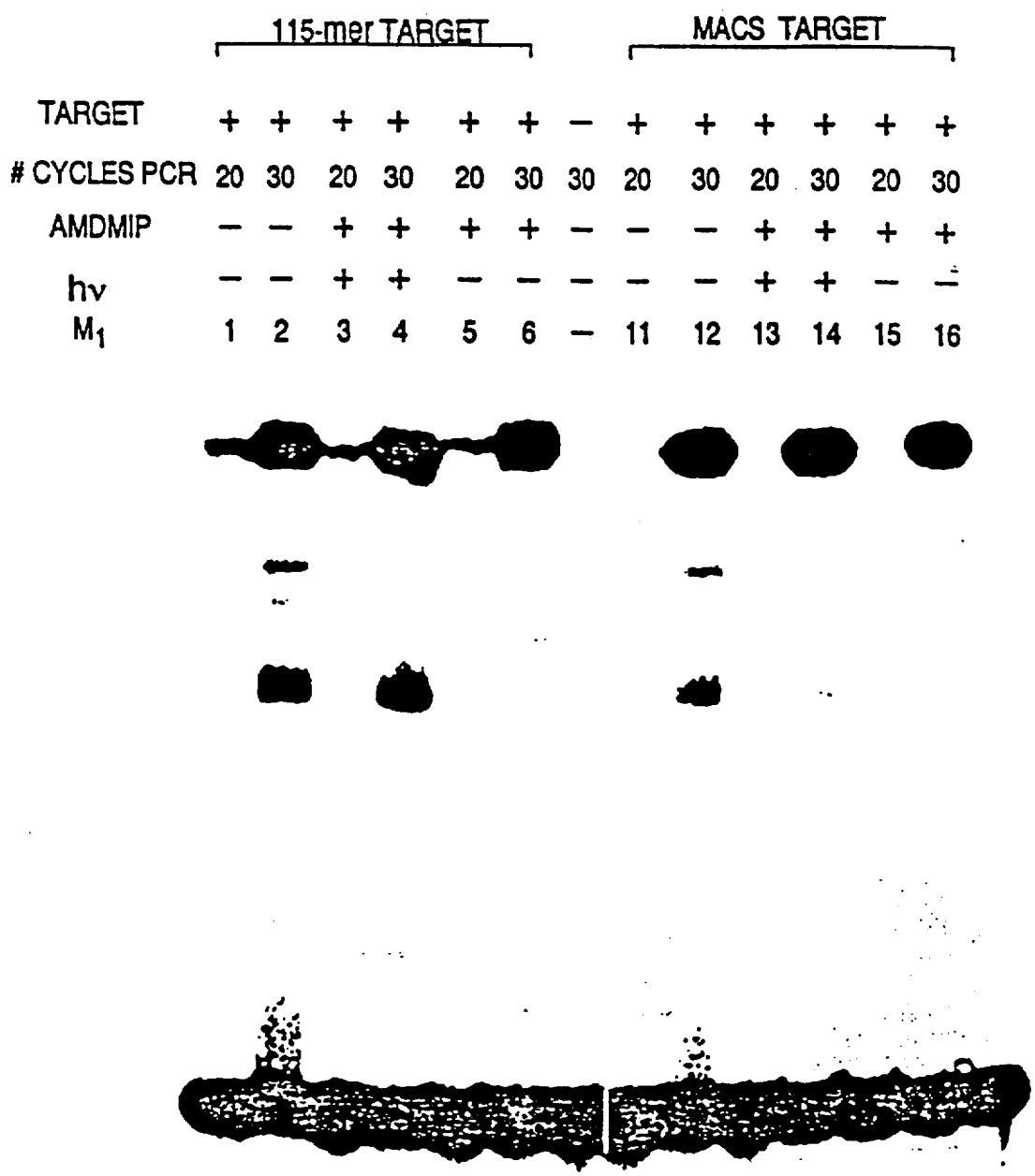

The first dark control was run with compounds 1-3. The results are shown in FIG. 49. All the compounds showed some inhibition of PCR at the higher concentrations used.

A separate experiment examined PCR inhibition with coumarin and methylene blue in the absence of light. The following concentrations of methylene blue were tried: $4.3 \times 10^{-2}$, $4.3 \times 10^{-3}$, $4.3 \times 10^{-4}$ and $4.3 \times 10^{-5}$M. Concentrations of coumarin tried included: $7 \times 10^{-3}$, $7 \times 10^{-4}$, $7 \times 10^{-5}$ and $7 \times 10^{-6}$M. Compound was added to PCR tube containing $\alpha$-$^{32}$P-dCTP and target (1 μl $10^{6.5}$×dil.; PCR'd MACS 1555 per assay-point). PCR was carried out for 30×cycles. Samples were loaded onto a 12%/8M urea gel. The results showed that methylene blue inhibited PCR at concentrations above $4.3 \times 10^{-5}$M. Coumarin did not inhibit PCR at any of the concentrations tested.

EXAMPLE 62

As discussed in Example 60, it cannot be assumed that the particular sterilizing compound concentration compatible with one PCR system will be compatible with another. The impact of a given concentration of sterilizing compound on PCR amplification efficiency must be determined on a system by system basis. For example, the HIV 115-mer system is compatible with concentrations of AMDMIP up to 400 μg/ml, and therefore this concentration of AMDMIP may be used for sterilization. However, this concentration of AMDMIP may not be compatible with other PCR systems. Indeed, the amplification efficiency of some PCR systems may be compromised by high concentrations of sterilizing compounds.

High concentrations of sterilizing compounds may function to stabilize PCR product (particularly long PCR products or PCR products which are exceptionally GC rich) such that less of the double stranded product will denature each cycle. This reduced availability of single stranded product for subsequent priming and extension would reduce the product yield in each PCR cycle. This reduced efficiency over many PCR cycles would result in drastic reduction in the yield of PCR product.

One method to overcome stabilization of PCR product is to modify the PCR conditions such that the melting temperature of the PCR product is lowered. In so doing, more of the double stranded PCR product is denatured each cycle thereby providing more single stranded target for subsequent priming and extension. The net result of the modified PCR conditions is a higher yield of PCR product.

One modification of PCR conditions which provides more denatured (single stranded) PCR product is to raise the pre-set denaturation temperature above 95° C. for each PCR cycle. This modification has the disadvantage of concomitant inactivation of Taq at temperatures above 95° C. Another modification is adding a co-solvent to the PCR buffer which allows denaturation of the PCR product to occur at a lower temperature. One such co-solvent is dimethyl sulfoxide (DMSO). Under some circumstances, DMSO has been shown to facilitate PCR. PCR Technology, H. A. Erlich (ed.) (Stockton Press 1989).

In this example, the effect of DMSO on PCR amplification in the presence of high concentrations of sterilizing compound (AMDMIP) was investigated. Samples were prepared for PCR which contained 1 μg of human placental DNA either with or without (unirradiated) AMDMIP (200 μg/ml). The samples were amplified 30 cycles under standard PCR conditions in the presence of 0%, 1%, 5% or 10% DMSO. The reaction mix contained $\alpha$-$^{32}$P-dCTP. Following amplification, the samples were analyzed by PAGE (data not shown).

The results indicated that, while (unirradiated) AMDMIP inhibits amplification at a concentration of 200 μg/ml to the point where there is virtually no detectable amplification product, addition of DMSO as a PCR co-solvent allowed amplification to proceed in the presence of AMDMIP. Excision and counting of the product bands provided the following results for the AMDMIP-containing samples (% DMSO/CPM): 0%/2500; 1%/2800; 5%/86,000; 10%/102,000).

Comparison of the control (no AMDMIP) PCR samples as a function of % DMSO showed a regular decrease in amplification yield. Excision and counting of the product bands (reported as the average of the duplicate samples) confirmed the visual observation that increasing concentrations of DMSO showed increased inhibition of PCR (% DMSO/CPM: 0%/139,000; 1%/137,000; 5%/94,000; 10%/76,000).

We claim:
1. A compound having the formula:

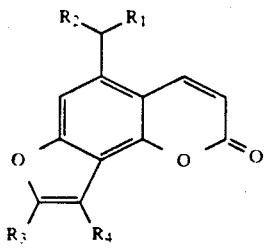

in which $R_1$ is —OH, —Br, —Cl, —I, —NH$_2$, or —NH$_3^+$X$^-$, where X$^-$ is Br$^-$, Cl$^-$ or I$^-$, and where $R_2$, $R_3$ and $R_4$, which may be the same or different, are —H or $^3$H.

2. A compound having the formula:

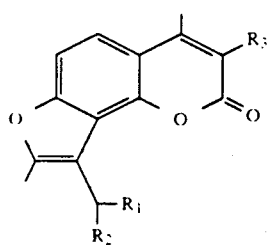

in which $R_1$ is —Br or —I, and where $R_2$ and $R_3$, which may be the same or different, are —H or $^3$H.

3. A compound having the formula:

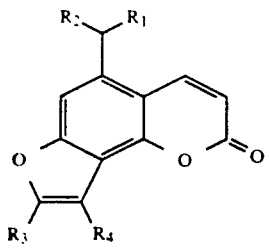

in which $R_1$ is

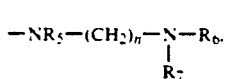

where n is a whole number between 6 and 16, where $R_2$, $R_3$ and $R_4$, in which may be the same or different, are —H or $^3$H, and where $R_5=R_7=$—CH$_3$, —C$_2$H$_5$, —C$_3$H$_7$ or —C$_4$H$_9$ and R$_6$ may have the formula —H or:

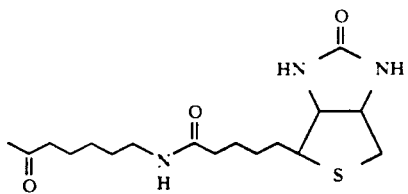

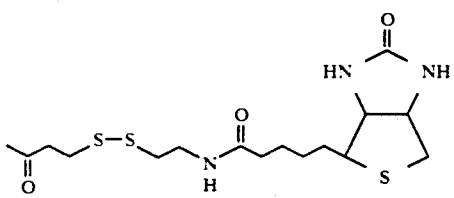

or

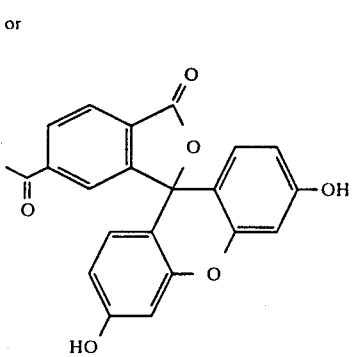

or a salt thereof.

4. A compound having the formula:

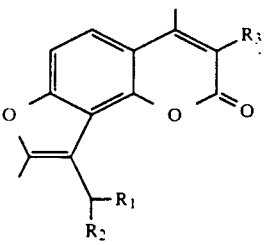

in which $R_1$ is

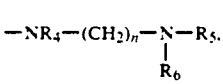

where n is a whole number between 6 and 16, where $R_2$ and $R_3$, which may be the same or different, are —H or $^3$H, and where $R_4=R_6=$—CH$_3$, —C$_2$H$_5$, —C$_3$H$_7$ or —C$_4$H$_9$ and R$_5$ may have the formula —H or:

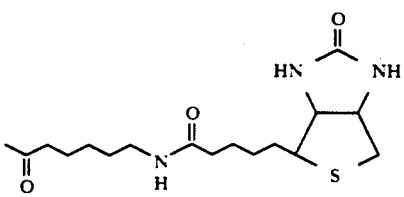

-continued

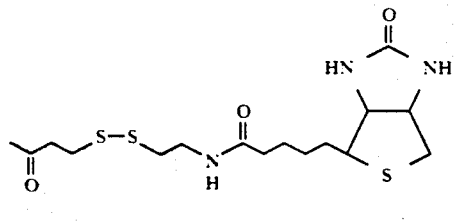

or

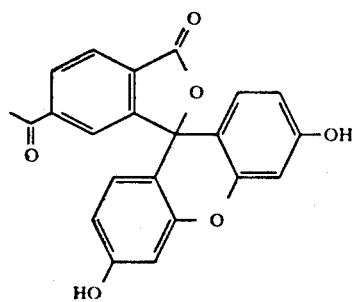

or a salt thereof.

5. A compound having the formula:

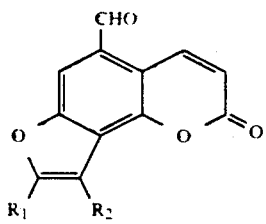

in which R₁ and R₂, which may be the same or different, are —H or ³H.

6. A compound having the formula:

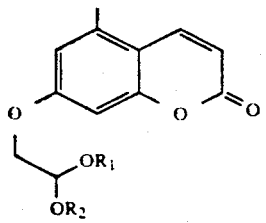

in which R₁ and R₂, which may be the same or different, are —CH₃, —C₂H₅, —C₃H₇ or —C₄H₉.

7. A compound having the formula:

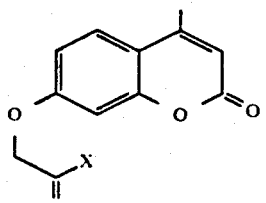

in which X is —Cl, —Br or —I.

8. A compound having the formula:

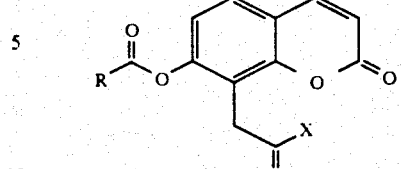

in which X is —Cl, —Br or —I and R is —CH₃, —C₂H₅, —C₃H₇ or —C₄H₉.

9. A compound having the formula:

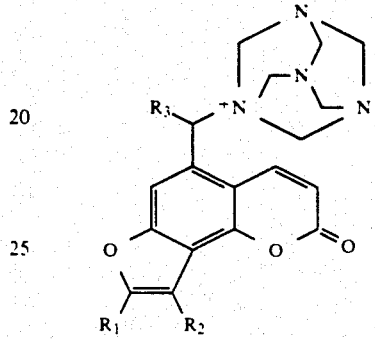

in which R₁, R₂ and R₃, which may be the same or different, are —H or ³H.

10. A complex, comprising one or more of the compounds of claims 1, 2, 3, 4, 5, or 9, coupled to nucleic acid.

11. A complex as in claim 10 wherein said coupling is non-covalent.

12. A complex as in claim 10 wherein said coupling is covalent.

13. A complex as in claim 10 wherein said nucleic acid is selected from the group consisting of viral, bacterial, fungal, mycoplasmal and protozoan DNA.

14. A complex as in claim 10 wherein said nucleic acid is human nucleic acid.

15. A complex, comprising 5-aminomethylisopsoralen coupled to nucleic acid at a level of addition greater than one 5-aminomethylisopsoralen molecule per fifty nucleic acid base pairs.

16. A complex, comprising 4'-aminomethyl-4,5'-dimethylisopsoralen coupled to nucleic acid at a level of addition greater than one 4'-aminomethyl-4,5'-dimethylisopsoralen molecule per fifty nucleic acid base pairs.

17. A complex as in claims 15 or 16 wherein said nucleic acid is DNA.

18. A complex as in claims 15 or 16 wherein said nucleic acid is RNA.

19. A method of synthesizing 5-methylisopsoralen, comprising the steps:
   a) providing 7-hydroxy-5-methylcoumarin; and
   b) treating 7-hydroxy-5-methylcoumarin with a haloethylene carbonate so that 5-methylisopsoralen is produced.

20. A method of synthesizing 5-methylisopsoralen, comprising the steps:
   a) providing 7-hydroxy-5-methylcoumarin;
   b) treating 7-hydroxy-5-methylcoumarin with a haloacetaldehyde diethylacetal so that 7-(2,2-diethoxyethyloxy)-5-methylcoumarin is produced; and c) treating 7-(2,2-diethoxyethyloxy)-5-methylcoumarin with acid so that 5-methylisopsoralen is produced.

21. A method of synthesizing 4,5'-dimethylisopsoralen, comprising the steps:

a) treating 7-(β-haloallyloxy)-4-methylcoumarin with heat and an alkyl anhydride to yield the esterified Claisen product 7-alkylcarbonyloxy-8-(β-haloallyl)-4-methylcoumarin; and b) treating 7-alkylcarbonyloxy-8-(β-halo-allyl)-4-methylcoumarin with an acid so that 4,5'-dimethylisopsoralen is produced.

22. A method of synthesizing 4'-aminomethyl-4,5'dimethylisopsoralen, comprising the steps:

a) treating 7-alkylcarbonyloxy-8-(β-haloallyl)-4-methylcoumarin with an acid so that 4,5'-dimethylisopsoralen is produced;

b) treating 4,5'-dimethylisopsoralen with a halomethyl methylether to yield a halomethyl derivative;

c) treating the halomethyl derivative with an alkali salt of phthalimide to yield the corresponding phthalimidomethyl derivative; and d) treating the phthalimidomethyl derivative with hydrazine to yield 4'-aminomethyl-4,5'dimethylisopsoralen.

23. A method of synthesizing 4'-aminomethyl-4,5'dimethylisopsoralen, comprising the steps:

a) providing 4,5'-dimethylisopsoralen;

b) reacting 4,5'-dimethylisopsoralen with a nitrogen donor so that 4'-phthalimidomethyl-4,5'-dimethylisopsoralen is produced; and c) treating 4'-phthalimidomethyl-4,5'-dimethylisopsoralen with hydrazine to yield 4'-aminomethyl-4,5'dimethylisopsoralen.

24. The method of claim 23 wherein said nitrogen donor may be selected from the group consisting of phthalimide salts, N-hydroxymethyl phthalimide and hexamethylene tetramine.

25. A method of synthesizing 4'-aminomethyl-4,5'dimethylisopsoralen, comprising the steps:

a) providing 4'-hydroxymethyl-4,5'-dimethylisopsoralen;

b) treating 4'-hydroxymethyl-4,5'-dimethylisopsoralen with a thionyl halide so that 4'-halomethyl-4,5'-dimethylisopsoralen is produced;

c) treating 4'-halomethyl-4,5'-dimethylisopsoralen with an alkali salt of phthalimide so that 4'-phthalimidomethyl-4,5'-dimethylisopsoralen is produced; and d) treating 4'-phthalimidomethyl-4,5'-dimethylisopsoralen with hydrazine so that 4'-aminomethyl-4,5'-dimethylisopsoralen is produced.

26. A method of synthesizing 5-aminomethyl-isopsoralen, comprising the steps:

a) providing a 5-halomethylisopsoralen;

b) treating said 5-halomethylisopsoralen with hexamethylenetetramine to create a hexamethylene-tetramine derivative; and c) treating said hexamethylenetetramine derivative with acid so that 5-aminomethylisopsoralen is produced.

27. The method of claim 26, wherein said providing of a 5-halomethylisopsoralen comprises synthesizing 5-bromomethylisopsoralen from 5-methylisopsoralen.

28. A method of synthesizing radiolabelled 5-aminomethylisopsoralen, comprising the steps:

a) providing formylisopsoralen;

b) treating said formylisopsoralen with radiolabelled sodium borohydride to yield the radiolabelled hydroxymethylisopsoralen;

c) treating hydroxymethylisopsoralen with a thionyl halide to yield the corresponding radiolabelled halomethylisopsoralen;

d) treating said halomethylisopsoralen with hexamethylene tetramine to create the corresponding radiolabelled hexamethylenetetramine derivative; and e) treating said hexamethylenetetramine derivative with an acid to produce radiolabelled 5-aminomethylisopsoralen.

29. A method for labelling nucleic acid, comprising the steps:

a) providing labelled 5-aminomethylisopsoralen and nucleic acid; and b) coupling said labelled 5-aminomethylisopsoralen to said nucleic acid by photoactivation.

30. A method for inhibiting template-dependent enzymatic synthesis of nucleic acid, comprising the steps:

a) providing one or more furocoumarins and nucleic acid; and b) coupling said one or more furocoumarins to said nucleic acid by photoactivation, so that it cannot be replicated by Taq polymerase.

31. A method for inhibiting template-dependent enzymatic synthesis of nucleic acid, comprising the steps:

a) providing one or more furocoumarins and nucleic acid; and b) coupling said one or more furocoumarins to said nucleic acid by photoactivation, so that it cannot be replicated by T4 polymerase.

32. The method as recited in claims 30 or 31 wherein said one or more furocoumarins are selected from the group consisting of 5-methylisopsoralen, 5-aminomethylisopsoralen and 4'-aminomethyl-4,5'-dimethylisopsoralen.

33. A method for inhibiting template-dependent enzymatic synthesis of nucleic acid, comprising the steps:

a) providing one or more isopsoralens and nucleic acid; and b) coupling said one or more isopsoralens to said nucleic acid by photoactivation, so that it cannot be replicated by reverse transcriptase.

34. The method as recited in claim 33 wherein said one or more isopsoralens are selected from the group consisting of 5-methylisopsoralen, 5-aminomethylisopsoralen and 4'-aminomethyl-4,5'-dimethylisopsoralen.

35. A method for inhibiting template-dependent enzymatic synthesis of nucleic acid, comprising the steps:

a) providing 4'-aminomethyl-4,5'-dimethylisopsoralen and nucleic acid; and b) binding said 4'-aminomethyl-4,5'-dimethylisopsoralen to nucleic acid by photoactivation, so that it cannot be replicated by E. coli DNA polymerase I.

36. A method for inhibiting template-dependent enzymatic synthesis of nucleic acid, comprising the steps:

a) providing 4'-aminomethyl-4,5'-dimethylisopsoralen and nucleic acid; and b) binding said 4'-aminomethyl-4,5'-dimethylisopsoralen to nucleic acid by photoactivation, so that it cannot be replicated by Klenow polymerase.

37. A method for modifying a target sequence, comprising the steps:

a) providing nucleic acid containing a target sequence;

b) providing 5-aminomethylisopsoralen; and c) coupling said 5-aminomethylisopsoralen to said target sequence by photoactivation.

38. A method for detecting a target sequence, comprising the steps:

a) providing nucleic acid containing a target sequence;

b) providing 5-aminomethylisopsoralen;

c) coupling said 5-aminomethylisopsoralen to said target sequence by photoactivation; and d) detecting said target sequence.

39. A method for detecting a target sequence, comprising the steps:

a) providing nucleic acid containing a target sequence;

b) providing 4'-aminomethyl-4,5'-dimethyl-isopsoralen; and c) coupling said 4'-aminomethyl-4,5'-dimethylisopsoralen to said target sequence by photoactivation; and d) detecting said target sequence.

40. A method of synthesizing photoproduct, comprising the steps:

a) providing one or more furocoumarins; and b) irradiating said one or more furocoumarins in the absence of nucleic acid.

41. The method as recited in claim 40 wherein said one or more furocoumarins are selected from the group consisting of 5-aminomethylisopsoralen and 4'-aminomethyl-4,5'-dimethylisopsoralen.

42. A method of binding photoproduct to nucleic acid, comprising the sequential steps:

a) providing in any order:
  i) one or more furocoumarin derivatives, and
  ii) nucleic acid;

b) exposing said furocoumarin derivatives to activating wavelengths of electromagnetic radiation;

c) mixing said irradiated furocoumarin derivatives with said nucleic acid in the absence of activating wavelengths of electromagnetic radiation.

* * * * *

UNITED STATES PATENT AND TRADEMARK OFFICE
CERTIFICATE OF CORRECTION

PATENT NO. : 5,139,940

DATED : 8/18/92

NVENTOR(S) : Stephen T. Isaacs et al.

It is certified that error appears in the above-identified patent and that said Letters Patent is hereby corrected as shown below:

In the INVENTORS:
 Line 5 should read "George D. Cimino...."
On the title page, item [56] References Cited:
In the OTHER PUBLICATIONS:
 The second line from the bottom of the column should read "Manipulation, . . . ."
 In the second column, line 21 should read, "Medicine Biologie Envir."
On the title page, item [57]:
In the ABSTRACT:

Line 5 should read "isopsoralens result in covalent . . . "

Line 9 should read ". . . Beside the isopsoralen -- compositions, . . ."

In col. 6, line 50, please delete "duced," and insert --duced;--

In col. 15, line 1, please delete "FIGS" and insert --FIG.--.

In col. 19, line 55, please delete "rhoduim" and insert --rhodium--.

In col. 21, line 15, please delete "VI #1 to #3, #3 to #5, #5 to #8 and #9 to #10" and insert --VI #1 to #3, #3 to #5, #5 to #8, #8 to #9, and #9 to #10--.

In col. 22, line 52, please delete "$\geq$" and insert --$\geq$--.

UNITED STATES PATENT AND TRADEMARK OFFICE
CERTIFICATE OF CORRECTION

PATENT NO. : 5,139,940

DATED : 8/18/92

INVENTOR(S) : Stephen T. Isaacs *et al.*

It is certified that error appears in the above-identified patent and that said Letters Patent is hereby corrected as shown below:

In col. 22, line 67, please delete "$_c2H_5$ $C_3H_7$ or $C_4H_7$" and insert --$C_2H_5$, $C_3H_7$ or $C_4H_9$--.

In col. 22, line 68, please delete "$_c2H_5$" and insert --$C_2H_5$--.

In col. 23, line 64, please delete "the" and insert --The--.

In col. 25, line 17, please delete "5 #5" and insert --#5--.

In col. 25, line 49, please delete "i.e., 5" and insert --i.e., #5--.

In col. 28, line 60, please delete "proprionic" and insert --propionic--.

In col. 29, line 13, please delete "trans" and insert --*trans*--.

In col. 29, line 24, please delete "rhoduim" and insert --rhodium--.

In col. 31, line 1, please delete "convarsion" and insert --conversion--.

UNITED STATES PATENT AND TRADEMARK OFFICE
CERTIFICATE OF CORRECTION

PATENT NO. : 5,139,940
DATED : 8/18/92
INVENTOR(S) : Stephen T. Isaacs et al.

It is certified that error appears in the above-identified patent and that said Letters Patent is hereby corrected as shown below:

In col. 31, line 52, please delete "$C_2H5$" and insert -- $C_2H_5$ --.

In col. 31, line 52, please delete "n" and insert --*n*--.

In col. 31, line 58, please delete "$\geq$" and insert --$\geq$--.

In col. 31, line 61, please delete "hinderance" and insert --hindrance--.

In col. 32, line 66, please delete "perferred" and insert --preferred--.

In col. 37, line 60, please delete "Eppendorph" and insert --Eppendorf--.

In col. 38, line 27, please delete "Eppendorph" and insert --Eppendorf--.

In col. 40, lines 32-33, please delete "compound #25a" and insert --Compound #25a--.

In col. 42, line 59, please delete "planer" and insert --planar--.

In col. 46, line 53, please delete "enhances" and insert --enhanced--.

In col. 47, line 14, please delete "Ka" and insert --*Ka*--.

In col. 50, line 64, please delete "diferential" and insert --differential--.

UNITED STATES PATENT AND TRADEMARK OFFICE
CERTIFICATE OF CORRECTION

PATENT NO. : 5,139,940

DATED : 8/18/92

INVENTOR(S) : Stephen T. Isaacs et al.

It is certified that error appears in the above-identified patent and that said Letters Patent is hereby corrected as shown below:

In col. 50, line 65, please delete "specifically" and insert --specificity--.

In col. 50, line 68, please delete "specifically" and insert --specificity--.

In col. 51, line 24, please delete "derivative," and insert --derivative;--.

In col. 51, line 26, please delete "ce(s)," and insert --ce(s); and--.

In col. 51, line 33, please delete "ve(s)," and insert --ve(s);--.

In col. 51, line 36, please delete "sequence(s)," and insert --sequence(s); and--.

In col. 54, line 65, please delete "&he" and insert --the--.

In col. 55, line 56, after "present" please insert --invention--.

In col. 56, line 47, after "later" please insert --be--.

In col. 58, line 5, please delete "compatablity" and insert --compatibility--.

In col. 60, line 39, please delete "anediamin]" and insert --anediamine]--.

UNITED STATES PATENT AND TRADEMARK OFFICE
CERTIFICATE OF CORRECTION

PATENT NO. : 5,139,940

DATED : 8/18/92

INVENTOR(S) : Stephen T. Isaacs et al.

It is certified that error appears in the above-identified patent and that said Letters Patent is hereby corrected as shown below:

In col. 61, line 66, please delete "their" and insert --there--.

In col. 62, line 60, please delete "ul" and insert --µl--.

In col. 63, at the footnote of Table 6, please delete "ug" and insert --µg--.

In Table 6, please delete "2.4 x 10⁻*" and insert --2.4 x $10^{-8}$--.

In col. 63, line 44, please delete "(a)" and insert --(a)--.

In col. 63, line 46, please delete "a adducts" and insert --a adducts--.

In col. 63, line 54, please delete "a" and insert --a--.

In col. 64, line 35, in the footnote to Table 7-continued, please delete "a" and insert --a--.

In col. 64, line 41, please delete "a" and insert --a--.

In col. 64, line 66, please delete "ul" and insert --µl--.

In col. 68, line 2, please delete "Eppendorph" and insert --Eppendorf--.

In col. 68, line 5, please delete "pendorph tubes have a transmittance IO of" and insert --pendorf tubes have a transmittance of--.

In col. 68, line 9, please delete "Eppendorph" and insert --Eppendorf--.

UNITED STATES PATENT AND TRADEMARK OFFICE
CERTIFICATE OF CORRECTION

PATENT NO. : 5,139,940

DATED : 8/18/92

INVENTOR(S) : Stephen T. Isaacs et al.

It is certified that error appears in the above-identified patent and that said Letters Patent is hereby corrected as shown below:

In col. 70, line 6, please center "EXAMPLE 2".

In col. 70, lines 42-43, please delete "chroloform" and insert --chloroform--.

In col. 70, line 44, please delete "strting" and insert --starting--.

In col. 70, line 46, please delete "[3,4, 4' ,5'-$^3H_4$-3," and insert --[3,4',5'-$^3H_4$]-3--.

In col. 70, line 61, please delete "chromatogrphy" and insert --chromatography--.

In col. 71, line 6, please delete "10 ug unlabelled MIP in 50 ul" and insert --10 µg unlabelled MIP in 50 µl--.

In col. 71, line 12, please delete "ul" and insert --µl--.

In col. 71, line 14, please delete "corresponding" and insert --corresponded--.

In col. 71, lines 22-23, please delete "1 65" and insert --1.65--.

In col. 74, line 57, after "aqueous" please insert --phase--.

In col. 75, line 7, before "was" please insert --phase--.

In col. 75, line 12, please delete "ug/ml" and insert --µg/ml--.

UNITED STATES PATENT AND TRADEMARK OFFICE
CERTIFICATE OF CORRECTION

PATENT NO. : 5,139,940
DATED : 8/18/92
INVENTOR(S) : Stephen T. Isaacs et al.

It is certified that error appears in the above-identified patent and that said Letters Patent is hereby corrected as shown below:

In col. 75, line 67, please delete "1 0 mmol" and insert -- 1.0 mmol--.

In col. 77, line 35, please delete "(1 0N)" and insert -- (1.0 N)--.

In col. 78, line 51, please delete "suIfosuccinimidyl" and insert --sulfosuccinimidyl--.

In col. 78, line 66, please delete "ug" and insert --µg--.

In col. 78, line 67, please delete "ul" and insert --µl--.

In col. 79, line 6, please delete "ul" and insert --µl--.

In col. 79, line 36, please delete "HCL" and insert --HCl--.

In col. 80, line 64, please delete "hour" and insert -- hours--.

In col. 81, line 28, after "6.26 (1" please delete "h" and insert --H--.

In col. 81, line 30, please delete "1 01-1 09 and insert -- 1.01-1.09--.

In col. 82, line 19, please delete "ug" and insert --µg--.

In col. 82, line 19, please delete "ul" and insert --µl--.

UNITED STATES PATENT AND TRADEMARK OFFICE
CERTIFICATE OF CORRECTION

PATENT NO. : 5,139,940
DATED : 8/18/92
INVENTOR(S) : Stephen T. Isaacs et al

It is certified that error appears in the above-indentified patent and that said Letters Patent is hereby corrected as shown below:

In col. 82, line 26, please delete "ul" and insert --µl--.

In col. 83, line 17, after "81%" please insert --yield--.

In col. 84, line 29, please delete "0 1 M" and insert --0.1 M--.

In col. 84, line 32, please delete "extracts" and insert --extract--.

In col. 84, line 43, please delete "HCL" and insert --HCl--.

In col. 84, line 57, please delete "3H-PHIMDMIP" and insert --³H-PHIMDMIP--.

In col. 85, line 16, please delete "chIoroform" and insert --chloroform--.

In col. 87, line 6, please delete "umol" and insert --µmol--.

In col. 87, line 23-24, please delete "chIoroform" and insert --chloroform--.

In col. 87, line 25, please delete "HCL" and insert --HCl--.

In col. 87, line 26, please delete "MgSO4" and insert --MgSO$_4$--.

In col. 88, line 7, please delete "3" and insert --2--.

In col. 88, line 21, please delete "is" and insert --in--.

UNITED STATES PATENT AND TRADEMARK OFFICE
CERTIFICATE OF CORRECTION

PATENT NO. : 5,139,940

DATED : 8/18/92

INVENTOR(S) : Stephen T. Isaacs et al.

It is certified that error appears in the above-identified patent and that said Letters Patent is hereby corrected as shown below:

In col. 89, line 12, please delete "FLOURDMIP" and insert --FLUORDMIP--.

In col. 89, line 58, please delete "was" and insert --were--.

In col. 90, line 10, please delete "0.2 u" and insert --0.2 µ--.

In col. 92, line 49, please delete "arrangment" and insert ---arrangement--.

In col. 94, line 42, please delete "embodimnt" and insert --embodiment--.

In col. 96, line 8, please delete "relation ship" and insert --relationship--.

In col. 96, line 22, please delete "Eppendorph" and insert --Eppendorf--.

In col. 96, line 27, please delete "Eppendorph" and insert --Eppendorf--.

In col. 96, line 28, please delete "Eppendorph" and insert --Eppendorf--.

In col. 98, line 46, please delete "reqardless" and insert --regardless--.

UNITED STATES PATENT AND TRADEMARK OFFICE
CERTIFICATE OF CORRECTION

PATENT NO. : 5,139,940
DATED : 8/18/92
INVENTOR(S) : Stephen T. Isaacs et al

It is certified that error appears in the above-indentified patent and that said Letters Patent is hereby corrected as shown below:

In col. 100, line 25, after "that" please insert --the--.

In col. 101, line 12-13, please delete "discreet" and insert --discrete--.

In col. 102, line 49, please delete "HRI-2" and insert --HRI-42--.

In col. 103, line 39, please delete "were" and insert --was--.

In col. 103, line 55, please delete "Polmerase" and insert --Polymerase--.

In col. 103, line 55, please delete "*E. Coli*" and insert --*E. coli*--.

In col. 104, line 12, please delete "*Thermus acuaticus*" and insert --*Thermus aquaticus*--.

In col. 104, line 65, please delete "stand" and insert --strand--.

In col. 106, line 36, please delete "55 C" and insert --55°C--.

In col. 106, line 41, please delete "was" and insert --were--.

In col. 107, line 16, after "watt" please insert --)--.

In col. 107, line 18, please delete "Eppendorph" and insert --Eppendorf--.

UNITED STATES PATENT AND TRADEMARK OFFICE
CERTIFICATE OF CORRECTION

PATENT NO. : 5,139,940
DATED : 8/18/92
INVENTOR(S) : Stephen T. Isaacs et al

It is certified that error appears in the above-indentified patent and that said Letters Patent is hereby corrected as shown below:

In col. 107, line 51, after "samples" please insert --to--.

In col. 108, line 40, please delete "indicats" and insert --indicates--.

In col. 109, line 19, please delete "Emmeryville" and insert --Emeryville--.

In col. 109, line 55, please delete "Eppendorph" and insert --Eppendorf--.

In col. 112, line 38, please delete "dependant" and insert --dependent--.

In col. 114, line 57, please delete "systems" and insert --system--.

In col. 116, line 43, please delete "44(d)" and insert --44(D)--.

In col. 116, line 57, please delete "α-32P" and insert --α-$^{32}$P--.

In col. 117, line 30, please delete "adressed" and insert --addressed--.

In col. 117, line 41, please delete "56.C" and insert --56°C--.

UNITED STATES PATENT AND TRADEMARK OFFICE
CERTIFICATE OF CORRECTION

PATENT NO. : 5,139,940

DATED : 8/18/92

INVENTOR(S) : Stephen T. Isaacs et al.

It is certified that error appears in the above-identified patent and that said Letters Patent is hereby corrected as shown below:

In col. 118, line 27, please delete "sterilize" and insert --sterilized--.

In col. 118, line 41, after "light" please insert --)--.

In col. 119, line 13, please delete "Amplification" and insert --Amplifications--.

In col. 119, line 22, please delete "autoradiaography" and insert --autoradiography--.

Figure 1B:
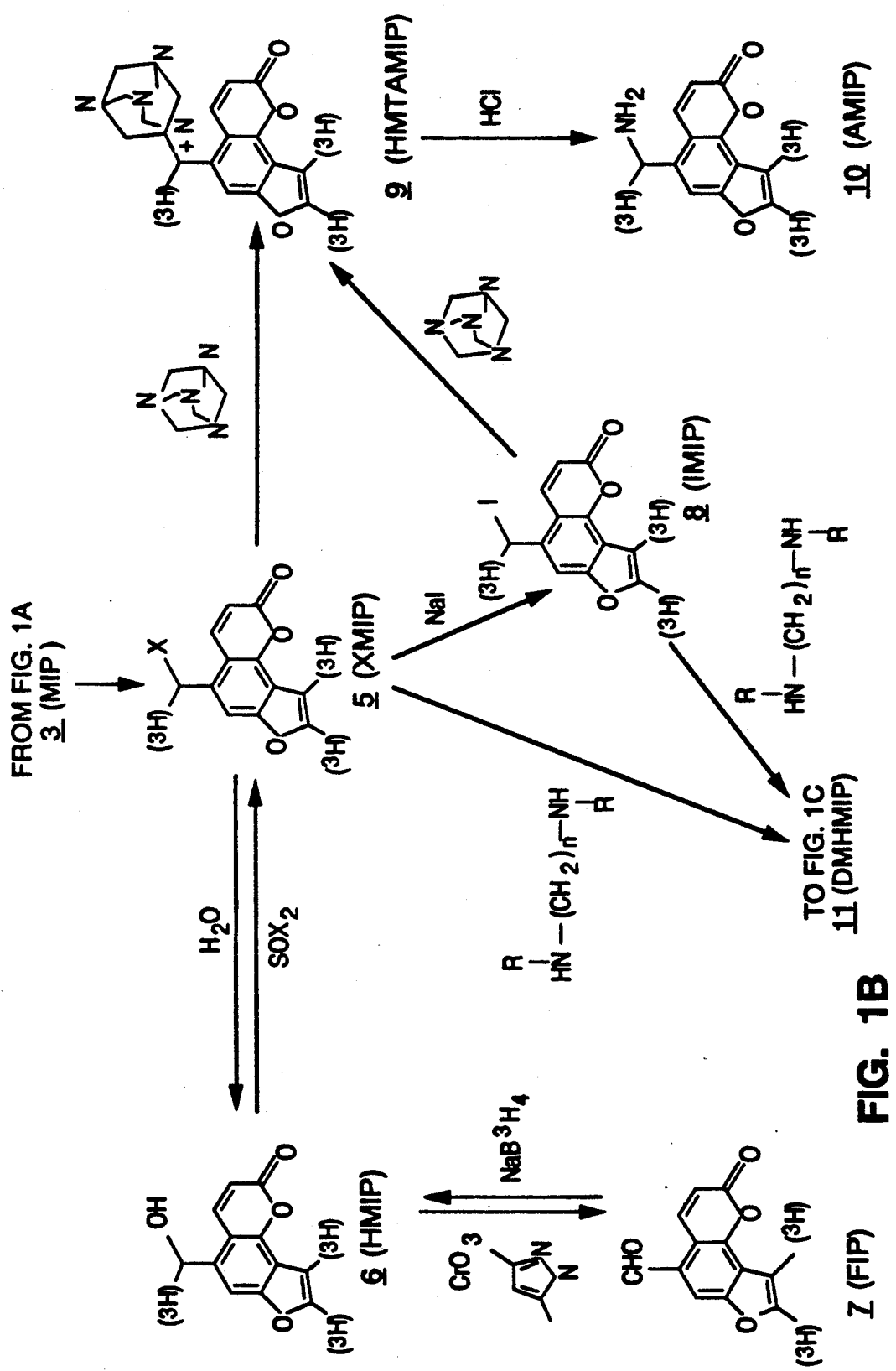
FIG. 1B details the compound synthesis scheme to Compound 10.
Figure 1C:
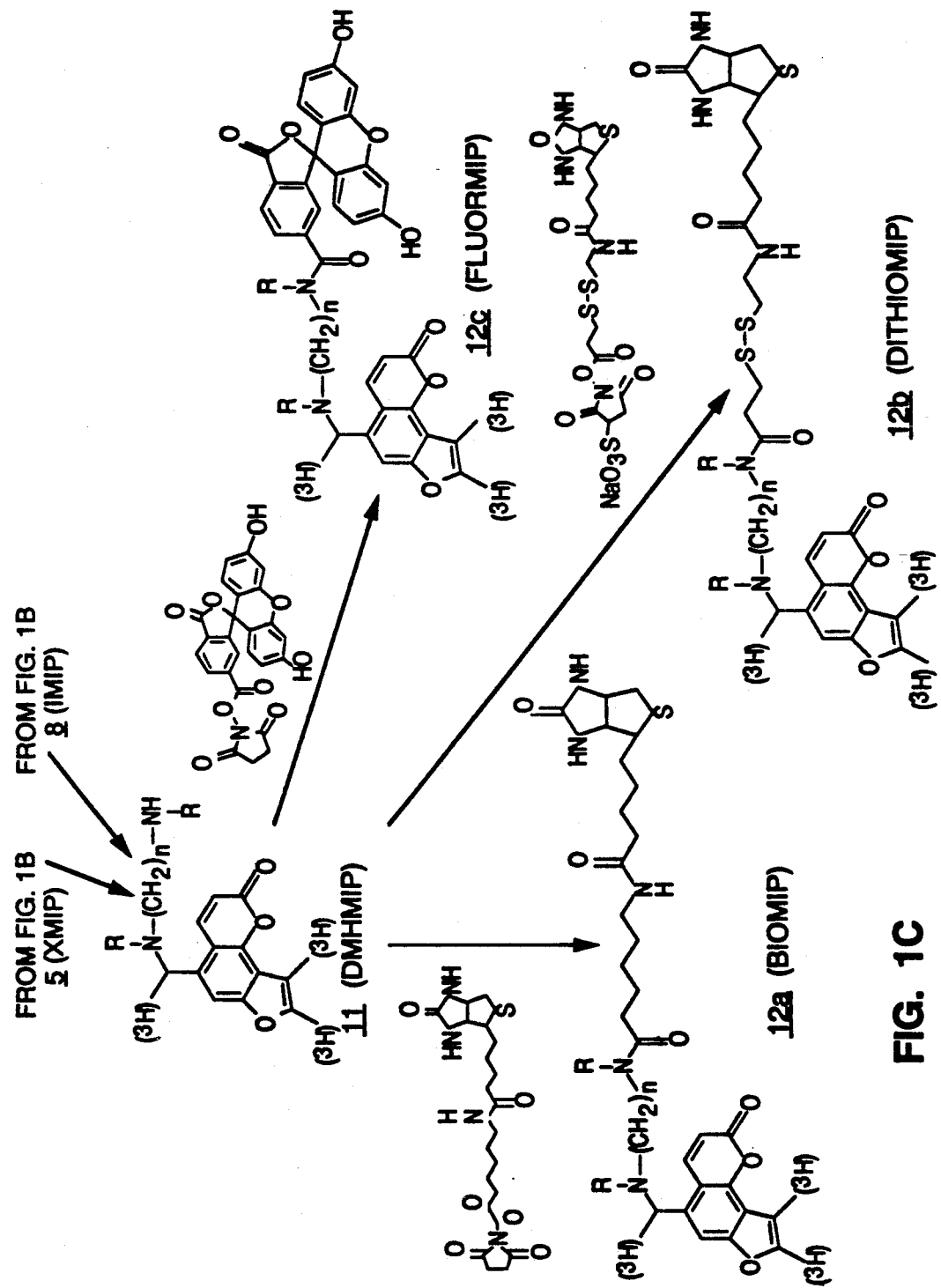
FIG. 1C details the compound synthesis scheme to Compound 12b.
Figure 2A:
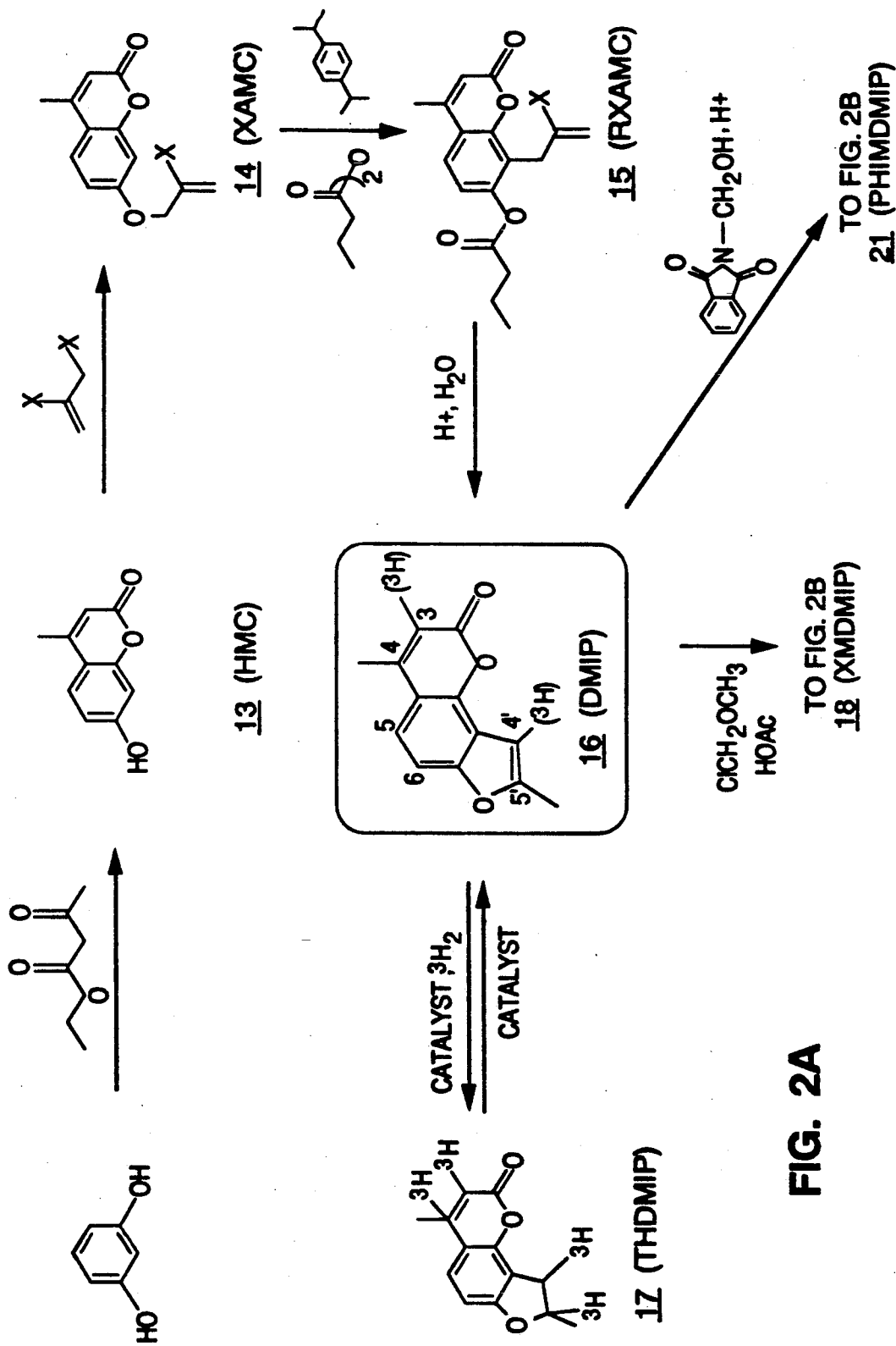
FIG. 2A details the compound synthesis scheme to Compound 16.
Figure 2B:
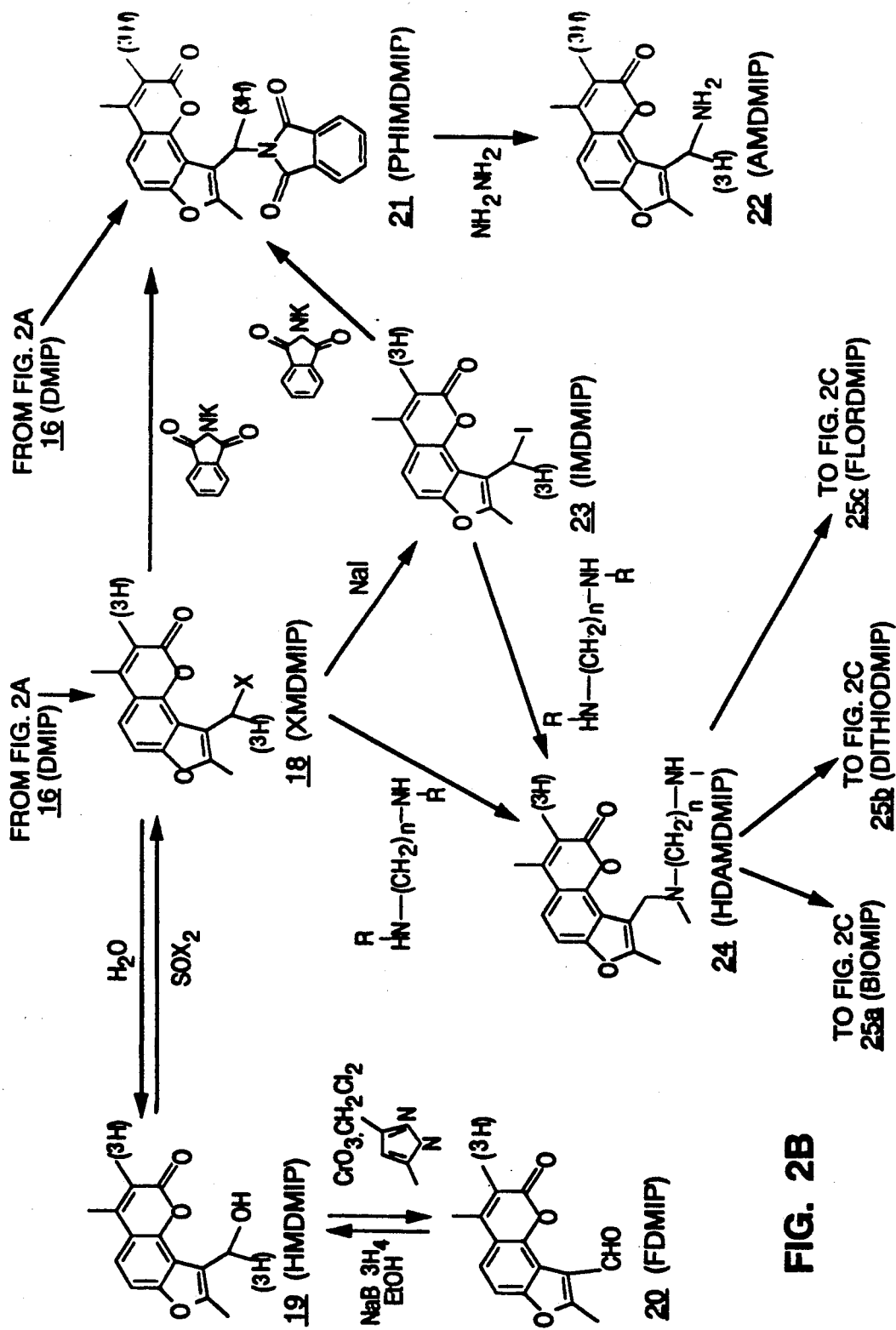
FIG. 2B details the compound synthesis scheme to Compound 24.
Figure 2C:
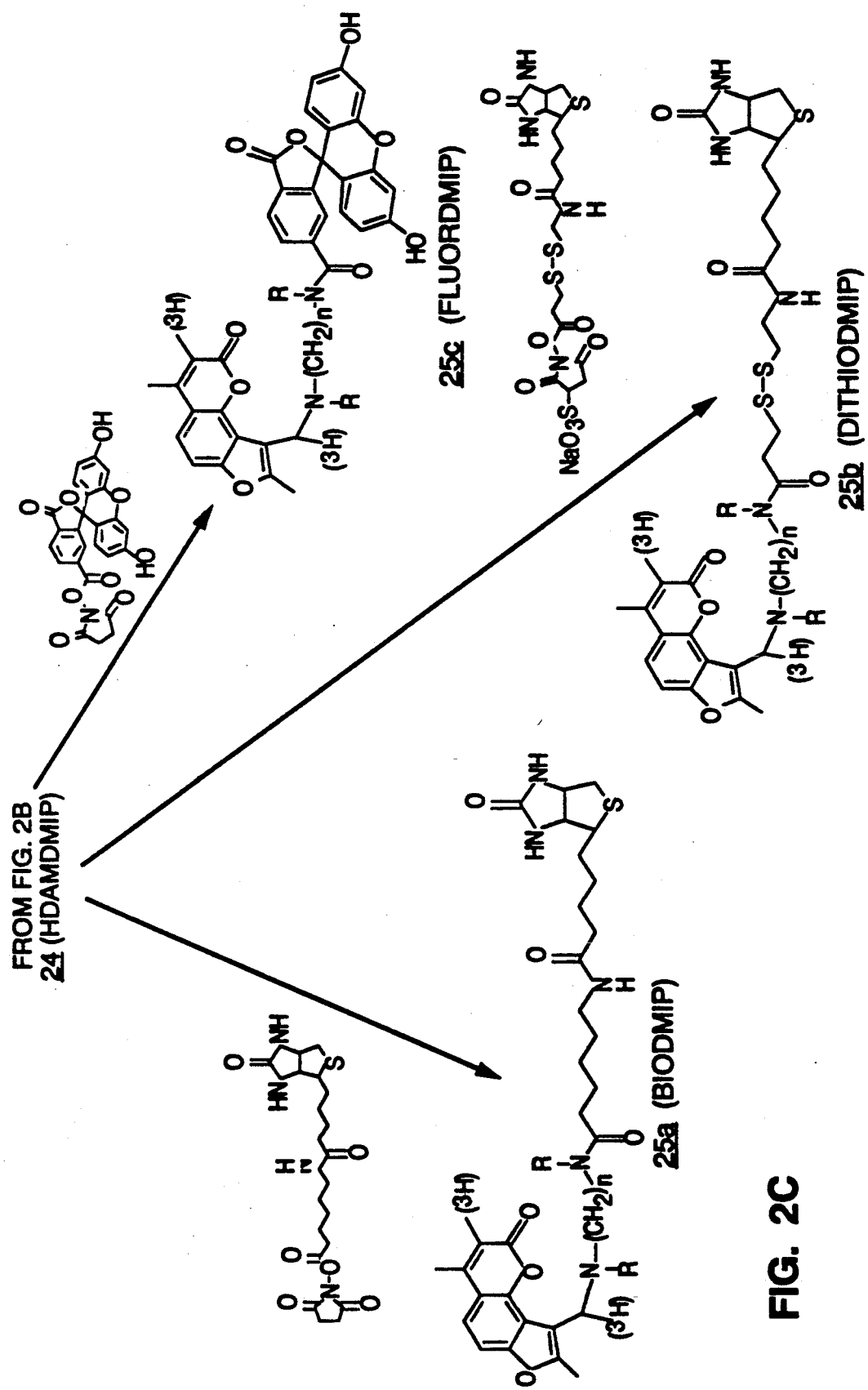
FIG. 2C details the compound synthesis scheme to Compound 25b.

In the DRAWINGS:

Sheets 2, 3, 4, 6, 7, 8, 11 50, 51 and 54 of the drawings, consisting of Figs. 1A, 1B, 1C. 2A, 2B, 2C, 5, 44A, 44B, 44C, 44D and 47, should be deleted to be replaced with the corrected Fig. 1A, 1B, 1C, 2A, 2B, 2C, 5, 44A, 44B, 44C, 44D and 47, as shown on the attached pages.

In FIG. 5, please delete "▽20°C" and insert --▲20°C--.

In FIG. 44(A) please delete "AMA" and insert --AMIP--.

In FIG. 44(B) please delete "AMA" and insert --AMIP--.

In FIG. 44(C) please delete "AMA" and insert --AMIP--.

In FIG. 44(D) please delete "AMDMA" and insert --AMDMIP--.

In the CLAIMS:

In col. 121, line 8, please delete "o%" and insert --0%--.

UNITED STATES PATENT AND TRADEMARK OFFICE
CERTIFICATE OF CORRECTION

PATENT NO. : 5,139,940
DATED : 8/18/92
INVENTOR(S) : Stephen T. Isaacs et al.

It is certified that error appears in the above-identified patent and that said Letters Patent is hereby corrected as shown below:

In col. 122, line 58, please delete "-$C_{4H9}$" and insert -- -$C_4H_9$ --.

In col. 126, line 4, please delete "radillabelled" and insert --radiolabelled--.

Signed and Sealed this

Second Day of May, 1995

BRUCE LEHMAN

Attest:

Attesting Officer

Commissioner of Patents and Trademarks